United States Patent
Merchiers et al.

(10) Patent No.: US 11,780,930 B2
(45) Date of Patent: Oct. 10, 2023

(54) CD38 MODULATING ANTIBODY

(71) Applicant: BLACK BELT THERAPEUTICS LIMITED, Stevenage (GB)

(72) Inventors: Pascal Merchiers, Stevenage (GB); Anne Goubier, Stevenage (GB); Kevin Moulder, Stevenage (GB); Nina Eissler, Stevenage (GB); Josephine Salimu, Stevenage (GB); Simone Filosto, Stevenage (GB); Beatriz Goyenechea Corzo, Stevenage (GB); Hemanta Baruah, Lebanon, NH (US); Bianka Prinz, Lebanon, NH (US)

(73) Assignee: BLACK BELT THERAPEUTICS LIMITED, Stevenage (GB)

( * ) Notice: Subject to any disclaimer, the term of this patent is extended or adjusted under 35 U.S.C. 154(b) by 824 days.

(21) Appl. No.: 16/620,584

(22) PCT Filed: Jun. 8, 2018

(86) PCT No.: PCT/EP2018/065237
§ 371 (c)(1),
(2) Date: Dec. 9, 2019

(87) PCT Pub. No.: WO2018/224682
PCT Pub. Date: Dec. 13, 2018

(65) Prior Publication Data
US 2020/0190209 A1 Jun. 18, 2020

Related U.S. Application Data

(60) Provisional application No. 62/582,681, filed on Nov. 7, 2017, provisional application No. 62/582,653, filed on Nov. 7, 2017, provisional application No. 62/582,628, filed on Nov. 7, 2017, provisional application No. 62/582,616, filed on Nov. 7, 2017, provisional application No. 62/582,666, filed on Nov. 7, 2017, provisional application No. 62/582,676, filed on Nov. 7, 2017, provisional application No. 62/546,330, filed on Aug. 16, 2017, provisional application No. 62/546,322, filed on Aug. 16, 2017, provisional application No. 62/517,740, filed on Jun. 9, 2017, provisional application No. 62/517,745, filed on Jun. 9, 2017, provisional application No. 62/517,165, filed on Jun. 9, 2017, provisional application No. 62/517,164, filed on Jun. 9, 2017, provisional application No. 62/517,753, filed on Jun. 9, 2017, provisional application No. 62/517,734, filed on Jun. 9, 2017, provisional application No. 62/517,149, filed on Jun. 8, 2017, provisional application No. 62/517,150, filed on Jun. 8, 2017.

(51) Int. Cl.
*C07K 16/28* (2006.01)
*A61P 35/00* (2006.01)
*A61K 39/00* (2006.01)

(52) U.S. Cl.
CPC ......... *C07K 16/2896* (2013.01); *A61P 35/00* (2018.01); *A61K 2039/505* (2013.01); *C07K 2317/21* (2013.01); *C07K 2317/24* (2013.01); *C07K 2317/31* (2013.01); *C07K 2317/54* (2013.01); *C07K 2317/55* (2013.01); *C07K 2317/565* (2013.01); *C07K 2317/569* (2013.01); *C07K 2317/622* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | |
|---|---|---|
| 8,263,746 B2 | 9/2012 | Tesar et al. |
| 9,200,061 B2 | 12/2015 | Tesar et al. |
| 9,758,590 B2 | 9/2017 | Tesar et al. |
| 2002/0164788 A1 | 11/2002 | Ellis |
| 2009/0123950 A1 | 5/2009 | Tesar |
| 2017/0088620 A1 | 3/2017 | Nioi |
| 2017/0114141 A1 | 4/2017 | Amann |

FOREIGN PATENT DOCUMENTS

| | | |
|---|---|---|
| EP | 2511297 A1 | 10/2012 |
| WO | 2006125640 A2 | 11/2006 |
| WO | 2007042309 A2 | 4/2007 |
| WO | 2010040209 | 4/2010 |
| WO | 2012076663 A1 | 6/2012 |
| WO | 2012092612 A1 | 7/2012 |
| WO | 2012092616 | 7/2012 |
| WO | 2015149077 A1 | 10/2015 |

(Continued)

OTHER PUBLICATIONS

Lammerts van Buren et al. (Blood, 2014, 124:3474 (Year: 2014).*
Rudikoff et al. (Proceedings of the National Academy of Sciences USA, vol. 79, p. 1979-1983, 1982) (Year: 1982).*
Lammerts van Bueren et al., "Direct in Vitro Comparison of Daratumumab with Surrogate Analogs of CD38 Antibodies MOR03087, SAR650984 and Ab79", Blood, 2014, 124(21):3474.
Decked et al., "SAR650984, A Novel Humanized CD38-Targeting Antibody, Demonstrates Potent Antitumor Activity in Models of Multiple Myeloma and Other CD38+ Hematologic Malignancies", Clinical Cancer Research, 2014, 20 (17):4574-4583.

(Continued)

*Primary Examiner* — Meera Natarajan
(74) *Attorney, Agent, or Firm* — Riverside Law LLP

(57) ABSTRACT

The present disclosure provides antibodies that bind to human CD38. In particular, the antibodies and antigen-binding portions thereof are defined by particular functional characteristics. The antibodies present features compatible for manufacturing and can be provided as fully human antibodies (e.g., fully human monoclonal antibodies or antigen-binding fragments) that can be useful for medical methods and compositions, in particular for treating cancer.

17 Claims, 51 Drawing Sheets
Specification includes a Sequence Listing.

(56) References Cited

FOREIGN PATENT DOCUMENTS

| WO | 2016071355 A1 | 5/2016 |
|---|---|---|
| WO | 2016164656 A1 | 10/2016 |
| WO | 2016210223 | 12/2016 |

OTHER PUBLICATIONS

Srinivasan et al., "Abstract B26: Immunomodulatory activity of Isatuximab", Cancer Immunol Res, 2017, 5(3 Suppl) Abstract.

Feng et al., "Targeting CD38 Suppresses Induction and Function of T Regulatory Cells to Mitigate Immunosuppression in Multiple Myeloma", Clin Cancer Res, 2017, 23(15):4290-4300.

Lonial et al., "Monoclonal antibodies in the treatment of multiple myeloma: current status and future perspectives", Leukemia, 2016, 30:526-535.

Niels W.C.J. van de Donk et al., "Monoclonal antibodies targeting CD38 in hematological malignancies and beyond", Immunological Reviews, 2016, 270:95-112.

Wong et al., "CD38 Monoclonal Antibody Therapies for Multiple Myeloma", Clinical Lymphoma, Myeloma & Leukemia, 2015, 15(11):635-45.

Karakasheva et al., "CD38-Expressing Myeloid-Derived Suppressor Cells Promote Tumor Growth in a Murine Model of Esophageal Cancer", Cancer Res, 2015, 75(19):4074-4085.

McEllistrim et al., "New developments in the treatment of multiple myeloma—clinical utility of daratumumab", Biologics: Targets and Therapy, 2017, 11:31-43.

Li et al., "Immuno-targeting the multifunctional CD38 using nanobody", Scientific Reports, 2016, 6(1), 27055.

Eissler et al., "Abstract 3812: A best in class anti-CD38 antibody with antitumor and immune-modulatory properties", 2018.

Moreno et al., "Critical Analysis on the Mechanism of Action (MoA) of the Anti-CD38 Monoclonal Antibody Isatuximab in Multiple Myeloma (MM)", Blood, 2016. 128(22):2105.

Boxhammer et al., "MOR202, a Human Anti-CD38 Monoclonal Antibody, Mediates Potent Tumoricidal Activity In Vivo and Shows Synergistic Efficacy in Combination with Different Antineoplastic Compounds", Blood, 2015, 126(23):3015.

Matas-Cespedes et al., "The Human CD38 Monoclonal Antibody Daratumumab Shows Antitumor Activity and Hampers Leukemia-Microenvironment Interactions in Chronic Lymphocytic Leukemia", Clin Cancer Res, 2016, 23 (6):1493-505.

European Medicines Agency: Committee for Medicinal Products for Human Use, "Darzalex: EPAR—Public Assessment Report", Apr. 1, 2016.

Eissler et al., "Targeting CD38 beyond haematological malignancies: a panel of anti-CD38 antibodies with unique functional properties", Nov. 7, 2017 (SITC—Abstract P320).

Eissler et al., "Targeting CD38 beyond haematological malignancies: a panel of anti-CD38 antibodies with unique functional properties", Nov. 11, 2017 (SITC—poster).

Henry et al., "Multimodality mapping and analysis of the CD38 expression landscape in various human cancers", Sep. 6, 2017 (CIMT—poster).

Eissler et al., "A best in class anti-CD38 antibody with anti-tumour and immune modulatory properties", Apr. 17, 2018 (AACR—poster).

Edwards et al. 2003. The remarkable flexibility of the human antibody repertoire; isolation of over one thousand different antibodies to a single protein, BlyS. Journal of Molecular Biology 334:103-118 (Year: 2003).

Murphy et al. "Enhancing recombinant antibody performance by optimally engineering its format," (Journal of Immunological Methods, vol. 463, p. 127-133, 2018) (Year: 2018).

Notice of Allowance dated Sep. 20, 2021 for U.S. Appl. No. 16/638,205 (pp. 1-9).

Rajpal A, Beyaz N, Haber L, et al. (A general method for greatly improving the affinity of antibodies by using combinatorial libraries. Proc Natl Acad Sci U S A. 2005;102(24):8466-8471) (Year: 2005).

* cited by examiner

| aCD38-a-323-HCDR1 | aCD38-a-323-HCDR2 | aCD38-a-323-HCDR3 |
|---|---|---|
| GSISSGSYYWS | YIYYSGSTYYNPSLKS | ARGSPYRWYNYYYMDV | aCD38-a-323-HCDR123

GSISSGSYYWSWIRQHPGKGLEWIGYIYYSGSTYYNPSLKSRVTISVDTSKNQFSLKLS
SVTAADTAVYYCARGSPYRWYNYYYMDVWGKGTTVTVSS

| aCD38-a-323-LCDR1 | aCD38-a-323-LCDR2 | aCD38-a-323-LCDR3 |
|---|---|---|
| RASQSISSWLA | DASSLES | QQHRSYPPT | aCD38-a-323-LCDR123

RASQSISSWLAWYQQKPGKAPKLLIYDASSLESGVPSRFSGSGSGTEFTLTISSLQPQ
DFATYYCQQHRSYPPTFGGGTKVEIK

FIGURE 3
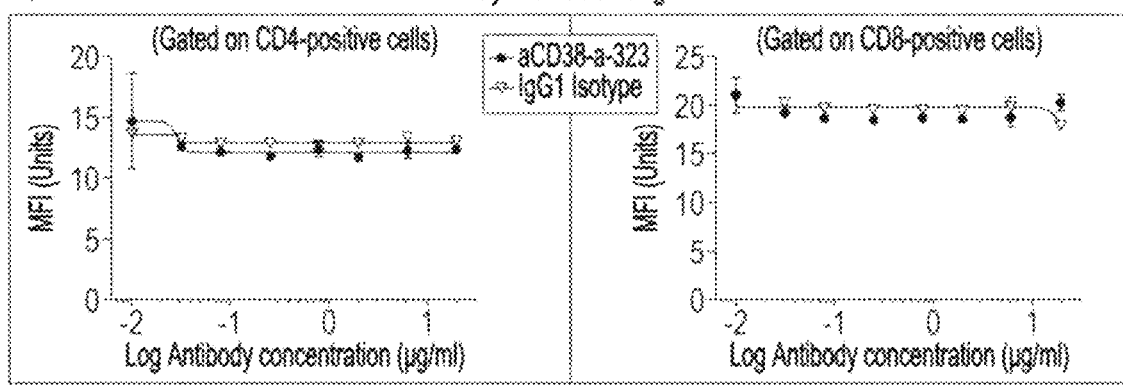
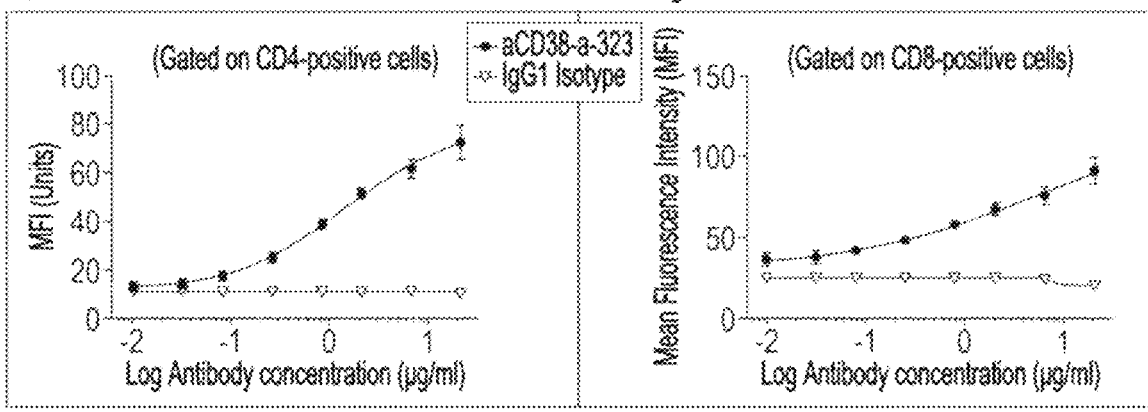

FIGURE 4
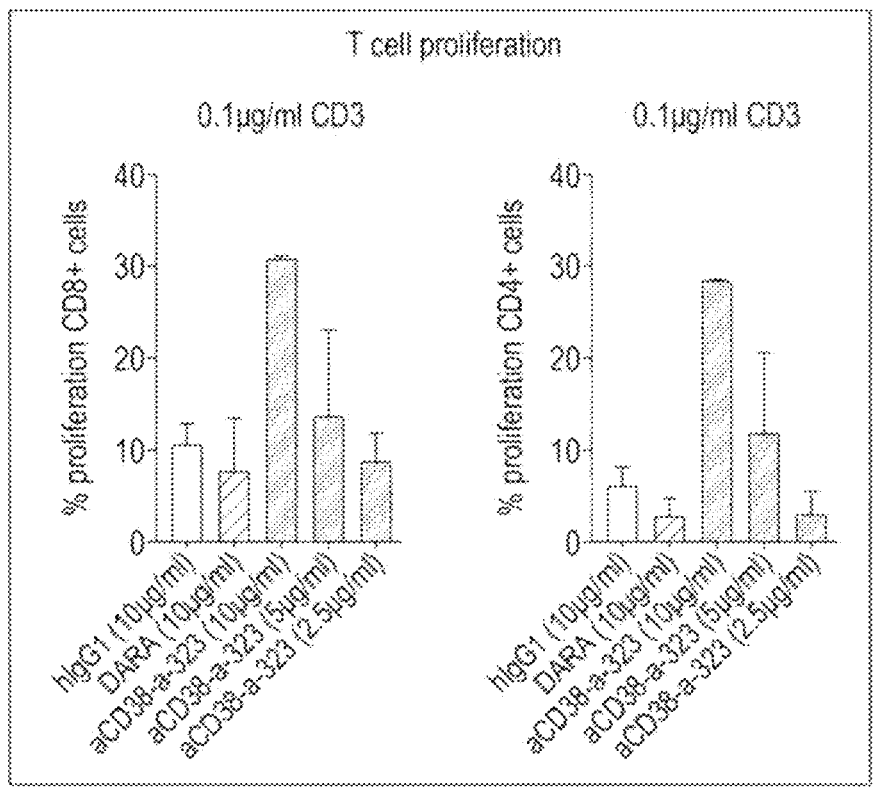
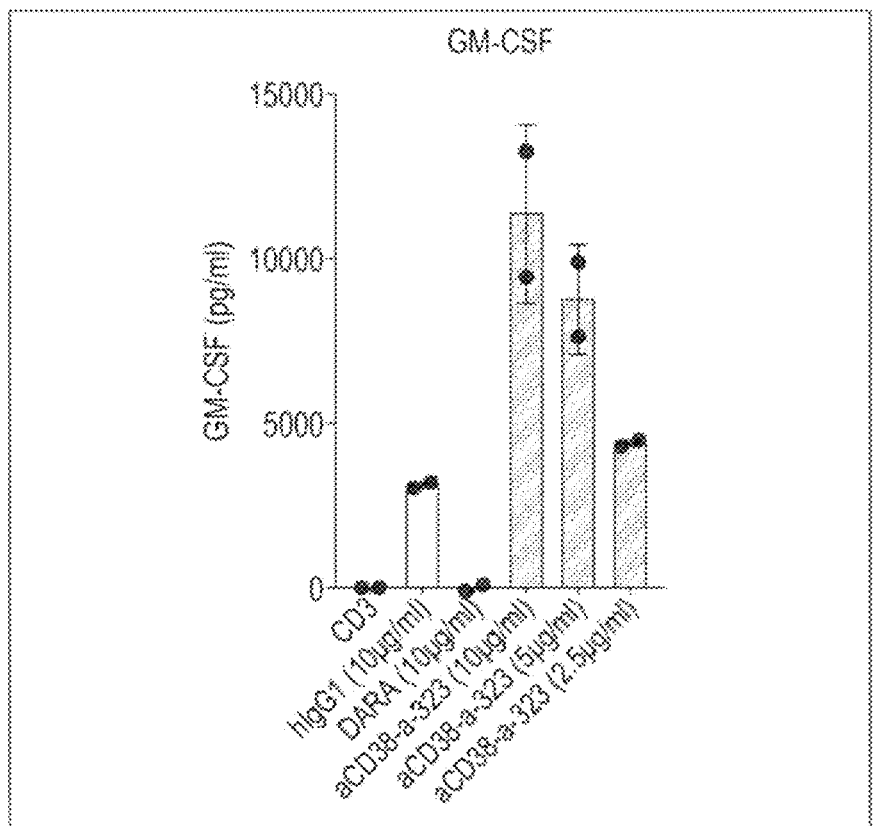

FIGURE 5
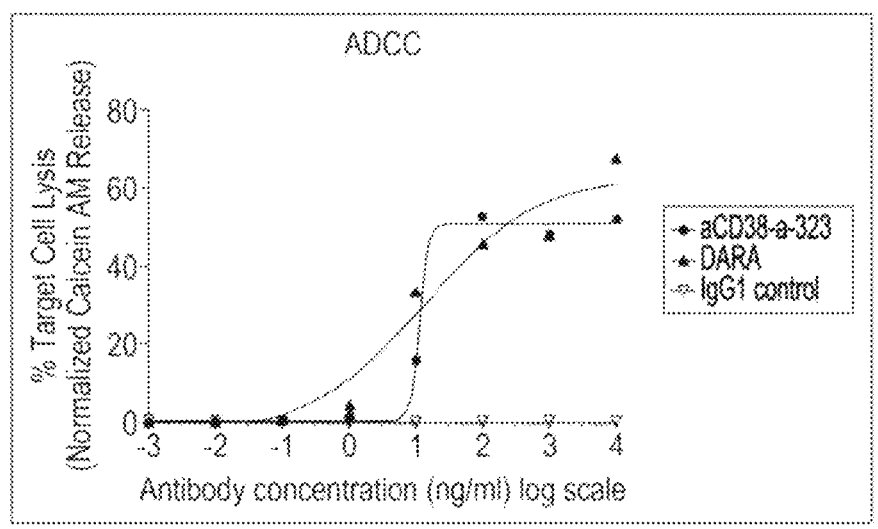
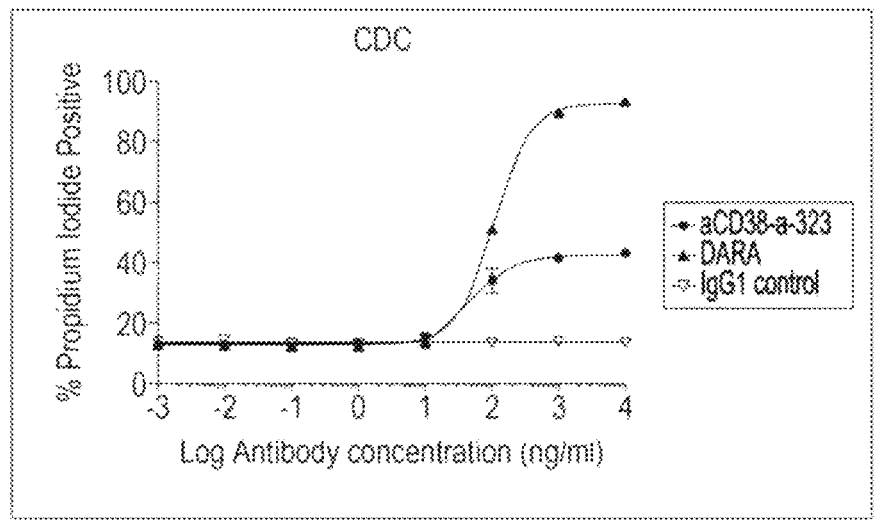

FIGURE 6
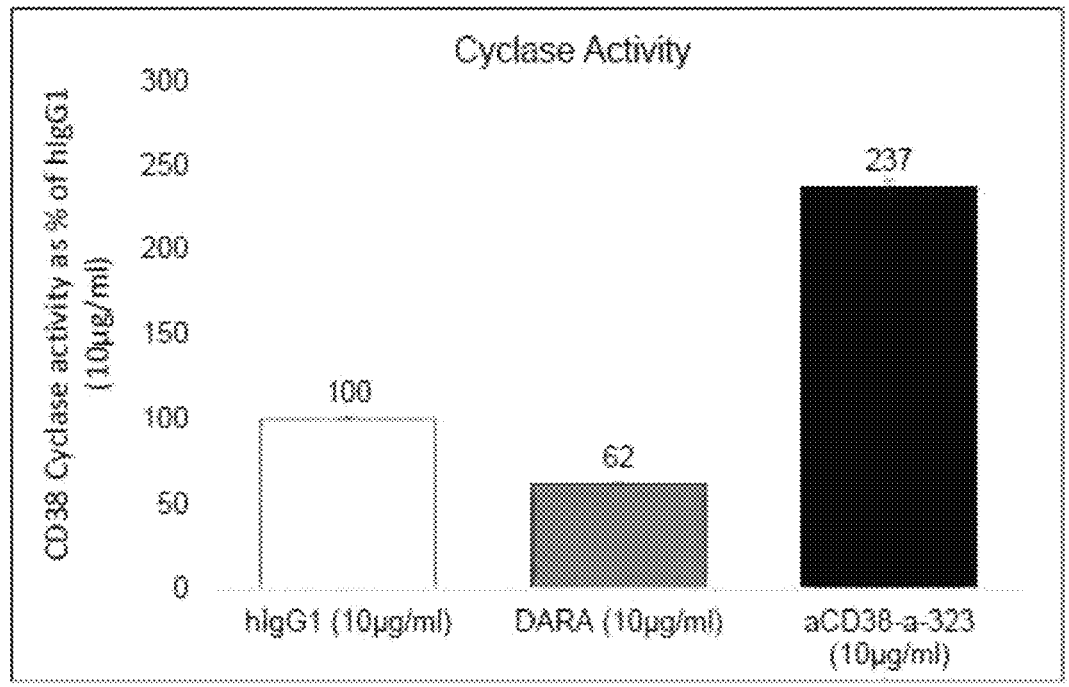
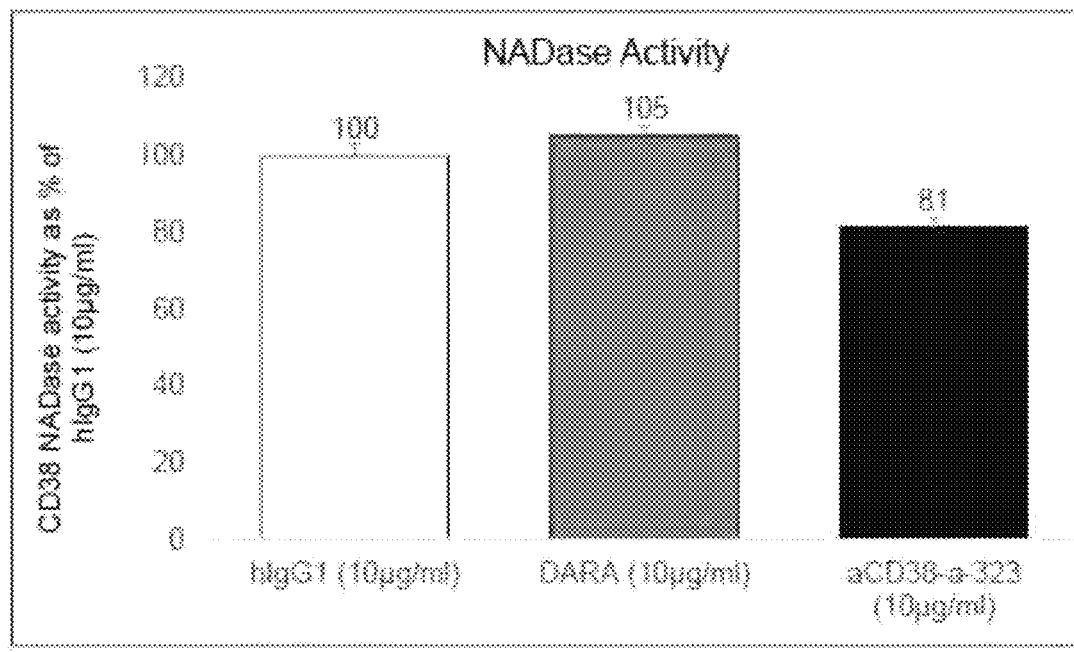

| aCD38-a-306-HCDR1 | aCD38-a-306-HCDR2 | aCD38-a-306-HCDR3 |
|---|---|---|
| YTFTGYYMH | WINPNSGGTNYAQKFQG | ARDQAHQRSSYD | aCD38-a-306-HCDR123

YTFTGYYMHWVRQAPGQGLEWMGWINPNSGGTNYAQKFQGRVTMTRDTSISTAYMELSRLRSDDTAVYYCARDQAHQRSSYDWGQGTLVTVSS

| aCD38-a-306-LCDR1 | aCD38-a-306-LCDR2 | aCD38-a-306-LCDR3 |
|---|---|---|
| RASQSISSYLN | GASSLQS | QQRSSTPIT | aCD38-a-306-LCDR123

RASQSISSYLNWYQQKPGKAPKLLIYGASSLQSGVPSRFSGSGSGTDFTLTISSLQPEDFATYYCQQRSSTPITFGGGTKVEIK

FIGURE 8
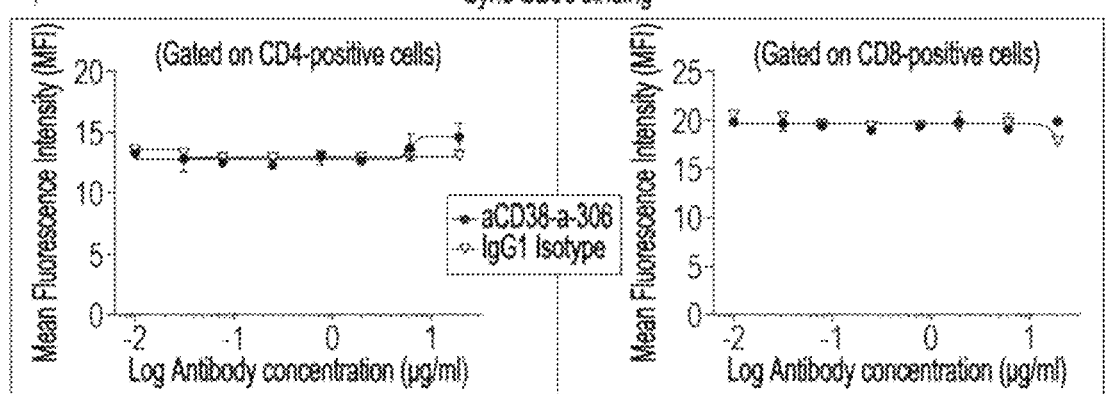
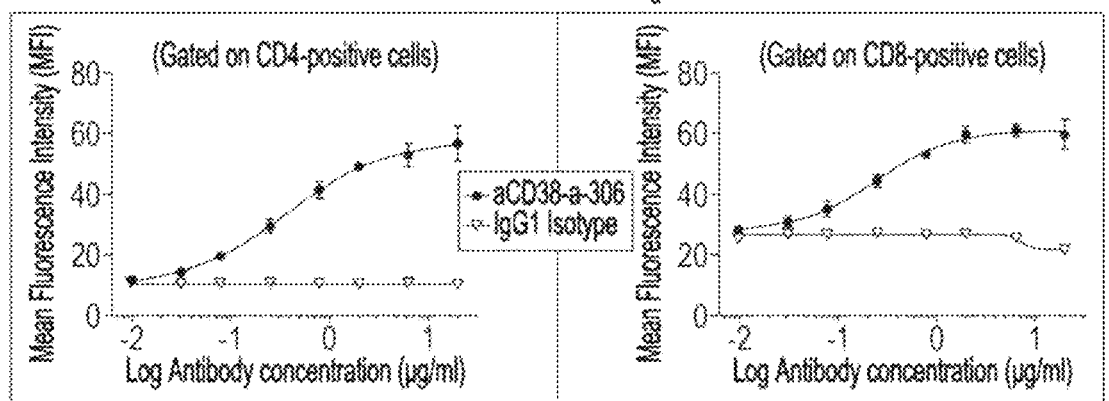

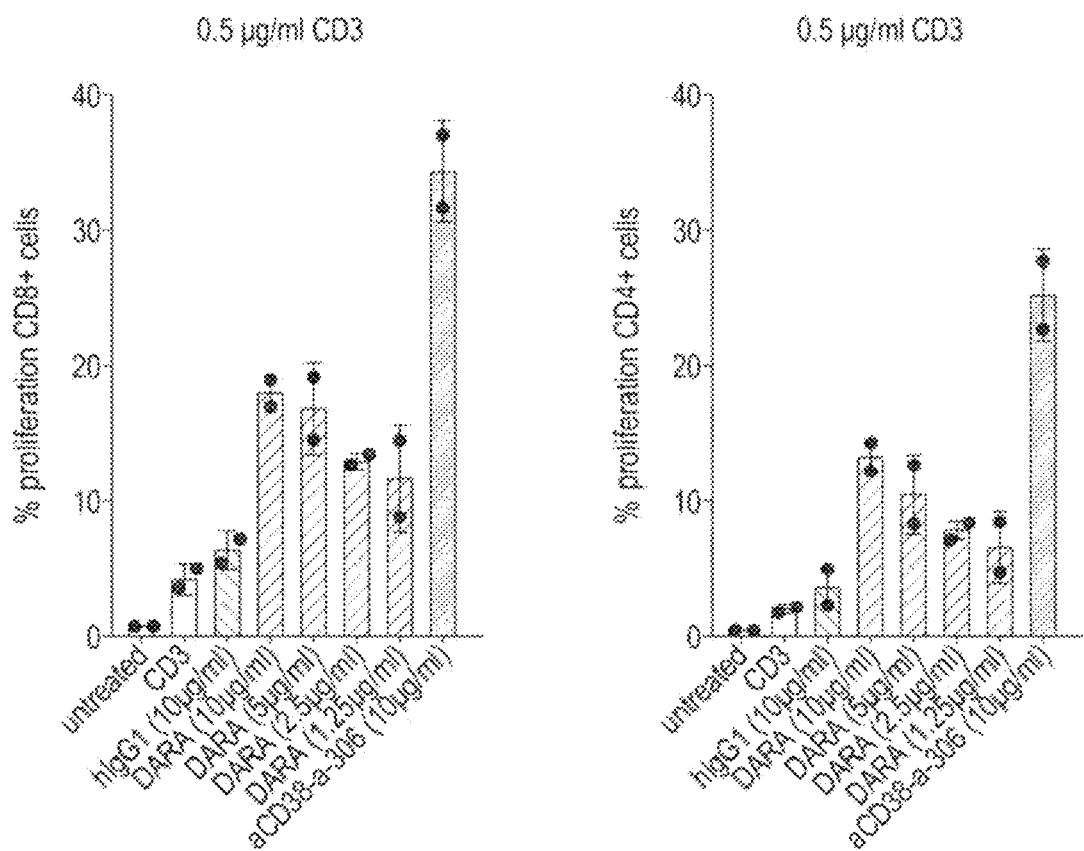

FIGURE 10
A)
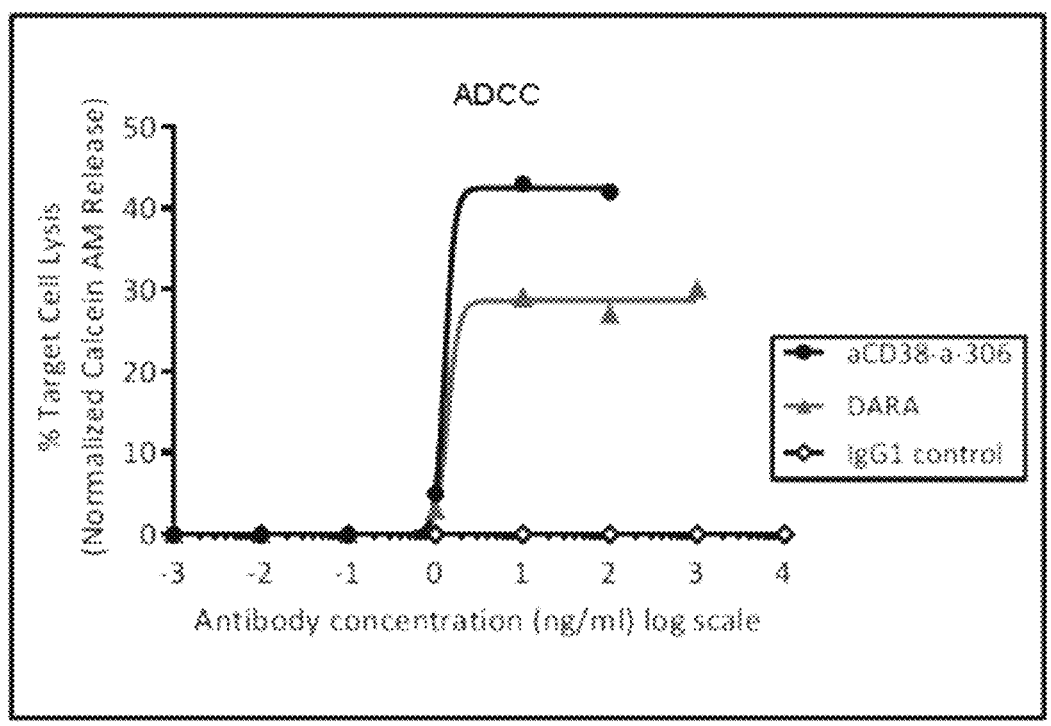
B)
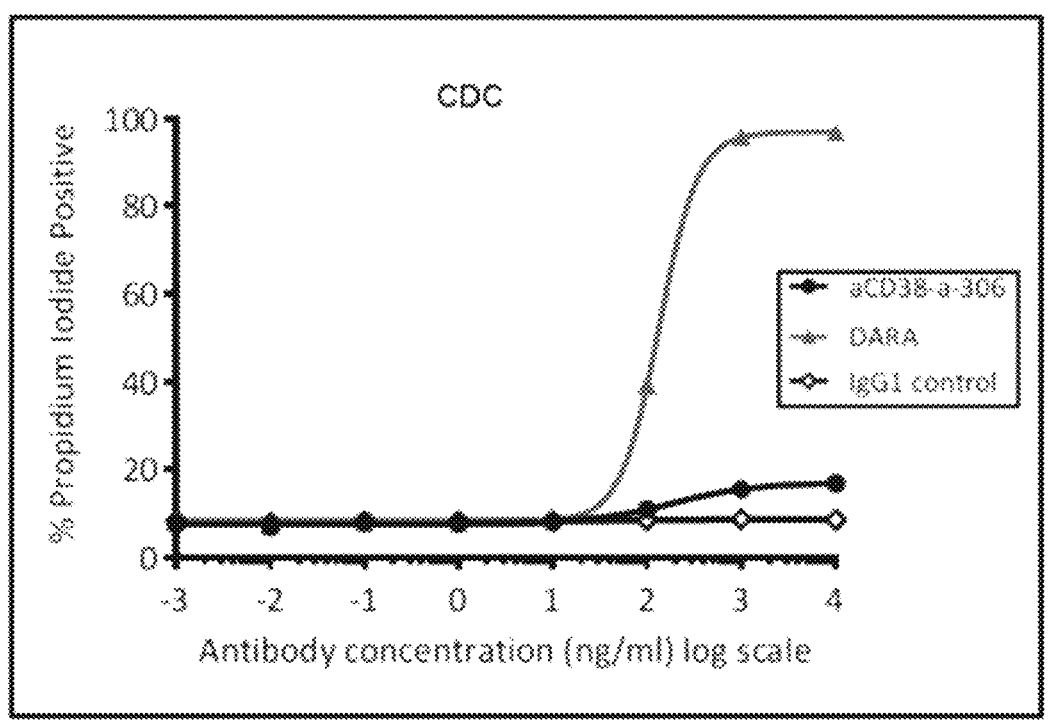

FIGURE 11

A)
aCD38-b-329-HCDR1      aCD38-b-329-HCDR2         aCD38-b-329-HCDR3
GSISSSDYYWG            SIYYSGSTYYNPSLKS          ARGQYSSGWYAYPFDM aCD38-b-329-HCDR123
GSISSSDYYWGWIRQPPGKGLEWIGSIYYSGSTYYNPSLKSRVTISVDTSKNQFSLKLS
SVTAADTAVYYCARGQYSSGWYAYPFDM aCD38-b-329-LCDR1      aCD38-b-329-LCDR2         aCD38-b-329-LCDR3
RASQSVRSSYLA           GASSRAT                   QQDGAVFT aCD38-b-329-LCDR123
RASQSVRSSYLAWYQQKPGQAPRLLIYGASSRATGIPDRFSGSGSGTDFTLTISRLEP
EDFAVYYCQQDGAVFT

B)

| Cytoplasmic | | Transmembrane | | |
|---|---|---|---|---|
| 10 | 20 | 30 | 40 | 50 |
| MANCEFSPVS | GDKPCCRLSR | RAQLCLGVSI | LVLILVVVLA | VVVPRWRQQW | aCD38-b-ep
  60          70          80          90          100
SGPGTTKRFP ETVLARCVKY TEIHPEMRHV DCQSVWDAFK GAFISKHPCN 110        120         130         140         150
ITEEDYQPLM KLGTQTVPCN KILLWSRIKD LAHQFTQVQR DMFTLEDTLL 160        170         180         190         200
GYLADDLTWC GEFNTSKINY QSCPDWRKDC SNNPVSVFWK TVSRRFAEAA

DARAep-a
  210        220         230         240         250
CDVVHVMLNG SRSKIFDKNS TFGSVEVHNL QPEKVQTLEA WVIHGGREDS

DARAep-b
  260        270         280         290         300
RDLCQDPTIK ELESIISKRN IQFSCKNIYR PDKFLQCVKN PEDSSCTSEI

FIGURE 13
A)
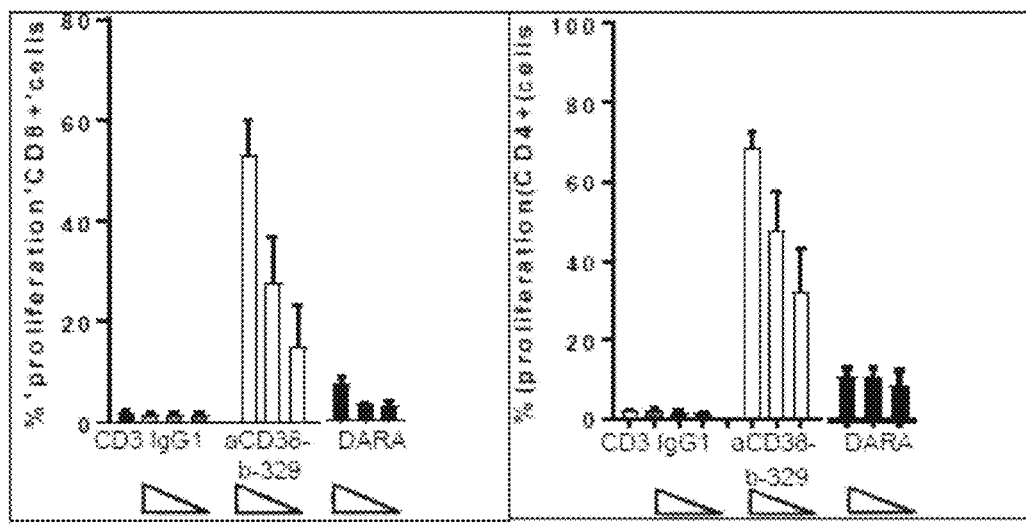
B)
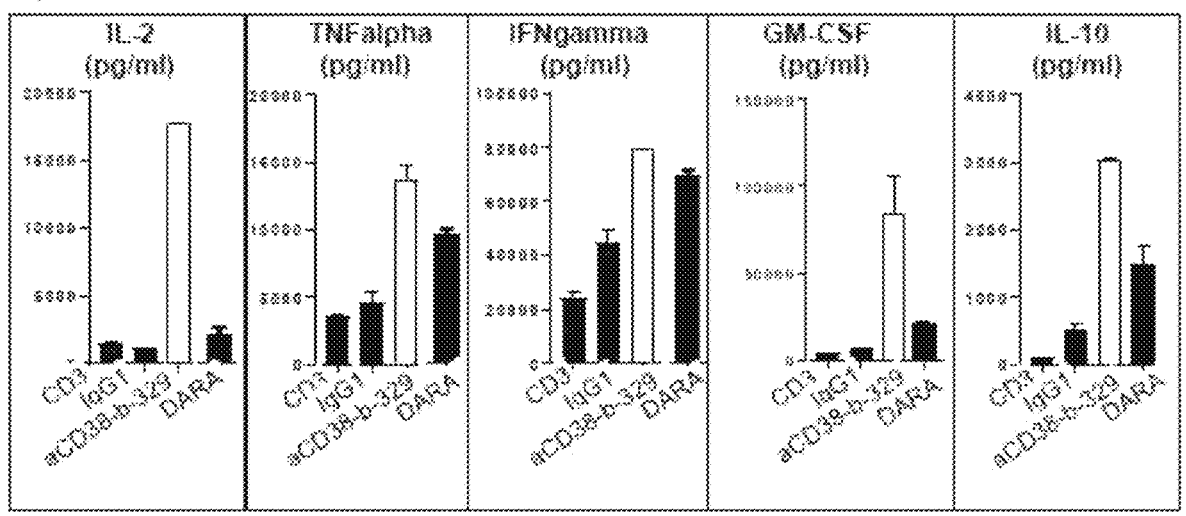

FIGURE 14
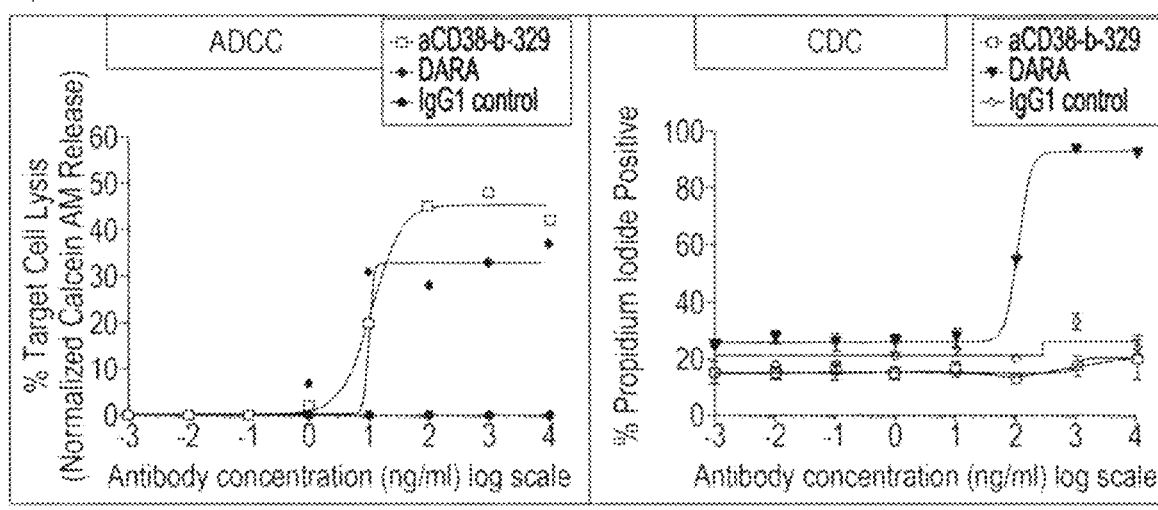
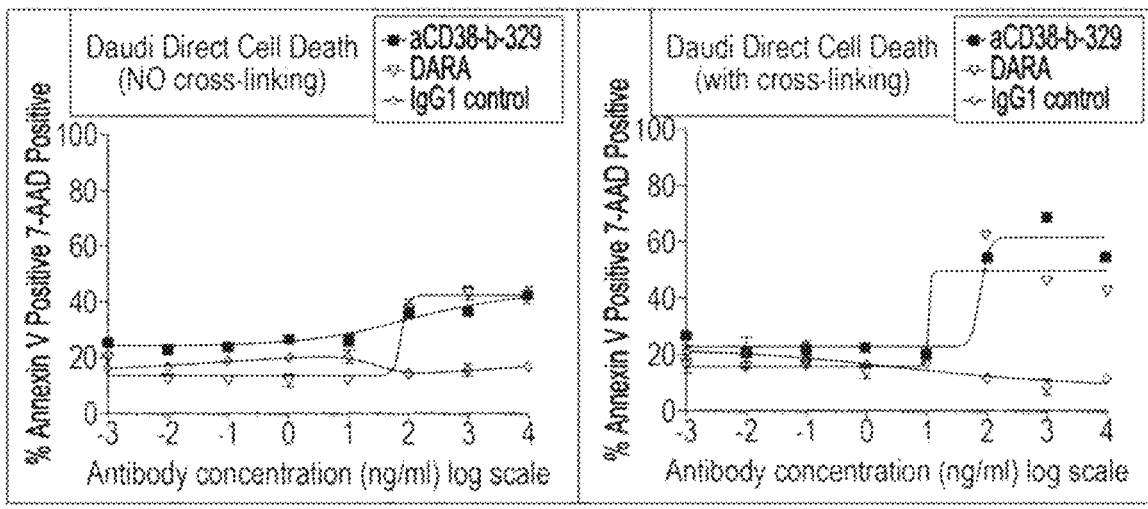

FIGURE 15
A)
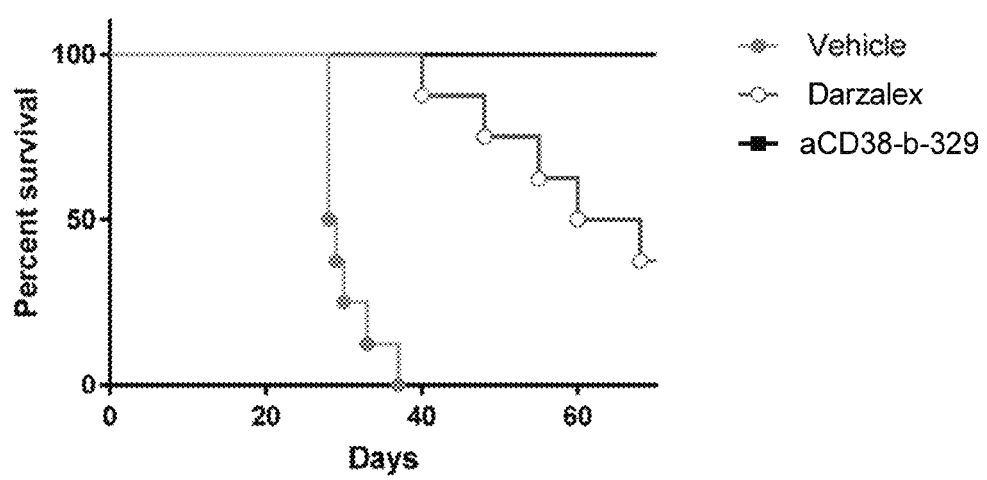
B)
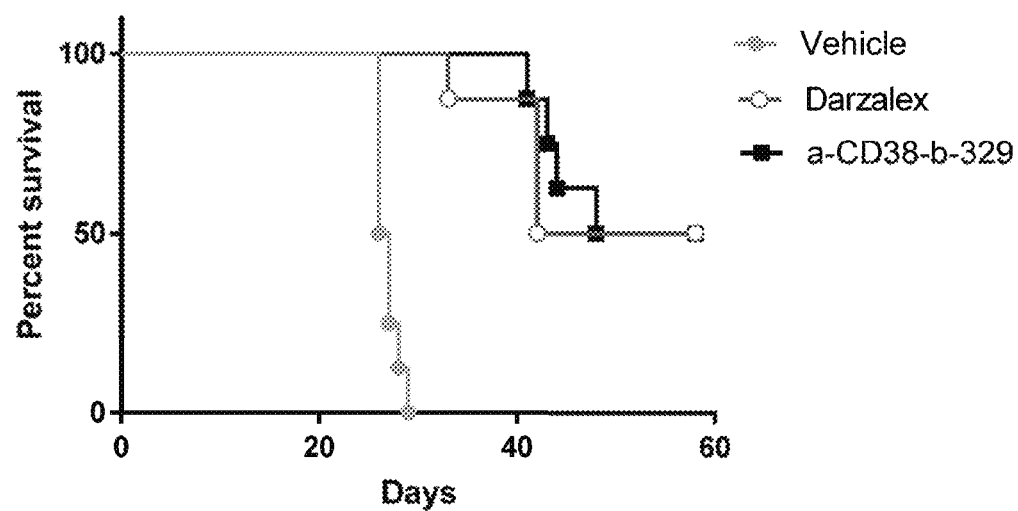

CD38-b-348-HCDR1
GSISSSDYYWG aCD38-b-348-HCDR2
SIYYSGSTYYNPSLKS aCD38-b-348-HCDR3
ARGQYSSGWYAYPFDM aCD38-b-348-HCDR123
GSISSSDYYWGWIRQPPGKGLEWIGSIYYSGSTYYNPSLKSRVTISVDTSKNQFSLKLS
SVTAADTAVYYCARGQYSSGWYAYPFDM aCD38-b-348-LCDR1
RASQSVRSSYLA aCD38-b-348-LCDR2
GASSRAT aCD38-b-348-LCDR3
QQDGNVYT aCD38-b-348-LCDR123
RASQSVRSSYLAWYQQKPGQAPRLLIYGASSRATGIPDRFSGSGSGTDFTLTISRLEP
EDFAVYYCQQDGNVYT

B)

| Cytoplasmic | | Transmembrane | | |
|---|---|---|---|---|
| 10 | 20 | 30 | 40 | 50 |

MANCEFSPVS GDKPCCRLSR RAQLCLGVSI LVLILVVVLA VVVPRWRQQW aCD38-b-ep
```
         60         70         80         90        100
SGPGTTKRFP ETVLARCVKY TEIHPEMRHV DCQSVWDAFK GAFISKHPCN
```

```
        110        120        130        140        150
ITEEDYQPLM KLGTQTVPCN KILLWSRIKD LAHQFTQVQR DMFTLEDTLL 160        170        180        190        200
GYLADDLTWC GEFNTSKINY QSCPDWRKDC SNNPVSVFWK TVSRRFAEAA
```

DARAep-a
```
        210        220        230        240        250
CDVVHVMLNG SRSKIFDKNS TFGSVEVHNL QPEKVQTLEA WVIHGGREDS
```

DARAep-b
```
        260        270        280        290        300
RDLCQDPTIK ELESIISKRN IQFSCKNIYR PDKFLQCVKN PEDSSCTSEI
```

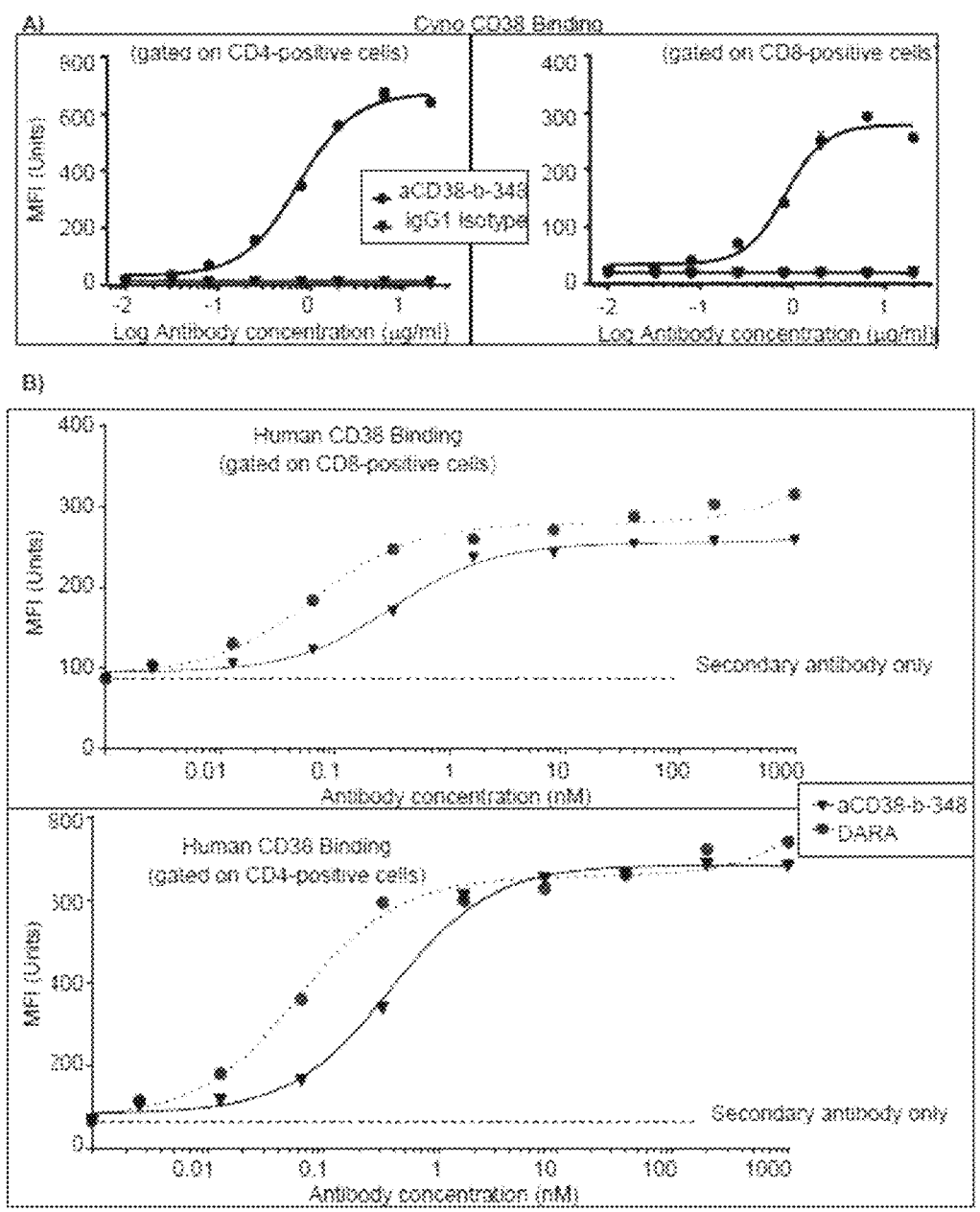

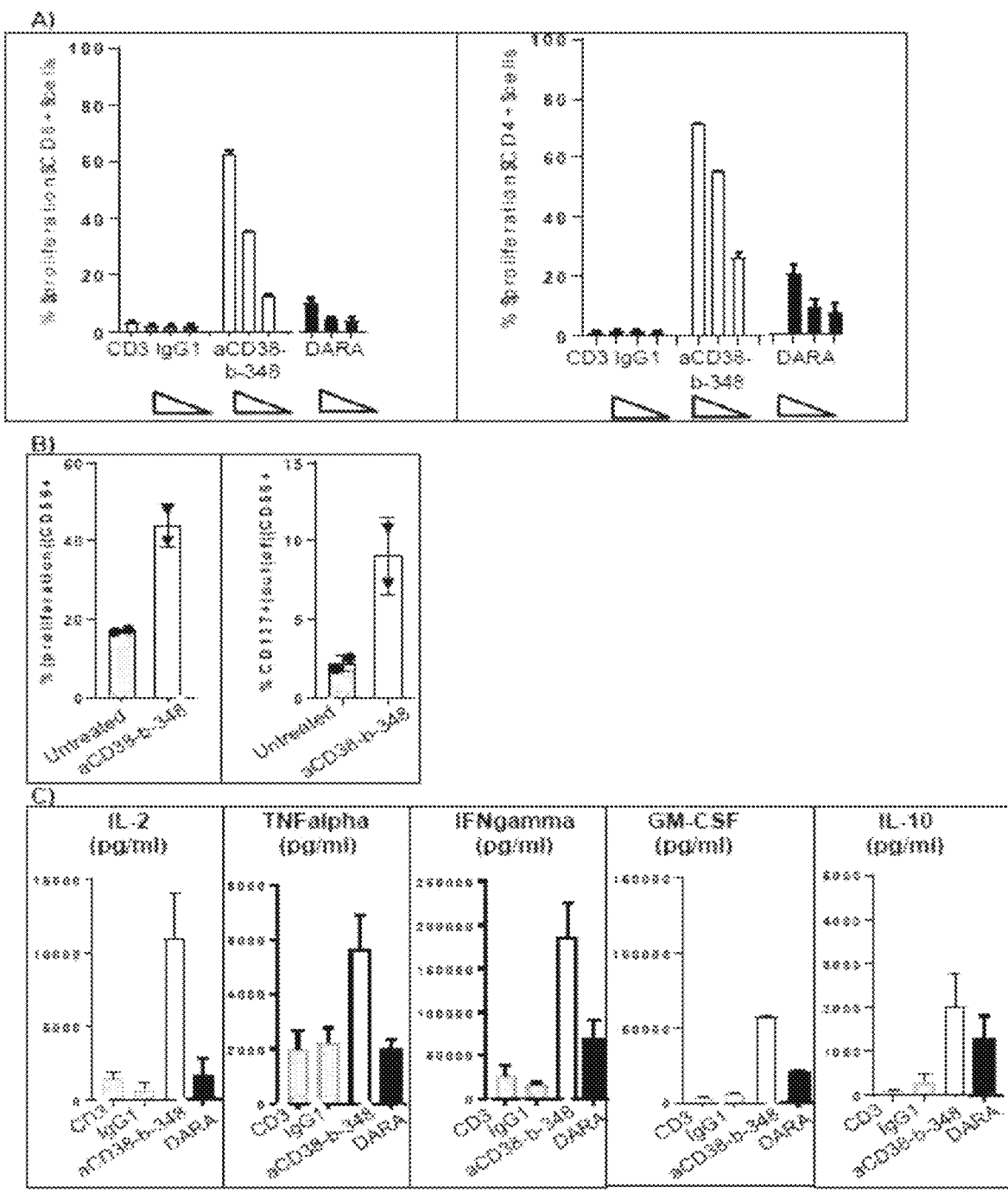

FIGURE 19
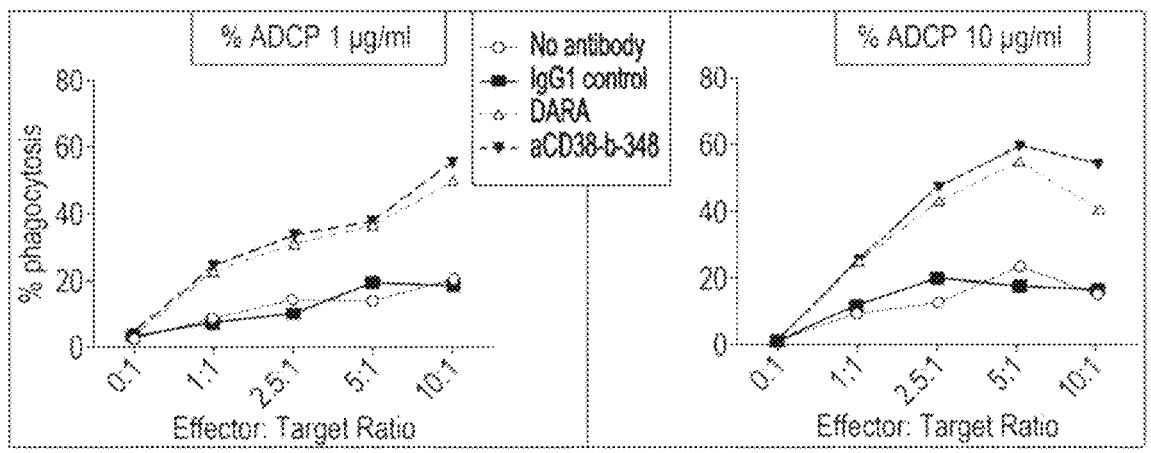
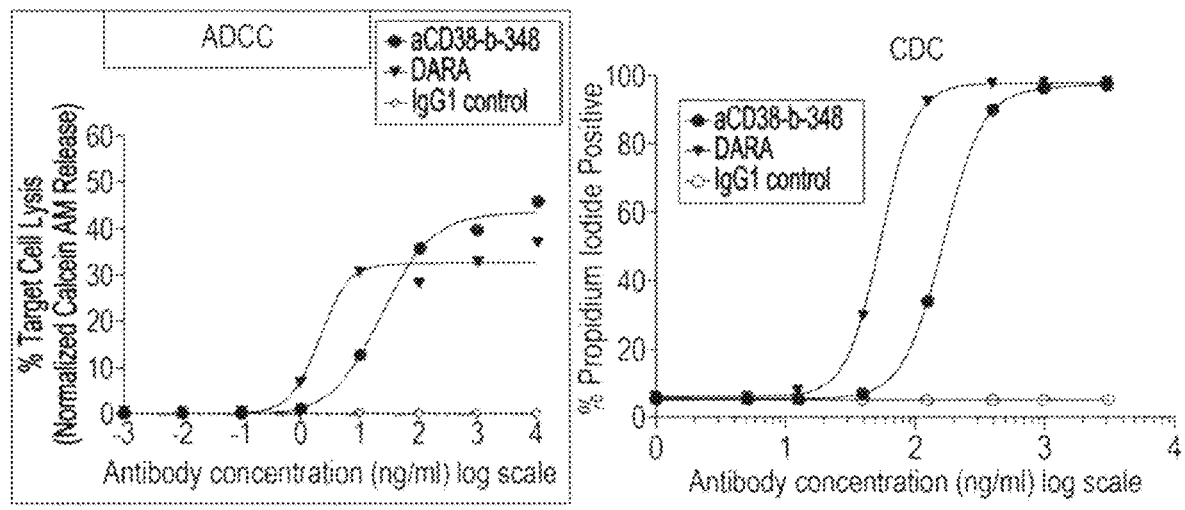
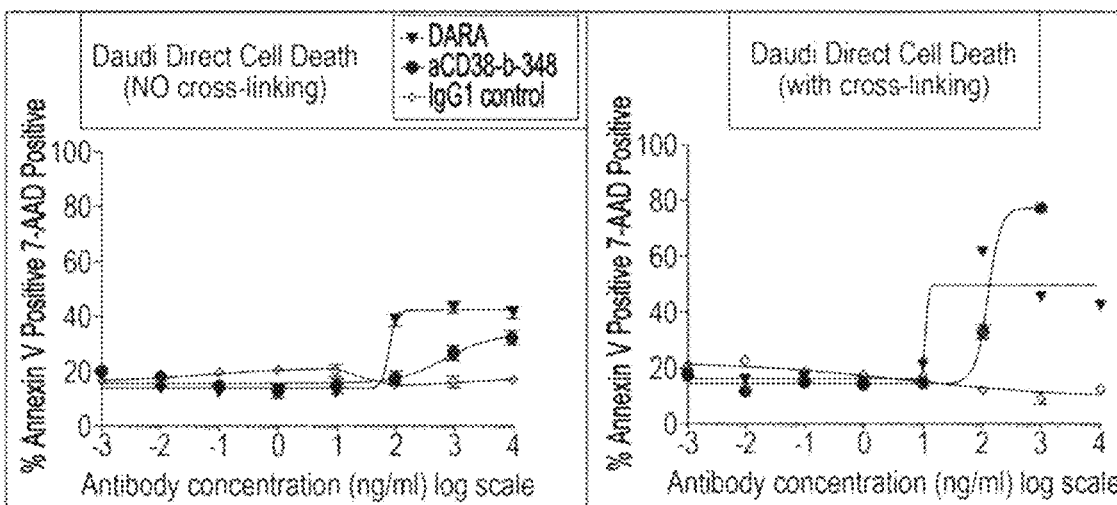

FIGURE 20
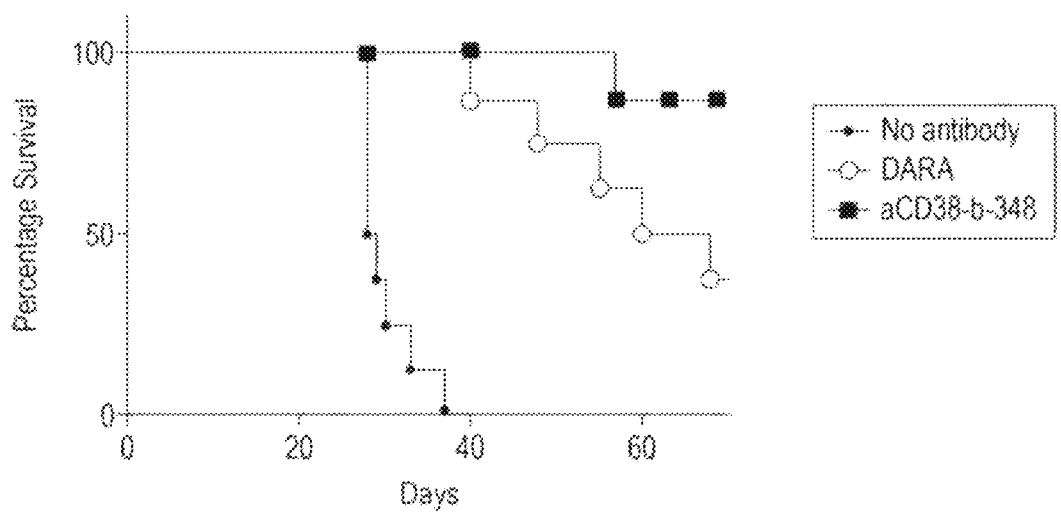
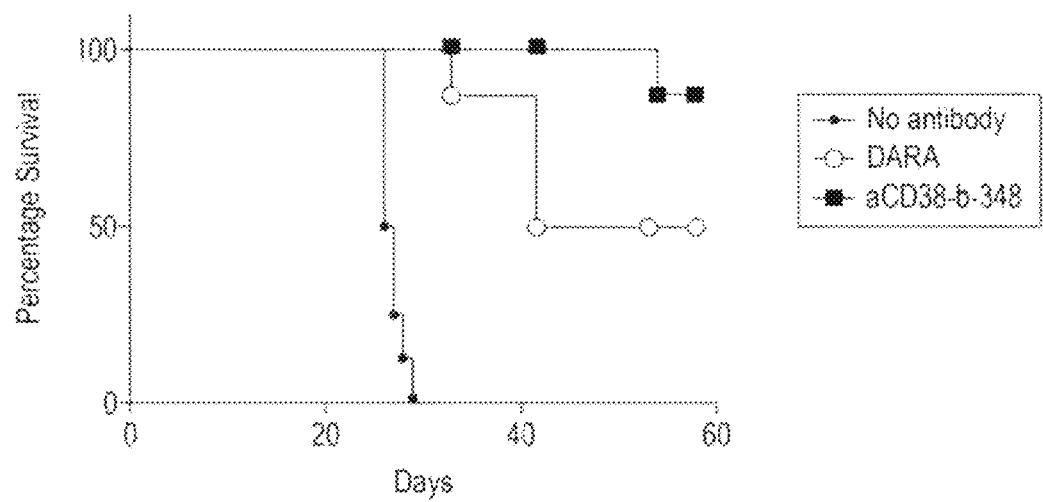

aCD38-a-327-HCDR1   aCD38-a-327-HCDR2   aCD38-a-327-HCDR3

GSISSGGYYWS            YIYYSGSTYYNPSLKS         ARAKSELVLPYYYYMDV aCD38-a-327-HCDR123

GSISSGGYYWSWIRQHPGKGLEWIGYIYYSGSTYYNPSLKSRVTISVDTSKNQFSLKLSSVTAADTAVYYCA
RAKSELVLPYYYYMDVWGKGTTVTVSS aCD38-a-327-LCDR1   aCD38-a-327-LCDR2   aCD38-a-327-LCDR3

KSSQSVLFSSNNKNYLA      WASTRES                  QQYYSLPPT aCD38-a-327-LCDR123

KSSQSVLFSSNNKNYLAWYQQKPGQPPKLLIYWASTRESGVPDRFSGSGSGTDFTLTISSLQAEDVAVYY
CQQYYSLPPTFGGGTKVEIK

B)

```
        Cytoplasmic                  Transmembrane
        10          20          30          40              50
MANCEFSPVS  GDKPCCRLSR  RAQLCLGVSI  LVLILVVVLA  VVVPRWRQQW aCD38ep-a
        60          70          80          90          100
SGPGTTKRFP  ETVLARCVKY  TEIHPEMRHV  DCQSVWDAFK  GAFISKHPCN aCD38ep-b
        110         120         130         140         150
ITEEDYQPLM  KLGTQTVPCN  KILLWSRIKD  LAHQFTQVQR  DMFTLEDTLL 160         170         180         190         200
GYLADDLTWC  GEFNTSKINY  QSCPDWRKDC  SNNPVSVFWK  TVSRRFAEAA DARAep-a
        210         220         230         240         250
CDVVHVMLNG  SRSKIFDKNS  TFGSVEVHNL  QPEKVQTLEA  WVIHGGREDS DARAep-b
        260         270         280         290         300
RDLCQDPTIK  ELESIISKRN  IQFSCKNIYR  PDKFLQCVKN  PEDSSCTSEI
```

FIGURE 22
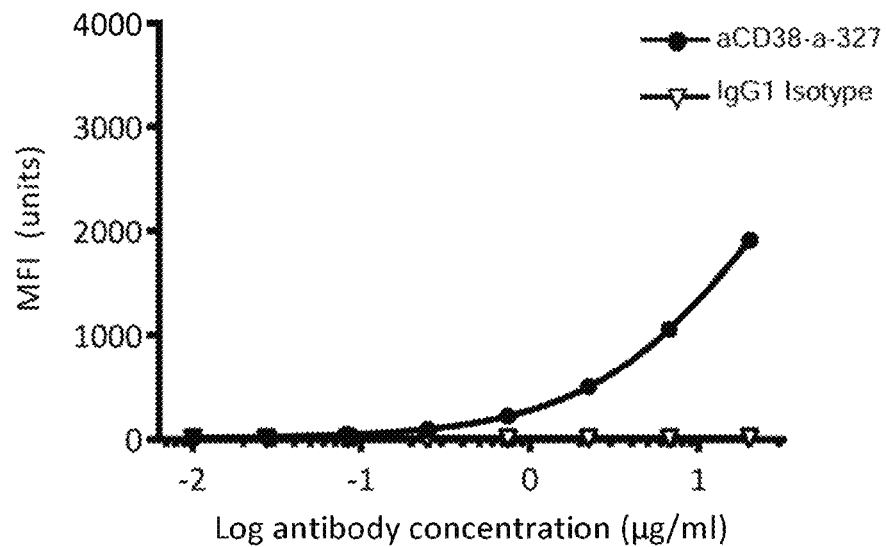
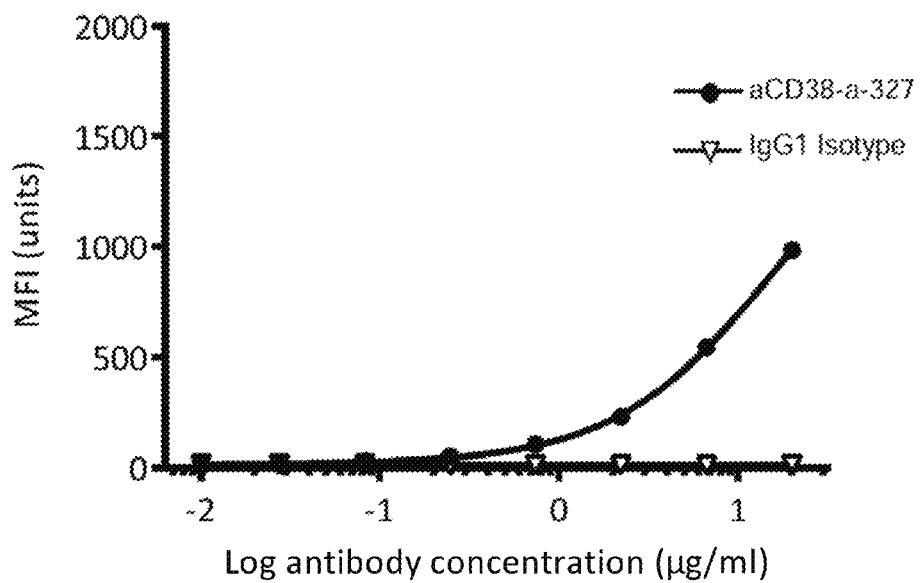

FIGURE 23
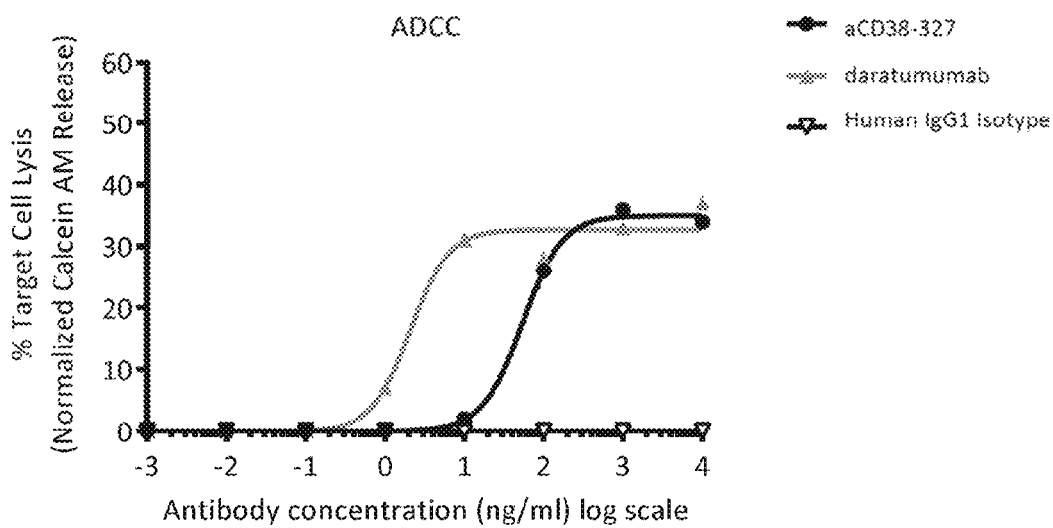
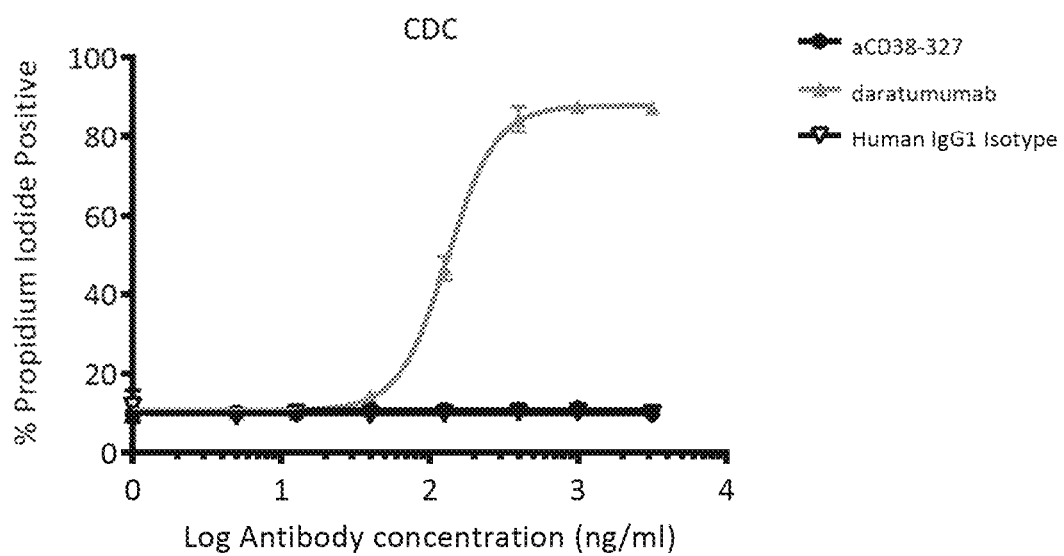

FIGURE 23 (Cont.)
C)
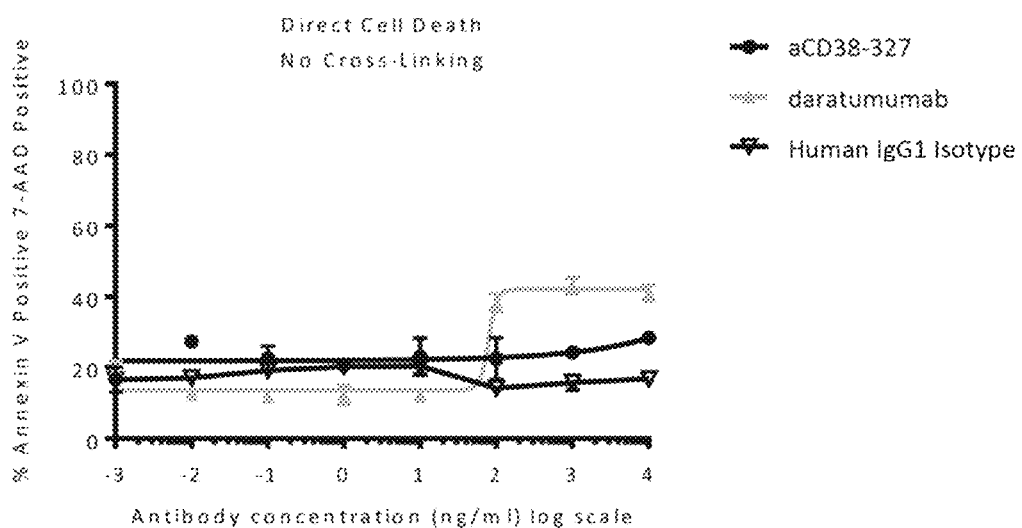
D)
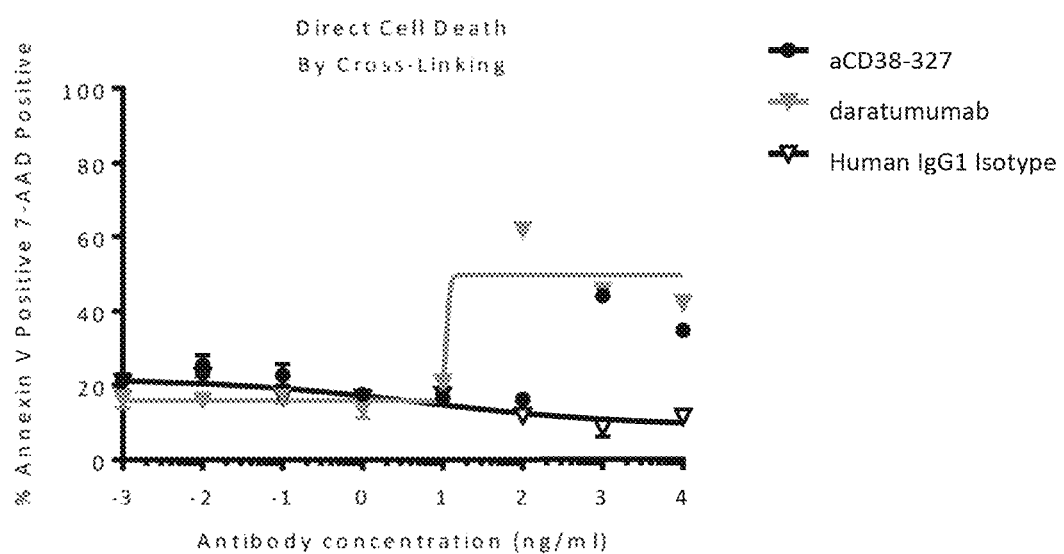

FIGURE 24
A)
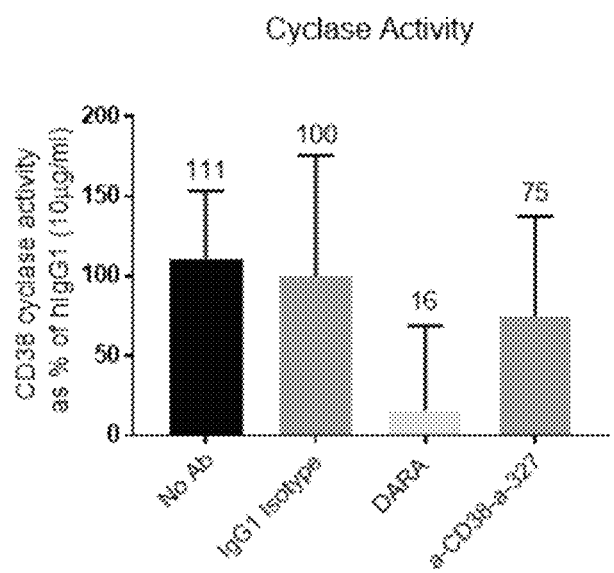
B)
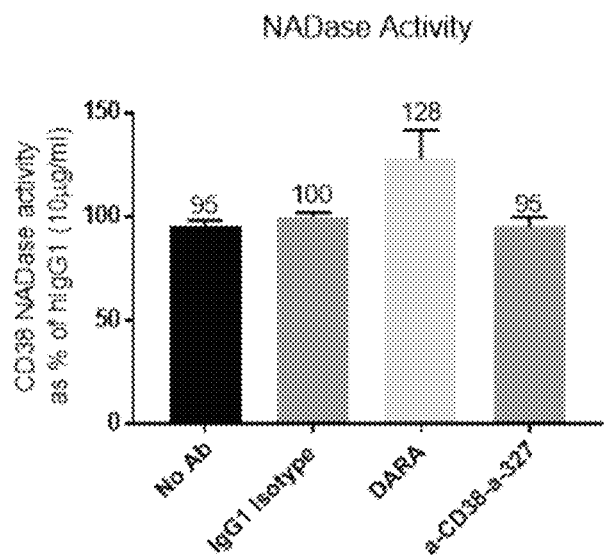

Figure 27
A)
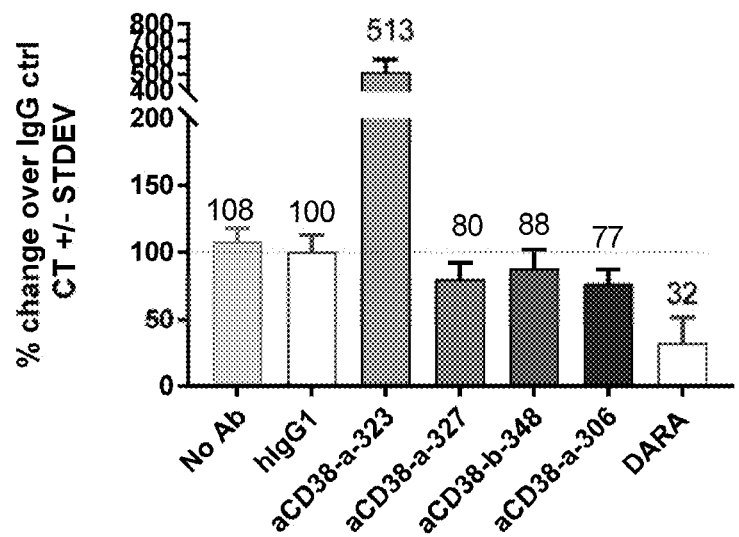
B)
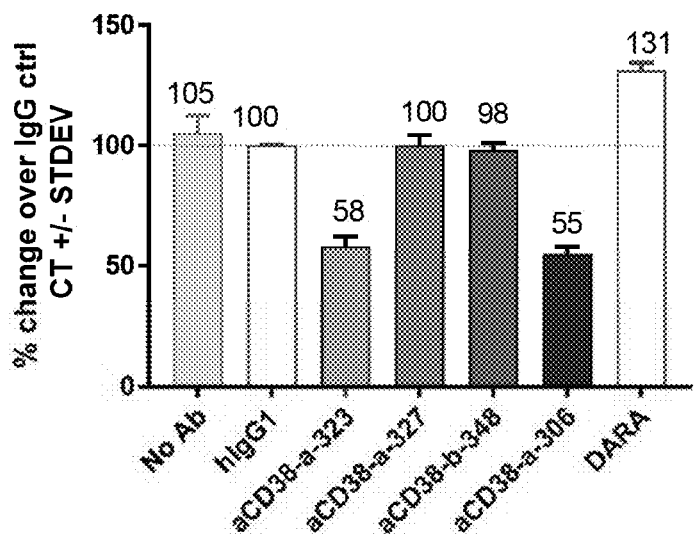

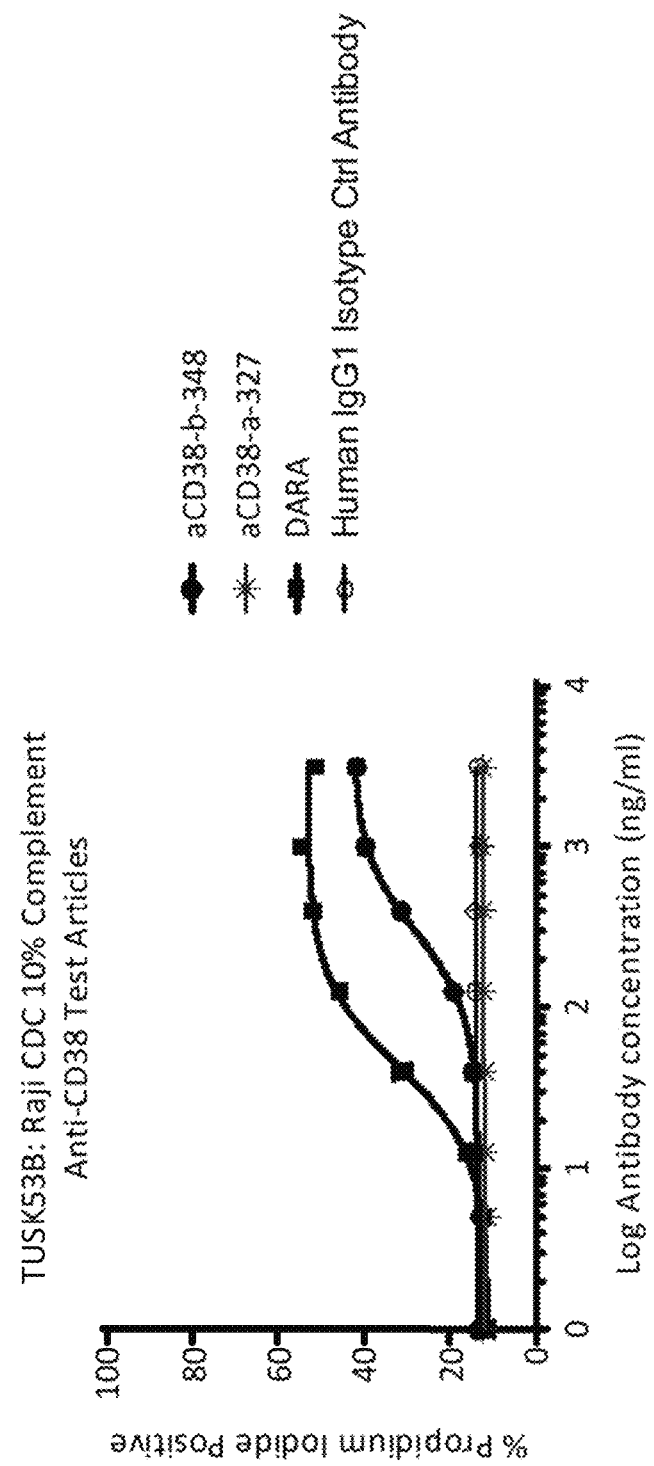

FIGURE 32
A)
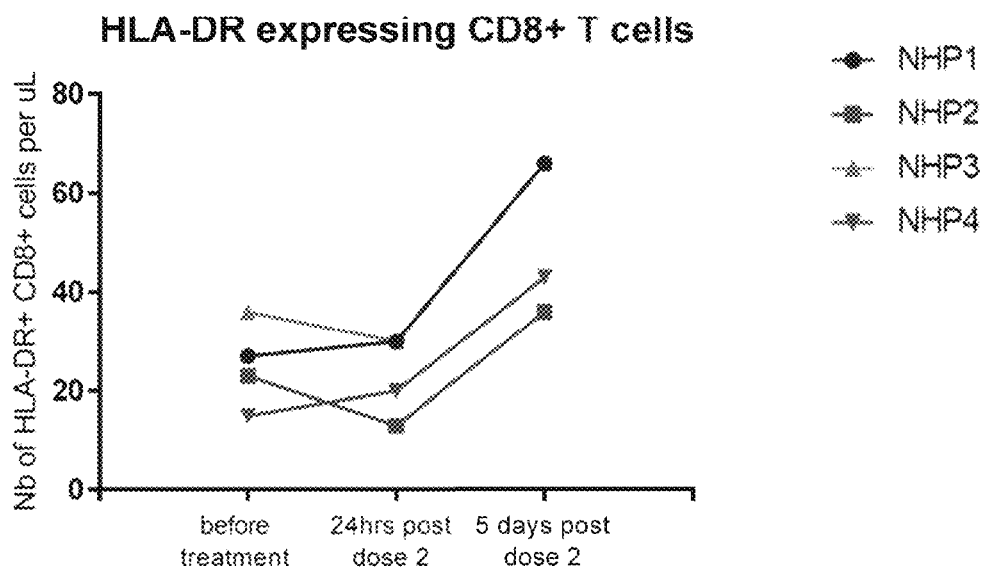
B)
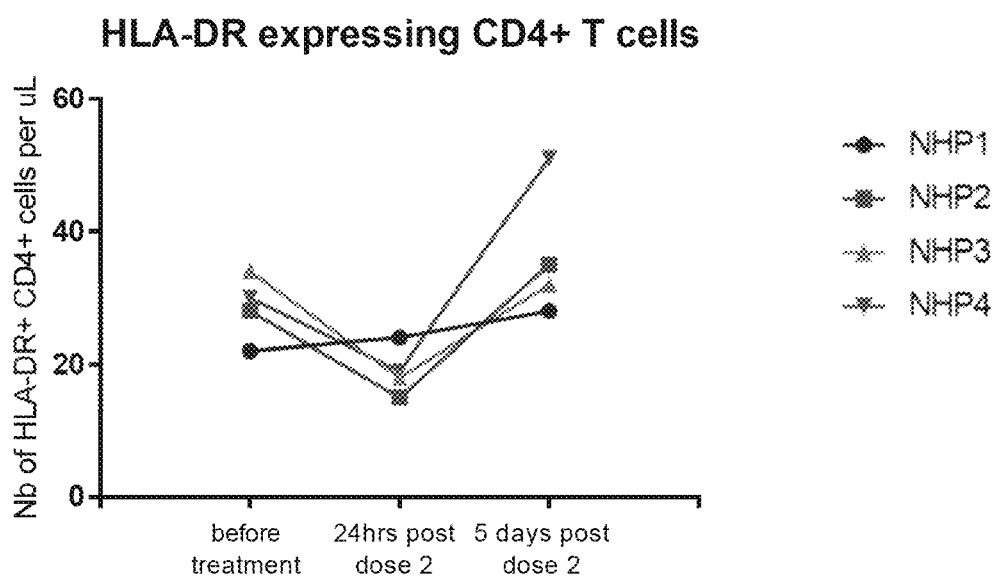

FIGURE 32 cont.
C)
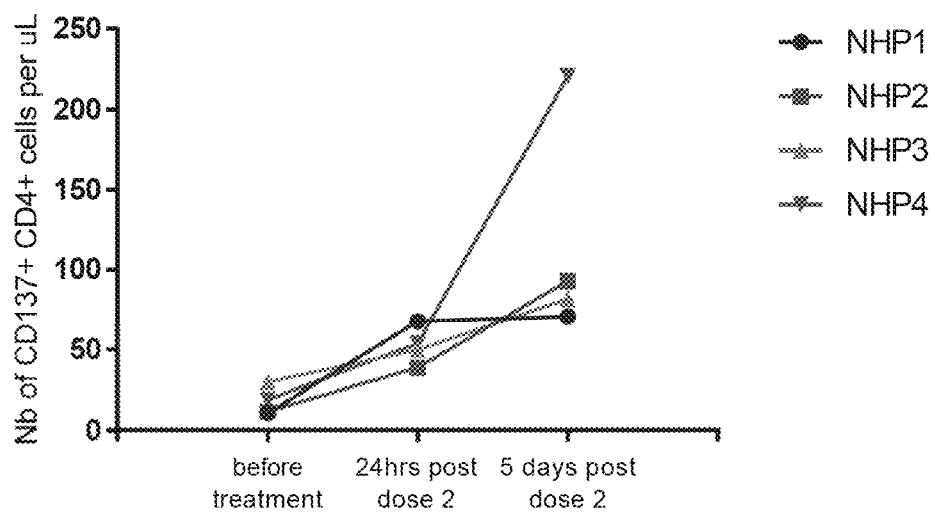
D)
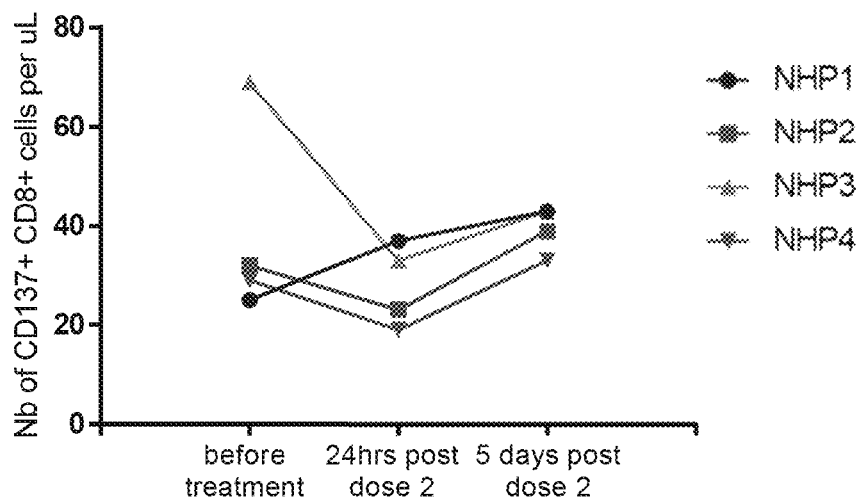

FIGURE 32 cont.
E)
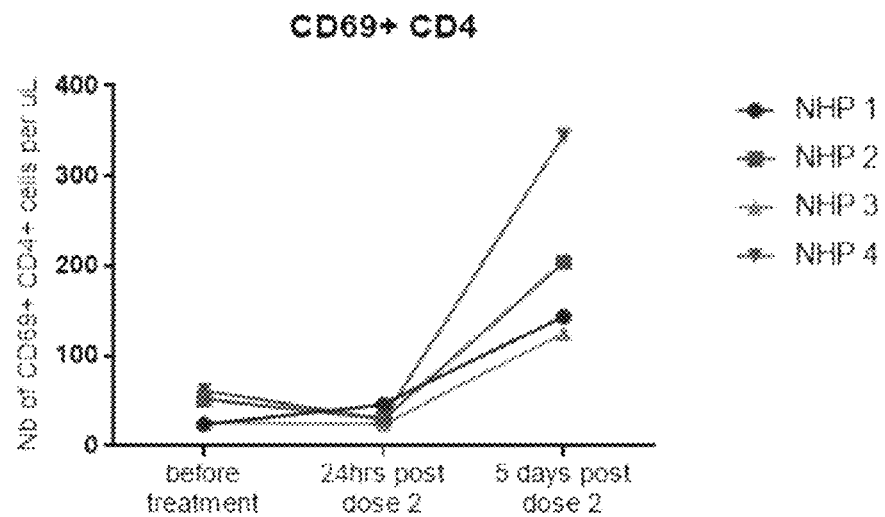
F)
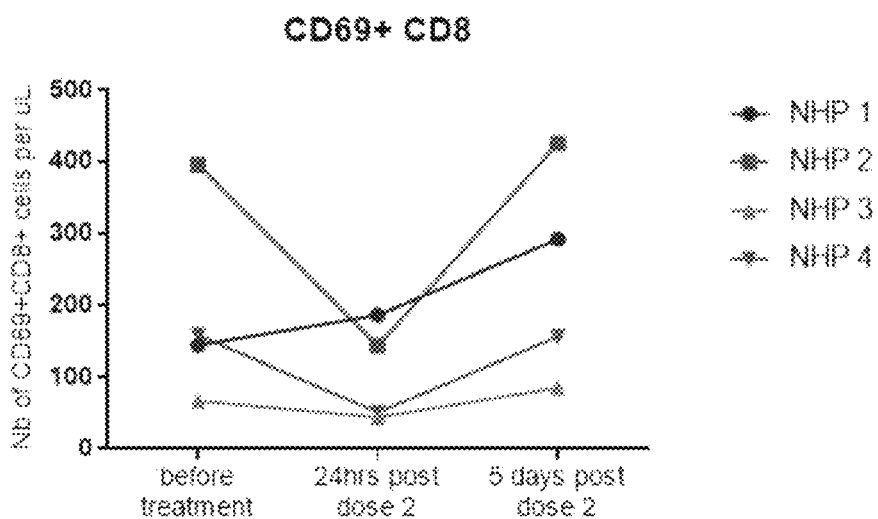

aCD38-b-329-m6-HCDR123

GSIS<u>SSDYYWG</u>WIRQPPGKGLEWIG<u>SIYYSGSTYYNPSLKS</u>RVTISVDTSKNQFSLK
LSSVTAADTAVYYC<u>ARGQYSSGWYAYPFDM</u> aCD38-b-329-m6-LCDR123

<u>RASQSVRSSYLA</u>WYQQKPGQAPRLLIY<u>GASSRAT</u>GIPDRFSGSGSGTDFTLTISRL
EPEDFAVYYC<u>QQDEAVFT</u>

B)

aCD38-b-329-m7-HCDR123

<u>GSISSSDYYWG</u>WIRQPPGKGLEWIG<u>SIYYSGSTYYNPSLKS</u>RVTISVDTSKNQFSLK
LSSVTAADTAVYYC<u>ARGQYSSGWYAYPFDM</u> aCD38-b-329-m7-LCDR123

<u>RASQSVRSSYLA</u>WYQQKPGQAPRLLIY<u>GASSRAT</u>GIPDRFSGSGSGTDFTLTISRL
EPEDFAVYYC<u>QQDSAVFT</u>

Daudi Binding

Daudi ADCC 4 hours Calcein AM Release
Donor 3627

aCD38-b-348-m1-HCDR123

<u>GSISSSDYYWG</u>WIRQPPGKGLEWIG<u>SIYYSGSTYYNPSLKS</u>RVTISVDTSKNQFSLKLSSVTAADTAVYYC<u>ARGQYSSGWYAYPFDM</u> aCD38-b-348-m1-LCDR123

<u>RASQSVRSSYLA</u>WYQQKPGQAPRLLIY<u>GASSRAT</u>GIPDRFSGSGSGTDFTLTISRLEPEDFAVYYC<u>QQEANVYT</u>

B)

aCD38-b-348-m2-HCDR123

<u>GSISSSDYYWG</u>WIRQPPGKGLEWIG<u>SIYYSGSTYYNPSLKS</u>RVTISVDTSKNQFSLKLSSVTAADTAVYYC<u>ARGQYSSGWYAYPFDM</u> aCD38-b-348-m2 LCDR123

<u>RASQSVRSSYLA</u>WYQQKPGQAPRLLIY<u>GASSRAT</u>GIPDRFSGSGSGTDFTLTISRLEPEDFAVYYC<u>QQDSNVYT</u>

C)

aCD38-b-348-m3 HCDR123

<u>GSISSSDYYWG</u>WIRQPPGKGLEWIG<u>SIYYSGSTYYNPSLKS</u>RVTISVDTSKNQFSLKLSSVTAADTAVYYC<u>ARGQYSSGWYAYPFDM</u> aCD38-b-348-m3-LCDR123

<u>RASQSVRSSYLA</u>WYQQKPGQAPRLLIY<u>GASSRAT</u>GIPDRFSGSGSGTDFTLTISRLEPEDFAVYYC<u>QQDANVYT</u>

D)

aCD38-b-348-m4-HCDR123

<u>GSISSSDYYWG</u>WIRQPPGKGLEWIG<u>SIYYSGSTYYNPSLKS</u>RVTISVDTSKNQFSLKLSSVTAADTAVYYC<u>ARGQYSSGWYAYPFDM</u> aCD38-b-348-m4-LCDR123

<u>RASQSVRSSYLA</u>WYQQKPGQAPRLLIY<u>GASSRAT</u>GIPDRFSGSGSGTDFTLTISRLEPEDFAVYYC<u>QQEGNVYT</u>

Daudi Binding

Daudi ADCC 4 hours Calcein AM Release
Donor 3627

FIGURE 39
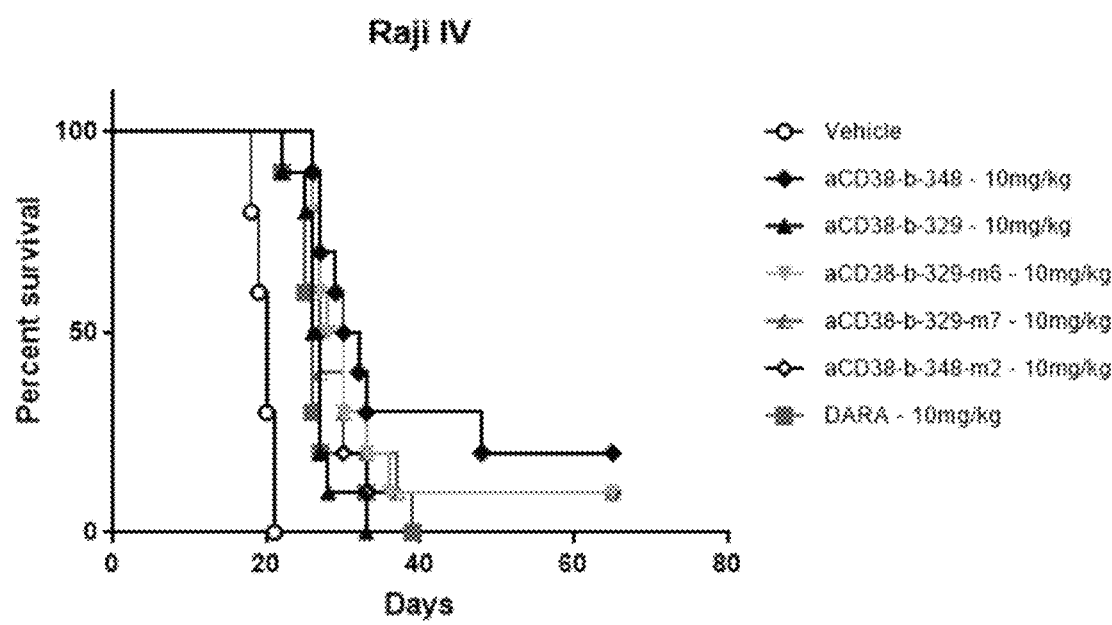
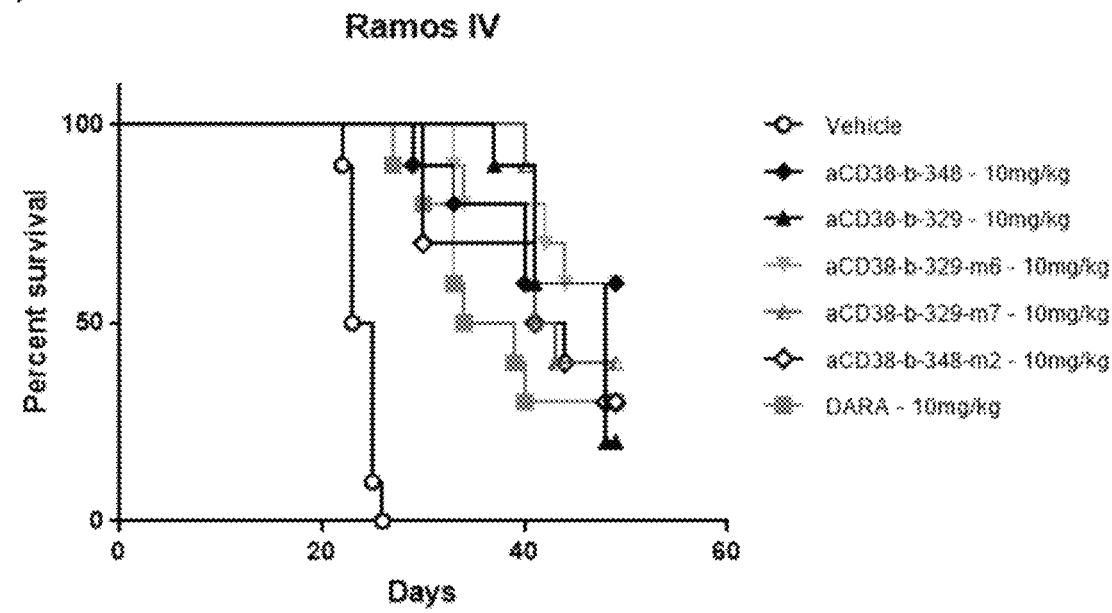

FIGURE 42
A)
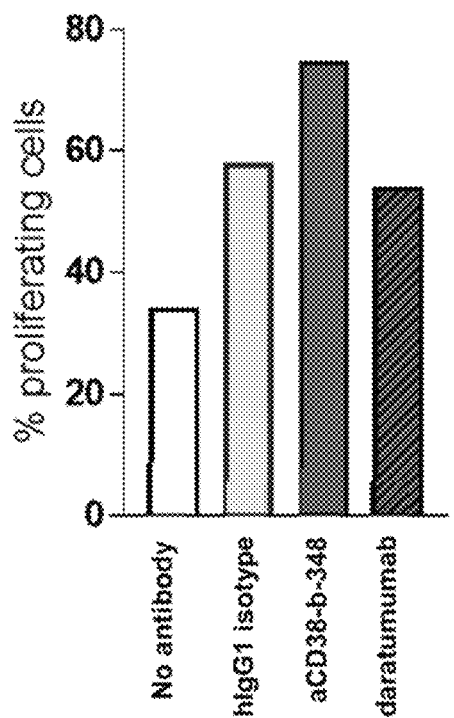
B)
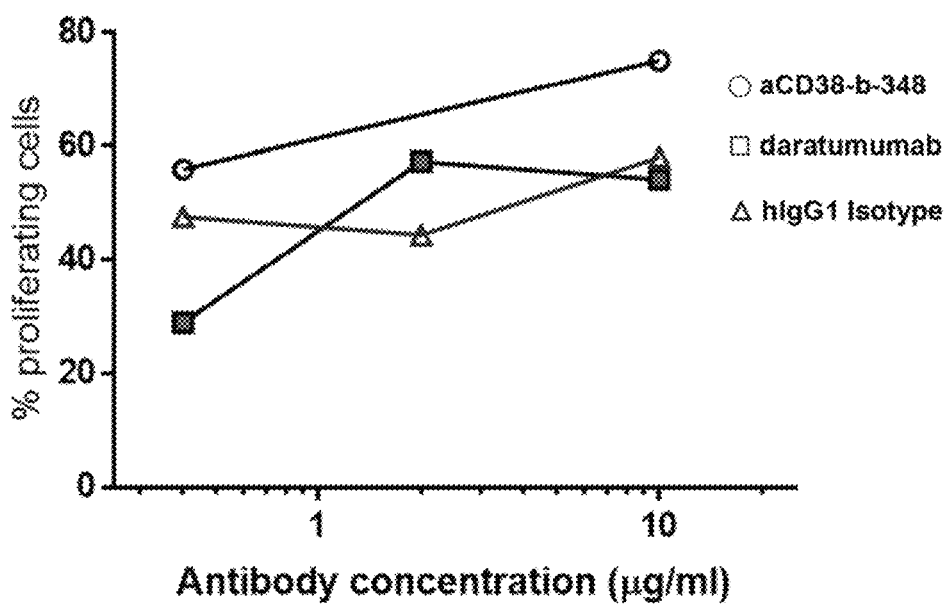

FIGURE 43
A)
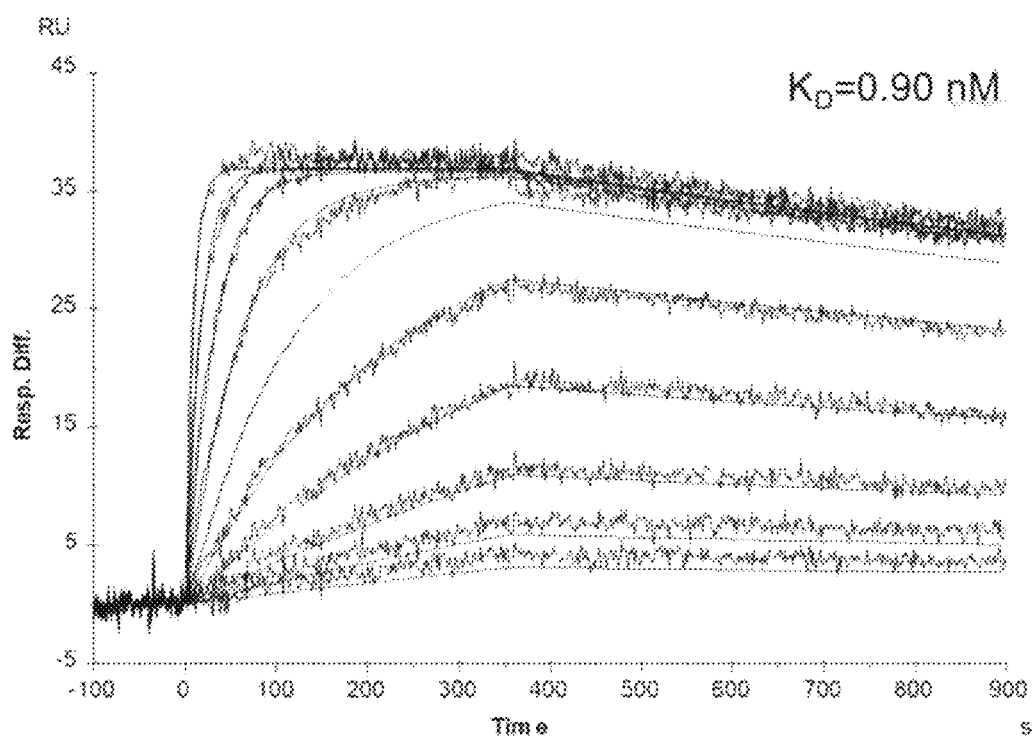
B)
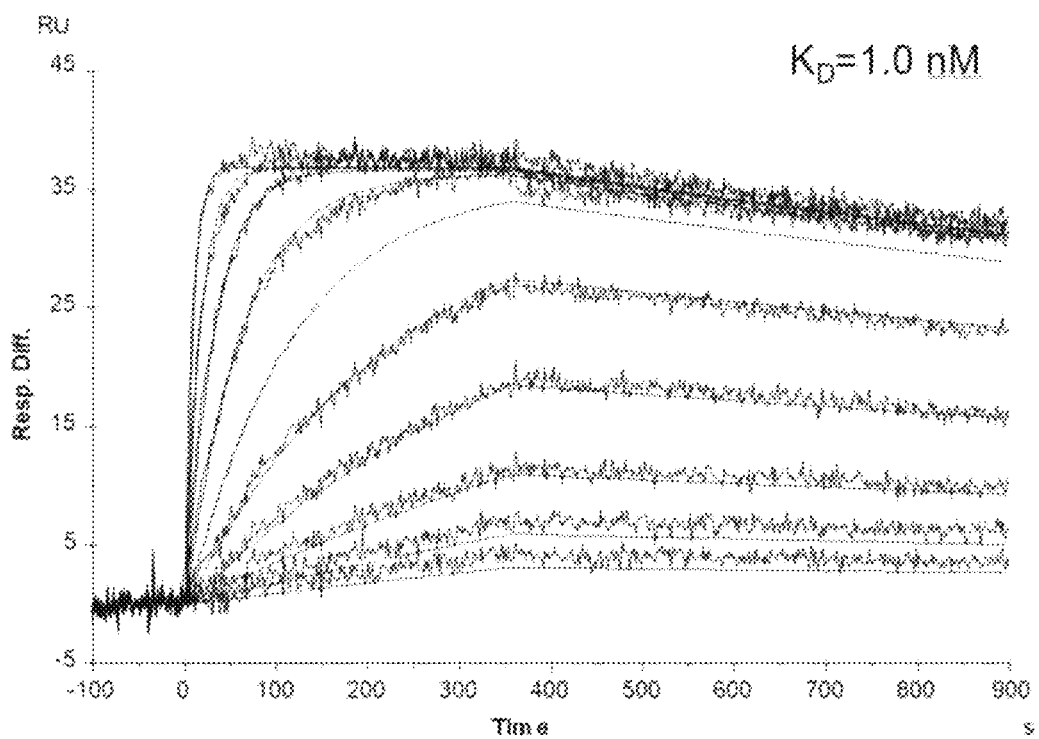

FIGURE 43 cont.
C)
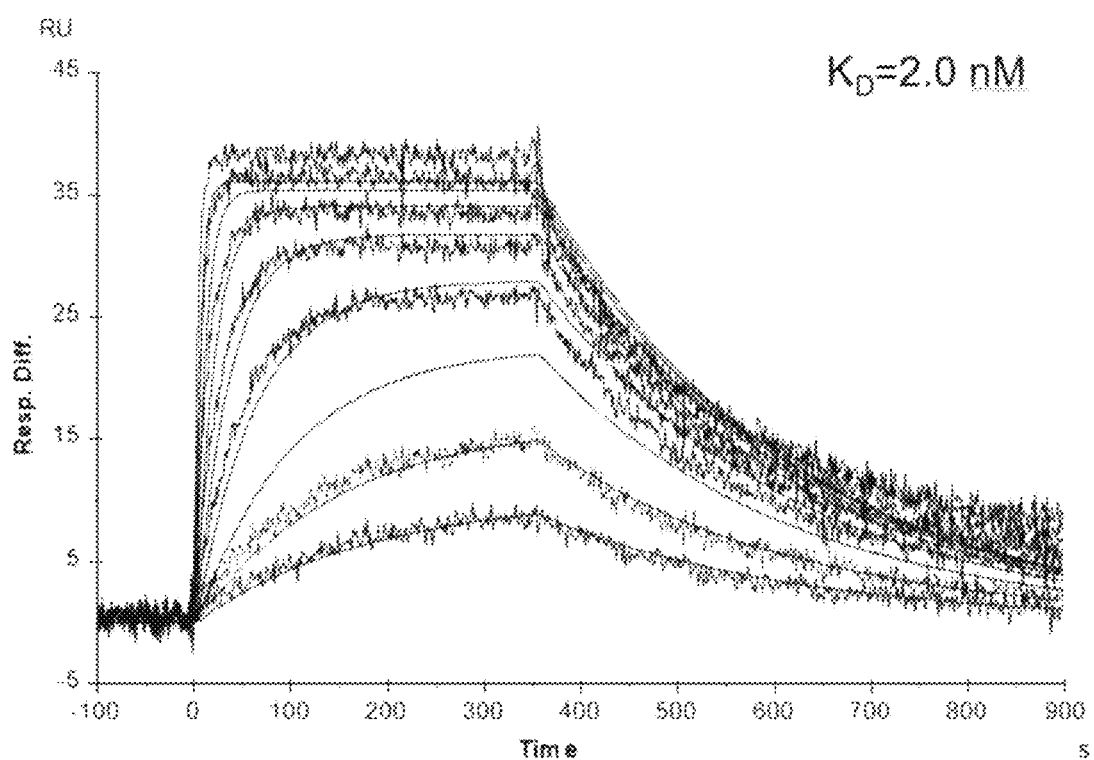
D)
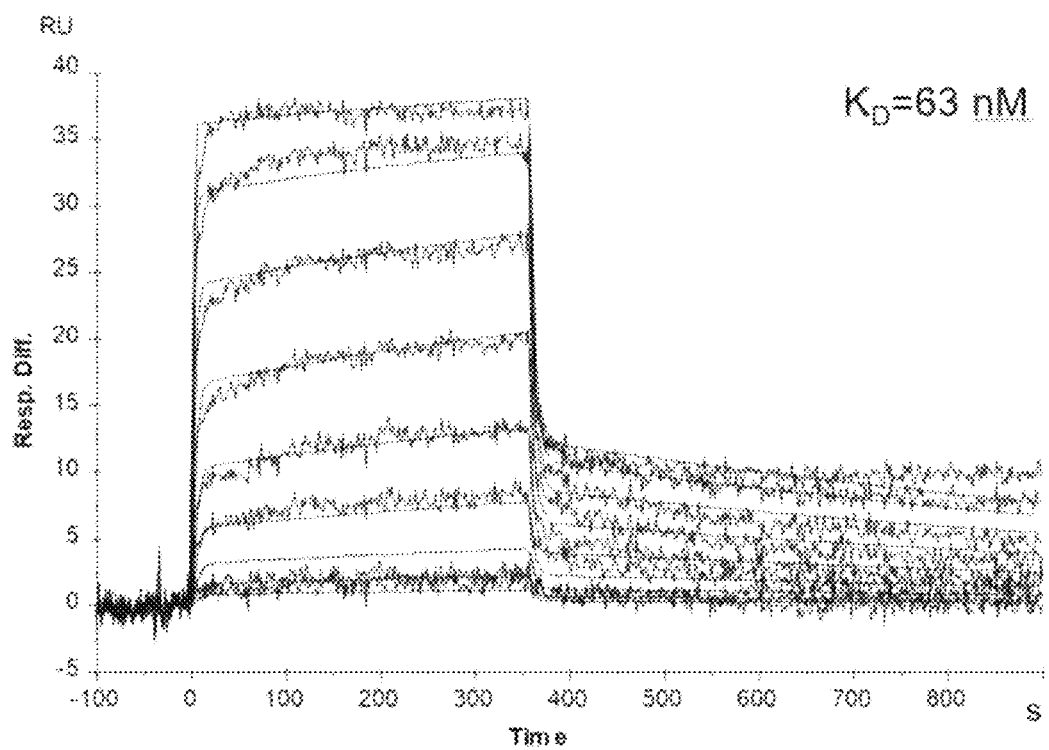

FIGURE 43 cont.
E)
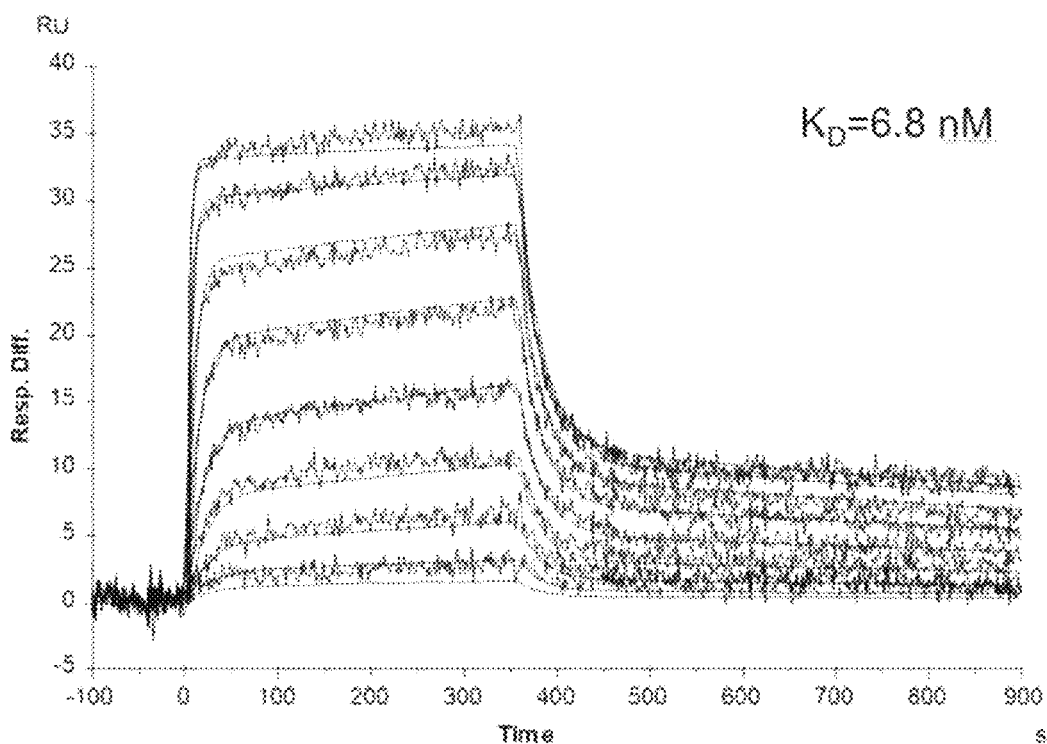
F)
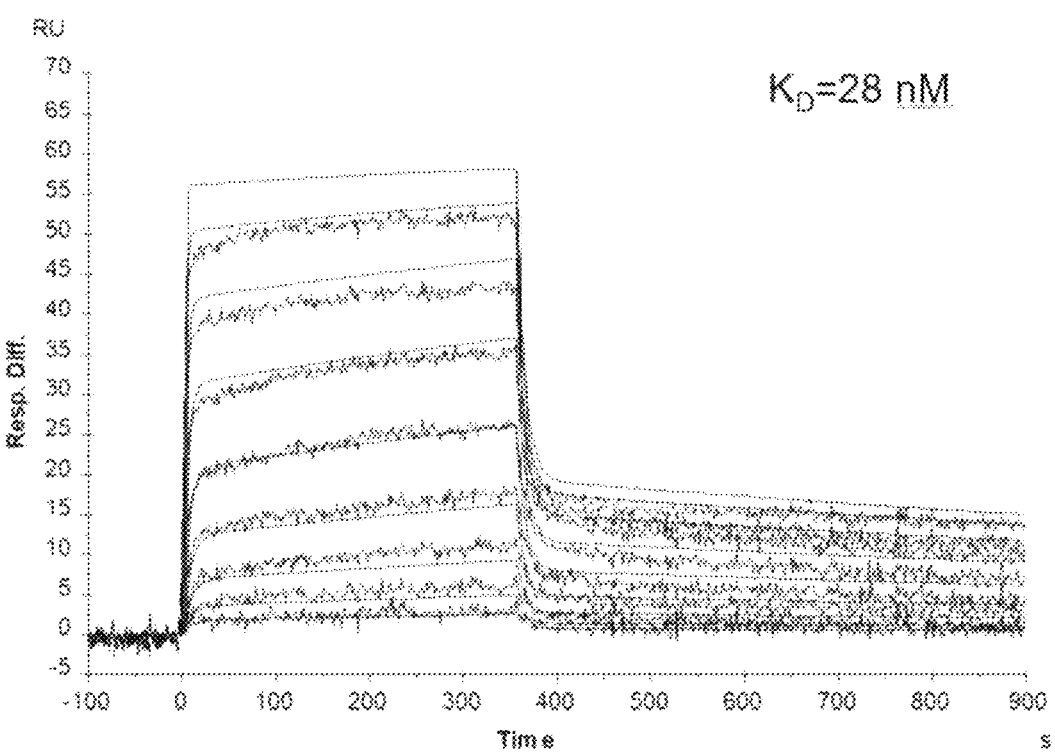

FIGURE 43 cont.
G)
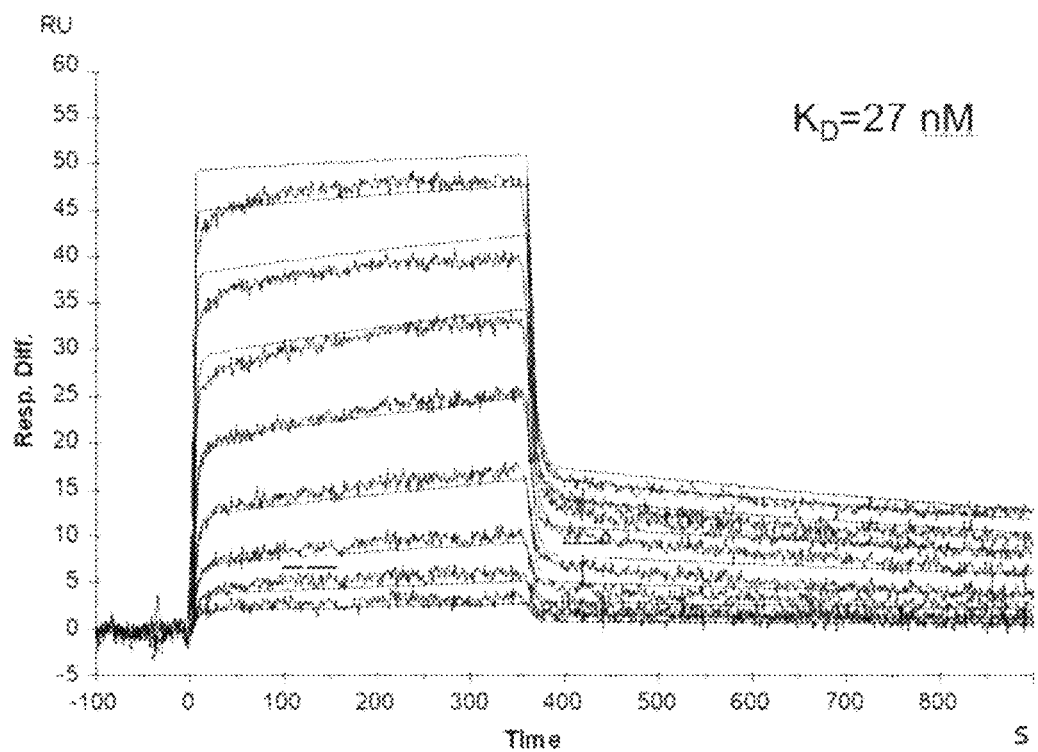
H)
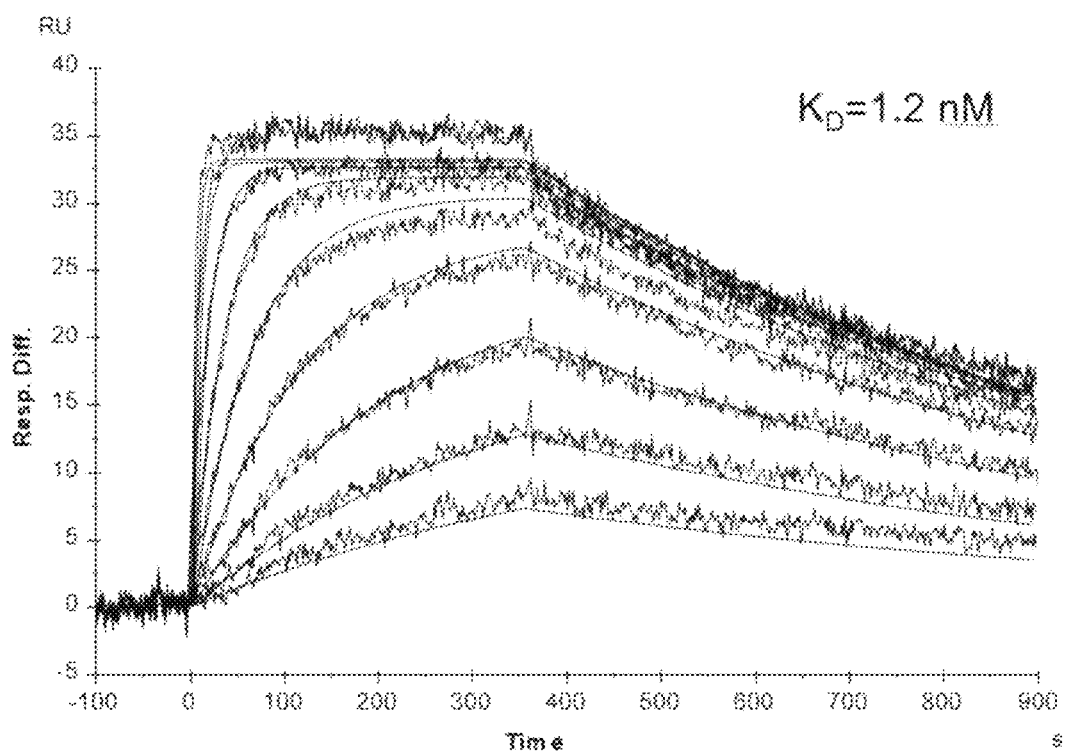

FIGURE 43 cont.
I)
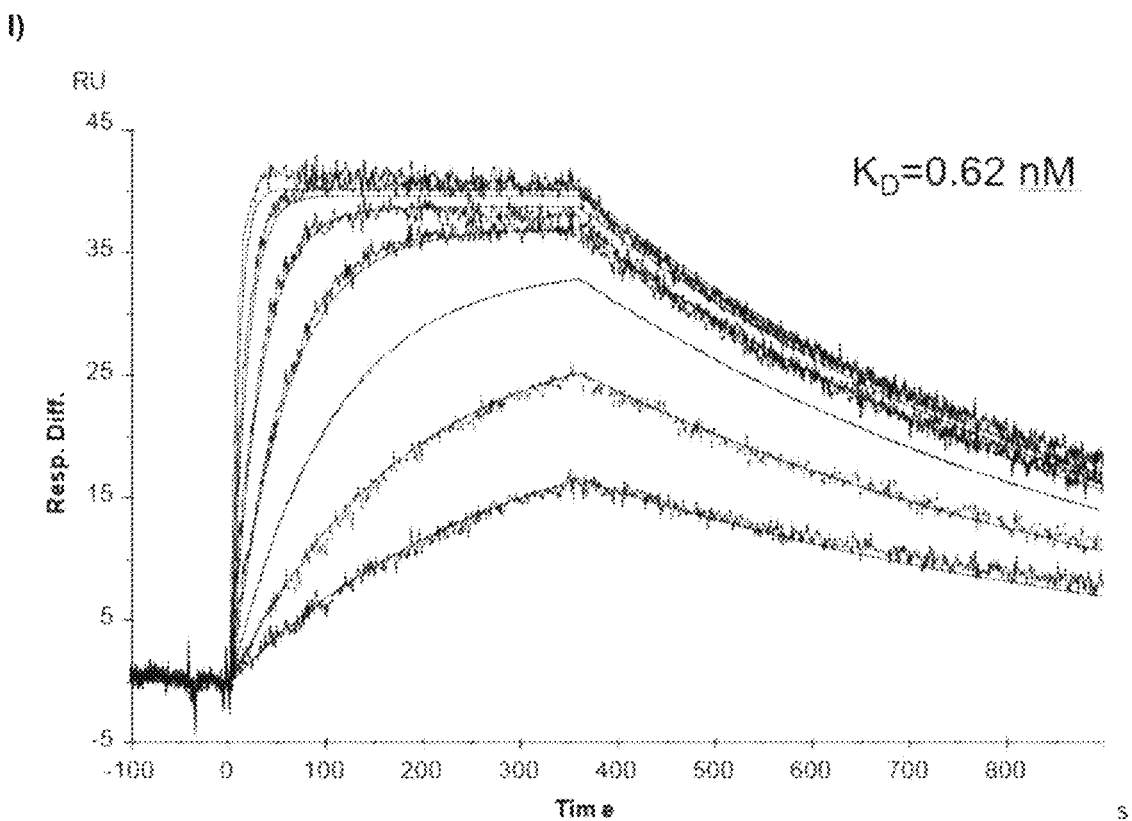
J)
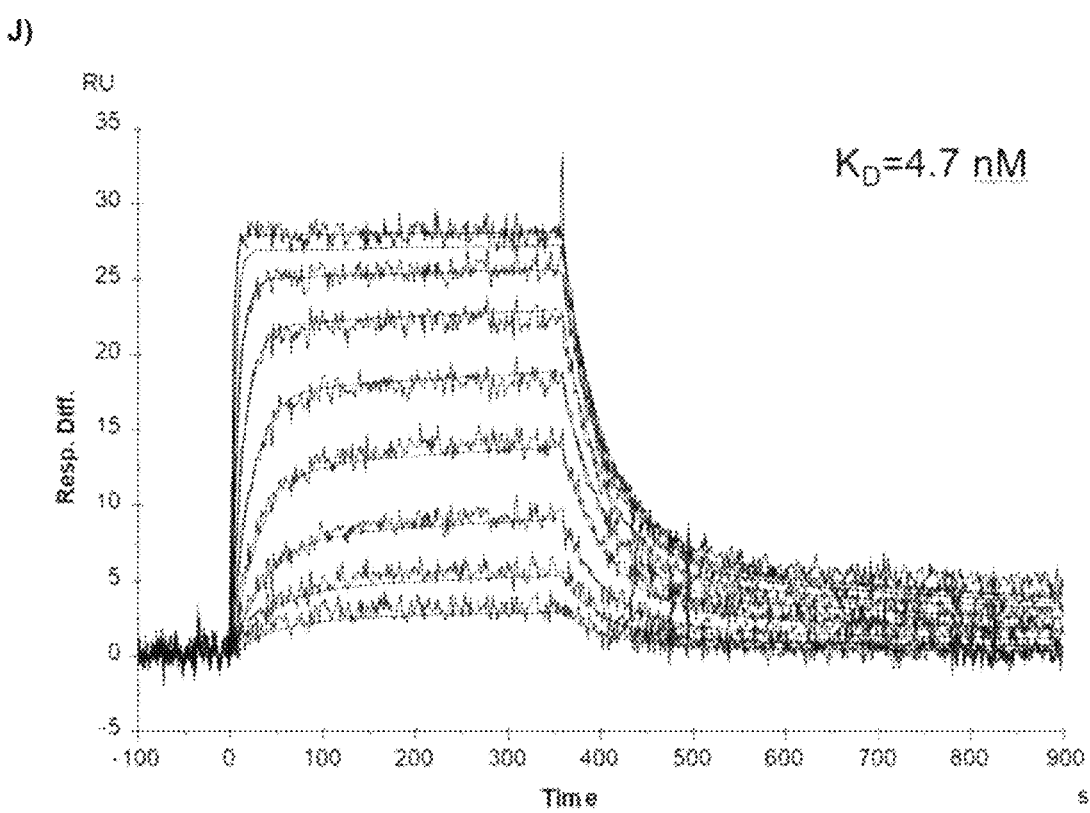

FIGURE 44
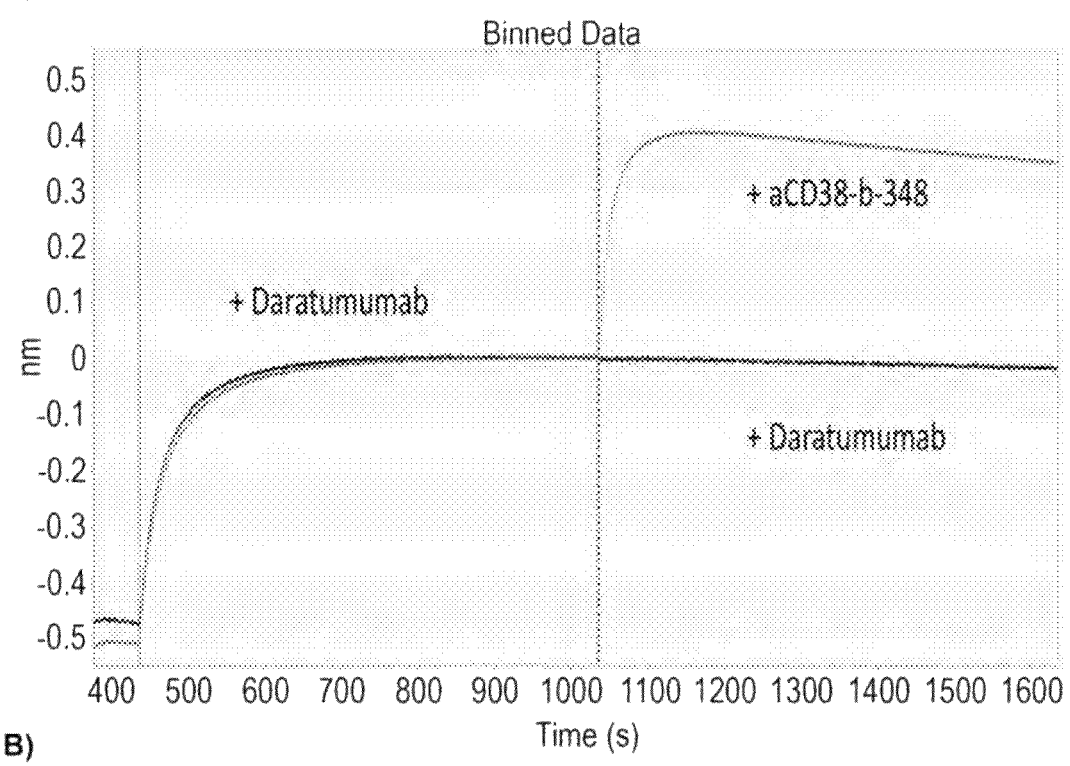
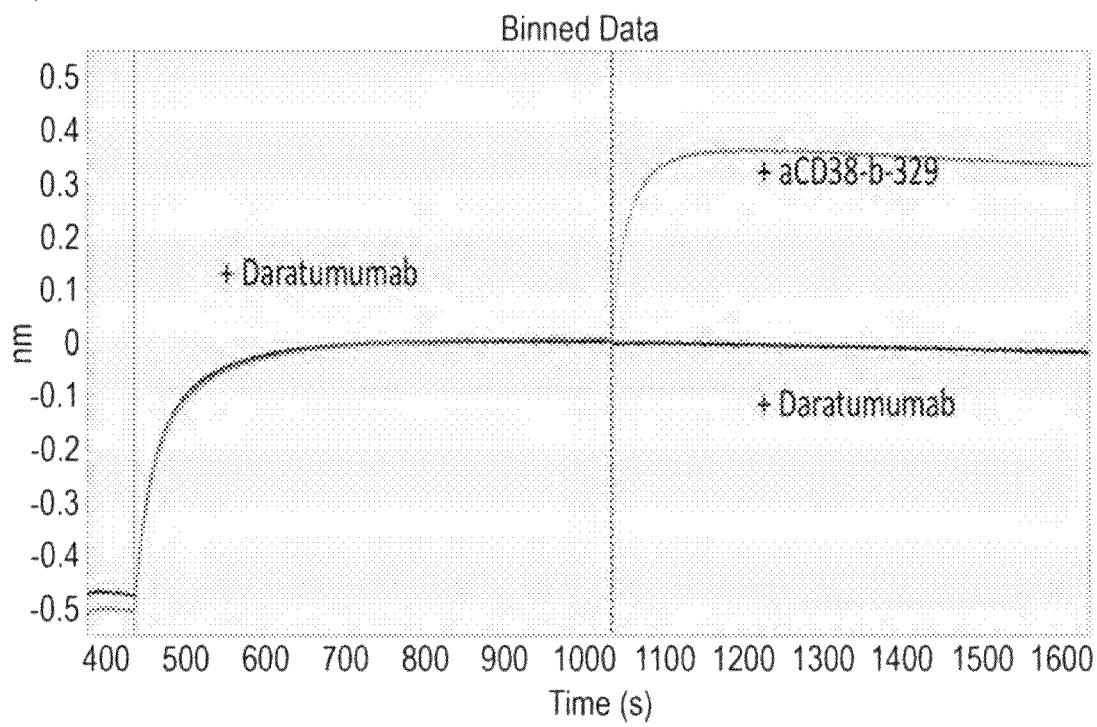

FIGURE 44 cont.
C)
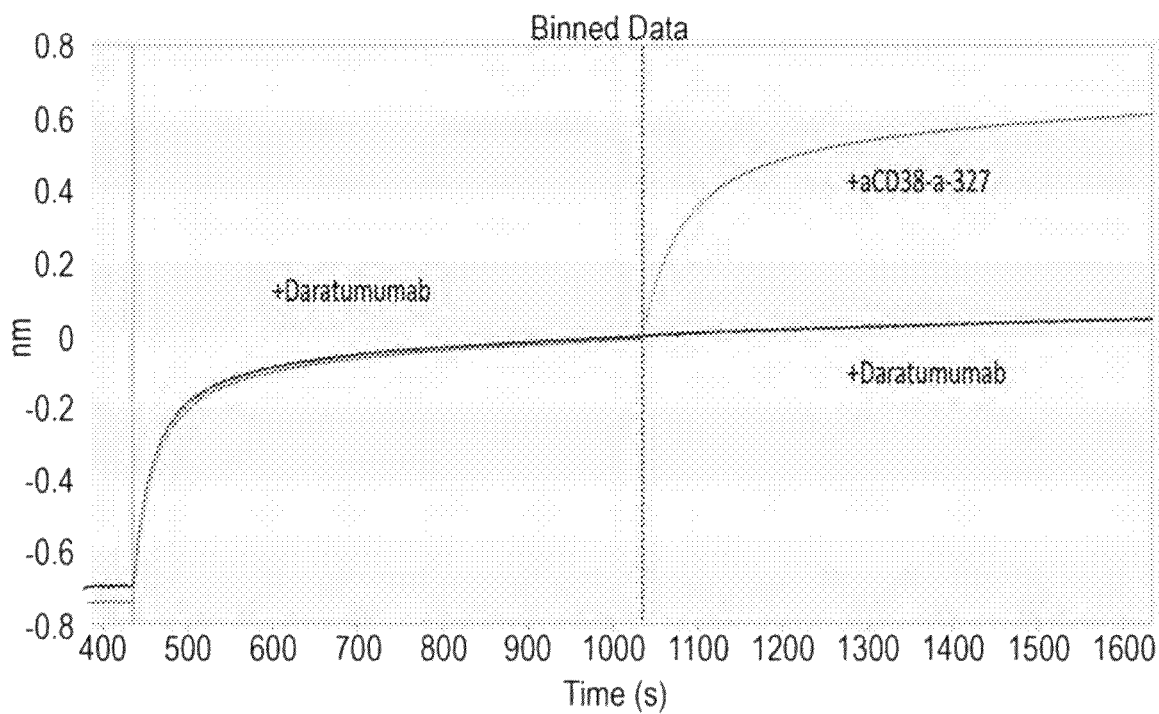
D)
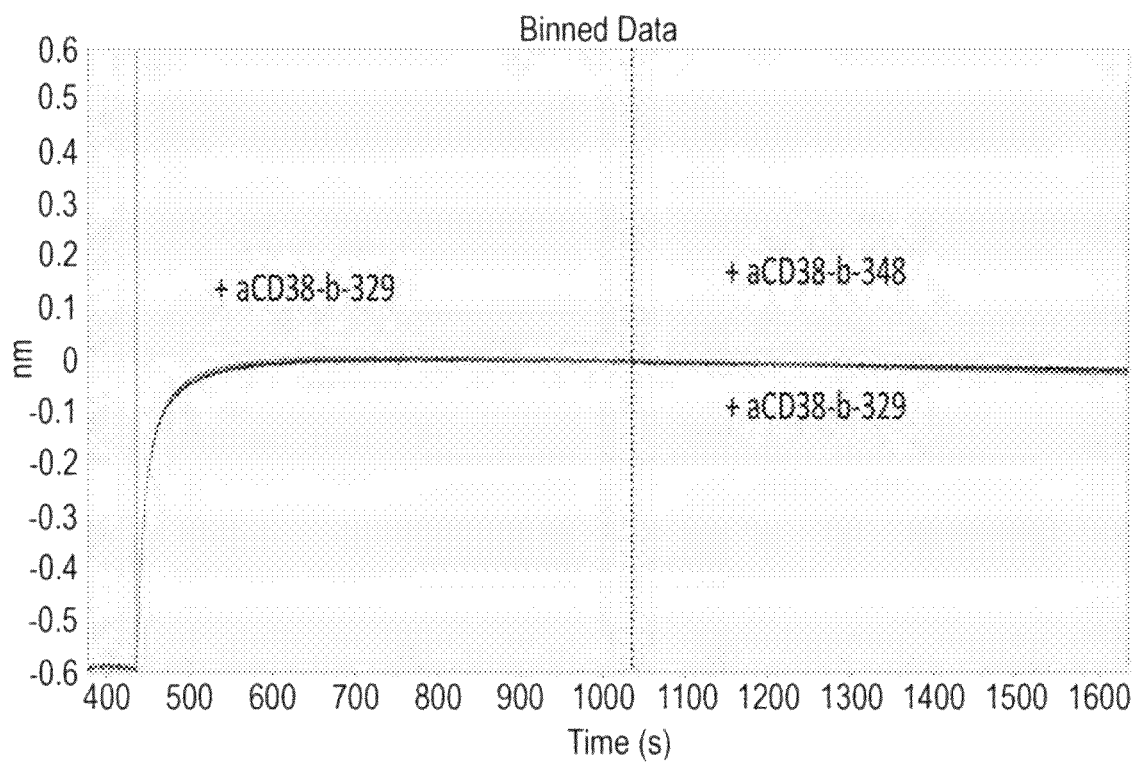

CD38 MODULATING ANTIBODY

CROSS-REFERENCE TO RELATED APPLICATION

This application is the U.S. national phase application filed under 35 U.S.C. § 371 claiming benefit to International Patent Application No. PCT/EP2018/065237, filed on Jun. 8, 2018, which is entitled to priority under 35 U.S.C. § 119(e) to U.S. Provisional Patent Application No. 62/517,150, filed Jun. 8, 2017, U.S. Provisional Patent Application No. 62/517,149, filed Jun. 8, 2017, U.S. Provisional Patent Application No. 62/517,165, filed Jun. 9, 2017, U.S. Provisional Patent Application No. 62/517,164, filed Jun. 9, 2017, U.S. Provisional Patent Application No. 62/517,734, filed Jun. 9, 2017, U.S. Provisional Patent Application No. 62/517,740, filed Jun. 9, 2017, U.S. Provisional Patent Application No. 62/517,745, filed Jun. 9, 2017, U.S. Provisional Patent Application No. 62/517,753, filed Jun. 9, 2017, U.S. Provisional Patent Application No. 62/546,322, filed Aug. 16, 2017, U.S. Provisional Patent Application No. 62/546,330, filed Aug. 16, 2017, U.S. Provisional Patent Application No. 62/582,676, filed Nov. 7, 2017, U.S. Provisional Patent Application No. 62/582,681, filed Nov. 7, 2017, U.S. Provisional Patent Application No. 62/582,666, filed Nov. 7, 2017, U.S. Provisional Patent Application No. 62/582,628, filed Nov. 7, 2017, U.S. Provisional Patent Application No. 62/582,653, filed Nov. 7, 2017, U.S. Provisional Patent Application No. 62/582,616, filed Nov. 7, 2017, the contents of each of which are incorporated by reference herein in their entireties.

BACKGROUND

CD38 is a type II membrane receptor glycoprotein having enzymatic activities, in particular as an important ADP-ribosyl cyclase that produces cyclic adenosine diphosphate ribose (cADPR) from nicotinamide adenine dinucleotide. CD38 can also hydrolyze NAD+ into ADPR. Generation of ADPR may modulate immunological responses as it is upstream of a pathway leading to the production of immune-suppressive adenosine. Different extracellular stimuli can induce cADPR production. cADPR is important to the mobilization of intracellular calcium stock that is involved in many cell functions such as cell proliferation, differentiation, adhesion, and signal transduction. CD38 was initially identified as a leukocyte activation marker but plays dual roles as receptor and ectoenzyme, endowed with cell signalling and cell homeostasis activities. CD38 has been linked to various human diseases, including malignancies such as chronic lymphocytic leukemia, myeloma and ovarian carcinoma (Quarona V, et al., 2013; Wei W, et al., 2014).

CD38 is found on the surface of many cell types that are involved in immunological responses (in short referred to as immune cells), including effector cells such as T and B lymphocytes and NK cells, but also immune suppressive cells such as regulatory T and B cells, myeloid derived suppressive cells (MDSCs) or tumour associated macrophages (Chevrier S et al. 2017). For instance, in lung cancer patients, anti-PD-1 treatment induced proliferation of PD-1 expressing T cells that expressed high levels of CD38 (Kamphorst A O et al., 2017). The importance of cADPR- and CD38-mediated Ca2+ signalling for biological activity of immune cells, in particular for the modulation of the immune response in physiological and pathological conditions, has been described in the literature (Morandi F et al., 2015; Rah S Y et al., 2015).

CD38 is highly expressed by cancer cells in multiple myeloma patients at all stages of disease and in CLL patients with a poor prognosis. Various CD38-targeting therapies are developed by generating compounds that act mainly as CD38 antagonists or inhibitors (de Weers M et al., 2011; van de Donk N W et al., 2016; Horenstein A L et al., 2017). Anti-CD38 monoclonal antibodies acting as CD38 agonists (such as the one named IB4) have also been characterized as inducing the mobilization of calcium ions, CD38 shedding, NK cell-mediated cytotoxicity, cytokine secretion (in particular Interleukin 6 and Interferon gamma), and proliferation of human T lymphocytes, among other activities, and were modified to deliver immunotoxins (Malavasi F et al., 2008; Hara-Yokoyama M et al., 2008; Frasca L et al, 2006; Karakasheva T et al., 2015). Such a positive effect on immune cells may be related to induction of Ca2+ mobilization, inhibition of CD38 enzymatic activity, and/or activation of intra-cellular signalling pathways.

Monoclonal antibodies were developed for targeted, direct killing of CD38-expressing tumor cells and have shown promising results in the clinic. However, the activity of such anti-CD38 antibodies may be restricted to tumors in which CD38 is highly expressed on the surface of cancer cells. In solid tumors, the expression of CD38 is generally lower or absent on the tumor cells and may be associated with tumor infiltrating immune cells, both effector and suppressive. Therefore, there is still a need for anti-CD38 antibodies presenting activities that result from the combination of different components, such as CD38-specific agonistic or modulating properties together with targeted cell killing or activation, and compatibility with pharmaceutical development, and that can be exploited for treating cancer, in particular for treating solid and haematological cancers.

SUMMARY

In some embodiments, the present invention provides new CD38 Modulating Antibody Agents. In some embodiments, provided CD38 Modulating Antibody Agents are antibodies or antigen-binding fragments that specifically bind to CD38, and particularly to human CD38, in many embodiments to a site in the human CD38 extracellular domain.

In some embodiments, provided antibodies or antigen binding fragments modulate one or more features of CD38. That is, in some embodiments, level and/or activity of CD38, and/or one or more downstream effects thereof, is detectably altered when a provided antibody is present as compared with when it is absent. Alternatively or additionally, in some embodiments, level and/or activity of CD38, and/or one or more downstream effects thereof, when a provided antibody is present, is comparable to or greater than that observed under comparable conditions when a reference CD38 Modulating Antibody Agent (e.g., a reference anti-CD38 antibody, such as IB-4, with a known desirable attribute; e.g., a known ability to agonize one or more features of CD38).

In many embodiments, one or more features of CD38 is enhanced when a provided CD38 Modulating Antibody Agent (e.g., anti-CD38 antibody or antigen-binding fragment thereof) is present. For example, in some embodiments, presence of a provided CD38 Modulating Antibody Agent (e.g., anti-CD38 antibody or antigen-binding fragment thereof) correlates with increased immune cell activation, and/or proliferation. Thus, provided CD38 Modulating Antibody Agents are often referred to herein as "agonists". Those skilled in the art, however, will appreciate that teachings of the present disclosure are not limited by particular mechanism of action of provided antibodies or antigen-binding fragments thereof. Relevant structural and/or functional features of provided antibodies are described herein and speak for themselves.

In some embodiments, provided CD38 Modulating Antibody Agents (e.g., CD38 antibodies or antigen-binding fragments) may be characterized, for example, by effects on certain immune effector cells (e.g., NK cells and/or T cells). Alternatively or additionally, in some embodiments, provided CD38 Modulating Antibody Agents (e.g., CD38 antibodies or antigen-binding fragments) may be characterized, for example, by effects on immune suppressive cells. For example, in some embodiments, provided CD38 Modulating Antibody Agents display activating properties with respect to immune effector cells such as NK cells and T cells and/or cytotoxic properties towards CD38 high expressing cells such as immune suppressive cells or tumour cells (e.g., in each case, that express CD38 on their surfaces). Alternatively or additionally, in some embodiments, provided CD38 Modulating Antibody Agents are characterized by one or more features that are associated with binding to a specific epitope in human CD38 extracellular domain and/or that render them particularly amenable to pharmaceutical use and/or manufacturing.

Provided technologies, including provided CD38 Modulating Antibody Agents (e.g., provided antibodies or antigen-binding fragments thereof (or variants of the same)), compositions including them, and/or uses for them, are useful in medicine. In some embodiments, such provided technologies are useful in cancer therapy and/or prophylaxis.

In one aspect, there is provided anti-CD38 antibodies or antigen-binding fragments thereof (or variants of the same), wherein the antibody or fragment thereof:
  exhibits antibody-dependent cell-mediated cytotoxicity (ADCC) activity against CD38+ target cells;
  exhibits no complement dependent cytotoxicity (CDC) or reduced CDC activity against a CD38+ target cell as compared to daratumumab under the same or substantially the same conditions; and
  induces immune effector cell activation.

In some embodiments, the anti-CD38 antibodies or antigen-binding fragments thereof having the above features are or are derived from, for example, aCD38-a-323, aCD38-b-329, aCD38-b-348 or aCD38-a-306. The antibodies or antigen-binding fragments thereof having the above features, may alternatively be derived from aCD38-a-327.

Antibody-dependent cell-mediated cytotoxicity (ADCC) activity of the anti-CD38 antibodies or antigen-binding fragments thereof may be determined in vitro using an assay as described in the Examples, e.g. using CD38+ Daudi cells as the target cell and human PBMC cells as effector cells, wherein the ratio of target cells to effector cells is from about 50 to 1 to about 25 to 1.

Complement dependent cytotoxicity (CDC) activity against a CD38+ target cell can be determined in vitro using an assay as described in the Examples, e.g. using CD38+ Daudi and/or Raji cells in the presence of 10% complement. CDC activity may be determined by treating the target cells with increasing concentrations up to 10 µg/ml of antibodies in the presence of human complement. In some embodiments CDC activity is determined by measuring the maximum percentage cell lysis of CD38+ cells, i.e. CD38+ Daudi cells in the presence of 10% complement. The maximum lysis for a given antibody may vary between experiments. It is therefore helpful to consider other metrics for measuring CDC activity, including, for example, EC50 values and/or fold difference in maximum % lysis and/or EC50 as compared with a reference antibody (such as daratumumab). A determination of a lower CDC activity as compared to daratumumab may therefore be in reference to maximum % lysis, EC50, and/or a fold change compared to daratumumab of either value.

In one preferred embodiment of the invention, the provided CD38 Modulating Antibody Agents may exhibit either no CDC or may exhibit CDC:
  a) with an EC50 that is at least 0.5-fold higher (or more preferably at least 1-fold higher) than daratumumab; or
  b) with a maximum % lysis as measured in Raji and/or Daudi cells in the presence of 10% complement that is no more than half that exhibited by daratumumab;

Of course, the CDC of daratumumab is determined in the same or substantially the same conditions for the comparison. Such anti-CD38 antibodies or antigen-binding fragments thereof may be, or may be derived from, for example, aCD38-a-323, aCD38-b-329, aCD38-b-348, aCD38-a-306 or aCD38-a-327. CDC activity can be determined using an antibody concentration of up to about 10 µg/mL. As the skilled person would understand, when determining maximum lysis of cells, a concentration of 10 µg/mL is not always required since maximum cell lysis may occur at a lower antibody concentration, although 10 µg/mL may be used if necessary.

In some embodiments, the reduction in CDC activity compared to daratumumab is such that the $EC_{50}$ of the antibody or antibody binding fragment thereof is at least about 0.5-fold greater (i.e. at least about 1.5 times greater), or preferably at least about 1-fold greater (i.e. at least about 2 times greater) than that of daratumumab under the same or substantially the same conditions. For example, the $EC_{50}$ of the antibody or antibody binding fragment thereof is at least about 0.5 fold greater, or preferably about 1-fold greater than that of daratumumab against Daudi cells and/or Raji in the presence of 10% complement. In some such embodiments, the anti-CD38 antibodies or antigen-binding fragments thereof having such features may be, or may be derived from, for example, aCD38-b-348.

In some embodiments, the reduction in CDC activity compared to daratumumab is such that the maximum % lysis is no more than half that exhibited by daratumamab under the same or substantially the same conditions. For example, the maximum % lysis may be no more than half that exhibited by daratumamab as measured in Raji and/or Daudi cells in the presence of 10% complement. In some such embodiments, the anti-CD38 antibodies or antigen-binding fragments thereof having such features may be or may be derived from, for example, aCD38-a-323 or aCD38-a-306.

In some embodiment, the anti-CD38 antibodies or antigen-binding fragments thereof (or variants of the same) do not exhibit CDC. In some such embodiments, the anti-CD38 antibodies or antigen-binding fragments thereof having such features may be or may be derived from, for example, aCD38-a-327.

In some embodiments, the antibody or fragment thereof (or variants of the same) causes less than 60% lysis of CD38+ expressing Daudi cells by CDC. In some embodiments, the antibody or fragment thereof causes less than about 50%, less than about 40%, less than about 30% or less than about 20% lysis of CD38+ expressing cells by CDC. In some embodiments, the antibody or fragment thereof causes less than about 60% lysis but more than about 10% lysis of CD38+ expressing cells by CDC. The percentage lysis can be measured in Daudi cells in the presence of 10% complement and increasing concentration up to 10 µg/mL of antibodies. In some embodiments, the anti-CD38 antibodies or antigen-binding fragments thereof having the above features may be, or may be derived from, for example, aCD38-a-323 or aCD38-a-306.

In some embodiments, the antibody or antigen-binding fragment thereof (or variants of the same) induces CDC with an $EC_{50}$ of at least about 0.05 µg/mL against CD38+ Daudi and/or Raji cells (and optionally causes less than 60% lysis of such CD38+ expressing cells by CDC). Such anti-CD38 antibodies or antigen-binding fragments thereof having an $EC_{50}$ value of at least about 0.05 µg/mL against CD38+ Daudi and/or Raji cells may be, or may be derived from, for example, aCD38-a-323, aCD38-b-348 or aCD38-a-306. In some embodiments, the antibody or fragment thereof induces CDC with an EC50 of at least about 0.05 µg/mL, at least about 0.10 µg/mL, or at least about 0.15 µg/mL against CD38+ Daudi and/or Raji cells (and optionally causes less than 60% lysis of such CD38+ expressing cells by CDC at an antibody concentration of up to about 10 µg/ml). Anti-CD38 antibodies or antigen-binding fragments thereof having an EC50 value of at least about 0.15 µg/mL against CD38+ Daudi and/or Raji cells include antibodies or fragments thereof that are, or are derived from, aCD38-b-348 or aCD38-a-306.

In some embodiments, the antibodies are or are derived from aCD38-b-348. Such antibodies exhibit antibody-dependent cell-mediated cytotoxicity (ADCC) activity against CD38+ target cells; exhibit reduced CDC activity against a CD38+ target cell as compared to daratumumab under the same or substantially the same conditions (for example, the EC50 value as measured as described herein may be at least twice that of daratumumab); induce immune effector cell activation; induce T cell proliferation; induce an increase in cytokine secretion, including IL-2, IFNγ, TNFα, GM-CSF and IL-10; and induce NK cell activation. Such antibodies may also exhibit a slight inhibitory effect on CD38 cyclase activity.

In some embodiments, the antibodies are or are derived from aCD38-a-323. Such antibodies exhibit antibody-dependent cell-mediated cytotoxicity (ADCC) activity against CD38+ target cells; exhibit reduced CDC activity against a CD38+ target cell as compared to daratumumab under the same or substantially the same conditions (for example, the maximum % lysis as measured as described herein may less than half that of daratumumab); induce immune effector cell activation; induce T cell proliferation; induce an increase in cytokine secretion, including GM-CSF; exhibit an inhibitory effect on CD38 NADase activity; and exhibit a stimulatory effect on CD38 cyclase activity.

In some embodiments, the antibodies are or are derived from aCD38-b-329. Such antibodies exhibit antibody-dependent cell-mediated cytotoxicity (ADCC) activity against CD38+ target cells; exhibit reduced CDC activity against CD38+ target cell as compared to daratumumab under the same or substantially the same conditions; induce immune effector cell activation; induce T cell proliferation; and induce an increase in cytokine secretion, including IL-2, TNFα, GM-CSF and IL-10.

In some embodiments, the antibodies are or are derived from aCD38-a-306. Such antibodies exhibit antibody-dependent cell-mediated cytotoxicity (ADCC) activity against CD38+ target cells; exhibit reduced CDC activity against a CD38+ target cell as compared to daratumumab under the same or substantially the same conditions (for example, the maximum % lysis as measured as described herein may less than half that of daratumumab); induce an increase in T cell proliferation; induce an increase in cytokine secretion, including IL-2, TNFα, IFNγ and IL-10; induce immune effector cell activation; and exhibit an inhibitory effect on CD38 NADase activity and on CD38 cyclase activity.

In some embodiments, the antibodies are or are derived from aCD38-a-327. Such antibodies exhibit antibody-dependent cell-mediated cytotoxicity (ADCC) activity against CD38+ target cells; exhibit reduced CDC activity against a CD38+ target cell as compared to daratumumab under the same or substantially the same conditions (or indeed does not exhibit any CDC activity at all); may induce T cell proliferation (or in some embodiments does not induce T cell proliferation); may induce immune effector cell activation (or in some embodiments does not induce T cell proliferation); and exhibit an inhibitory effect on CD38 cyclase activity.

In some embodiments, the anti-CD38 antibody or antigen-binding fragment thereof (or variants of the same) exhibits antibody-dependent cellular phagocytosis (ADCP) against CD38-expressing cells. In such embodiments, the anti-CD38 antibody or antigen-binding fragment thereof may be, or may be derived from, for example, aCD38-b-348. ADCP activity may be determined by a reporter cell assay measuring FcgRIIa engagement in Jurkat cells as the effector cells expressing FcgRIIa. The effector cells also express NFAT-induced luciferase. The target cell in the assay may be a CD38 expressing Raji cell. NFAT signalling can be measured to determine the activity.

In some embodiments, the anti-CD38 antibody or antigen-binding fragment thereof (or variants of the same) may induce ADCP against in vitro generated T reg cells. This may be measured as discussed in the Examples.

In some embodiments, the anti-CD38 antibody or antigen-binding fragment thereof (or variants of the same) does not exhibit ADCP activity against CD38-expressing cells, for example when ADCP is determined in a reporter cell assay measuring FcgRIIa engagement. In such embodiments, the anti-CD38 antibody or antigen-binding fragment thereof may be, or may be derived from, for example, aCD38-a-323, or aCD38-a-306.

In some embodiments, the anti-CD38 antibody or antigen-binding fragment thereof (or variants of the same) induces T cell activation at a greater amount as compared to daratumumab under the same or substantially the same conditions. In some embodiments T cell activation is determined by measuring NFAT signalling in luc_reporter Jurkat cells. In some embodiments, the NFAT signalling induced by the anti-CD38 antibody or antigen-binding fragment thereof, as measured in luc_reporter Jurkat cells, is at least about 10% higher than that of daratumumab measured under the same or substantially the same conditions. In some embodiments, the NFAT signalling is at least about 15%, at least about 20%, or at least about 30% higher than NFAT signalling of daratumumab measured under the same or substantially the same conditions.

In a NFAT luc_reporter assay in Jurkat cells, NFAT signalling can be measured in the presence of soluble CD3 monoclonal antibody in relative luminescence units (RLU). The CD3 monoclonal antibody may be at a concentration of 1 µg/ml and the Jurkat cells may be stimulated with the anti-CD38 antibody at a concentration of from about 5 µg/ml to about 40 µg/ml (for example 10 µg/ml). Using such an assay, NFAT signalling may be at least about 30% higher than NFAT signalling of daratumumab measured under the same or substantially the same conditions, when the RLU of CD3 only stimulation is used as a baseline.

T cell activation can be further characterised by an increase in T cell proliferation, and/or an increase in cytokine secretion, wherein the cytokines may be selected from the group consisting of IL-2, TNF-α, IFN-γ, IL-10 and GM-CSF.

T cell proliferation can be measured as in the Examples, for example as determined at an antibody concentration of 10 µg/ml after 72 hours incubation and in the presence of 0.1 µg/ml or 0.5 µg/ml anti-CD3 antibody. In some embodiments, the anti-CD38 antibody or antigen-binding fragment thereof increases T cell proliferation of CD4+ and/or CD8+ cells by at least about 20% as compared to untreated cells. In some embodiments, T cell proliferation increases by at least about 25%, by at least about 30%, by at least about 35%, or by at least about 40% as compared to untreated cells.

Preferably the anti-CD38 antibody or antigen-binding fragment thereof (or variants of the same) increases T cell proliferation in CD4+ and/or CD8+ cells by at least about 0.5-fold (i.e. at least 1.5 times as much) or at least 1-fold (i.e. at least 2 times as much) or at least 2-fold (i.e. at least 3 times as much) or at least 3-fold (i.e. at least 4 times as much) as compared to cells treated with human IgG1 in the same or substantially the same conditions (for example incubation at the same antibody concentration for 72 hours).

In some embodiments, the anti-CD38 antibody or antigen-binding fragment thereof (or variants of the same) induces the secretion of a cytokine selected from the group consisting of IL-2, TNF-α, IFN-γ, IL-10 and/or GM-CSF in CD4+ and/or CD8+ cells in an amount greater than is induced by daratumumab under the same or substantially the same conditions. In some embodiments, the anti-CD38 antibody or antigen-binding fragment thereof increases the secretion of GM-CSF as compared to a daratumumab. In such embodiments, the anti-CD38 antibody or antigen-binding fragment thereof may be, or may be derived from, for example, aCD38-a-323, aCD38-b-329, or aCD38-b-348. In some embodiments, the anti-CD38 antibody or antigen-binding fragment thereof increases the secretion of IL-2 as compared to a daratumumab, e.g. aCD38-a-323, aCD38-b-329, aCD38-a-327 or aCD38-b-348. In some embodiments, the anti-CD38 antibody or antigen-binding fragment thereof increases the secretion of IL-2, TNF-α, IFN-γ, IL-10 and GM-CSF as compared to daratumumab. In such embodiments, the anti-CD38 antibody or antigen-binding fragment thereof may be, or may be derived from, for example, aCD38-b-329, or aCD38-b-348. Cytokine secretion may be measured as provided in the Examples, for example as determined at an antibody concentration of 10 µg/ml after 72 hours incubation.

In some embodiments, the anti-CD38 antibody or antigen-binding fragment thereof (or variants of the same) induces NK cell activation. In such embodiments, the anti-CD38 antibody or antigen-binding fragment thereof may be, or may be derived from, for example, aCD38-b-348. NK cell activation can be characterised by an increase in NK cell proliferation. NK cell activation may alternatively or additionally be determined by an increase in showing intracellular IFNg production and/or as increased expression of the degranulation marker CD107a.

In some embodiments, the anti-CD38 antibody or antigen-binding fragment thereof (or variants of the same) has an inhibitory effect on CD38 NADase activity. In such embodiments, the anti-CD38 antibody or antigen-binding fragment thereof may be, or may be derived from, for example, aCD38-a-323 or aCD38-a-306. The inhibitory effect on the CD38 NADase activity can be measured as in the assays of the Examples, e.g. by measuring the conversion of E-NAD+ into 5'-eAMP in Jurkat cells. In some embodiments, the inhibitory effect on CD38 NADase activity is at least about 10% lower compared to the CD38 NADase activity in the presence of an IgG non-binding control antibody as measured by the conversion of E-NAD+ into 5'-eAMP in Jurkat cells. In some embodiments, the inhibitory effect can be at least about 15%, at least about 20% or at least about 25% lower compared to the CD38 NADase activity in the presence of an IgG non-binding control activity.

In some embodiments, the anti-CD38 antibody or antigen-binding fragment thereof (or variants of the same) reduces the CD38 NADase activity to no less than about 25% of the CD38 NADase activity in the presence of an IgG non-binding control antibody as measured by the conversion of E-NAD+ into 5'-eAMP in Jurkat cells. Preferable the antibody reduces the CD38 NADase activity to no less than about 30%, to no less than about 40% or to no less than about 50% of the CD38 NADase activity in the presence of an IgG non-binding control antibody. Preferably the antibody reduces the CD38 NADase activity to between 25%-95%, between about 30%-90% or between about 40% to 90% of the CD38 cyclase activity in the presence of an IgG non-binding control antibody This means that in the presence of the anti-CD38 antibody or antigen-binding fragment thereof, CD38 NADase activity is still present in the Jurkat cells, however at a reduced amount as compared to in the presence of an IgG non-binding control antibody.

In some embodiments, the anti-CD38 antibody or antigen-binding fragment thereof (or variants of the same) has a stimulatory effect on CD38 cyclase activity. In such embodiments, the anti-CD38 antibody or antigen-binding fragment thereof may be, or may be derived from, for example, aCD38-a-323. The stimulatory effect on the CD38 cyclase activity can be measured as in the assays of the Examples, for example by measuring the conversion of NGD+ into cGDPR in Jurkat cells. In some embodiments, the stimulatory effect on CD38 cyclase activity can be at least 10% higher compared to the CD38 cyclase activity in the presence of an IgG non-binding control antibody as measured by the conversion of NGD+ into cGDPR in Jurkat cells. In some embodiments, the stimulatory effect can be at least about 15%, at least about 20%, at least about 25% higher, at least about 50% higher, at last about 100% higher, at least about 200% higher, at least about 300% higher, at least about 400% higher compared to the CD38 cyclase in the presence of an IgG non-binding control activity. In some embodiments, the anti-CD38 antibody or antigen-binding fragment thereof, has a greater stimulatory effect on CD38 cyclase as compared to daratumumab.

In some embodiments, the anti-CD38 antibody or antigen-binding fragment thereof (or variants of the same) has an inhibitory effect on CD38 cyclase activity. In such embodiments, the anti-CD38 antibody or antigen-binding fragment thereof may be, or may be derived from, for example, aCD38-b-348, aCD38-a-306 or aCD38-a-327. The inhibitory effect on the CD38 cyclase activity can be measured as in the assays of the Examples, for example by measuring the conversion of NGD+ into cGDPR in Jurkat cells. The inhibitory effect on CD38 cyclase activity can result in CD38 activity at least 10% lower compared to the CD38 cyclase activity in the presence of an IgG non-binding control antibody as measured by the conversion of NGD+ into cGDPR in Jurkat cells. In some embodiments, the anti-CD38 antibody or antigen-binding fragment thereof, has an inhibitory effect on CD38 cyclase which is less than the inhibitory effect of daratumumab on CD38 cyclase activity in the same or substantially the same conditions. In some embodiments, the anti-CD38 antibody or antigen-binding fragment thereof reduces the CD38 cyclase activity to no less than about 25% of the CD38 cyclase activity in the presence of an IgG non-binding control antibody as measured by the conversion of NGD+ into cGDPR in Jurkat cells. Preferably the antibody reduces the CD38 cyclase activity to no less than about 30%, to no less than about 40% or to no less than about 50% of the CD38 cyclase activity in the presence of an IgG non-binding control antibody. Preferably the antibody reduces the CD38 cyclase activity to between 25%-95%, between about 30%-90% or between about 50% to 90% of the CD38 cyclase activity in the presence of an IgG non-binding control antibody. This means that in the presence of the anti-CD38 antibody or antigen-binding fragment thereof, CD38 cyclase activity is still present in the Jurkat cells, however at a reduced amount as compared to in the presence of an IgG non-binding control antibody. In such embodiments, the anti-CD38 antibody or antigen-binding fragment thereof may be, or may be derived from, for example, aCD38-b-348, aCD38-a-306 or aCD38-a-327.

In some embodiments, the anti-CD38 antibody or antigen-binding fragment thereof (or variants of the same) has an inhibitory effect on CD38 cyclase activity and an inhibitory effect on CD38 NADase activity. In such embodiments, the anti-CD38 antibody or antigen-binding fragment thereof may be, or may be derived from, for example, aCD38-a306. In some embodiments, the anti-CD38 antibody or antigen-binding fragment thereof has a stimulatory effect on CD38 cyclase activity and an inhibitory effect on CD38 NADase activity e.g. an antibody or antigen-binding fragment thereof that may be, or may be derived from, for example, aCD38-a-323.

Daratumumab has been shown to inhibit cyclase activity and stimulate NADase activity. In contrast, the antibodies of the present invention either stimulate cyclase activity, have no effect on cyclase activity, or inhibit cyclase activity to a lesser degree than daratumumab (for example cyclase activity is at least twice as high in the presence of an antibody of the invention compared to cyclase activity in the presence of daratumumab in the same or substantially the same conditions) and the antibodies of the present invention either have no effect on NADase activity or they inhibit NADase activity.

In some embodiments, provided CD38 Modulating Antibody Agents are exemplified by the antibodies having the sequence of aCD38-a-323, and more in general antibodies or agents that are or comprise one or more antigen-binding fragments or portions thereof, for example that comprise the aCD38-a-323-HCDR3 amino acid sequence (SEQ ID NO: 3) as variable heavy chain complementarity determining region 3, and/or, in some embodiments, comprise one or both of the aCD38-a-323 HCDR1 (SEQ ID NO: 1) and HCDR2 (SEQ ID NO: 2) sequences, and/or that compete with aCD38-a-323 for binding human CD38 extracellular domain.

In some embodiments, provided CD38 Modulating Antibody Agents are exemplified by the antibodies having the sequence of aCD38-a-306, and more in general antibodies or agents that are or comprise one or more antigen-binding fragments or portions thereof, for example that comprise the aCD38-a-306-HCDR3 amino acid sequence (SEQ ID NO: 11) as variable heavy chain complementarity determining region 3, and/or, in some embodiments, comprise one or both of the aCD38-a-306 HCDR1 (SEQ ID NO: 9) and HCDR2 (SEQ ID NO: 10) sequences, and/or that compete with aCD38-a-306 for binding human CD38 extracellular domain.

In some embodiments, provided CD38 Modulating Antibody Agents are exemplified by the antibodies having the sequence of aCD38-b-329, and more in general antibodies or agents that are or comprise one or more antigen-binding fragments or portions thereof, for example that comprise the aCD38-b-329-HCDR3 (SEQ ID NO: 19) amino acid sequence as variable heavy chain complementarity determining region 3, and/or, in some embodiments, comprise one or both of the aCD38-b-329 HCDR1 (SEQ ID NO: 17) and HCDR2 (SEQ ID NO: 18) sequences, and/or that compete with aCD38-b-329 for binding human CD38 extracellular domain.

In some embodiments, provided CD38 Modulating Antibody Agents are exemplified by the antibodies having the sequence of aCD38-b-348, and more in general antibodies or agents that are or comprise one or more antigen-binding fragments or portions thereof, for example that comprise the aCD38-b-348-HCDR3 amino acid sequence (SEQ ID NO: 27) as variable heavy chain complementarity determining region 3, and/or, in some embodiments, comprise one or both of the aCD38-b-348 HCDR1 (SEQ ID NO: 25) and HCDR2 (SEQ ID NO: 26) sequences, and/or that compete with aCD38-b-348 for binding human CD38 extracellular domain.

In some embodiments, provided CD38 Modulating Antibody Agents are exemplified by the antibodies having the sequence of aCD38-a-327, and more in general antibodies or agents that are or comprise one or more antigen-binding fragments or portions thereof, for example that comprise the aCD38-a-327-HCDR3 amino acid sequence (SEQ ID NO: 35) as variable heavy chain complementarity determining region 3, and/or, in some embodiments, comprise one or both of the aCD38-a-327 HCDR1 (SEQ ID NO: 33) and HCDR2 (SEQ ID NO: 34) sequences, and/or that compete with aCD38-a-327 for binding human CD38 extracellular domain.

In some embodiments, provided antibodies or antigen-binding fragments thereof bind to human CD38 with a Kd of in the $10^{-8}$M range, or below (for example in the $10^{-9}$M range, $10^{-10}$M range, $10^{-11}$M range, or below). In some embodiments, the Kd is from $10^{-11}$M to $10^{-8}$M. The Kd to evaluate the binding affinity of the antibodies or antigen binding fragments thereof can be obtained by standard methodologies including surface plasmon resonance (SPR) such as Biacore analysis or analysis using Forte Bio Octet Systems.

In some embodiments, CD38 Modulating Antibody Agents (e.g. antibodies or antigen-binding fragments thereof) are provided that bind to an epitope on human CD38 that is bound by aCD38-a-323, aCD38-a-306, aCD38-b-329, aCD38-a-327, or aCD38-b-348. In some embodiments, such provided CD38 Modulating Antibody Agents may bind to human CD38 extracellular domain. In some embodiments, provided CD38 Modulating Antibody Agents may bind to an epitope of CD38 (e.g., when assessed using one or more assays as described herein or otherwise known in the art). In some embodiments, provided antibodies or antigen-binding fragments thereof may bind to human and Cynomolgus Monkey CD38 (e.g., to an extracellular epitope on human and Cynomolgus Monkey CD38) with Kd value in the $10^{-8}$M range or below (for example in the $10^{-9}$M range or below).

In some embodiments, provided antibodies or antigen-binding fragments thereof do bind to a mutant human CD38

(as compared to non-mutant human CD38 (SEQ ID NO:47)), wherein in the mutant human CD38, the serine residue in position 274 has been substituted with a phenylalanine. In such embodiments, the anti-CD38 antibody or antigen-binding fragment thereof may be, or may be derived from, for example, aCD38-a-327, aCD38-b-329, aCD38-b-348 or aCD38-a-323.

In some embodiments, provided antibodies or antigen-binding fragments thereof do bind to a mutant human CD38 (as compared to non-mutant human CD38 (SEQ ID NO: 47)), wherein in the mutant human CD38, the aspartate residue in position 202 has been substituted with a glycine residue. In such embodiments, the anti-CD38 antibody or antigen-binding fragment thereof may be, or may be derived from, for example, aCD38-a-327, aCD38-b-329, aCD38-b-348, aCD38-a-323, or aCD38-a-306.

In some embodiments, provided antibodies or antigen-binding fragments thereof do bind to a mutant human CD38 (as compared to non-mutant human CD38 (SEQ ID NO: 47)), wherein in the mutant human CD38, the serine residue in position 274 has been substituted with a phenylalanine and the aspartate residue in position 202 has been substituted with a glycine residue. In such embodiments, the anti-CD38 antibody or antigen-binding fragment thereof may be, or may be derived from, for example, aCD38-a-327, aCD38-b-329, aCD38-b-348 or aCD38-a-323.

In some embodiments, provided antibodies or antigen-binding fragments thereof do not bind to a mutant human CD38 or binds with a reduced affinity to a mutant human CD38 (as compared to non-mutant human CD38 (SEQ ID NO: 47)), wherein in the mutant human CD38, the serine residue in position 274 has been substituted with a phenylalanine, and do bind to a mutant human CD38 wherein in the mutant human CD38, the aspartate residue in position 202 has been substituted with a glycine residue. In such embodiments, the anti-CD38 antibody or antigen-binding fragment thereof may be, or may be derived from, for example, aCD38-a-306.

Among other things, the present disclosure provides a procedure (FIG. 1) that can be utilized to identify and/or characterize particularly useful CD38 Modulating Antibody Agents (e.g., anti CD38 antibodies or antigen-binding fragments thereof) as described herein (e.g., anti-CD38 antibodies or antigen-binding fragments thereof characterized by certain structural and/or functional features, such as specific binding to human CD38 (e.g., to an extracellular epitope thereof), inclusion of one or more CDR sequence elements as described herein (and particularly inclusion of an HCDR3 sequence element, optionally in combination with HCDR1 and/or HCDR2 elements), cell activating activity as described herein, cytotoxic activity as described herein (e.g., with respect to immune regulatory cells with relatively high levels of CD38 on their surfaces), and combinations thereof). In some embodiments, particularly useful anti-CD38 antibodies as described herein are characterized by a plurality of such features. In some embodiments, one or more antibodies described herein may be characterized as a CD38 Modulating Antibody Agent.

Thus, as exemplified herein, certain antibodies and/or antigen-binding fragments comprising aCD38-a-323 sequences (in particular aCD38-a-323-HCDR3 (SEQ ID NO: 3) and/or aCD38-a-323-LCDR3 (SEQ ID NO: 7)), CD38-a-306 sequences (in particular aCD38-a-306-HCDR3 (SEQ ID NO: 11) and/or aCD38-a-306-LCDR3 (SEQ ID NO: 15)), aCD38-b-329 sequences (in particular aCD38-b-329-HCDR3 (SEQ ID NO: 19) and/or aCD38-b-329-LCDR3 (SEQ ID NO: 23)), aCD38-a-327 sequences (in particular aCD38-a-327-HCDR3 (SEQ ID NO: 35) and/or aCD38-a-327-LCDR3 (SEQ ID NO: 39), or aCD38-b-348 sequences (in particular aCD38-b-348-HCDR3 (SEQ ID NO: 27) and/or aCD38-b-348-LCDR3 (SEQ ID NO: 31)), are characterized by such desirable structural and/or functional features; such antibodies and/or antigen-binding fragments thereof (and variants of the same) may be referred to herein as CD38 Modulating Antibody Agents. Additionally, in accordance with the present disclosure, antibodies and antigen-binding fragments thereof compete with aCD38-a-323, aCD38-a-306, aCD38-b-329, aCD38-a-327 or aCD38-b-348 may be particularly useful antibodies; such antibodies and/or antigen-binding fragments thereof may also be referred to herein as CD38 Modulating Antibody Agents.

Antibodies (and/or antigen-binding fragments thereof) described herein may be particularly useful in medicine (e.g., in therapy and/or in prophylaxis, for example in the treatment of cancer), and/or for use with respect to methods that require or involve targeting an epitope within human CD38 extracellular domain such as the one identified as aCD38-b-ep, as for aCD38-b-348 and aCD38-b-329, or aCD38ep-a and aCD38ep-b, as for CD38-a-327, within human CD38 extracellular domain. Provided antibodies or antigen-binding fragments thereof may be prepared as presenting the most appropriate isotype, in particular human isotype from the group consisting of IgG1, IgG2, IgG3, and IgG4 isotype antibodies, more particularly human IgG1.

In one aspect, the present invention provides aCD38-a-323-HCDR3 amino acid sequence and polypeptides that include it, such as, for example, antibodies or antigen-binding fragments comprising the aCD38-a-323-HCDR3 amino acid sequence (SEQ ID NO: 3) as variable heavy chain complementarity determining region 3. In some embodiments, such antibody or antigen-binding fragment may be further characterized by comprising further aCD38-a-323 amino acid sequence elements such as:

a) aCD38-a-323-HCDR1 amino acid sequence (SEQ ID NO: 1) as variable heavy chain complementarity determining region 1; and/or
b) aCD38-a-323-HCDR2 amino acid sequence (SEQ ID NO: 2) as variable heavy chain complementarity determining region 2.

In some embodiments, provided antibodies or antigen-binding fragments thereof may comprise variable heavy chain complementarity determining regions defined above (i.e. aCD38-a-323 amino acid sequence elements) further in the correct order, specifically separated by antibody frame sequences, such as the one included in aCD38-a-323-HCDR123 amino acid sequence (SEQ ID NO: 4), in particular for exerting correctly their binding and functional properties. For example, in some embodiments, a provided antibody or antigen-binding fragment thereof can comprise aCD38-a-323-HCDR123 amino acid sequence (SEQ ID NO: 4, or the HCDR1, HCDR2 and HCDR3 sequences thereof) and, optionally:

a) aCD38-a-323-LCDR1 amino acid sequence (SEQ ID NO: 5) as variable light chain complementarity determining region 1;
b) aCD38-a-323-LCDR2 amino acid sequence (SEQ ID NO: 6) as variable light chain complementarity determining region 2; and
c) aCD38-a-323-LCDR3 amino acid sequence (SEQ ID NO: 7) as variable light chain complementarity determining region 3.

Thus, in some embodiments, the present invention provides an isolated antibody or antigen-binding fragments thereof comprising a variable heavy chain comprising aCD38-a-323-HCDR123 amino acid sequence (SEQ ID NO: 4). Preferably, such isolated antibody or antigen-binding fragments thereof further comprises a variable light chain comprising aCD38-a-323-LCDR123 amino acid sequence (SEQ ID NO: 8), as described in the Examples.

In some embodiments the present invention provides an isolated antibody or antigen-binding fragments thereof comprising a variable heavy chain comprising the sequence:

(SEQ ID NO: 72)
GSISSGSYYWSWIRQHPGKGLEWIGYIYYSGSTYYNPSLKSRVTISVDTS

KNQFSLKLSSVTAADTAVYYCARGSPYRWYNYYYMDV and/or the variable light chain comprising the sequence (SEQ ID NO: 73)
RASQSISSWLAWYQQKPGKAPKLLIYDASSLESGVPSRFSGSGSGTEFTL

TISSLQPDDFATYYCQQHRSYPPT.

In some embodiments the variable heavy chain sequence of aCD38-a-323 comprises the sequence:

(SEQ ID NO: 48)
QVQLQESGPGLVKPSQTLSLTCTVSGGSISSGSYYWSWIRQHPGKGLEWI

GYIYYSGSTYYNPSLKSRVTISVDTSKNQFSLKLSSVTAADTAVYYCARG

SPYRWYNYYYMDVWGKGTTVTVSS and the variable light chain sequence of aCD38-a-323 comprises the sequence:

(SEQ ID NO: 49)
DIQMTQSPSTLSASVGDRVTITCRASQSISSWLAWYQQKPGKAPKLLIYD

ASSLESGVPSRFSGSGSGTEFTLTISSLQPDDFATYYCQQHRSYPPTFGG

GTKVEIK.

The present invention also provides an antibody or antigen-binding fragment thereof comprising the sequence of aCD38-a-323-HCDR3 as an HCDR3 and the sequence of aCD38-a-323-LCDR3 as an LCDR3.

The present invention also provides variant antibodies and antigen binding fragments thereof that have certain % identities relative to a reference sequence, such as a CDR sequence or a heavy or light chain variable sequence of aCD38-a-323. Such antibodies and antigen binding fragments thereof may also be referred to herein as CD38 Modulating Antibody Agents.

For example, in some embodiments the anti-CD38 antibody or antigen binding fragment thereof comprises a variable heavy chain sequence comprising an amino acid sequence having at least 90% sequence identity to SEQ ID NO: 48. In some embodiments the anti-CD38 antibody or antigen binding fragment thereof comprises a variable heavy chain sequence comprising an amino acid sequence having at least 95% sequence identity to SEQ ID NO: 48. In some embodiments the anti-CD38 antibody or antigen binding fragment thereof comprises a variable heavy chain sequence comprising an amino acid sequence having at least 98% sequence identity to SEQ ID NO: 48. In some embodiments the anti-CD38 antibody or antigen binding fragment thereof comprises a variable heavy chain sequence comprising the amino acid sequence of SEQ ID NO: 48.

In some embodiments the anti-CD38 antibody or antigen binding fragment thereof comprises a variable light chain sequence comprising an amino acid sequence having at least 90% sequence identity to SEQ ID NO: 49. In some embodiments the anti-CD38 antibody or antigen binding fragment thereof comprises a variable light chain sequence comprising an amino acid sequence having at least 95% sequence identity to SEQ ID NO: 49. In some embodiments the anti-CD38 antibody or antigen binding fragment thereof comprises a variable light chain sequence comprising an amino acid sequence having at least 98% sequence identity to SEQ ID NO: 49. In some embodiments the anti-CD38 antibody or antigen binding fragment thereof comprises a variable light chain sequence comprising the amino acid sequence of SEQ ID NO: 49.

In some embodiments the anti-CD38 antibody or antigen binding fragment thereof comprises a variable heavy chain sequence comprising an amino acid sequence having at least 90% sequence identity to SEQ ID NO: 48 and a variable light chain sequence comprising an amino acid sequence having at least 90% sequence identity to SEQ ID NO: 49. In some embodiments the anti-CD38 antibody or antigen binding fragment thereof comprises a variable heavy chain sequence comprising an amino acid sequence having at least 95% sequence identity to SEQ ID NO: 48 and a variable light chain sequence comprising an amino acid sequence having at least 95% sequence identity to SEQ ID NO: 49. In some embodiments the anti-CD38 antibody or antigen binding fragment thereof comprises a variable heavy chain sequence comprising an amino acid sequence having at least 98% sequence identity to SEQ ID NO: 48 and a variable light chain sequence comprising an amino acid sequence having at least 98% sequence identity to SEQ ID NO: 49. In some embodiments the anti-CD38 antibody or antigen binding fragment thereof comprises a variable heavy chain sequence comprising the amino acid sequence of SEQ ID NO: 48 and a variable light chain sequence comprising the amino acid sequence of SEQ ID NO: 49.

In some embodiments the anti-CD38 antibody or antigen binding fragment thereof comprises a variable heavy chain sequence comprising an amino acid sequence having at least 90% sequence identity to SEQ ID NO: 72. In some embodiments the anti-CD38 antibody or antigen binding fragment thereof comprises a variable heavy chain sequence comprising an amino acid sequence having at least 95% sequence identity to SEQ ID NO: 72. In some embodiments the anti-CD38 antibody or antigen binding fragment thereof comprises a variable heavy chain sequence comprising an amino acid sequence having at least 98% sequence identity to SEQ ID NO: 72. In some embodiments the anti-CD38 antibody or antigen binding fragment thereof comprises a variable heavy chain sequence comprising the amino acid sequence of SEQ ID NO: 72.

In some embodiments the anti-CD38 antibody or antigen binding fragment thereof comprises a variable light chain sequence comprising an amino acid sequence having at least 90% sequence identity to SEQ ID NO: 73. In some embodiments the anti-CD38 antibody or antigen binding fragment thereof comprises a variable light chain sequence comprising an amino acid sequence having at least 95% sequence identity to SEQ ID NO: 73. In some embodiments the anti-CD38 antibody or antigen binding fragment thereof comprises a variable light chain sequence comprising an amino acid sequence having at least 98% sequence identity to SEQ ID NO: 73. In some embodiments the anti-CD38 antibody or antigen binding fragment thereof comprises a variable light chain sequence comprising the amino acid sequence of SEQ ID NO: 73.

In some embodiments the anti-CD38 antibody or antigen binding fragment thereof comprises a variable heavy chain sequence comprising an amino acid sequence having at least 90% sequence identity to SEQ ID NO: 72 and a variable light chain sequence comprising an amino acid sequence having at least 90% sequence identity to SEQ ID NO: 73. In some embodiments the anti-CD38 antibody or antigen binding fragment thereof comprises a variable heavy chain sequence comprising an amino acid sequence having at least 95% sequence identity to SEQ ID NO: 72 and a variable light chain sequence comprising an amino acid sequence having at least 95% sequence identity to SEQ ID NO: 73. In some embodiments the anti-CD38 antibody or antigen binding fragment thereof comprises a variable heavy chain sequence comprising an amino acid sequence having at least 98% sequence identity to SEQ ID NO:72 and a variable light chain sequence comprising an amino acid sequence having at least 98% sequence identity to SEQ ID NO: 73. In some embodiments the anti-CD38 antibody or antigen binding fragment thereof comprises a variable heavy chain sequence comprising the amino acid sequence of SEQ ID NO: 72 and a variable light chain sequence comprising the amino acid sequence of SEQ ID NO: 73.

In some embodiments the anti-CD38 antibody or antigen binding fragment thereof comprises a variable heavy chain sequence comprising an amino acid sequence having at least 90% sequence identity to SEQ ID NO: 4. In some embodiments the anti-CD38 antibody or antigen binding fragment thereof comprises a variable heavy chain sequence comprising an amino acid sequence having at least 95% sequence identity to SEQ ID NO: 4. In some embodiments the anti-CD38 antibody or antigen binding fragment thereof comprises a variable heavy chain sequence comprising an amino acid sequence having at least 98% sequence identity to SEQ ID NO: 4. In some embodiments the anti-CD38 antibody or antigen binding fragment thereof comprises a variable heavy chain sequence comprising the amino acid sequence of SEQ ID NO: 4.

In some embodiments the anti-CD38 antibody or antigen binding fragment thereof comprises a variable light chain sequence comprising an amino acid sequence having at least 90% sequence identity to SEQ ID NO: 8. In some embodiments the anti-CD38 antibody or antigen binding fragment thereof comprises a variable light chain sequence comprising an amino acid sequence having at least 95% sequence identity to SEQ ID NO: 8. In some embodiments the anti-CD38 antibody or antigen binding fragment thereof comprises a variable light chain sequence comprising an amino acid sequence having at least 98% sequence identity to SEQ ID NO: 8. In some embodiments the anti-CD38 antibody or antigen binding fragment thereof comprises a variable light chain sequence comprising the amino acid sequence of SEQ ID NO: 8.

In some embodiments the anti-CD38 antibody or antigen binding fragment thereof comprises a variable heavy chain sequence comprising an amino acid sequence having at least 90% sequence identity to SEQ ID NO: 4 and a variable light chain sequence comprising an amino acid sequence having at least 90% sequence identity to SEQ ID NO: 8. In some embodiments the anti-CD38 antibody or antigen binding fragment thereof comprises a variable heavy chain sequence comprising an amino acid sequence having at least 95% sequence identity to SEQ ID NO: 4 and a variable light chain sequence comprising an amino acid sequence having at least 95% sequence identity to SEQ ID NO: 8. In some embodiments the anti-CD38 antibody or antigen binding fragment thereof comprises a variable heavy chain sequence comprising an amino acid sequence having at least 98% sequence identity to SEQ ID NO: 4 and a variable light chain sequence comprising an amino acid sequence having at least 98% sequence identity to SEQ ID NO: 8. In some embodiments the anti-CD38 antibody or antigen binding fragment thereof comprises a variable heavy chain sequence comprising the amino acid sequence of SEQ ID NO: 4 and a variable light chain sequence comprising the amino acid sequence of SEQ ID NO: 8.

Such variant antibodies and antigen binding fragments thereof may retain or exhibit the same (or substantially the same) functional and pharmacological properties as described for the antibodies and antigen binding fragments thereof having the heavy and light chain variable sequences disclosed herein for aCD38-a-323.

Moreover, aCD38-a-323 amino acid sequences also refer to antibody sequences that are defined by the number of substitution with respect to the aCD38-a-323 amino acid sequence elements defined above. For example, such sequence may comprise, as variable heavy chain complementarity determining region 3 (HCDR3) a sequence containing up to 1, 2, 3, or 4, amino acid substitutions within aCD38-a-323-HCDR3. In a further embodiment, aCD38-a-323 amino acid sequences also refer to antibody sequences comprising, as variable heavy chain complementarity determining regions 1, 2 and 3 (HCDR1, HCDR2, and HCDR3) a sequence containing up to 1, 2, 3, 4, 5, 6, 7, 8, 9, or 10 amino acid substitutions within aCD38-a-323-HCDR1, aCD38-a-323-HCDR2, and aCD38-a-323-HCDR3, and more preferably a sequence containing up to 1, 2, 3, 4, 5, 6, 7, 8, 9, or 10 amino acid substitutions within aCD38-a-323-HCDR123 (SEQ ID NO: 4), or within SEQ ID NO: 48 or SEQ ID NO: 72. In some embodiments aCD38-a-323 amino acid sequences also refer to antibody sequences comprising as a variable heavy chain sequence a sequence containing up to 1, 2, 3, 4, 5, 6, 7, 8, 9, 10 amino acid substitutions within the framework regions of the variable heavy chain sequence. The antibodies presenting such aCD38-a-323 amino acid sequence elements and such substitutions can still present the binding and/or functional properties of aCD38-a-323, and of a CD38 Modulating Antibody Agent in general.

Such aCD38-a-323 amino acid sequences may also comprise, as variable light chain complementarity determining region 3 (LCDR3) a sequence containing up to 1, 2, 3, 4, amino acid substitutions within aCD38-a-323-LCDR3. In a further embodiment, aCD38-a-323 amino acid sequences also refer to antibody sequences comprising, as variable light chain complementarity determining regions 1, 2 and 3 (LCDR1, LCDR2, and LCDR3) a sequence containing up to 1, 2, 3, 4, 5, 6, 7, 8, 9, or 10 amino acid substitutions within aCD38-a-323-LCDR1, aCD38-a-323-LCDR2, and aCD38-a-323-LCDR3, and more preferably a sequence containing up to 1, 2, 3, 4, 5, 6, 7, 8, 9, or 10 amino acid substitutions within aCD38-a-323-LCDR123 (SEQ ID NO: 8) or within SEQ ID NO: 49 or SEQ ID NO: 73. In some embodiments aCD38-a-323 amino acid sequences also refer to antibody sequences comprising as a variable light chain sequence a sequence containing up to 1, 2, 3, 4, 5, 6, 7, 8, 9, or 10 amino acid substitutions within the framework regions of the variable light chain sequence. The antibodies presenting such aCD38-a-323 amino acid sequence elements and such substitutions can still present the binding and/or functional properties of aCD38-a-323, and of a CD38 Modulating Antibody Agent in general.

Accordingly, in one embodiment, the present invention provides an anti-CD38 Antibody Agent (i.e. an antibody or antigen-binding fragment thereof, and variants thereof as described herein, such as variants mutated to remove the DG motif) comprising:
  a. the variable heavy chain region sequence of aCD38-a-323 (or a variant thereof, such as an affinity matured variant thereof) or a variable heavy chain region sequence having up to 5 amino acid substitutions compared to the variable heavy chain region sequence of aCD38-a-323 (or a variant thereof, such as an affinity matured variant thereof); and/or
  b. the variable light chain region sequence of aCD38-a-323 (or a variant thereof, such as an affinity matured variant thereof) or a variable light chain region sequence having up to 5 amino acid substitutions compared to the variable light chain region sequence of aCD38-a-323 (or a variant thereof, such as an affinity matured variant thereof).

The aCD38-a-323 heavy chains that may incorporate amino acid substitutions include SEQ ID NOs 4, 48 and 72. The aCD38-a-323 light chains that may incorporate amino acid substitutions include SEQ ID NOs 8, 49 and 73.

The amino acid substitutions preferably do not adversely effect, or not substantially adversely effect, the functional properties of the antibodies. The substitutions may therefore be considered conservative amino acid substitutions. Preferably, when amino acid substitutions do occur, they occur in a ratio of 1:1, such that the total length of the heavy and/or light chain variable region does not change.

In one aspect, the present invention provides aCD38-a-306-HCDR3 amino acid sequence and polypeptides that include it, such as, for example, antibodies or antigen-binding fragments comprising the aCD38-a-306-HCDR3 amino acid sequence (SEQ ID NO: 11) as variable heavy chain complementarity determining region 3. In some embodiments, such antibody or antigen-binding fragment may be further characterized by comprising further aCD38-a-306 amino acid sequence elements such as:
a) aCD38-a-306-HCDR1 amino acid sequence (SEQ ID NO: 9) as variable heavy chain complementarity determining region 1; and/or
b) aCD38-a-306-HCDR2 amino acid sequence (SEQ ID NO: 10) as variable heavy chain complementarity determining region 2.

In some embodiments, provided antibodies or antigen-binding fragments thereof may comprise variable heavy chain complementarity determining regions defined above (i.e. aCD38-a-306 amino acid sequence elements) further in the correct order, specifically separated by antibody frame sequences, such as the one included in aCD38-a-306-HCDR123 amino acid sequence (SEQ ID NO: 12), in particular for exerting correctly their binding and functional properties. For example, in some embodiments, a provided antibody or antigen-binding fragment thereof can comprise aCD38-a-306-HCDR123 amino acid sequence (SEQ ID NO: 12, or the HCDR1, HCDR2 and HCDR3 sequences thereof) and, optionally:
a) aCD38-a-306-LCDR1 amino acid sequence (SEQ ID NO: 13) as variable light chain complementarity determining region 1;
b) aCD38-a-306-LCDR2 amino acid sequence (SEQ ID NO: 14) as variable light chain complementarity determining region 2; and
c) aCD38-a-306-LCDR3 amino acid sequence (SEQ ID NO: 15) as variable light chain complementarity determining region 3.

Thus, in some embodiments, the present invention provides an isolated antibody or antigen-binding fragments thereof comprising a variable heavy chain comprising aCD38-a-306-HCDR123 amino acid sequence (SEQ ID NO: 12). Preferably, such isolated antibody or antigen-binding fragments thereof further comprises a variable light chain comprising aCD38-a-306-LCDR123 amino acid sequence (SEQ ID NO: 16), as described in the Examples.

In some embodiments the present invention provides an isolated antibody or antigen-binding fragments thereof comprising a variable heavy chain comprising the sequence:

(SEQ ID NO: 74)
YTFTGYYMHWVRQAPGQGLEWMGWINPNSGGTNYAQKFQGRVTMTRDTSI

STAYMELSRLRSDDTAVYYCARDQAHQRSSYD and/or the variable light chain comprising the sequence:

(SEQ ID NO: 75)
RASQSISSYLNWYQQKPGKAPKLLIYGASSLQSGVPSRFSGSGSGTDFTL

TISSLQPEDFATYYCQQRSSTPIT.

In some embodiments the variable heavy chain sequence of aCD38-a-306 comprises the sequence:

(SEQ ID NO: 50)
QVQLVQSGAEVKKPGASVKVSCKASGYTFTGYYMHWVRQAPGQGLEWMGW

INPNSGGTNYAQKFQGRVTMTRDTSISTAYMELSRLRSDDTAVYYCARDQ

AHQRSSYDWGQGTLVTVSS and the variable light chain sequence of aCD38-a-306 comprises the sequence:

(SEQ ID NO: 51)
DIQMTQSPSSLSASVGDRVTITCRASQSISSYLNWYQQKPGKAPKLLIYG

ASSLQSGVPSRFSGSGSGTDFTLTISSLQPEDFATYYCQQRSSTPITFGG

GTKVEIK.

The present invention also provides an antibody or antigen-binding fragment thereof comprising the sequence of aCD38-a-306-HCDR3 as an HCDR3 and the sequence of aCD38-a-306-LCDR3 as an LCDR3.

The present invention also provides variant antibodies and antigen binding fragments thereof that have certain % identities relative to a reference sequence, such as a CDR sequence or a heavy or light chain variable sequence of aCD38-a-306. Such antibodies and antigen binding fragments thereof may also be referred to herein as CD38 Modulating Antibody Agents.

For example, in some embodiments the anti-CD38 antibody or antigen binding fragment thereof comprises a variable heavy chain sequence comprising an amino acid sequence having at least 90% sequence identity to SEQ ID NO: 50. In some embodiments the anti-CD38 antibody or antigen binding fragment thereof comprises a variable heavy chain sequence comprising an amino acid sequence having at least 95% sequence identity to SEQ ID NO: 50. In some embodiments the anti-CD38 antibody or antigen binding fragment thereof comprises a variable heavy chain sequence comprising an amino acid sequence having at least 98% sequence identity to SEQ ID NO: 50. In some embodiments the anti-CD38 antibody or antigen binding fragment thereof comprises a variable heavy chain sequence comprising the amino acid sequence of SEQ ID NO: 50.

In some embodiments the anti-CD38 antibody or antigen binding fragment thereof comprises a variable light chain sequence comprising an amino acid sequence having at least 90% sequence identity to SEQ ID NO: 51. In some embodiments the anti-CD38 antibody or antigen binding fragment thereof comprises a variable light chain sequence comprising an amino acid sequence having at least 95% sequence identity to SEQ ID NO: 51. In some embodiments the anti-CD38 antibody or antigen binding fragment thereof comprises a variable light chain sequence comprising an amino acid sequence having at least 98% sequence identity to SEQ ID NO: 51. In some embodiments the anti-CD38 antibody or antigen binding fragment thereof comprises a variable light chain sequence comprising the amino acid sequence of SEQ ID NO: 51.

In some embodiments the anti-CD38 antibody or antigen binding fragment thereof comprises a variable heavy chain sequence comprising an amino acid sequence having at least 90% sequence identity to SEQ ID NO: 50 and a variable light chain sequence comprising an amino acid sequence having at least 90% sequence identity to SEQ ID NO: 51. In some embodiments the anti-CD38 antibody or antigen binding fragment thereof comprises a variable heavy chain sequence comprising an amino acid sequence having at least 95% sequence identity to SEQ ID NO: 50 and a variable light chain sequence comprising an amino acid sequence having at least 95% sequence identity to SEQ ID NO: 51. In some embodiments the anti-CD38 antibody or antigen binding fragment thereof comprises a variable heavy chain sequence comprising an amino acid sequence having at least 98% sequence identity to SEQ ID NO: 50 and a variable light chain sequence comprising an amino acid sequence having at least 98% sequence identity to SEQ ID NO: 51. In some embodiments the anti-CD38 antibody or antigen binding fragment thereof comprises a variable heavy chain sequence comprising the amino acid sequence of SEQ ID NO: 50 and a variable light chain sequence comprising the amino acid sequence of SEQ ID NO: 51.

In some embodiments the anti-CD38 antibody or antigen binding fragment thereof comprises a variable heavy chain sequence comprising an amino acid sequence having at least 90% sequence identity to SEQ ID NO: 74. In some embodiments the anti-CD38 antibody or antigen binding fragment thereof comprises a variable heavy chain sequence comprising an amino acid sequence having at least 95% sequence identity to SEQ ID NO: 74. In some embodiments the anti-CD38 antibody or antigen binding fragment thereof comprises a variable heavy chain sequence comprising an amino acid sequence having at least 98% sequence identity to SEQ ID NO: 74. In some embodiments the anti-CD38 antibody or antigen binding fragment thereof comprises a variable heavy chain sequence comprising the amino acid sequence of SEQ ID NO: 74.

In some embodiments the anti-CD38 antibody or antigen binding fragment thereof comprises a variable light chain sequence comprising an amino acid sequence having at least 90% sequence identity to SEQ ID NO: 75. In some embodiments the anti-CD38 antibody or antigen binding fragment thereof comprises a variable light chain sequence comprising an amino acid sequence having at least 95% sequence identity to SEQ ID NO: 75. In some embodiments the anti-CD38 antibody or antigen binding fragment thereof comprises a variable light chain sequence comprising an amino acid sequence having at least 98% sequence identity to SEQ ID NO: 75. In some embodiments the anti-CD38 antibody or antigen binding fragment thereof comprises a variable light chain sequence comprising the amino acid sequence of SEQ ID NO: 75.

In some embodiments the anti-CD38 antibody or antigen binding fragment thereof comprises a variable heavy chain sequence comprising an amino acid sequence having at least 90% sequence identity to SEQ ID NO: 74 and a variable light chain sequence comprising an amino acid sequence having at least 90% sequence identity to SEQ ID NO: 75. In some embodiments the anti-CD38 antibody or antigen binding fragment thereof comprises a variable heavy chain sequence comprising an amino acid sequence having at least 95% sequence identity to SEQ ID NO: 74 and a variable light chain sequence comprising an amino acid sequence having at least 95% sequence identity to SEQ ID NO: 75. In some embodiments the anti-CD38 antibody or antigen binding fragment thereof comprises a variable heavy chain sequence comprising an amino acid sequence having at least 98% sequence identity to SEQ ID NO:74 and a variable light chain sequence comprising an amino acid sequence having at least 98% sequence identity to SEQ ID NO: 75. In some embodiments the anti-CD38 antibody or antigen binding fragment thereof comprises a variable heavy chain sequence comprising the amino acid sequence of SEQ ID NO: 74 and a variable light chain sequence comprising the amino acid sequence of SEQ ID NO: 75.

In some embodiments the anti-CD38 antibody or antigen binding fragment thereof comprises a variable heavy chain sequence comprising an amino acid sequence having at least 90% sequence identity to SEQ ID NO: 12. In some embodiments the anti-CD38 antibody or antigen binding fragment thereof comprises a variable heavy chain sequence comprising an amino acid sequence having at least 95% sequence identity to SEQ ID NO: 12. In some embodiments the anti-CD38 antibody or antigen binding fragment thereof comprises a variable heavy chain sequence comprising an amino acid sequence having at least 98% sequence identity to SEQ ID NO: 12. In some embodiments the anti-CD38 antibody or antigen binding fragment thereof comprises a variable heavy chain sequence comprising the amino acid sequence of SEQ ID NO: 12.

In some embodiments the anti-CD38 antibody or antigen binding fragment thereof comprises a variable light chain sequence comprising an amino acid sequence having at least 90% sequence identity to SEQ ID NO: 16. In some embodiments the anti-CD38 antibody or antigen binding fragment thereof comprises a variable light chain sequence comprising an amino acid sequence having at least 95% sequence identity to SEQ ID NO: 16. In some embodiments the anti-CD38 antibody or antigen binding fragment thereof comprises a variable light chain sequence comprising an amino acid sequence having at least 98% sequence identity to SEQ ID NO: 16. In some embodiments the anti-CD38 antibody or antigen binding fragment thereof comprises a variable light chain sequence comprising the amino acid sequence of SEQ ID NO: 16.

In some embodiments the anti-CD38 antibody or antigen binding fragment thereof comprises a variable heavy chain sequence comprising an amino acid sequence having at least 90% sequence identity to SEQ ID NO: 12 and a variable light chain sequence comprising an amino acid sequence having at least 90% sequence identity to SEQ ID NO: 16. In some embodiments the anti-CD38 antibody or antigen binding fragment thereof comprises a variable heavy chain sequence comprising an amino acid sequence having at least 95% sequence identity to SEQ ID NO: 12 and a variable light chain sequence comprising an amino acid sequence having at least 95% sequence identity to SEQ ID NO: 16. In some embodiments the anti-CD38 antibody or antigen binding fragment thereof comprises a variable heavy chain sequence comprising an amino acid sequence having at least 98% sequence identity to SEQ ID NO: 12 and a variable light chain sequence comprising an amino acid sequence having at least 98% sequence identity to SEQ ID NO: 16. In some embodiments the anti-CD38 antibody or antigen binding fragment thereof comprises a variable heavy chain sequence comprising the amino acid sequence of SEQ ID NO: 12 and a variable light chain sequence comprising the amino acid sequence of SEQ ID NO: 16.

Such variant antibodies and antigen binding fragments thereof may retain or exhibit the same (or substantially the same) functional and pharmacological properties as described for the antibodies and antigen binding fragments thereof having the heavy and light chain variable sequences disclosed herein for aCD38-a-306.

Moreover, aCD38-a-306 amino acid sequences also refer to antibody sequences that are defined by the number of substitution with respect to the aCD38-a-306 amino acid sequence elements defined above. For example, such sequence may comprise, as variable heavy chain complementarity determining region 3 (HCDR3) a sequence containing up to 1, 2, 3, or 4 amino acid substitutions within aCD38-a-306-HCDR3. In a further embodiment, aCD38-a-306 amino acid sequences also refer to antibody sequences comprising, as variable heavy chain complementarity determining regions 1, 2 and 3 (HCDR1, HCDR2, and HCDR3) a sequence containing up to 1, 2, 3, 4, 5, 6, 7, 8, 9, or 10 amino acid substitutions within aCD38-a-306-HCDR1, aCD38-a-306-HCDR2, and aCD38-a-306-HCDR3, and more preferably a sequence containing up to 1, 2, 3, 4, 5, 6, 7, 8, 9, or 10 amino acid substitutions within aCD38-a-306-HCDR123 (SEQ ID NO: 12), or within SEQ ID NO: 50 or SEQ ID NO: 74. In some embodiments aCD38-a-306 amino acid sequences also refer to antibody sequences comprising as a variable heavy chain sequence a sequence containing up to 1, 2, 3, 4, 5, 6, 7, 8, 9, or 10 amino acid substitutions within the framework regions of the variable heavy chain sequence. The antibodies presenting such aCD38-a-306 amino acid sequence elements and such substitutions can still present the binding and/or functional properties of aCD38-a-306, and of a CD38 Modulating Antibody Agent in general.

Such aCD38-a-306 amino acid sequences may also comprise, as variable light chain complementarity determining region 3 (LCDR3) a sequence containing up to 1, 2, 3, 4, amino acid substitutions within aCD38-a-306-LCDR3. In a further embodiment, aCD38-a-306 amino acid sequences also refer to antibody sequences comprising, as variable light chain complementarity determining regions 1, 2 and 3 (LCDR1, LCDR2, and LCDR3) a sequence containing up to 1, 2, 3, 4, 5, 6, 7, 8, 9, or 10 amino acid substitutions within aCD38-a-306-LCDR1, aCD38-a-306-LCDR2, and aCD38-a-306-LCDR3, and more preferably a sequence containing up to 1, 2, 3, 4, 5, 6, 7, 8, 9, or 10 amino acid substitutions within aCD38-a-306-LCDR123 (SEQ ID NO: 16), or within SEQ ID NO: 51 or SEQ ID NO: 75. In some embodiments aCD38-a-306 amino acid sequences also refer to antibody sequences comprising as a variable light chain sequence a sequence containing up to 1, 2, 3, 4, 5, 6, 7, 8, 9, or 10 amino acid substitutions within the framework regions of the variable light chain sequence. The antibodies presenting such aCD38-a-306 amino acid sequence elements and such substitutions can still present the binding and/or functional properties of aCD38-a-306, and of a CD38 Modulating Antibody Agent in general.

Accordingly, in one embodiment, the present invention provides an anti-CD38 Antibody Agent (i.e. an antibody or antigen-binding fragment thereof, and variants thereof as described herein, such as variants mutated to remove the DG motif) comprising:

a. the variable heavy chain region sequence of aCD38-a-306 (or a variant thereof, such as an affinity matured variant thereof) or a variable heavy chain region sequence having up to 5 amino acid substitutions compared to the variable heavy chain region sequence of aCD38-a-306 (or a variant thereof, such as an affinity matured variant thereof); and/or b. the variable light chain region sequence of aCD38-a-306 (or a variant thereof, such as an affinity matured variant thereof) or a variable light chain region sequence having up to 5 amino acid substitutions compared to the variable light chain region sequence of aCD38-a-306 (or a variant thereof, such as an affinity matured variant thereof).

The aCD38-a-306 heavy chains that may incorporate amino acid substitutions include SEQ ID NOs 12, 50 and 74. The aCD38-a-306 light chains that may incorporate amino acid substitutions include SEQ ID NOs 16, 51 and 75.

The amino acid substitutions preferably do not adversely effect, or not substantially adversely effect, the functional properties of the antibodies. The substitutions may therefore be considered conservative amino acid substitutions. Preferably, when amino acid substitutions do occur, they occur in a ratio of 1:1, such that the total length of the heavy and/or light chain variable region does not change.

In one aspect, the present invention provides aCD38-b-329-HCDR3 amino acid sequence and polypeptides that include it, such as, for example, the antibodies or antigen-binding fragments comprising the aCD38-b-329-HCDR3 amino acid sequence (SEQ ID NO: 19) as variable heavy chain complementarity determining region 3. In some embodiments, such antibody or antigen-binding fragment may be further characterized by comprising further aCD38-b-329 amino acid sequence elements such as:

a) aCD38-b-329-HCDR1 amino acid sequence as variable heavy chain complementarity determining region 1 (SEQ ID NO: 17); and/or b) aCD38-b-329-HCDR2 amino acid sequence (SEQ ID NO: 18) as variable heavy chain complementarity determining region 2.

In some embodiments, provided antibodies or antigen-binding fragments thereof may comprise variable heavy chain complementarity determining regions defined above (i.e. aCD38-b-329 amino acid sequence elements) further in the correct order, specifically separated by antibody frame sequences, such as the one included in aCD38-b-329-HCDR123 amino acid sequence (SEQ ID NO: 20), in particular for exerting correctly their binding and functional properties. For example, in some embodiments, a provided antibody or antigen-binding fragment thereof can comprise aCD38-b-329-HCDR123 amino acid sequence (SEQ ID NO: 20, or the HCDR1, HCDR2 and HCDR3 sequences thereof) and, optionally:

a) aCD38-b-329-LCDR1 amino acid sequence as variable light chain complementarity determining region 1 (SEQ ID NO: 21);

b) aCD38-b-329-LCDR2 amino acid sequence as variable light chain complementarity determining region 2 (SEQ ID NO: 22); and c) aCD38-b-329-LCDR3 amino acid sequence (SEQ ID NO: 23) as variable light chain complementarity determining region 3.

Thus, in some embodiments, the present invention provides an isolated antibody or antigen-binding fragments thereof comprising a variable heavy chain comprising aCD38-b-329-HCDR123 amino acid sequence (SEQ ID NO: 20). Preferably, such isolated antibody or antigen-binding fragments thereof further comprises a variable light chain comprising aCD38-b-329-LCDR123 amino acid sequence (SEQ ID NO: 24), as described in the Examples.

In some embodiments the variable heavy chain sequence of aCD38-b-329 comprises the sequence:

```
                                            (SEQ ID NO: 52)
QLQLQESGPGLVKPSETLSLTCTVSGGSISSSDYYWGWIRQPPGKGLE

WIGSIYYSGSTYYNPSLKSRVTISVDTSKNQFSLKLSSVTAADTAVYY

CARGQYSSGWYAYPFDMWGQGTMVTVSS
``` and the variable light chain sequence of aCD38-b-329 comprises the sequence:

```
                                            (SEQ ID NO: 53)
EIVLTQSPGTLSLSPGERATLSCRASQSVRSSYLAWYQQKPGQAPRLL

IYGASSRATGIPDRFSGSGSGTDFTLTISRLEPEDFAVYYCQQDGAVF

TFGGGTKVEIK.
```

The present invention also provides an antibody or antigen-binding fragment thereof comprising the sequence of aCD38-b-329-HCDR3 as an HCDR3 and comprising an LCDR3 having a sequence selected from the group consisting of aCD38-b-329-LCDR3, aCD38-b-329-m6-LCDR3, and aCD38-b-329-m7-LCDR3.

The present invention also provides an antibody or antigen-binding fragment thereof comprising the sequence of aCD38-b-329-HCDR1 as an HCDR1, the sequence of aCD38-b-329-HCDR2 as an HCDR2, the sequence aCD38-b-329-HCDR3 as an HCDR3, the sequence of aCD38-b-329-LCDR1 as an LCDR1, the sequence of aCD38-b-329-LCDR2 as an LCDR2 and comprising an LCDR3 having a sequence selected from the group consisting of aCD38-b-329-LCDR3, aCD38-b-329-m6-LCDR3 and aCD38-b-329-m7-LCDR3.

The present invention also provides an antibody or antigen-binding fragment thereof comprising the sequence of aCD38-b-329-HCDR123 as a variable heavy chain region and comprising a variable light chain region having a sequence selected from the group consisting of aCD38-b-329-LCDR123, aCD38-b-329-m6-LCDR123, and aCD38-b-329-m7-LCDR123.

The present invention also provides an antibody or antigen-binding fragment thereof comprising the sequence of aCD38-b-329-VH as a variable heavy chain region and comprising a variable light chain region having a sequence selected from the group consisting of aCD38-b-329-VL, aCD38-b-329-m6-VL, and aCD38-b-329-m7-VL.

The present invention also provides variant antibodies and antigen binding fragments thereof that have certain % identities relative to a reference sequence, such as a CDR sequence or a heavy or light chain variable sequence of aCD38-b-329. Such antibodies and antigen binding fragments thereof may also be referred to herein as CD38 Modulating Antibody Agents.

For example, in some embodiments the anti-CD38 antibody or antigen binding fragment thereof comprises a variable heavy chain sequence comprising an amino acid sequence having at least 90% sequence identity to SEQ ID NO: 52. In some embodiments the anti-CD38 antibody or antigen binding fragment thereof comprises a variable heavy chain sequence comprising an amino acid sequence having at least 95% sequence identity to SEQ ID NO: 52. In some embodiments the anti-CD38 antibody or antigen binding fragment thereof comprises a variable heavy chain sequence comprising an amino acid sequence having at least 98% sequence identity to SEQ ID NO: 52. In some embodiments the anti-CD38 antibody or antigen binding fragment thereof comprises a variable heavy chain sequence comprising the amino acid sequence of SEQ ID NO: 52.

In some embodiments the anti-CD38 antibody or antigen binding fragment thereof comprises a variable light chain sequence comprising an amino acid sequence having at least 90% sequence identity to SEQ ID NO: 53. In some embodiments the anti-CD38 antibody or antigen binding fragment thereof comprises a variable light chain sequence comprising an amino acid sequence having at least 95% sequence identity to SEQ ID NO: 53. In some embodiments the anti-CD38 antibody or antigen binding fragment thereof comprises a variable light chain sequence comprising an amino acid sequence having at least 98% sequence identity to SEQ ID NO: 53. In some embodiments the anti-CD38 antibody or antigen binding fragment thereof comprises a variable light chain sequence comprising the amino acid sequence of SEQ ID NO: 53.

In some embodiments the anti-CD38 antibody or antigen binding fragment thereof comprises a variable heavy chain sequence comprising an amino acid sequence having at least 90% sequence identity to SEQ ID NO: 52 and a variable light chain sequence comprising an amino acid sequence having at least 90% sequence identity to SEQ ID NO: 53. In some embodiments the anti-CD38 antibody or antigen binding fragment thereof comprises a variable heavy chain sequence comprising an amino acid sequence having at least 95% sequence identity to SEQ ID NO: 52 and a variable light chain sequence comprising an amino acid sequence having at least 95% sequence identity to SEQ ID NO: 53. In some embodiments the anti-CD38 antibody or antigen binding fragment thereof comprises a variable heavy chain sequence comprising an amino acid sequence having at least 98% sequence identity to SEQ ID NO: 52 and a variable light chain sequence comprising an amino acid sequence having at least 98% sequence identity to SEQ ID NO: 53. In some embodiments the anti-CD38 antibody or antigen binding fragment thereof comprises a variable heavy chain sequence comprising the amino acid sequence of SEQ ID NO: 52 and a variable light chain sequence comprising the amino acid sequence of SEQ ID NO: 53.

In some embodiments the anti-CD38 antibody or antigen binding fragment thereof comprises a variable heavy chain sequence comprising an amino acid sequence having at least 90% sequence identity to SEQ ID NO: 20. In some embodiments the anti-CD38 antibody or antigen binding fragment thereof comprises a variable heavy chain sequence comprising an amino acid sequence having at least 95% sequence identity to SEQ ID NO: 20. In some embodiments the anti-CD38 antibody or antigen binding fragment thereof comprises a variable heavy chain sequence comprising an amino acid sequence having at least 98% sequence identity to SEQ ID NO: 20. In some embodiments the anti-CD38 antibody or antigen binding fragment thereof comprises a variable heavy chain sequence comprising the amino acid sequence of SEQ ID NO: 20.

In some embodiments the anti-CD38 antibody or antigen binding fragment thereof comprises a variable light chain sequence comprising an amino acid sequence having at least 90% sequence identity to SEQ ID NO: 24. In some embodiments the anti-CD38 antibody or antigen binding fragment thereof comprises a variable light chain sequence comprising an amino acid sequence having at least 95% sequence identity to SEQ ID NO: 24. In some embodiments the anti-CD38 antibody or antigen binding fragment thereof comprises a variable light chain sequence comprising an amino acid sequence having at least 98% sequence identity to SEQ ID NO: 24. In some embodiments the anti-CD38 antibody or antigen binding fragment thereof comprises a variable light chain sequence comprising the amino acid sequence of SEQ ID NO: 24.

In some embodiments the anti-CD38 antibody or antigen binding fragment thereof comprises a variable heavy chain sequence comprising an amino acid sequence having at least 90% sequence identity to SEQ ID NO: 20 and a variable light chain sequence comprising an amino acid sequence having at least 90% sequence identity to SEQ ID NO: 24. In some embodiments the anti-CD38 antibody or antigen binding fragment thereof comprises a variable heavy chain sequence comprising an amino acid sequence having at least 95% sequence identity to SEQ ID NO: 20 and a variable light chain sequence comprising an amino acid sequence having at least 95% sequence identity to SEQ ID NO: 24. In some embodiments the anti-CD38 antibody or antigen binding fragment thereof comprises a variable heavy chain sequence comprising an amino acid sequence having at least 98% sequence identity to SEQ ID NO: 20 and a variable light chain sequence comprising an amino acid sequence having at least 98% sequence identity to SEQ ID NO: 24. In some embodiments the anti-CD38 antibody or antigen binding fragment thereof comprises a variable heavy chain sequence comprising the amino acid sequence of SEQ ID NO: 20 and a variable light chain sequence comprising the amino acid sequence of SEQ ID NO: 24.

Such variant antibodies and antigen binding fragments thereof may retain or exhibit the same (or substantially the same) functional and pharmacological properties as described for the antibodies and antigen binding fragments thereof having the heavy and light chain variable sequences disclosed herein for aCD38-b-329.

Moreover, aCD38-b-329 amino acid sequences also refer to antibody sequences that are defined by the number of substitution with respect to the aCD38-b-329 amino acid sequence elements defined above. For example, such sequence may comprise, as variable heavy chain complementarity determining region 3 (HCDR3) a sequence containing up to 1, 2, 3, 4, amino acid substitutions within aCD38-b-329-HCDR3. In a further embodiment, aCD38-b-329 amino acid sequences also refer to antibody sequences comprising, as variable heavy chain complementarity determining regions 1, 2 and 3 (HCDR1, HCDR2, and HCDR3) a sequence containing up to 1, 2, 3, 4, 5, 6, 7, 8, 9, or 10 amino acid substitutions within aCD38-b-329-HCDR1, aCD38-b-329-HCDR2, and aCD38-b-329-HCDR3, and more preferably a sequence containing up to 1, 2, 3, 4, 5, 6, 7, 8, 9, or 10 amino acid substitutions within aCD38-b-329-HCDR123 (SEQ ID NO: 20), or within SEQ ID NO: 52. In some embodiments aCD38-b-329 amino acid sequences also refer to antibody sequences comprising as a variable heavy chain sequence a sequence containing up to 1, 2, 3, 4, 5, 6, 7, 8, 9, or 10 amino acid substitutions within the framework regions of the variable heavy chain sequence. The antibodies presenting such aCD38-b-329 amino acid sequence elements and such substitutions can still present the binding and/or functional properties of aCD38-b-329, and of a CD38 Modulating Antibody Agent in general.

Such aCD38-b-329 amino acid sequences may also comprise, as variable light chain complementarity determining region 3 (LCDR3) a sequence containing up to 1, 2, 3, or 4, amino acid substitutions within aCD38-b-329-LCDR3. In a further embodiment, aCD38-b-329 amino acid sequences also refer to antibody sequences comprising, as variable light chain complementarity determining regions 1, 2 and 3 (LCDR1, LCDR2, and LCDR3) a sequence containing up to 1, 2, 3, 4, 5, 6, 7, 8, 9, or 10 amino acid substitutions within aCD38-b-329-LCDR1, aCD38-b-329-LCDR2, and aCD38-b-329-LCDR3, and more preferably a sequence containing up to 1, 2, 3, 4, 5, 6, 7, 8, 9, or 10 amino acid substitutions within aCD38-b-329-LCDR123 (SEQ ID NO: 24), or within SEQ ID NO: 53. In some embodiments aCD38-b-329 amino acid sequences also refer to antibody sequences comprising as a variable light chain sequence a sequence containing up to 1, 2, 3, 4, 5, 6, 7, 8, 9, or 10 amino acid substitutions within the framework regions of the variable light chain sequence. The antibodies presenting such aCD38-b-329 amino acid sequence elements and such substitutions can still present the binding and/or functional properties of aCD38-b-329, and of a CD38 Modulating Antibody Agent in general.

Accordingly, in one embodiment, the present invention provides an anti-CD38 Antibody Agent (i.e. an antibody or antigen-binding fragment thereof and variants thereof as described herein, such as variants mutated to remove the DG motif) comprising:

a. the variable heavy chain region sequence of aCD38-b-329 (or a variant thereof, such as an affinity matured variant thereof) or a variable heavy chain region sequence having up to 5 amino acid substitutions compared to the variable heavy chain region sequence of aCD38-b-329 (or a variant thereof, such as an affinity matured variant thereof); and/or b. the variable light chain region sequence of aCD38-b-329 (or a variant thereof, such as an affinity matured variant thereof) or a variable light chain region sequence having up to 5 amino acid substitutions compared to the variable light chain region sequence of aCD38-b-329 (or a variant thereof, such as an affinity matured variant thereof).

The aCD38-b-329 heavy chains that may incorporate amino acid substitutions include SEQ ID NOs 20 and 52. The aCD38-b-329 light chains that may incorporate amino acid substitutions include SEQ ID NOs 24, 53, 62, 63, 68 and 69.

The amino acid substitutions preferably do not adversely effect, or not substantially adversely effect, the functional properties of the antibodies. The substitutions may therefore be considered conservative amino acid substitutions. Preferably, when amino acid substitutions do occur, they occur in a ratio of 1:1, such that the total length of the heavy and/or light chain variable region does not change.

In one aspect, the present invention provides aCD38-b-348-HCDR3 amino acid sequence and polypeptides that include it, such as, for example, the antibodies or antigen-binding fragments comprising the aCD38-b-348-HCDR3 amino acid sequence (SEQ ID NO: 27) as variable heavy chain complementarity determining region 3. In some embodiments, such antibody or antigen-binding fragment may be further characterized by comprising further aCD38-b-348 amino acid sequence elements such as:

a) aCD38-b-348-HCDR1 amino acid sequence as variable heavy chain complementarity determining region 1 (SEQ ID NO: 25); and/or
b) aCD38-b-348-HCDR2 amino acid sequence as variable heavy chain complementarity determining region 2 (SEQ ID NO: 26).

In some embodiments, provided antibodies or antigen-binding fragments thereof may comprise variable heavy chain complementarity determining regions defined above (i.e. aCD38-b-348 amino acid sequence elements) further in the correct order, specifically separated by antibody frame sequences, such as the one included in aCD38-b-348-HCDR123 amino acid sequence (SEQ ID NO: 28), in particular for exerting correctly their binding and functional properties. For example, in some embodiments, a provided antibody or antigen-binding fragment thereof can comprise aCD38-b-348-HCDR123 amino acid sequence (SEQ ID NO: 28, or the HCDR1, HCDR2 and HCDR3 sequences thereof) and, optionally:

a) aCD38-b-348-LCDR1 amino acid sequence (SEQ ID NO: 29) as variable light chain complementarity determining region 1;
b) aCD38-b-348-LCDR2 amino acid sequence (SEQ ID NO: 30) as variable light chain complementarity determining region 2; and
c) aCD38-b-348-LCDR3 amino acid sequence (SEQ ID NO: 31) as variable light chain complementarity determining region 3.

Thus, in some embodiments, the present invention provides an isolated antibody or antigen-binding fragments thereof comprising a variable heavy chain comprising aCD38-b-348-HCDR123 amino acid sequence (SEQ ID NO: 28). Preferably, such isolated antibody or antigen-binding fragments thereof further comprises a variable light chain comprising aCD38-b-348-LCDR123 amino acid sequence (SEQ ID NO: 32), as described in the Examples.

In some embodiments the variable heavy chain sequence of aCD38-b-348 comprises the sequence:

(SEQ ID NO: 54)
QLQLQESGPGLVKPSETLSLTCTVSGG<u>SISSSDYYWG</u>WIRQPPGKGLEWI

G<u>SIYYSGSTYYNPSLKS</u>RVTISVDTSKNQFSLKLSSVTAADTAVYYC<u>ARG</u>

<u>QYSSGWYAYPFDMW</u>GQGTMVTVSS and the variable light chain sequence of aCD38-a-348 comprises the sequence:

(SEQ ID NO: 55)
EIVLTQSPGTLSLSPGERATLSC<u>RASQSVRSSYLA</u>WYQQKPGQAPRLLIY

<u>GASSRAT</u>GIPDRFSGSGSGTDFTLTISRLEPEDFAVYYC<u>QQDGNVYT</u>FGG

GTKVEIK.

The present invention also provides an antibody or antigen-binding fragment thereof comprising the sequence of aCD38-b-348-HCDR3 as an HCDR3 and comprising an LCDR3 having a sequence selected from the group consisting of aCD38-b-348-LCDR3, aCD38-b-348-m1-LCDR3, aCD38-b-348-m2-LCDR3, aCD38-b-348-m3-LCDR3 and aCD38-b-348-m4-LCDR3.

The present invention also provides an antibody or antigen-binding fragment thereof comprising the sequence of aCD38-b-348-HCDR1 as an HCDR1, the sequence of aCD38-b-348-HCDR2 as an HCDR2, the sequence aCD38-b-348-HCDR3 as an HCDR3, the sequence of aCD38-b-348-LCDR1 as an LCDR1, the sequence of aCD38-b-348-LCDR2 as an LCDR2 and comprising an LCDR3 having a sequence selected from the group consisting of aCD38-b-348-LCDR3, aCD38-b-348-m1-LCDR3, aCD38-b-348-m2-LCDR3, aCD38-b-348-m3-LCDR3 and aCD38-b-348-m4-LCDR3.

The present invention also provides an antibody or antigen-binding fragment thereof comprising the sequence of aCD38-b-348-HCDR123 as a variable heavy chain region and comprising a variable light chain region having a sequence selected from the group consisting of aCD38-b-348-LCDR123, aCD38-b-348-m1-LCDR123, aCD38-b-348-m2-LCDR123, aCD38-b-348-m3-LCDR123 and aCD38-b-348-m4-LCDR123.

The present invention also provides an antibody or antigen-binding fragment thereof comprising the sequence of aCD38-b-348-VH as a variable heavy chain region and comprising a variable light chain region having a sequence selected from the group consisting of aCD38-b-348-VL, aCD38-b-348-m1-VL, aCD38-b-348-m2-VL, aCD38-b-348-m3-VL and aCD38-b-348-m4-VL.

The present invention also provides variant antibodies and antigen binding fragments thereof that have certain % identities relative to a reference sequence, such as a CDR sequence or a heavy or light chain variable sequence of aCD38-b-348. Such antibodies and antigen binding fragments thereof may also be referred to herein as CD38 Modulating Antibody Agents.

For example, in some embodiments the anti-CD38 antibody or antigen binding fragment thereof comprises a variable heavy chain sequence comprising an amino acid sequence having at least 90% sequence identity to SEQ ID NO: 54. In some embodiments the anti-CD38 antibody or antigen binding fragment thereof comprises a variable heavy chain sequence comprising an amino acid sequence having at least 95% sequence identity to SEQ ID NO: 54. In some embodiments the anti-CD38 antibody or antigen binding fragment thereof comprises a variable heavy chain sequence comprising an amino acid sequence having at least 98% sequence identity to SEQ ID NO: 54. In some embodiments the anti-CD38 antibody or antigen binding fragment thereof comprises a variable heavy chain sequence comprising the amino acid sequence of SEQ ID NO: 54.

In some embodiments the anti-CD38 antibody or antigen binding fragment thereof comprises a variable light chain sequence comprising an amino acid sequence having at least 90% sequence identity to SEQ ID NO: 55. In some embodiments the anti-CD38 antibody or antigen binding fragment thereof comprises a variable light chain sequence comprising an amino acid sequence having at least 95% sequence identity to SEQ ID NO: 55. In some embodiments the anti-CD38 antibody or antigen binding fragment thereof comprises a variable light chain sequence comprising an amino acid sequence having at least 98% sequence identity to SEQ ID NO: 55. In some embodiments the anti-CD38 antibody or antigen binding fragment thereof comprises a variable light chain sequence comprising the amino acid sequence of SEQ ID NO: 55.

In some embodiments the anti-CD38 antibody or antigen binding fragment thereof comprises a variable heavy chain sequence comprising an amino acid sequence having at least 90% sequence identity to SEQ ID NO: 54 and a variable light chain sequence comprising an amino acid sequence having at least 90% sequence identity to SEQ ID NO: 55. In some embodiments the anti-CD38 antibody or antigen binding fragment thereof comprises a variable heavy chain sequence comprising an amino acid sequence having at least 95% sequence identity to SEQ ID NO: 54 and a variable light chain sequence comprising an amino acid sequence having at least 95% sequence identity to SEQ ID NO: 55. In some embodiments the anti-CD38 antibody or antigen binding fragment thereof comprises a variable heavy chain sequence comprising an amino acid sequence having at least 98% sequence identity to SEQ ID NO: 54 and a variable light chain sequence comprising an amino acid sequence having at least 98% sequence identity to SEQ ID NO: 55. In some embodiments the anti-CD38 antibody or antigen binding fragment thereof comprises a variable heavy chain sequence comprising the amino acid sequence of SEQ ID NO: 54 and a variable light chain sequence comprising the amino acid sequence of SEQ ID NO: 55.

In some embodiments the anti-CD38 antibody or antigen binding fragment thereof comprises a variable heavy chain sequence comprising an amino acid sequence having at least 90% sequence identity to SEQ ID NO: 28. In some embodiments the anti-CD38 antibody or antigen binding fragment thereof comprises a variable heavy chain sequence comprising an amino acid sequence having at least 95% sequence identity to SEQ ID NO: 28. In some embodiments the anti-CD38 antibody or antigen binding fragment thereof comprises a variable heavy chain sequence comprising an amino acid sequence having at least 98% sequence identity to SEQ ID NO: 28. In some embodiments the anti-CD38 antibody or antigen binding fragment thereof comprises a variable heavy chain sequence comprising the amino acid sequence of SEQ ID NO: 28.

In some embodiments the anti-CD38 antibody or antigen binding fragment thereof comprises a variable light chain sequence comprising an amino acid sequence having at least 90% sequence identity to SEQ ID NO: 32. In some embodiments the anti-CD38 antibody or antigen binding fragment thereof comprises a variable light chain sequence comprising an amino acid sequence having at least 95% sequence identity to SEQ ID NO: 32. In some embodiments the anti-CD38 antibody or antigen binding fragment thereof comprises a variable light chain sequence comprising an amino acid sequence having at least 98% sequence identity to SEQ ID NO: 32. In some embodiments the anti-CD38 antibody or antigen binding fragment thereof comprises a variable light chain sequence comprising the amino acid sequence of SEQ ID NO: 32.

In some embodiments the anti-CD38 antibody or antigen binding fragment thereof comprises a variable heavy chain sequence comprising an amino acid sequence having at least 90% sequence identity to SEQ ID NO: 28 and a variable light chain sequence comprising an amino acid sequence having at least 90% sequence identity to SEQ ID NO: 32. In some embodiments the anti-CD38 antibody or antigen binding fragment thereof comprises a variable heavy chain sequence comprising an amino acid sequence having at least 95% sequence identity to SEQ ID NO: 28 and a variable light chain sequence comprising an amino acid sequence having at least 95% sequence identity to SEQ ID NO: 32. In some embodiments the anti-CD38 antibody or antigen binding fragment thereof comprises a variable heavy chain sequence comprising an amino acid sequence having at least 98% sequence identity to SEQ ID NO: 28 and a variable light chain sequence comprising an amino acid sequence having at least 98% sequence identity to SEQ ID NO: 32. In some embodiments the anti-CD38 antibody or antigen binding fragment thereof comprises a variable heavy chain sequence comprising the amino acid sequence of SEQ ID NO: 28 and a variable heavy chain sequence comprising the amino acid sequence of SEQ ID NO: 32.

Such variant antibodies and antigen binding fragments thereof may retain or exhibit the same (or substantially the same) functional and pharmacological properties as described for the antibodies and antigen binding fragments thereof having the heavy and light chain variable sequences disclosed herein for aCD38-b-348.

Moreover, aCD38-b-348 amino acid sequences also refer to antibody sequences that are defined by the number of substitution with respect to the aCD38-b-348 amino acid sequence elements defined above. For example, such sequence may comprise, as variable heavy chain complementarity determining region 3 (HCDR3) a sequence containing up to 1, 2, 3, 4, amino acid substitutions within aCD38-b-348-HCDR3. In a further embodiment, aCD38-b-348 amino acid sequences also refer to antibody sequences comprising, as variable heavy chain complementarity determining regions 1, 2 and 3 (HCDR1, HCDR2, and HCDR3) a sequence containing up to 1, 2, 3, 4, 5, 6, 7, 8, 9, or 10 amino acid substitutions within aCD38-b-348-HCDR1, aCD38-b-348-HCDR2, and aCD38-b-348-HCDR3, and more preferably a sequence containing up to 1, 2, 3, 4, 5, 6, 7, 8, 9, or 10 amino acid substitutions within aCD38-b-348-HCDR123 (SEQ ID NO: 28) or within SEQ ID NO: 54. In some embodiments aCD38-b-348 amino acid sequences also refer to antibody sequences comprising as a variable heavy chain sequence a sequence containing up to 1, 2, 3, 4, 5, 6, 7, 8, 9, or 10 amino acid substitutions within the framework regions of the variable heavy chain sequence. The antibodies presenting such aCD38-b-348 amino acid sequence elements and such substitutions can still present the binding and/or functional properties of aCD38-b-348, and of a CD38 Modulating Antibody Agent in general.

Such aCD38-b-348 amino acid sequences may also comprise, as variable light chain complementarity determining region 3 (LCDR3) a sequence containing up to 1, 2, 3, 4, amino acid substitutions within aCD38-b-348-LCDR3. In a further embodiment, aCD38-b-348 amino acid sequences also refer to antibody sequences comprising, as variable light chain complementarity determining regions 1, 2 and 3 (LCDR1, LCDR2, and LCDR3) a sequence containing up to 1, 2, 3, 4, 5, 6, 7, 8, 9, or 10 amino acid substitutions within aCD38-b-348-LCDR1, aCD38-b-348-LCDR2, and aCD38-b-348-LCDR3, and more preferably a sequence containing up to 1, 2, 3, 4, 5, 6, 7, 8, 9, or 10 amino acid substitutions within aCD38-b-348-LCDR123 (SEQ ID NO: 32) or within SEQ ID NO: 55. In some embodiments aCD38-b-348 amino acid sequences also refer to antibody sequences comprising as a variable light chain sequence a sequence containing up to 1, 2, 3, 4, 5, 6, 7, 8, 9, or 10 amino acid substitutions within the framework regions of the variable light chain sequence. The antibodies presenting such aCD38-b-348 amino acid sequence elements and such substitutions can still present the binding and/or functional properties of aCD38-b-348, and of a CD38 Modulating Antibody Agent in general.

Accordingly, in one embodiment, the present invention provides an anti-CD38 Antibody Agent (i.e. an antibody or antigen-binding fragment thereof and variants thereof as described herein, such as variants mutated to remove the DG motif) comprising:
  a. the variable heavy chain region sequence of aCD38-b-348 (or a variant thereof, such as an affinity matured variant thereof) or a variable heavy chain region sequence having up to 5 amino acid substitutions compared to the variable heavy chain region sequence of aCD38-b-348 (or a variant thereof, such as an affinity matured variant thereof); and/or b. the variable light chain region sequence of aCD38-b-348 (or a variant thereof, such as an affinity matured variant thereof) or a variable light chain region sequence having up to 5 amino acid substitutions compared to the variable light chain region sequence of aCD38-b-348 (or a variant thereof, such as an affinity matured variant thereof).

The aCD38-b-348 heavy chains that may incorporate amino acid substitutions include SEQ ID NOs 28 and 54. The aCD38-b-348 light chains that may incorporate amino acid substitutions include SEQ ID NOs 32, 55, 58, 59, 60, 61, 64, 65, 66, and 67.

The amino acid substitutions preferably do not adversely effect, or not substantially adversely effect, the functional properties of the antibodies. The substitutions may therefore be considered conservative amino acid substitutions. Preferably, when amino acid substitutions do occur, they occur in a ratio of 1:1, such that the total length of the heavy and/or light chain variable region does not change.

In one aspect, the present invention provides aCD38-a-327-HCDR3 amino acid sequence and polypeptides that include it, such as, for example, antibodies or antigen-binding fragments comprising the aCD38-a-327-HCDR3 amino acid sequence (SEQ ID NO: 35) as variable heavy chain complementarity determining region 3. In some embodiments, such antibody or antigen-binding fragment may be further characterized by comprising further aCD38-a-327 amino acid sequence elements such as:

a) aCD38-a-327-HCDR1 amino acid sequence (SEQ ID NO: 33) as variable heavy chain complementarity determining region 1; and/or
b) aCD38-a-327-HCDR2 amino acid sequence (SEQ ID NO: 34) as variable heavy chain complementarity determining region 2.

In some embodiments, provided antibodies or antigen-binding fragments thereof may comprise variable heavy chain complementarity determining regions defined above (i.e. aCD38-a-327 amino acid sequence elements) further in the correct order, specifically separated by antibody frame sequences, such as the one included in aCD38-a-327-HCDR123 amino acid sequence (SEQ ID NO: 36), in particular for exerting correctly their binding and functional properties. For example, in some embodiments, a provided antibody or antigen-binding fragment thereof can comprise aCD38-a-327-HCDR123 amino acid sequence (SEQ ID NO: 36, or the HCDR1, HCDR2 and HCDR3 sequences thereof) and, optionally:

a) aCD38-a-327-LCDR1 amino acid sequence (SEQ ID NO: 37) as variable light chain complementarity determining region 1;
b) aCD38-a-327-LCDR2 amino acid sequence (SEQ ID NO: 38) as variable light chain complementarity determining region 2; and
c) aCD38-a-327-LCDR3 amino acid sequence (SEQ ID NO: 39) as variable light chain complementarity determining region 3.

Thus, in some embodiments, the present invention provides an isolated antibody or antigen-binding fragments thereof comprising a variable heavy chain comprising aCD38-a-327-HCDR123 amino acid sequence (SEQ ID NO: 36). Preferably, such isolated antibody or antigen-binding fragments thereof further comprises a variable light chain comprising aCD38-a-327-LCDR123 amino acid sequence (SEQ ID NO: 40), as described in the Examples.

In some embodiments the present invention provides an isolated antibody or antigen-binding fragments thereof comprising a variable heavy chain comprising the sequence:

(SEQ ID NO: 76)
GSISSGGYYWSWIRQHPGKGLEWIGYIYYSGSTYYNPSLKSRVTISVDTS

KNQFSLKLSSVTAADTAVYYCARAKSELVLPYYYYMDV and/or the variable light chain comprising the sequence:

(SEQ ID NO: 77)
KSSQSVLFSSNNKNYLAWYQQKPGQPPKLLIYWASTRESGVPDRFSGSGS

GTDFTLTISSLQAEDVAVYYCQQYYSLPPT.

In some embodiments the variable heavy chain sequence of aCD38-a-327 comprises the sequence:

(SEQ ID NO: 56)
QVQLQESGPGLVKPSQTLSLTCTVSGGSISSGGYYWSWIRQHPGKGLEWI

GYIYYSGSTYYNPSLKSRVTISVDTSKNQFSLKLSSVTAADTAVYYCARA

KSELVLPYYYYMDVWGKGTTVTVSS and the variable light chain sequence of aCD38-a-327 comprises the sequence:

(SEQ ID NO: 57)
DIVMTQSPDSLAVSLGERATINCKSSQSVLFSSNNKNYLAWYQQKPGQPP

KLLIYWASTRESGVPDRFSGSGSGTDFTLTISSLQAEDVAVYYCQQYYSL

PPTFGGGTKVEIK.

The present invention also provides an antibody or antigen-binding fragment thereof comprising the sequence of aCD38-a-327-HCDR3 as an HCDR3 and the sequence of aCD38-a-327-LCDR3 as an LCDR3.

The present invention also provides variant antibodies and antigen binding fragments thereof that have certain % identities relative to a reference sequence, such as a CDR sequence or a heavy or light chain variable sequence of aCD38-a-327. Such antibodies and antigen binding fragments thereof may also be referred to herein as CD38 Modulating Antibody Agents.

For example, in some embodiments the anti-CD38 antibody or antigen binding fragment thereof comprises a variable heavy chain sequence comprising an amino acid sequence having at least 90% sequence identity to SEQ ID NO: 56. In some embodiments the anti-CD38 antibody or antigen binding fragment thereof comprises a variable heavy chain sequence comprising an amino acid sequence having at least 95% sequence identity to SEQ ID NO: 56. In some embodiments the anti-CD38 antibody or antigen binding fragment thereof comprises a variable heavy chain sequence comprising an amino acid sequence having at least 98% sequence identity to SEQ ID NO: 56. In some embodiments the anti-CD38 antibody or antigen binding fragment thereof comprises a variable heavy chain sequence comprising the amino acid sequence of SEQ ID NO: 56.

In some embodiments the anti-CD38 antibody or antigen binding fragment thereof comprises a variable light chain sequence comprising an amino acid sequence having at least 90% sequence identity to SEQ ID NO: 57. In some embodiments the anti-CD38 antibody or antigen binding fragment thereof comprises a variable light chain sequence comprising an amino acid sequence having at least 95% sequence identity to SEQ ID NO: 57. In some embodiments the anti-CD38 antibody or antigen binding fragment thereof comprises a variable light chain sequence comprising an amino acid sequence having at least 98% sequence identity to SEQ ID NO: 57. In some embodiments the anti-CD38 antibody or antigen binding fragment thereof comprises a variable light chain sequence comprising the amino acid sequence of SEQ ID NO: 57.

In some embodiments the anti-CD38 antibody or antigen binding fragment thereof comprises a variable heavy chain sequence comprising an amino acid sequence having at least 90% sequence identity to SEQ ID NO: 56 and a variable light chain sequence comprising an amino acid sequence having at least 90% sequence identity to SEQ ID NO: 57. In some embodiments the anti-CD38 antibody or antigen binding fragment thereof comprises a variable heavy chain sequence comprising an amino acid sequence having at least 95% sequence identity to SEQ ID NO: 56 and a variable light chain sequence comprising an amino acid sequence having at least 95% sequence identity to SEQ ID NO: 57. In some embodiments the anti-CD38 antibody or antigen binding fragment thereof comprises a variable heavy chain sequence comprising an amino acid sequence having at least 98% sequence identity to SEQ ID NO: 56 and a variable light chain sequence comprising an amino acid sequence having at least 98% sequence identity to SEQ ID NO: 57. In some embodiments the anti-CD38 antibody or antigen binding fragment thereof comprises a variable heavy chain sequence comprising the amino acid sequence of SEQ ID NO: 56 and a variable light chain sequence comprising the amino acid sequence of SEQ ID NO: 57.

In some embodiments the anti-CD38 antibody or antigen binding fragment thereof comprises a variable heavy chain sequence comprising an amino acid sequence having at least 90% sequence identity to SEQ ID NO: 76. In some embodiments the anti-CD38 antibody or antigen binding fragment thereof comprises a variable heavy chain sequence comprising an amino acid sequence having at least 95% sequence identity to SEQ ID NO: 76. In some embodiments the anti-CD38 antibody or antigen binding fragment thereof comprises a variable heavy chain sequence comprising an amino acid sequence having at least 98% sequence identity to SEQ ID NO: 76. In some embodiments the anti-CD38 antibody or antigen binding fragment thereof comprises a variable heavy chain sequence comprising the amino acid sequence of SEQ ID NO: 76.

In some embodiments the anti-CD38 antibody or antigen binding fragment thereof comprises a variable light chain sequence comprising an amino acid sequence having at least 90% sequence identity to SEQ ID NO: 77. In some embodiments the anti-CD38 antibody or antigen binding fragment thereof comprises a variable light chain sequence comprising an amino acid sequence having at least 95% sequence identity to SEQ ID NO: 77. In some embodiments the anti-CD38 antibody or antigen binding fragment thereof comprises a variable light chain sequence comprising an amino acid sequence having at least 98% sequence identity to SEQ ID NO: 77. In some embodiments the anti-CD38 antibody or antigen binding fragment thereof comprises a variable light chain sequence comprising the amino acid sequence of SEQ ID NO: 77.

In some embodiments the anti-CD38 antibody or antigen binding fragment thereof comprises a variable heavy chain sequence comprising an amino acid sequence having at least 90% sequence identity to SEQ ID NO: 76 and a variable light chain sequence comprising an amino acid sequence having at least 90% sequence identity to SEQ ID NO: 77. In some embodiments the anti-CD38 antibody or antigen binding fragment thereof comprises a variable heavy chain sequence comprising an amino acid sequence having at least 95% sequence identity to SEQ ID NO: 76 and a variable light chain sequence comprising an amino acid sequence having at least 95% sequence identity to SEQ ID NO: 77. In some embodiments the anti-CD38 antibody or antigen binding fragment thereof comprises a variable heavy chain sequence comprising an amino acid sequence having at least 98% sequence identity to SEQ ID NO:76 and a variable light chain sequence comprising an amino acid sequence having at least 98% sequence identity to SEQ ID NO: 77. In some embodiments the anti-CD38 antibody or antigen binding fragment thereof comprises a variable heavy chain sequence comprising the amino acid sequence of SEQ ID NO: 76 and a variable light chain sequence comprising the amino acid sequence of SEQ ID NO: 77.

In some embodiments the anti-CD38 antibody or antigen binding fragment thereof comprises a variable heavy chain sequence comprising an amino acid sequence having at least 90% sequence identity to SEQ ID NO: 36. In some embodiments the anti-CD38 antibody or antigen binding fragment thereof comprises a variable heavy chain sequence comprising an amino acid sequence having at least 95% sequence identity to SEQ ID NO: 36. In some embodiments the anti-CD38 antibody or antigen binding fragment thereof comprises a variable heavy chain sequence comprising an amino acid sequence having at least 98% sequence identity to SEQ ID NO: 36. In some embodiments the anti-CD38 antibody or antigen binding fragment thereof comprises a variable heavy chain sequence comprising the amino acid sequence of SEQ ID NO: 36.

In some embodiments the anti-CD38 antibody or antigen binding fragment thereof comprises a variable light chain sequence comprising an amino acid sequence having at least 90% sequence identity to SEQ ID NO: 40. In some embodiments the anti-CD38 antibody or antigen binding fragment thereof comprises a variable light chain sequence comprising an amino acid sequence having at least 95% sequence identity to SEQ ID NO: 40. In some embodiments the anti-CD38 antibody or antigen binding fragment thereof comprises a variable light chain sequence comprising an amino acid sequence having at least 98% sequence identity to SEQ ID NO: 40. In some embodiments the anti-CD38 antibody or antigen binding fragment thereof comprises a variable light chain sequence comprising the amino acid sequence of SEQ ID NO: 40.

In some embodiments the anti-CD38 antibody or antigen binding fragment thereof comprises a variable heavy chain sequence comprising an amino acid sequence having at least 90% sequence identity to SEQ ID NO: 36 and a variable light chain sequence comprising an amino acid sequence having at least 90% sequence identity to SEQ ID NO: 40. In some embodiments the anti-CD38 antibody or antigen binding fragment thereof comprises a variable heavy chain sequence comprising an amino acid sequence having at least 95% sequence identity to SEQ ID NO: 36 and a variable light chain sequence comprising an amino acid sequence having at least 95% sequence identity to SEQ ID NO: 40. In some embodiments the anti-CD38 antibody or antigen binding fragment thereof comprises a variable heavy chain sequence comprising an amino acid sequence having at least 98% sequence identity to SEQ ID NO: 36 and a variable light chain sequence comprising an amino acid sequence having at least 98% sequence identity to SEQ ID NO: 40. In some embodiments the anti-CD38 antibody or antigen binding fragment thereof comprises a variable heavy chain sequence comprising the amino acid sequence of SEQ ID NO: 36 and a variable light chain sequence comprising the amino acid sequence of SEQ ID NO: 40.

Such variant antibodies and antigen binding fragments thereof may retain or exhibit the same (or substantially the same) functional and pharmacological properties as described for the antibodies and antigen binding fragments thereof having the heavy and light chain variable sequences disclosed herein for aCD38-a-327.

Moreover, aCD38-a-327 amino acid sequences also refer to antibody sequences that are defined by the number of substitution with respect to the aCD38-a-327 amino acid sequence elements defined above. For example, such sequence may comprise, as variable heavy chain complementarity determining region 3 (HCDR3) a sequence containing up to 1, 2, 3, or 4, amino acid substitutions within aCD38-a-327-HCDR3. In a further embodiment, aCD38-a-327 amino acid sequences also refer to antibody sequences comprising, as variable heavy chain complementarity determining regions 1, 2 and 3 (HCDR1, HCDR2, and HCDR3) a sequence containing up to 1, 2, 3, 4, 5, 6, 7, 8, 9, or 10 amino acid substitutions within aCD38-a-327-HCDR1, aCD38-a-327-HCDR2, and aCD38-a-327-HCDR3, and more preferably a sequence containing up to 1, 2, 3, 4, 5, 6, 7, 8, 9, or 10 amino acid substitutions within aCD38-a-27-HCDR123 (SEQ ID NO: 36), or within SEQ ID NO: 56 or SEQ ID NO: 76. In some embodiments aCD38-a-327 amino acid sequences also refer to antibody sequences comprising as a variable heavy chain sequence a sequence containing up to 1, 2, 3, 4, 5, 6, 7, 8, 9, or 10 amino acid substitutions within the framework regions of the variable heavy chain sequence. The antibodies presenting such aCD38-a-327 amino acid sequence elements and such substitutions can still present the binding and/or functional properties of aCD38-a-327, and of a CD38 Modulating Antibody Agent in general.

Such aCD38-a-327 amino acid sequences may also comprise, as variable light chain complementarity determining region 3 (LCDR3) a sequence containing up to 1, 2, 3, or 4 amino acid substitutions within aCD38-a-327-LCDR3. In a further embodiment, aCD38-a-327 amino acid sequences also refer to antibody sequences comprising, as variable light chain complementarity determining regions 1, 2 and 3 (LCDR1, LCDR2, and LCDR3) a sequence containing up to 1, 2, 3, 4, 5, 6, 7, 8, 9, or 10 amino acid substitutions within aCD38-a-327-LCDR1, aCD38-a-327-LCDR2, and aCD38-a-327-LCDR3, and more preferably a sequence containing up to 1, 2, 3, 4, 5, 6, 7, 8, 9, or 10 amino acid substitutions within aCD38-a-327-LCDR123 (SEQ ID NO: 40), or within SEQ ID NO: 57 or SEQ ID NO: 77. In some embodiments aCD38-a-327 amino acid sequences also refer to antibody sequences comprising as a variable light chain sequence a sequence containing up to 1, 2, 3, 4, 5, 6, 7, 8, 9, or 10 amino acid substitutions within the framework regions of the variable light chain sequence. The antibodies presenting such aCD38-a-327 amino acid sequence elements and such substitutions can still present the binding and/or functional properties of aCD38-a-327, and of a CD38 Modulating Antibody Agent in general.

Accordingly, in one embodiment, the present invention provides an anti-CD38 Antibody Agent (i.e. an antibody or antigen-binding fragment thereof and variants thereof as described herein, such as variants mutated to remove the DG motif) comprising:

a. the variable heavy chain region sequence of aCD38-a-327 (or a variant thereof, such as an affinity matured variant thereof) or a variable heavy chain region sequence having up to 5 amino acid substitutions compared to the variable heavy chain region sequence of aCD38-a-327 (or a variant thereof, such as an affinity matured variant thereof); and/or b. the variable light chain region sequence of aCD38-a-327 (or a variant thereof, such as an affinity matured variant thereof) or a variable light chain region sequence having up to 5 amino acid substitutions compared to the variable light chain region sequence of aCD38-a-327 (or a variant thereof, such as an affinity matured variant thereof).

The aCD38-a-327 heavy chains that may incorporate amino acid substitutions include SEQ ID NOs 36, 56, and 76. The aCD38-a-327 light chains that may incorporate amino acid substitutions include SEQ ID NOs 40, 57 and 77.

The amino acid substitutions preferably do not adversely effect, or not substantially adversely effect, the functional properties of the antibodies. The substitutions may therefore be considered conservative amino acid substitutions. Preferably, when amino acid substitutions do occur, they occur in a ratio of 1:1, such that the total length of the heavy and/or light chain variable region does not change.

Accordingly the invention also provides variant antibodies or antigen-binding fragments thereof of the antibodies described herein. The invention provides antibodies or antigen-binding fragments thereof, wherein any DG motif in the light or heavy chains of the antibodies may be altered, for example to reduce aspartate isomerization and/or wherein any methionine in the light or heavy chains of the antibodies may be altered, for example to reduce methionine oxidation. For example, a DG motif may be altered to substitute one or both of the amino acids in the motif with a different amino acid. For example, such motifs may be mutated to EG, DQ or DA. A methionine residue may be altered to replaced it with a different amino acid, for example leucine or phenylalanine.

In such embodiments, the anti-CD38 antibody or antigen-binding fragment thereof may be, or may be derived from, for example, aCD38-b-348 or aCD38-b-329, although variants of all antibodies disclosed herein are specifically contemplated and provided. The variant anti-CD38 antibodies provide further antibodies having any, and possibly all, binding and functional properties of aCD38-b-348 and aCD38-b-329.

Accordingly, in some embodiments, the antibodies or fragments thereof provided herein can be mutated to remove or modify DG motifs, in particular DG motifs appearing in the CDR regions, as is standard in the art to reduce susceptibility to aspartate isomerisation. Such antibodies that have been modified in this may way need to undergo further modification (for example affinity maturation) before arriving at a final sequence.

In one embodiment of the invention, there is provided a variant antibody having CDR1, CDR2 and CDR3 sequences of an antibody as disclosed herein (for example the CDR1, CDR2 and CDR3 sequences of any of aCD38-a-323, aCD38-b-329, aCD38-b-348, aCD38-a-306 or aCD38-a-327), or the variable heavy and variable light chain of any antibody as disclosed herein (for example the variable heavy and variable light chain of any of aCD38-a-323, aCD38-b-329, aCD38-b-348, aCD38-a-306 or aCD38-a-327), but differing from the specified sequence in that at least one or at least two DG motifs in the CDRs (if present) have been changed to a different motif. The disclosed variants may be used and formulated as described for any of aCD38-a-323, aCD38-b-329, aCD38-b-348, aCD38-a-306 or aCD38-a-327.

For example, aCD38-b-329 contains a DG motif in its LCDR3 sequence. In some embodiments, the aspartate of the DG motif may be changed to a different amino acid and/or the glycine of the DG motif may be changed to a different amino acid. In such embodiments, the anti-CD38 antibody or antigen-binding fragment thereof may be, or may be derived from, for example, aCD38-b-329. In some of the embodiments the variant antibodies or antigen-binding fragments thereof have a VL CDR3 sequence as provided in Table 5 (labelled aCD38-b-329-m6 and aCD38-b-329-m7). For example, a variant LCDR3 sequence (for example aCD38-b-329-m6 variant LCDR3 sequence or aCD38-b-329-m7 variant LCDR3 sequence) can be incorporated into an antibody that comprises the LCDR1 and/or LCDR2 sequences of aCD38-b-329. In one embodiment, a variant LCDR3 sequence (for example aCD38-b-329-m6 variant LCDR3 sequence or aCD38-b-329-m7 variant LCDR3 sequence) can be incorporated into an antibody that comprises the LCDR1, LCDR2, HCDR1, HCDR2 and HCDR3 sequences of aCD38-b-329. In some embodiments, the variant antibody or antibody binding fragment thereof may comprise the variable heavy and variable light chain sequences of aCD38-b-329, but with a LCDR3 sequence mutated to remove the DG motif (for example aCD38-b-329-m6-LCDR3 or aCD38-b-329-m7-LCDR3 may be present as a LCDR3 instead). The variant anti-CD38 antibodies provide further antibodies having any, and possibly all, binding and functional properties of the parental aCD38-b-329. The disclosed variants may be used and formulated as described for aCD38-b-329.

Accordingly, the variant antibody aCD38-b-329-m6 may be characterised as comprising a heavy chain variable region comprising the sequence of:

(SEQ ID NO: 52)
QLQLQESGPGLVKPSETLSLTCTVSGGSISSSDYYWGWIRQPPGKGLEWI

GSIYYSGSTYYNPSLKSRVTISVDTSKNQFSLKLSSVTAADTAVYYCARG

QYSSGWYAYPFDMWGQGTMVTVSS and a variant light chain region comprising the sequence:

(SEQ ID NO: 68)
EIVLTQSPGTLSLSPGERATLSCRASQSVRSSYLAWYQQKPGQAPRLLIY

GASSRATGIPDRFSGSGSGTDFTLTISRLEPEDFAVYYCQQDEAVFTFGG

GTKVEIK.

The variant antibody aCD38-b-329-m7 may be characterised as comprising a heavy chain variable region comprising the sequence of:

(SEQ ID NO: 52)
QLQLQESGPGLVKPSETLSLTCTVSGGSISSSDYYWGWIRQPPGKGLE

WIGSIYYSGSTYYNPSLKSRVTISVDTSKNQFSLKLSSVTAADTAVYY

CARGQYSSGWYAYPFDMWGQGTMVTVSS and a variant light chain region comprising the sequence:

(SEQ ID NO: 69)
EIVLTQSPGTLSLSPGERATLSCRASQSVRSSYLAWYQQKPGQAPRLL

-continued
IYGASSRATGIPDRFSGSGSGTDFTLTISRLEPEDFAVYYCQQDSAVF

TFGGGTKVEIK.

The antibody aCD38-b-348 contains a DG motif in its LCDR3 sequence. In some embodiments, the aspartate of the DG motif may be changed to a different amino acid and/or the glycine of the DG motif may be changed to a different amino acid. In such embodiments, the anti-CD38 antibody or antigen-binding fragment thereof may be, or may be derived from, for example, aCD38-b-348. In some of the embodiments the variant antibodies or antigen-binding fragments thereof have a VL CDR3 sequence as provided in Table 8 (labelled aCD38-b-348-m1, aCD38-b-348-m2, aCD38-b-348-m3 and aCD38-b-348-m4). For example, a variant LCDR3 sequence (for example a aCD38-b-348-m1 variant LCDR3 sequence, aCD38-b-348-m2 variant LCDR3 sequence, aCD38-b-348-m3 variant LCDR3 sequence or aCD38-b-348-m4 variant LCDR3 sequence) can be incorporated into an antibody that comprises the LCDR1 and/or LCDR2 sequences of aCD38-b-348. In one embodiment, a variant LCDR3 sequence (for example the aCD38-b-348-m1 variant LCDR3 sequence, aCD38-b-348-m2 variant LCDR3 sequence, aCD38-b-348-m3 variant LCDR3 sequence or aCD38-b-348-m4 variant LCDR3 sequence) can be incorporated into an antibody that comprises the LCDR1, LCDR2, HCDR1, HCDR2 and HCDR3 sequences of aCD38-b-348. In some embodiments, the variant antibody or antibody binding fragment thereof may comprise the variable heavy and variable light chain sequences of aCD38-b-348, but with the LCDR3 sequence mutated to remove the DG motif (for example aCD38-b-348-m1-LCDR3, aCD38-b-348-m2-LCDR3, aCD38-b-348-m3-LCDR3 or aCD38-b-348-m4-LCDR3 may be present as a LCDR3 instead). The variant anti-CD38 antibodies provide further antibodies having any, and possibly all, binding and functional properties of the parental aCD38-b-348. The disclosed variants may be used and formulated as described for aCD38-b-348.

Accordingly, the variant antibody aCD38-b-348-m1 may be characterised as comprising a heavy chain variable region comprising the sequence of:

(SEQ ID NO: 54)
QLQLQESGPGLVKPSETLSLTCTVSGGSISSSDYYWGWIRQPPGKGLE

WIGSIYYSGSTYYNPSLKSRVTISVDTSKNQFSLKLSSVTAADTAVYY

CARGQYSSGWYAYPFDMWGQGTMVTVSS and a variant light chain region comprising the sequence:

(SEQ ID NO: 64)
EIVLTQSPGTLSLSPGERATLSCRASQSVRSSYLAWYQQKPGQAPRLL

IYGASSRATGIPDRFSGSGSGTDFTLTISRLEPEDFAVYYCQQEANVY

TFGGGTKVEIK.

The variant antibody aCD38-b-348-m2 may be characterised as comprising a heavy chain variable region comprising the sequence of:

(SEQ ID NO: 54)
QLQLQESGPGLVKPSETLSLTCTVSGGSISSSDYYWGWIRQPPGKGLE

```
                                                    -continued
WIGSIYYSGSTYYNPSLKSRVTISVDTSKNQFSLKLSSVTAADTAVYY

CARGQYSSGWYAYPFDMWGQGTMVTVSS
``` and a variant light chain region comprising the sequence:

```
                                                  (SEQ ID NO: 65)
EIVLTQSPGTLSLSPGERATLSCRASQSVRSSYLAWYQQKPGQAPRLL

IYGASSRATGIPDRFSGSGSGTDFTLTISRLEPEDFAVYYCQQDSNVY

TFGGGTKVEIK.
```

The variant antibody aCD38-b-348-m3 may be characterised as comprising a heavy chain variable region comprising the sequence of:

```
                                                  (SEQ ID NO: 54)
QLQLQESGPGLVKPSETLSLTCTVSGGSISSSDYYWGWIRQPPGKGLE

WIGSIYYSGSTYYNPSLKSRVTISVDTSKNQFSLKLSSVTAADTAVYY

CARGQYSSGWYAYPFDMWGQGTMVTVSS
``` and a variant light chain region comprising the sequence:

```
                                                  (SEQ ID NO: 66)
EIVLTQSPGTLSLSPGERATLSCRASQSVRSSYLAWYQQKPGQAPRLL

IYGASSRATGIPDRFSGSGSGTDFTLTISRLEPEDFAVYYCQQDANVY

TFGGGTKVEIK.
```

The variant antibody aCD38-b-348-m4 may be characterised as comprising a heavy chain variable region comprising the sequence of:

```
                                                  (SEQ ID NO: 54)
QLQLQESGPGLVKPSETLSLTCTVSGGSISSSDYYWGWIRQPPGKGLE

WIGSIYYSGSTYYNPSLKSRVTISVDTSKNQFSLKLSSVTAADTAVYY

CARGQYSSGWYAYPFDMWGQGTMVTVSS
``` and a variant light chain region comprising the sequence:

```
                                                  (SEQ ID NO: 67)
EIVLTQSPGTLSLSPGERATLSCRASQSVRSSYLAWYQQKPGQAPRLL

IYGASSRATGIPDRFSGSGSGTDFTLTISRLEPEDFAVYYCQQEGNVY

TFGGGTKVEIK.
```

The invention also provides affinity matured antibodies, for example an affinity matured variant derived from any of the antibodies disclosed herein. In one embodiment, the affinity matured antibodies are affinity matured antibodies additionally having an altered DG motif and/or NG motif and/or altered to remove or mutate any methionine residues. The disclosed affinity matured variants may be used and formulated as described for any of aCD38-a-323, aCD38-b-329, aCD38-b-348, aCD38-a-306 or aCD38-a-327. In some embodiments the invention provides a method of preparing an anti-CD38 antibody comprising providing an antibody as herein described (e.g., aCD38-a-323, aCD38-b-329, aCD38-b-348, aCD38-a-306 or aCD38-a-327 or an antigen binding fragment or variant thereof), and subjecting the antibody to affinity maturation, wherein the antibody produced binds to CD38 with greater affinity than the parental antibody. Preferably the produced antibody binds to CD38 with at least 20%, at least 30%, at least 40%, more preferably at least 50% greater affinity than the parental antibody binds to CD38, for example as measured by the Kd. Methods for measuring affinity are known in the art and described in the Examples below. The affinity matured antibodies produced by such methods can be formulated and used as described herein for the other anti-CD38 Antibody Agents.

Affinity maturation may be carried out according to any suitable method known to the skilled person. For example, in vitro antibody display systems are widely used for the generation of specific antibodies with high affinity. In these systems, the phenotype (i.e., the antibody fragment) is coupled to the genotype (i.e., the antibody gene) allowing the direct determination of the sequence of the antibody. Several systems have been developed to achieve display of antibody repertoires to allow subsequent selection of binders and by increasing the stringency of selection allows for the selection of higher and higher affinity variants. The antibody fragments can be expressed in yeast, ribosomes, phage display particles or by direct coupling to DNA.

Current antibody affinity maturation methods belong to two mutagenesis categories: stochastic and non-stochastic. Error-prone polymerase chain reaction (PCR), mutator bacterial strains, and saturation mutagenesis are typical examples of stochastic mutagenesis methods. Non-stochastic techniques often use alanine-scanning or site-directed mutagenesis to generate limited collections of specific variants. In addition, shuffling approaches to obtain shuffled variants of the parent antibody can also be used to improve antibodies affinity further.

Accordingly, in one embodiment of the invention, the method of affinity maturation is selected from the group consisting of stochastic mutagenesis (for example error-prone polymerase chain reaction (PCR), mutator bacterial strains, or saturation mutagenesis), non-stochastic mutagenesis (for example alanine-scanning or site-directed mutagenesis), shuffling (for example DNA shuffling, chain shuffling or CDR shuffling) and the use of the CRISPR-Cas9 system to introduce modifications.

Affinity maturation methods are described in, for example, Rajpal et al., Proc Natl Acad Sci USA, 2005, 102(24):8466-71, Steinwand et al., MAbs, 2014, 6(1):204-18, as well as in Handbook of Therapeutic Antibodies, Wiley, 2014, Chapter 6, Antibody Affinity (pages 115-140).

In some embodiments there is provided a method of preparing a pharmaceutical composition comprising providing an antibody prepared according to a method above, (i.e. for producing an antibody by affinity maturation) and co-formulating the antibody with at least one or more pharmaceutically acceptable excipients. The antibody used in the preparation of the pharmaceutical composition can be an affinity matured variant of aCD38-a-323, aCD38-b-329, aCD38-b-348, aCD38-a-306 or aCD38-a-327. The pharmaceutical compositions produced by such methods can be used in the methods of treatment of the present invention as described herein for the other anti-CD38 Antibody Agents.

Antibodies and/or antigen-binding fragments thereof as described herein (e.g., a CD38 Modulating Antibody Agent that may include one or more aCD38-a-323 amino acid sequence elements such aCD38-a-323-HCDR3 or aCD38-a-323-HCDR123, one or more aCD38-a-306 amino acid sequence elements such aCD38-a-306-HCDR3 or aCD38-a-306-HCDR123, one or more aCD38-b-329 amino acid sequence elements such aCD38-b-329-HCDR3 or aCD38-b-329-HCDR123; one or more aCD38-b-348 amino acid sequence elements such aCD38-b-348-HCDR3 or aCD38-b-348-HCDR123, one or more aCD38-a-327 amino acid sequence elements such aCD38-a-327-HCDR3 or aCD38-a-327-HCDR123 and/or that may compete with aCD38-a-323, aCD38-a-306, aCD38-b-329, aCD38-b-348 or aCD38-a-327 for binding to human CD38 and non-human primate CD38, for example Cynomolgus monkey CD38, etc.) may be provided in any of a variety of formats. For example, in some embodiments an appropriate format may be or comprise a monoclonal antibody, a domain antibody, a single chain antibody, a Fab fragment, a F(ab')2 fragment, a single chain variable fragment (scFv), a scFv-Fc fragment, a single chain antibody (scAb), an aptamer, or a single domain antibody. In some embodiments, an antibody or antigen-binding fragment thereof (and particularly a monoclonal antibody), may be a rabbit, mouse, chimeric, humanized or fully human antibody or antigen-binding fragment thereof. In some embodiments, a provided antibody or antigen-binding fragment thereof may be of an IgG, IgA, IgE, or IgM isotype (preferably human ones), as it can be most appropriate for a given use. In some embodiments, a provided antibody or antigen-binding fragment thereof is an IgG isotype, more particularly an IgG1, IgG2, IgG3, or IgG4 isotype (preferably human IgG1). In some embodiments, a provided antibody or antigen-binding fragment thereof (e.g., is provided as part of a multi-specific binding agent such as, for example, when it is desirable to associate further binding and/or functional moieties to a CD38 Modulating Antibody Agent such as a aCD38-a-323, aCD38-a-306, aCD38-b-329, aCD38-b-348 or aCD38-a-327 amino acid sequence, the isolated antibody or antigen-binding can be comprised in a bispecific antibody, a multispecific antibody, or other multi-specific format that may be available in the art.

In some embodiments, a provided CD38 Modulating Antibody Agent comprises a CD38-binding entity (e.g., an anti-CD38 antibody or antigen-binding fragment thereof) and a conjugated payload such as a therapeutic or diagnostic agent. In many such embodiments, the agent is considered and/or referred to as an "immunoconjugate". Examples of technologies and compounds that can be used for generating specific immunoconjugates such as antibody-drug are disclosed in the literature (Beck A et al., 2017) and described as applicable to several known anti-CD38 antibodies (WO2016166304).

In some embodiments, the present invention provides aCD38-a-323, aCD38-a-306, aCD38-b-329, aCD38-b-348 or aCD38-a-327 amino acid sequences that identify provided antibodies or antigen-binding fragments thereof. In some embodiments, such sequences identify provided antibodies or antigen-binding fragments thereof that bind an epitope in the extracellular domain of human CD38 (such as aCD38-b-ep as for aCD38-b-348 and aCD38-b-329), or aCD38ep-a and aCD38ep-b as for CD38-a-327), and optionally also a corresponding epitope of Cynomolgus monkey and/or murine CD38, either as isolated proteins or on the surface of cells expressing CD38 (such as immune cells or cell lines, e.g. Raji cells).

The invention also provides CD38 Modulating Antibody Agents binding the same (or similar) epitope as bound by the CD38 Modulating Antibody Agents of the invention. For example, in one embodiment there is provided an antibody that binds the same (or similar) epitope as (aCD38-a-323, aCD38-a-306, aCD38-b-329, aCD38-b-348 or aCD38-a-327 (or variants thereof)).

In some embodiments, the present invention provides anti-CD38 antibodies or antigen-binding fragments that specifically bind to an epitope of human CD38, wherein the epitope comprises one or more amino acid residues comprised in the amino acids 65-79 of SEQ ID NO: 47 (i.e. aCD38-b-ep). In such embodiments, the anti-CD38 antibody or antigen-binding fragment thereof may be, or may be derived from, for example, aCD38-b-348 or aCD38-b-329. Preferably the epitope comprises at least 4 amino acids wherein the epitope comprises one or more amino acids comprised in amino acids 65-79 of SEQ ID NO: 47. Preferably the epitope comprises at least 5 amino acids, at least 6 amino acids, at least seven amino acids, at least eight amino acids, at least nine amino acids, at least ten amino acids, at least eleven amino acids, at least twelve amino acids, at least thirteen amino acids, or at least fourteen or more amino acids wherein the epitope comprises one or more amino acids comprised in amino acids 65-79 of SEQ ID NO: 47. The epitope may be either linear or conformational, i.e. discontinuous. In some embodiments, the anti-CD38 antibodies or antigen-binding fragments specifically bind to an epitope of human CD38 wherein the epitope comprises at least two, at least three, at least four, at least five, at least six, at least seven, at least eight, at least nine, at least ten, at least eleven, at least twelve, at least thirteen, or at least fourteen or more amino acid residues comprised in amino acids 65-79 of SEQ ID NO: 47. In some embodiments, the anti-CD38 antibodies or antigen-binding fragments bind to an epitope comprising amino acids 65-79 of SEQ ID NO: 47.

In some embodiments, the present invention provides anti-CD38 antibodies or antigen-binding fragments that specifically bind to an epitope of human CD38, wherein the epitope comprises one or more amino acid residues comprised in the amino acids 47-66 and 126-138 of SEQ ID NO: 47 (i.e. aCD38ep-a and aCD38ep-b). In such embodiments, the anti-CD38 antibody or antigen-binding fragment thereof may be, or may be derived from, for example, aCD38-a-327. Preferably the epitope comprises at least 4 amino acids wherein the epitope comprises one or more amino acids comprised in amino acids 47-66 and 126-138 of SEQ ID NO: 47. Preferably the epitope comprises at least five amino acids, at least six amino acids, at least seven amino acids, at least eight amino acids, at least nine amino acids, at least ten amino acids, at least eleven amino acids, at least twelve amino acids, at least thirteen amino acids, or at least fourteen or more amino acids wherein the epitope comprises one or more amino acids comprised in amino acids 47-66 and 126-138 of SEQ ID NO:47. The epitope may be either linear or conformational, i.e. discontinuous. In some embodiments, the anti-CD38 antibodies or antigen-binding fragments specifically bind to an epitope of human CD38 wherein the epitope comprises at least two, at least three, at least four, at least five, at least six, at least seven, at least eight, at least nine, at least ten, at least eleven, at least twelve, at least thirteen, or at least fourteen or more amino acid residues comprised in amino acids 47-66 and 126-138 of SEQ ID NO: 47. In some embodiments, the anti-CD38 antibodies or antigen-binding fragments bind to an epitope comprising amino acids 47-66 and 126-138 of SEQ ID NO: 47. In some embodiments the anti-CD38 antibodies or antigen-binding fragments further bind amino acid 68 of SEQ ID NO: 47.

In some embodiments, the present invention provides anti-CD38 antibodies or antigen-binding fragments that specifically bind to an epitope of human CD38, wherein the epitope comprises amino acids 120, 121 and 141 of SEQ ID NO: 47. In some embodiments the anti-CD38 antibodies or antigen-binding fragments further bind amino acid 241 of SEQ ID NO: 47. In such embodiments, the anti-CD38 antibody or antigen-binding fragment thereof may be, or may be derived from, for example, aCD38-a-323.

In some embodiments, the present invention provides procedures for screening and/or characterizing antibodies or antigen-binding fragments thereof that comprise aCD38-a-323, aCD38-a-306, aCD38-b-329, aCD38-b-348 or aCD38-a-327 amino acid sequences and/or that present binding features comparable to antibodies or antigen-binding fragments thereof comprising one or more aCD38-a-323, aCD38-a-306, aCD38-b-329, aCD38-b-348, aCD38-a-327 amino acid sequence elements (e.g. including aCD38-a-323-HCDR3 amino acid sequence and/or competing with aCD38-a-323, aCD38-a-306-HCDR3 amino acid sequence and/or competing with aCD38-a-306, aCD38-b-329-HCDR3 amino acid sequence and/or competing with aCD38-b-329, aCD38-b-348-HCDR3 amino acid sequence and/or competing with aCD38-b-348, and aCD38-a-327-HCDR3 amino acid sequence and/or competing with aCD38-a-327) that allow binding to human CD38 extracellular domain as isolated protein and on the surface of cells expressing human CD38, competing for the same epitope, in particular the epitopes identified in the Examples as aCD38-b-ep (protein sequence ARCVKYTEIHPEMRH; amino acids 65-79 in Uniprot sequence P28907, SEQ ID NO: 47) for aCD38-b-348 and aCD38b-329 (or variants thereof), as aCD38ep-a (protein sequence RQQWSGPGTTKRFPETV-LAR; amino acids 47-66 in Uniprot sequence P28907, SEQ ID NO: 47) and as aCD38ep-b (protein sequence SRIKD-LAHQFTQV; amino acids 126-138 in Uniprot sequence P28907, SEQ ID NO: 47) for aCD38-a-327 (or variants thereof). Antibody aCD38-a-327 (or variants thereof) may further bind amino acid 68 of SEQ ID NO:47. Antibody aCD38-a-323 (or variants thereof) may bind an epitope that comprises amino acid residues 120, 121 and 141 of SEQ ID NO: 47 and may optionally bind amino acid residue 241 of SEQ ID NO:47.

Furthermore, the present invention also provides procedures for screening antibodies or antigen-binding fragments thereof that present functional features comparable to antibodies or antigen-binding fragments thereof comprising one or more aCD38-a-323, aCD38-a-306, aCD38-b-329, aCD38-b-348 or aCD38-a-327 amino acid sequence elements, such features being cell activating and cytotoxic activities, and acting as CD38 Modulating Antibody Agents. At these scopes, the candidate antibodies can be tested in the assays that are described in the Examples (see e.g. FIG. 1) or other assays that are known in the art for establishing the presence of any of such features, but possibly all of them when evaluated in in vitro/ex vivo assays, cell-based assays, and/or animal models.

In some embodiments, the present invention provides nucleic acid molecules encoding an isolated antibody or antigen-binding fragment thereof that comprises a CD38 Modulating Antibody Agent such as a aCD38-a-323, aCD38-a-306, aCD38-b-329, aCD38-b-348 or aCD38-a-327 amino acid sequence, or variants thereof. In some embodiments, such provided nucleic acid molecules may contain codon-optimized nucleic acid sequences, and/or may be included in expression cassettes within appropriate nucleic acid vectors for the expression in host cells such as, for example, bacterial, yeast, insect, piscine, murine, simian, or human cells.

In some embodiments, the present invention provides host cells comprising heterologous nucleic acid molecules (e.g. DNA vectors) that express a provided CD38 Modulating Antibody Agent (e.g., an antibody or antigen-binding fragment thereof) having one or more properties, e.g., as described herein, of a CD38 Modulating Antibody Agent (e.g., comprising a aCD38-a-323, aCD38-a-306, aCD38-b-329, aCD38-b-348 or aCD38-a-327 amino acid sequence or variants thereof). In some embodiments, the present disclosure provides methods of preparing a CD38 Modulating Antibody Agent (e.g., an antibody or antigen-binding fragment thereof) having one or more properties, e.g., as described herein, of a CD38 Modulating Antibody Agent (e.g. comprising a aCD38-a-323, aCD38-a-306, aCD38-b-329, aCD38-b-348 or aCD38-a-327 amino acid sequence or variants thereof). In some embodiments, such methods may comprise culturing a host cell that comprises nucleic acids (e.g., heterologous nucleic acids that may comprise and/or be delivered to the host cell via vectors). In some embodiments, such a host cell (and/or the heterologous nucleic acid sequences) is/are arranged and constructed so that the CD38 Modulating Antibody Agent (e.g., the antibody or antigen-binding fragment thereof) is secreted from the host cell (e.g., so that it can be isolated from cell culture supernatants), and/or exposed on the cell surface (for instance, if such aCD38-a-323, aCD38-a-306, aCD38-b-329, aCD38-b-348 or aCD38-a-327 amino acid sequences (or variants thereof) and sequence elements are intended to be used in the context of, or together with, such cells, as in artificial T cell receptors grafting the specificity of a monoclonal antibody onto T cells).

In some embodiments the antibody or antigen-binding fragment thereof (or variants of the same) may be afucosylated. It is well known that antibody glycosylation may have impact on the activity, pharmacokinetics and pharmacodynamics of antibodies (e.g., monoclonal antibodies, recombinant antibodies, and/or antibodies that are otherwise engineered or isolated) and Fc-fusion proteins and specific technology may be exploited to obtain an antibody with the desired glycosylation profile (Liu L, 2015). Effector functions supporting the cytotoxicity of an antibody for use in accordance with the present invention (e.g., an anti-CD38 antibody as described herein, including for example an antibody which may be or be described as a CD38 Modulating Antibody Agent) can be enhanced using methods to decrease antibody fucosylation levels. Antibodies comprising specific aCD38-a-323, aCD38-a-306, aCD38-b-329, aCD38-a-327, or aCD38-b-348 sequence elements presenting such properties can be generated, for example, by expressing a aCD38-a-323, aCD38-a-306, aCD38-b-329, aCD38-a-327, or aCD38-b-348 sequence using technologies for genetically engineering cell lines which may produce antibodies with absent or reduced fucosylation capacity, some of them commercially available such as Potelligent (Lonza) GlyMAXX (ProBiogen), or by manipulating the manufacturing process, for example by controlling osmolarity and/or using enzyme inhibitors, see also for example the methods described in EP2480671.

In some embodiments, the present invention provides compositions (e.g. pharmaceutical compositions) comprising a provided antibody or an antigen-binding fragment thereof having desirable properties as described herein (e.g., as described for antibodies that are herein termed CD38 Modulating Antibody Agents, specifically including, for example, aCD38-a-323, aCD38-a-306, aCD38-b-329, aCD38-a-327, or aCD38-b-348 antibodies or antigen-binding fragments thereof, and variants of the same). In some embodiments, such provided compositions are intended for and/or are for use in a medical use, such as a therapeutic, diagnostic, or prophylactic use. In some embodiments, such a provided composition can further comprise a pharmaceutically acceptable carrier or excipient and/or may be for use in the treatment of cancer. In some embodiments, a pharmaceutical composition may be formulated with one or more carrier, excipients, salts, buffering agents, etc., as is known in the art. Those of skill in the art will be aware of and readily able to utilize a variety of formulation technologies, including as may be particularly desirable and/or useful for a given method and/or site of administration, for instance for parenteral (e.g. subcutaneous, intramuscular, or intravenous injection), mucosal, intratumoral, peritumoral, oral, or topical administration. In many embodiments, provided pharmaceutical compositions, comprising a CD38 Modulating Antibody Agent as described herein (e.g., an anti-CD38 antibody or antigen binding portion thereof), are formulated for parenteral delivery (e.g., by injection and/or infusion). In some embodiments, such a provided pharmaceutical composition may be provided, for example, in a pre-loaded syringe or vial format. In some embodiments, such a provided pharmaceutical composition may be provided and/or utilized, for example, in dry (e.g., lyophilized) form; alternatively, in some embodiments, such a provided pharmaceutical composition may be provided and/or utilized in a liquid form (e.g., as a solution, suspension, dispersion, emulsion, etc.), in a gel form, etc.

In some embodiments, the present invention provides uses of CD38 Modulating Antibody Agents (e.g., anti-CD38 antibodies or antigen-binding fragments thereof) as described herein (e.g. comprising a aCD38-a-323, aCD38-a-306, aCD38-b-329, aCD38-a-327, or a aCD38-b-348 amino acid sequence element), and/or of a composition comprising them, in treatment of and/or in the manufacture of a medicament for treatment of, a cancer, such as a B cell malignancy, a lymphoma, (Hodgkins Lymphoma, non-Hodgkins lymphoma, chronic lymphocytic, leukemia, acute lymphoblastic leukemia, myelomas), a myeloproliferative disorders, a solid tumor (such as a breast carcinoma, a squamous cell carcinoma, a colon cancer, a head and neck cancer, a lung cancer, a genitourinary cancer, a rectal cancer, a gastric cancer, sarcoma, melanoma, an esophageal cancer, liver cancer, testicular cancer, cervical cancer, mastocytoma, hemangioma, eye cancer, laryngeal cancer, mouth cancer, mesothelioma, skin cancer, rectal cancer, throat cancer, bladder cancer, breast cancer, uterine cancer, prostate cancer, lung cancer, pancreatic cancer, renal cancer, gastric cancer, non-small cell lung cancer, and ovarian cancer). The cancer can be also defined on the basis of presence of specific tumor-relevant markers and antigens such as CD20, HER2, PD-1, PD-L1, SLAM7F, CD47, CD137, CD134, TIM3, CD25, CD38, GITR, EGFR, etc., or a cancer that has been identified as having a biomarker referred to as microsatellite instability-high (MSI-H) or mismatch repair deficient (dMMR). Furthermore, such conditions may also be considered when defining precancerous, non-invasive states of the above cancers, such as cancer in-situ, smouldering myeloma, monoclonal gammopathy of undetermined significance, cervical intra-epithelial neoplasia, MALTomas/GALTomes and various lymphoproliferative disorders. Preferably in some embodiments the subject being treated has a solid tumor. In one embodiment the subject has a haematological cancer. In some embodiments the subject has a CD38 positive tumor.

Thus, in some embodiments, the present invention provides methods of treating cancer in a subject, comprising administering to the subject an effective amount of a composition comprising a provided CD38 Modulating Antibody Agent (e.g., anti-CD38 antibodies or antigen-binding fragments thereof) as described herein (e.g. comprising aCD38-a-323, aCD38-a-306, aCD38-b-329, aCD38-a-327, or aCD38-b-348 amino acid sequences or variants thereof). In some embodiments, provided methods may further comprise administering, simultaneously or sequentially in any order, at least one additional agent or therapy to the subject (i.e., so that the subject receives a combination therapy). In some embodiments, such an at least one additional agent or therapy can be or comprise an anticancer drug (e.g., a chemotherapeutic agent), radiotherapy (by applying irradiation externally to the body or by administering radio-conjugated compounds), an anti-tumor antigen or marker antibody (the antigen or marker being for example CD4, CD25, CA125, PSMA, c-MET, VEGF, CD137, VEGFR2, CD20, HER2, HER3, SLAMF7, CD326, CAIX, CD40, CD47, or EGF receptor), a checkpoint inhibitor or an immunomodulating antibody (for example an antibody targeting PD-1. PD-L1, TIM3, CD25, GITR, CD134, CD134L, CD137L, CD80, CD86, B7-H3, B7-H4, B7RP1, LAG3, ICOS, TIM3, GAL9, CD28, AP2M1, SHP-2, OX-40 etc.), a vaccine, an adjuvant, standard-of-use protocol, one or more other compounds targeting cancer cells or stimulating an immune response against cancer cells, or any combination thereof. In certain particular embodiments, when such at least one additional agent or therapy is or comprises an antibody, the format of and/or the antigen targeted by such antibody can be chosen among those listed in the literature and possibly adapted to a given cancer (Sliwkowski M & Mellman I, 2013; Redman J M et al., 2015; Kijanka M et al., 2015).

Still further, the present invention provides a variety of kits or articles of manufacture containing a provided CD38 Modulating Antibody Agent (e.g., anti-CD38 antibody or antigen-binding fragment thereof) as described herein (e.g. comprising aCD38-a-323, aCD38-a-306, aCD38-b-329, aCD38-a-327, or aCD38-b-348 amino acid sequences or variants thereof) or related compositions that allow the administration, storage, or other use of such an isolated antibody or antigen-binding fragment. In some embodiments, a provided kit comprises a vessel, syringe, a vial, or other container comprising such compositions, optionally together with one or more articles of manufactures, diluents, reagents, solid phases, and/or instructions for the correct use of the kit.

In some embodiments, identification, characterization, and/or validation of particular CD38 Modulating Antibody Agent (e.g., anti-CD38 antibody or antigen-binding fragment thereof) as described herein (e.g. comprising aCD38-a-323, aCD38-a-306, aCD38-b-329, aCD38-a-327, or aCD38-b-348 amino acid sequences or variants thereof) for a particular use, such as a medical use, and in particular for treating cancer, can be performed by using one or more assays or systems as described herein. In some embodiments, such identification, characterization, and/or validation may involve analysis of activity in one or more cell-based assays, for example using different experimental set-ups and/or a panel of selected (e.g., cancer-derived cell lines). In some embodiments, particularly given the proposed immunological mechanism associated certain desirable CD38 Modulating Antibody Agents as described herein activities, desirable identification, characterization, and/or validation can involve collection of relevant data generated in animal models wherein cancers are induced or wherein cancer cells are implanted as a xenograft or as a syngeneic/allogeneic cancer-derived cells. Alternatively or additionally, in some embodiments, animal models may be utilized that involve transfer of human cells such as PBMC (i.e. humanized PBMC mouse models) or CD34+ hematopoietic stem cells (i.e. CD34+ humanized mice) to allow evaluating activity of the CD38 Modulating Antibody Agents on human immune cells within a model system.

In some embodiments, relevant sequences of CD38 Modulating Antibody Agents (e.g., anti-CD38 antibody or antigen-binding fragments thereof) as described herein (e.g. comprising aCD38-a-323, aCD38-a-306, aCD38-b-329, aCD38-a-327, or aCD38-b-348 amino acid sequences (or variants thereof) or otherwise including structural and/or functional characteristics of an agent described herein as a CD38 Modulating Antibody Agent) can be cloned into and/or expressed in context of an antibody frame that is more appropriate or desirable for pharmaceutical and/or technical reasons. For example, such sequences (possibly as codon-optimized VH and VL coding sequences) can be cloned together with human IgG1 constant regions (hIgG1) and expressed using an appropriate antibody expression vectors and cell line (such as a CHO-derived cell line, e.g. CHO-S). In some particular embodiments, expression and secretion of provided antibody sequences in human IgG1 format antibodies can be analyzed after transfection in reduced conditions in cell lysates and in non-reduced conditions in supernatants that will be later used to purify the antibody (by affinity chromatography, gel filtration, and/or other appropriate technique). Binding and/or other functional properties of provided anti-CD38 antibody sequences, in human IgG1 format (e.g., CD38 Modulating Antibody Agents-hIgG1) can be analysed, for example by using one or more assays described in Examples below. For instance, such hIgG1-format provided antibodies can be evaluated for binding to human and cynomolgus PBMC, e.g., using flow cytometry. Alternatively or additionally, binding to specific immune cell populations can be assessed, for example using flow cytometry that may employ one or more specific markers for specific immune cell populations, like CD3, CD45, CD56 and CD159 (NKG2A) for NK cells, CD14 (for monocytes), CD19 (for B cells), and/or CD4/CD8 (for T cells).

Moreover, the effect of one or more CD38 Modulating Antibody Agents (e.g., anti-CD38 antibody or antigen-binding fragments thereof) as described herein (e.g. comprising aCD38-a-323, aCD38-a-306, aCD38-b-329, aCD38-a-327, or aCD38-b-348 amino acid sequences (or variants thereof) or otherwise including structural and/or functional characteristics of an agent described herein as a CD38 Modulating Antibody Agent—such as a CD38 Modulating Antibody Agent-hIgG1) on human primary tumor cells and/or immune cells isolated from human healthy donors and/or patients can be assessed. In order to investigate potential effects on individual immune cell populations in more detail, such CD38 Modulating Antibody Agents can be used to treat PBMC and/or cells isolated from tumors (and/or organs such as lymph nodes) and/or purified human CD8 and CD4 T cells, Treg cells, MDSC cells, dendritic cells, macrophages and monocytes, neutrophils, NK cells and other cell types. Potential read outs comprise cytokine release, tumor cell killing, cell proliferation, and/or activation, apoptosis, antigen-specific and/or allogenic responses, or any combination thereof. Alternatively or additionally, mice or non-human primates can be treated and cellular status can be followed using flow cytometry or after isolation of various organs and/or cells from the animals.

Alternatively or additionally, one or more properties of CD38 Modulating Antibody Agents (e.g., anti-CD38 antibody or antigen-binding fragments thereof) as described herein (e.g. comprising aCD38-a-323, aCD38-a-306, aCD38-b-329, aCD38-a-327, or aCD38-b-348 amino acid sequences (or variants thereof) or otherwise including structural and/or functional characteristics of an agent described herein as a CD38 Modulating Antibody Agent—such as a CD38 Modulating Antibody Agent-hIgG1) may be evaluated, alone or in combination, by studying the effects of such CD38 Modulating Antibody Agents on CD38 expressing cells (e.g. NK cells or T-cells); CD38 enzymatic activity, CD38 induced $Ca^{2+}$ levels and protein phosphorylation, CD38 shedding and/or internalization, CD38-induced activation of intra-cellular pathways (e.g. NFκB pathway), and/or interaction with CD31 and other receptor proteins (e.g., CD16, TCR, BCR, etc.). Involvement of the latter processes in the CD38 downstream activity can also be evaluated using specific inhibitors of these processes.

In order to gain further insights into the molecular interactions between a provided CD38 Modulating Antibody Agent and human CD38, the crystal structure of the CD38 Modulating Antibody Agent (e.g., a aCD38-a-323-hIgG1 aCD38-a-306-hIgG1, aCD38-b-329-hIgG1, aCD38-a-327-hIgG1, or aCD38-b-348-hIgG1 antibody) and human CD38 protein can be determined. Solubility and/or stability of provided CD38 Modulating Antibody Agents (specifically including, for example, aCD38-a-323-hIgG1, aCD38-a-306-hIgG1, aCD38-b-329-hIgG1, aCD38-a-327-hIgG1, or aCD38-b-348-hIgG1 antibodies) can be assessed through solubility studies, accelerated stress studies, freeze thaw studies and formal stability studies. Aggregation of the antibodies can be followed by visual inspection, size exclusion chromatography and dynamic light scattering and $OD_{280/320}$ absorbance.

The present invention includes variants or derivates of the antibodies disclosed herein, such as any of aCD38-a-323, aCD38-a-306, aCD38-b-329, aCD38-a-327, and aCD38-b-348. Variant or derivative antibodies or antigen binding fragments thereof (for example aCD38-b-329-m6, aCD38-b-329-m7, aCD38-b-348-m1, aCD38-b-348-m2, aCD38-b-348-m3 and aCD38-b-348-m4) may share the same functional profile (i.e. pharmacological properties) as for the antibody from which they are derived. Similarly, the present invention includes antibodies or antigen binding fragments that compete for binding to CD38 with any of the antibodies disclosed herein, such as any of aCD38-a-323, aCD38-a-306, aCD38-b-329, aCD38-a-327, and aCD38-b-348 (or variants thereof). Such competing antibodies may have the same functional profile (i.e. pharmacological properties) as the antibody with which they compete for binding to CD38.

BRIEF DESCRIPTION OF DRAWINGS

FIG. 2: relevant protein sequences aCD38-a-323 protein sequences. Each CDR for the heavy (aCD38-a-323-HCDR1 (SEQ ID NO: 1), aCD38-a-323-HCDR2 (SEQ ID NO: 2), and aCD38-a-323-HCDR3 (SEQ ID NO: 3)) and the light (aCD38-a-323-LCDR1 (SEQ ID NO: 5), aCD38-a-323-LCDR2 (SEQ ID NO: 6), and aCD38-a-323-LCDR3 (SEQ ID NO: 7)) chain is indicated separately and, underlined, within the frame sequence of the heavy and light chain antibody as initially identified by the screening procedure (aCD38-a-323-HCDR123 (SEQ ID NO: 4) and aCD38-a-323-LCDR123 (SEQ ID NO: 8), respectively).

FIG. 3: characterization of aCD38-a-323 binding to CD38 expressed in PBMCs, using cells of either Cynomolgus Monkey (A) or human origin (B) at increasing antibody concentration and by restricting the analysis to CD8-positive or CD4-positive cells and comparing with human IgG1 isotype control.

FIG. 4: functional characterization of aCD38-a-323 compared to Daratumumab (DARA) or negative control antibodies (anti-human CD3 or human IgG1 isotype), in cell-based models independently from the administration of any further tumor targeting antibody. (A) aCD38-a-323 increases the percentage of TCR-mediated CD4 and CD8 T cell proliferation, as indicated in each graph. (aCD38-a-323 at 10-5-2.5 µg/ml; hIgG1 and DARA tested at 10 µg/ml; the anti-CD3 concentration to provide baseline activation is 0.1 µg/ml). (B) aCD38-a-323 increases the secretion of GM-CSF by TCR-activated CD4/CD8 T cells (similar pattern in 3 out of 3 donors tested), (aCD38-a-323 at 10-5-2.5 µg/ml; hIgG1 and DARA tested at 10 µg/ml, anti-CD3 is tested at 0.1 µg/ml).

FIG. 5: functional characterization of aCD38-a-323 compared to DARA with respect to cytotoxicity. (A) Both aCD38-a-323 and DARA induce killing of CD38 expressing Daudi cells by antibody-dependent cell-mediated cytotoxicity (ADCC). Further, both aCD38-a-323 and Daratumumab (DARA) induce complement dependent cytotoxicity (CDC), (B), DARA to a higher extent than aCD38-a-323, which induces only 40% cell lysis by CDC, while DARA induces >90% cell lysis (CDC is particularly significant for DARA, as described in the literature).

FIG. 6: functional characterization of aCD38-a-323 compared to Daratumumab (DARA) and control antibody (human IgG1 isotype) with respect to enzymatic activity. Tested is the inhibition or activation of CD38 cyclase or NADase (hydrolase) activity in Daudi cells by aCD38-323 and control antibodies. (A) aCD38-a-323 increases cyclase activity compared to human IgG1 antibody, while DARA decreases the cyclase activity (N=2 experiments). (B) aCD38-a-323 decreases the NADase activity while DARA does not (N=2 experiments).

FIG. 7: relevant protein sequences aCD38-a-306 protein sequences. Each CDR for the heavy (aCD38-a-306-HCDR1 (SEQ ID NO: 9), aCD38-a-306-HCDR2 (SEQ ID NO: 10), and aCD38-a-306-HCDR3 (SEQ ID NO: 11)) and the light (aCD38-a-306-LCDR1 (SEQ ID NO: 13), aCD38-a-306-LCDR2 (SEQ ID NO: 14), and aCD38-a-306-LCDR3 (SEQ ID NO: 15)) chain is indicated separately and, underlined, within the frame sequence of the heavy and light chain antibody as initially identified by the screening procedure (aCD38-a-306-HCDR123 (SEQ ID NO: 12) and aCD38-a-306-LCDR123 (SEQ ID NO: 16), respectively).

FIG. 8: characterization of aCD38-a-306 binding to CD38 expressed in PBMCs, using cells of either Cynomolgus Monkey (A) or human origin (B) at increasing antibody concentration and by restricting the analysis to CD8-positive or CD4-positive cells and comparing with human IgG1 isotype control.

FIG. 10: functional characterization of aCD38-a-306 compared to DARA with respect to cytotoxicity. (A) Both aCD38-a-306 and DARA induce killing of CD38 expressing target cells by antibody-dependent cell-mediated cytotoxicity (ADCC) (B) but, differently from DARA aCD38-a-306 does not induce killing by complement-dependent cytotoxicity (CDC, particularly significant for DARA, as described in the literature).

FIG. 11: relevant protein sequences (A) aCD38-b-329 protein sequences. Each CDR for the heavy (aCD38-b-329-HCDR1 (SEQ ID NO: 17), aCD38-b-329-HCDR2 (SEQ ID NO: 18), and aCD38-b-329-HCDR3 (SEQ ID NO: 19)) and the light (aCD38-b-329-LCDR1 (SEQ ID NO: 21), aCD38-b-329-LCDR2 (SEQ ID NO: 22), and aCD38-b-329-LCDR3 (SEQ ID NO: 23)) chain is indicated separately and, underlined, within the frame sequence of the heavy and light chain antibody as initially identified by the screening procedure (aCD38-b-329-HCDR123 (SEQ ID NO: 20) and aCD38-b-329-HCDR123 (SEQ ID NO: 24), respectively). The DG motif (double underlined) is indicate as hotspot for isomerization and degradation of antibodies (Sydow J et al. 2014) and may be mutated for providing alternative anti-CD38 antibodies having any, and possibly all, binding and functional properties of aCD38-b-329. (B) sequence of human CD38 (Uniprot code P28907) (SEQ ID NO: 47) in which different boxes identify cytoplasmic domain, transmembrane domain, and, within the extracellular domain, the position of aCD38-b-329 major epitope as preliminarily identified (aCD38-b-ep) compared to the one of Daratumumab epitope (DARA, as identified and disclosed in WO2006099875 being formed by two human CD38 regions, here indicated as DARAep-a and DARAep-b).

FIG. 13: functional characterization of aCD38-b-329 compared to Daratumumab (DARA) or negative control antibodies (anti-human CD3 or human IgG1 isotype), in cell-based models independently from the administration of any further tumor targeting antibody. (A) aCD38-b-329 increases the percentage of TCR-mediated CD4 and CD8 T cell proliferation, as indicated in each graph. (IgG1 and each of anti-CD38 antibodies were tested at 10-5-2.5 µg/ml; anti-CD3 is tested at 0.1 µg/ml). (B) aCD38-b-329 increases the secretion of selected cytokines by TCR-activated CD4/CD8 T cells (similar pattern in 5 out of 5 donors tested).

FIG. 14: functional characterization of aCD38-b-329 compared to DARA with respect to cytotoxicity. (A) This direct antibody-mediated killing effect is accompanied by antibody-dependent cell-mediated cytotoxicity (ADCC) as with Daratumumab (DARA). The data also suggest that this antibody exhibits reduced complement dependent cytotoxicity (CDC) compared to DARA. (B) Moreover, targets cell killing, as determined in Daudi cells, is strongly induced by antibody cross-linking when aCD38-b-329 is compared to DARA, whose activity is poorly increased by antibody cross-linking.

FIG. 15: functional characterization of aCD38-b-329 (administered at 10 mg/kg) with respect to animal survival in two cancer model based on the intra-venous administration of Daudi Cells (A) and Ramos cells (B) over the indicated number of days. The treatment with aCD38-b-329 increases animal survival when compared to negative control. In the Daubi model aCD38-b-329 also increases survival when compared to Daratumumab (DARA).

FIG. 16: relevant protein sequences (A) aCD38-b-348 protein sequences. Each CDR for the heavy (aCD38-b-348-HCDR1 (SEQ ID NO: 25), aCD38-b-348-HCDR2 (SEQ ID NO: 26), and aCD38-b-348-HCDR3 (SEQ ID NO: 27)) and the light (aCD38-b-348-LCDR1 (SEQ ID NO: 29), aCD38-b-348-LCDR2 (SEQ ID NO: 30), and aCD38-b-348-LCDR3 (SEQ ID NO: 31)) chain is indicated separately and, underlined, within the frame sequence of the heavy and light chain antibody as initially identified by the screening procedure (aCD38-b-348-HCDR123 (SEQ ID NO: 28) and aCD38-b-348-HCDR123 (SEQ ID NO: 32), respectively). The DG motif (double underlined) is indicate as hotspot for isomerization and degradation of antibodies (Sydow J et al. 2014) and may be mutated for providing alternative anti-CD38 antibodies having any, and possibly all, binding and functional properties of aCD38-b-348. (B) sequence of human CD38 (Uniprot code P28907) (SEQ ID NO: 47) in which different boxes identify cytoplasmic domain, transmembrane domain, and, within the extracellular domain, the position of aCD38-b-348 major epitope as preliminarily identified (aCD38-b-ep) compared to the one of Daratumumab epitope (DARA, as identified and disclosed in WO2006099875 being formed by two human CD38 regions, here indicated as DARAep-a and DARAep-b).

FIG. 17: characterization of aCD38-b-348 binding to CD38 expressed in PBMCs, using cells of either Cynomolgus Monkey (A) or human origin (B) at increasing antibody concentration and by restricting the analysis to CD8-positive or CD4-positive cells and comparing with either human IgG1 isotype control, Daratumumab (DARA), or in absence of a primary antibody.

FIG. 18: functional characterization of aCD38-b-348 compared to Daratumumab (DARA) or negative control antibodies (anti-human CD3 or human IgG1 isotype), in cell-based models independently from the administration of any further tumor targeting antibody. (A) aCD38-b-348 increases the percentage of TCR-mediated CD4 and CD8 T cell proliferation, as indicated in each graph. (IgG1 and each of anti-CD38 antibodies were tested at 10-5-2.5 µg/ml; anti-CD3 is tested at 0.1 µg/ml). (B) aCD38-b-348 increases NK proliferation and activation in PBMC-MDA-MB-231 co-culture (ratio 100:1). The percentage of proliferating CD56-positive and of CD56-positive, CD137-positive NK cells is indicated in each graph. (C) aCD38-b-348 increases the secretion of selected cytokines by TCR-activated CD4/CD8 T cells (similar pattern in 5 out of 5 donors tested).

FIG. 19: functional characterization of aCD38-b-348 compared to DARA with respect to cytotoxicity. (A) Both aCD38-b-348 and DARA induce killing of Regulatory T cells at 1 µg/ml and at 10 µg/ml by inducing phagocytosis of CD38-positive regulatory T cells. (B) This direct antibody-mediated killing effect is accompanied by antibody-dependent cell-mediated cytotoxicity (ADCC) as in Daratumumab (DARA) but, differently from DARA, by lower complement-dependent cytotoxicity (CDC, particularly significant for DARA, as described in the literature). (C) Moreover, targets cell killing, as determined in Daudi cells, is strongly induced by antibody cross-linking when aCD38-b-348 is compared to DARA, whose activity is poorly increased by antibody cross-linking.

FIG. 20: functional characterization of aCD38-b-348 (administered at 10 mg/kg) with respect to animal survival in two cancer model based on intra-venous administration of Daudi Cells (A) and Ramos cells (B) over the indicated number of days. The treatment with aCD38-b-348 increases animal survival not only when compared to negative control but also when compared to Daratumumab (DARA).

FIG. 21: relevant protein sequences (A) aCD38-a-327 protein sequences. Each CDR for the heavy (aCD38-a-327-HCDR1 (SEQ ID NO: 33), aCD38-a-327-HCDR2 (SEQ ID NO: 34), and aCD38-a-327-HCDR3 (SEQ ID NO: 35)) and the light (aCD38-a-327-LCDR1 (SEQ ID NO: 37), aCD38-a-327-LCDR2 (SEQ ID NO: 38), and aCD38-a-327-LCDR3 (SEQ ID NO: 39)) chain is indicated separately and, underlined, within the frame sequence of the heavy and light chain antibody as initially identified by the screening procedure (aCD38-a-327-HCDR123 (SEQ ID NO: 36) and aCD38-a-327-LCDR123 (SEQ ID NO: 40), respectively) (B) sequence of human CD38 (Uniprot code P28907) (SEQ ID NO: 47) in which different boxes identify cytoplasmic domain, transmembrane domain, and, within the extracellular domain, the position of the aCD38-a-327 major epitopes as preliminarily identified, identified as (aCD38ep-a and aCD38ep-b) compared to the one of Daratumumab epitope (DARA, as identified and disclosed in WO2006099875 being formed by two human CD38 regions, here indicated as DARAep-a and DARAep-b).

FIG. 22: characterization of aCD38-a-327 binding to CD38 expressed in human cell lines using human lymphoma cell lines, Daudi and Raji, expressing CD38, at increasing antibody concentration and comparing with human IgG1 isotype control.

FIG. 23: functional characterization of aCD38-a-327 compared to DARA with respect to cytotoxicity. (A) Both aCD38-a-327 and DARA induce killing of CD38 expressing Daudi cells by antibody-dependent cell-mediated cytotoxicity (ADCC). (B) Further, Daratumumab (DARA) but not aCD38-a-327 induces complement dependent cytotoxicity (CDC), CDC is particularly significant for DARA, as described in the literature. (C) and (D) Moreover, targets cell killing, as determined in Daudi cells, is not induced by antibody cross-linking when aCD38-a-327 is compared to DARA whose activity is also poorly increased by antibody cross-linking.

FIG. 24: functional characterization of aCD38-a-327 compared to Daratumumab (DARA) and control antibody (human IgG1 isotype) with respect to enzymatic activity. Tested is the inhibition or activation of CD38 cyclase or NADase (hydrolase) activity in Jurkat cells by aCD38-327 and control antibodies. (A) aCD38-a-327 moderately inhibits cyclase activity (about 20%) compared to human IgG1 antibody, while DARA strongly decreases the cyclase activity (about 70% inhibition) (N=2 experiments). (B) aCD38- a-327 does not interfere with NADase activity while DARA increases the NADase activity (about 30% increase)(N=2 experiments).

Figure 25:
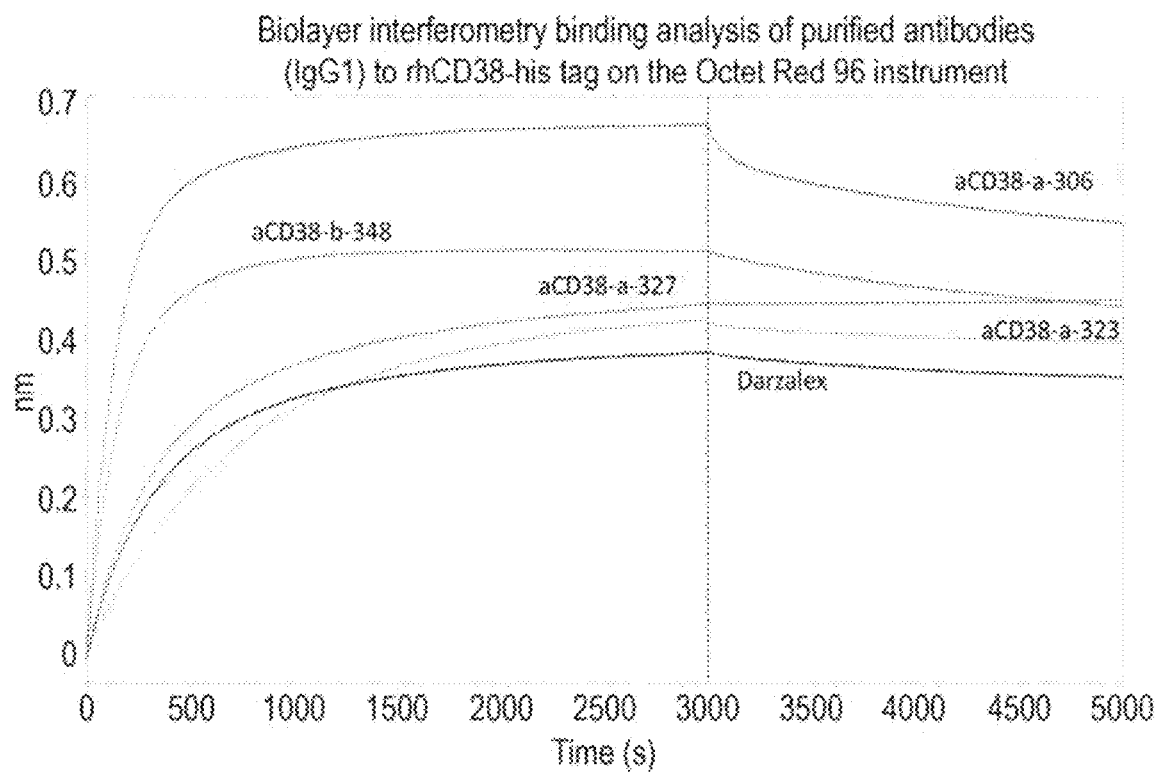

FIG. 25: shows the binding of anti-CD38 antibodies aCD38-b-348, aCD38-a-323 and aCD38-a-306 and aCD38-a-327 as compared to daratumumab to recombinant human CD38 his tagged measured by biolayer interferometry on the Octet Red 96 instrument. 4.2 nM of rhCD38-his was loaded to the Ni NTA biosensor followed by 7 nM of antibody and then let them to dissociate in Kinetics Buffer.

Figure 26:
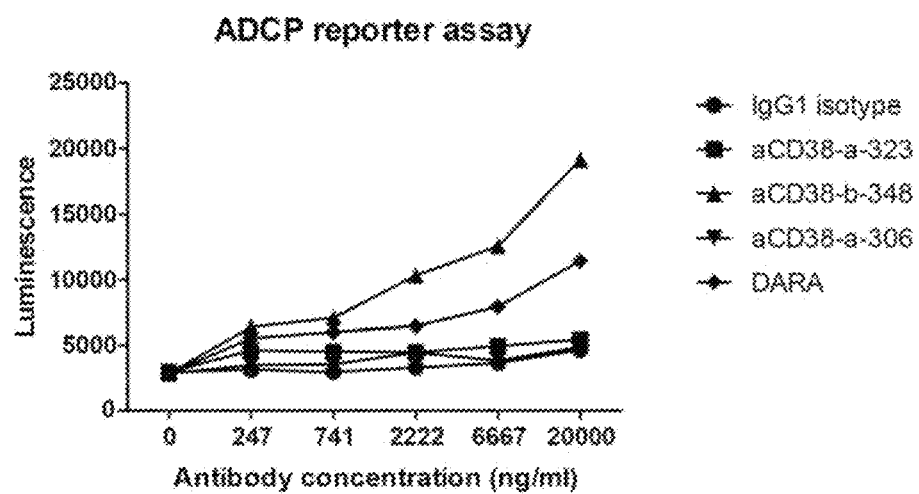

FIG. 26: functional characterization of aCD38-b-348, aCD38-a-323 and aCD38-a-306 compared to DARA with respect to cytotoxicity. aCD38-b-348 shows ADCP activity as measured using a NFAT report assay in Jurkat cells.

FIG. 27: Functional characterization of aCD38-b-348, aCD38-a-323, aCD38-a-306 and aCD38-a-327 compared to Daratumumab and human IgG1 isotype control with respect to enzymatic activity. Tested is the inhibition or activation of CD38 cyclase or NADase (hydrolase) activity in Jurkat cells by aCD38-b-348, aCD38-a-323, aCD38-a-306 and aCD38-a-327 and control antibodies. (A) aCD38-a-323 induces cyclase activity compared to human IgG1 antibody, while aCD38-b-348 (p=0.34), aCD38-a-306 (p=0.07), aCD38-a-327 (p=0.12), and DARA decrease the cyclase activity. Hence aCD38-a-306 shows a trend of inhibition (p=0.07), while the minor inhibition observed for aCD38-b-348 and aCD38-a-327 were not statistically significant. (B) aCD38-a-323 and aCD38-a-306 decrease the NADase activity while aCD38-b-348, aCD38-a-327 and DARA do not. The results in FIG. 27 for aCD38-a-327 confirm the results of FIG. 24; FIG. 24 presents data from only 1 experiment (n=1). FIG. 27 presents data as average of 3 independent experiments (n=3).

Figure 28:
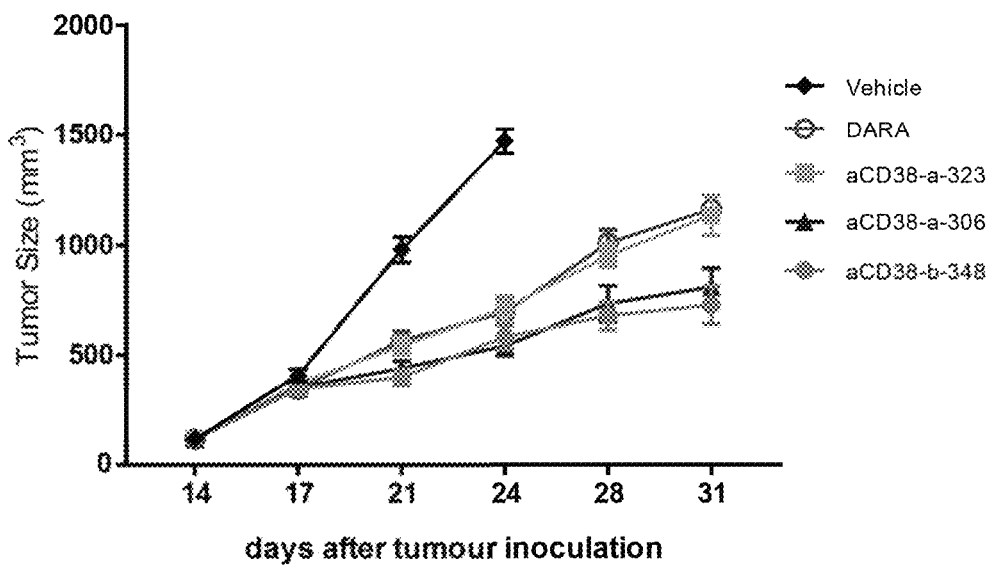

FIG. 28: Characterization of aCD38-b-348, aCD38-a-323 and aCD38-a-306 (administered at 10 mg/kg) with respect to animal survival in an in vivo solid tumor cancer model based over the indicated number of days. The treatment with aCD38-b-348 and aCD38-a-306 increased animal survival not only when compared to negative control but also when compared to Daratumumab (DARA).

Figure 29:
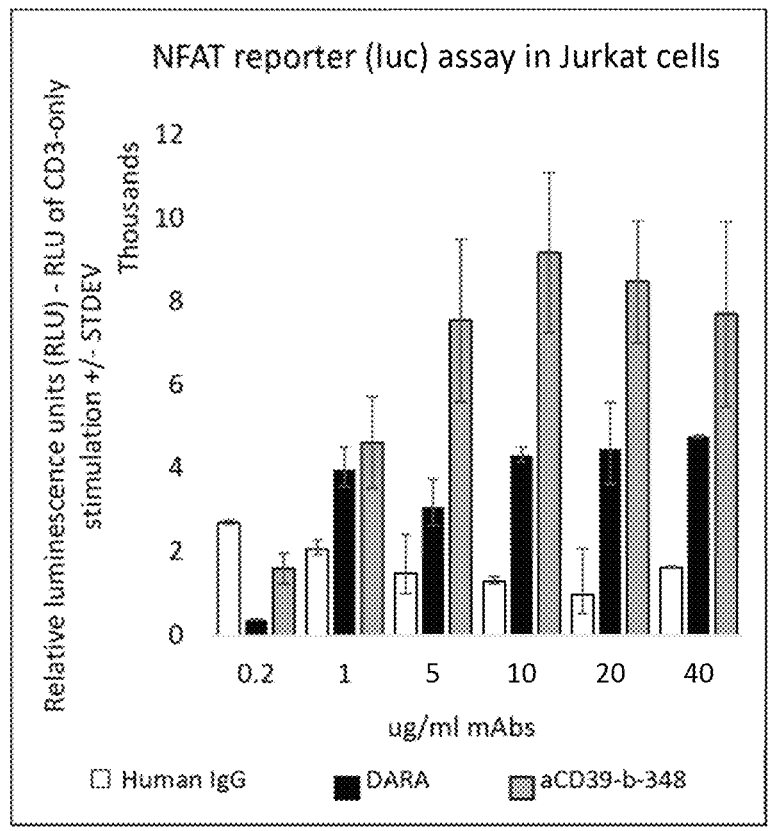
Figure 30A:
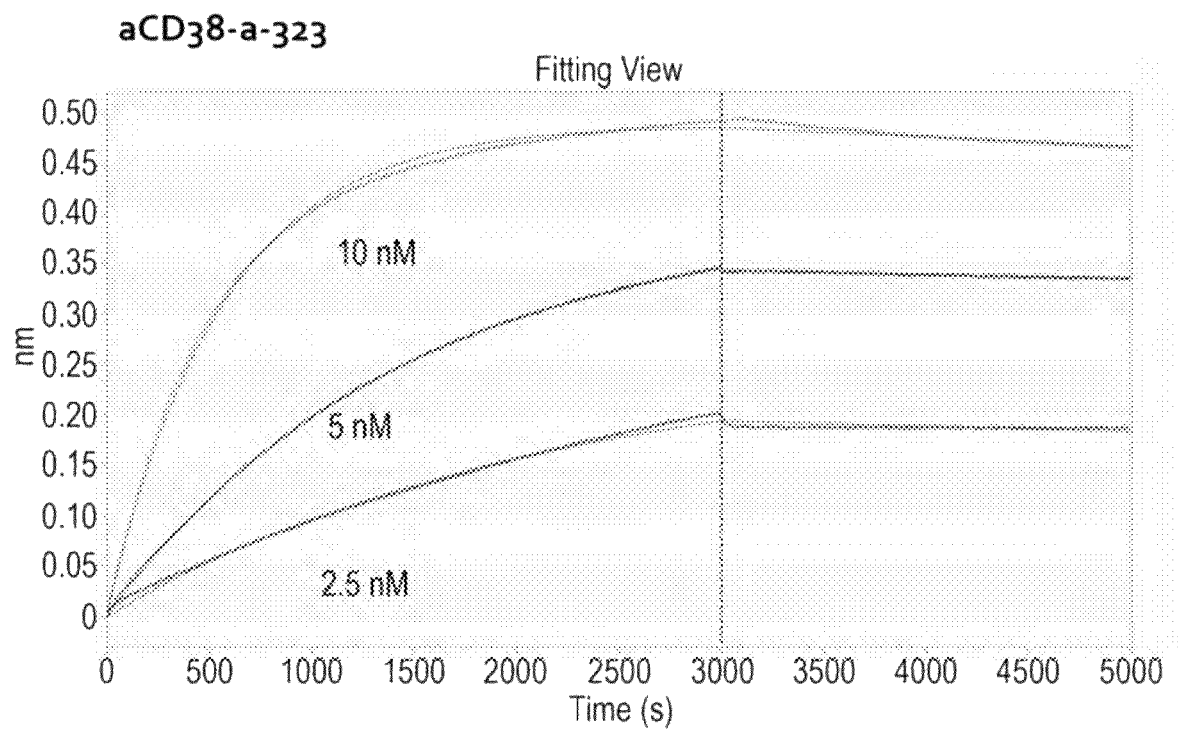
Figure 30B:
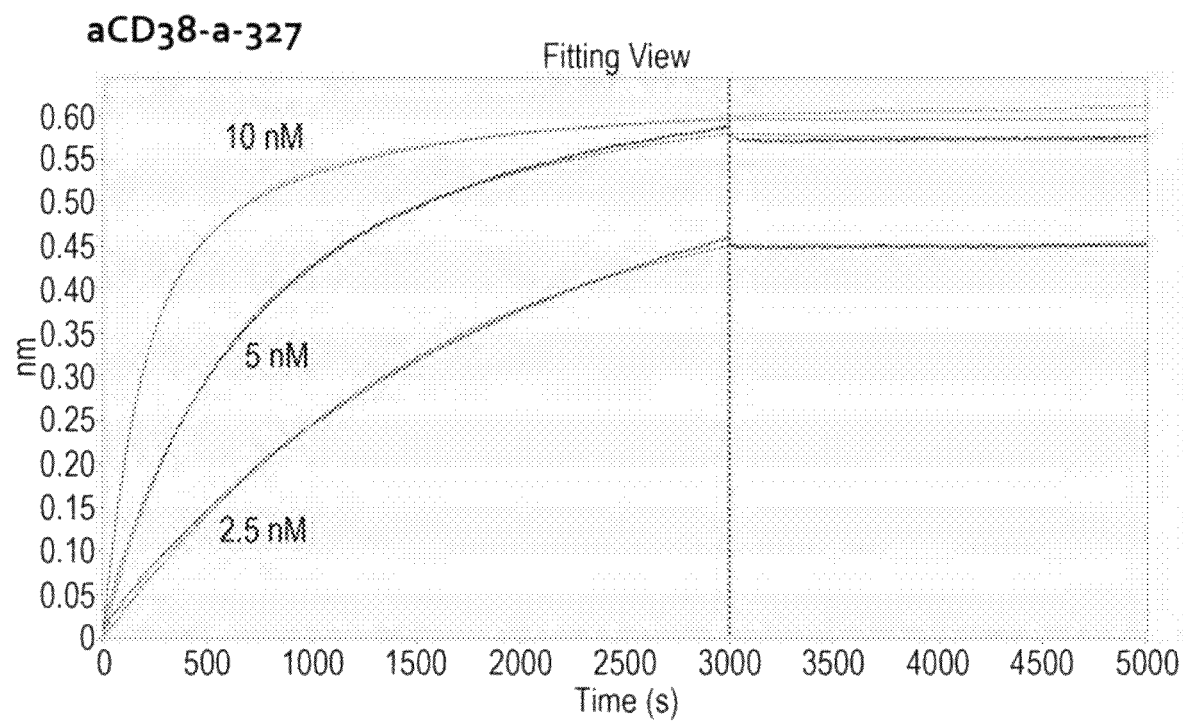
Figure 30C:
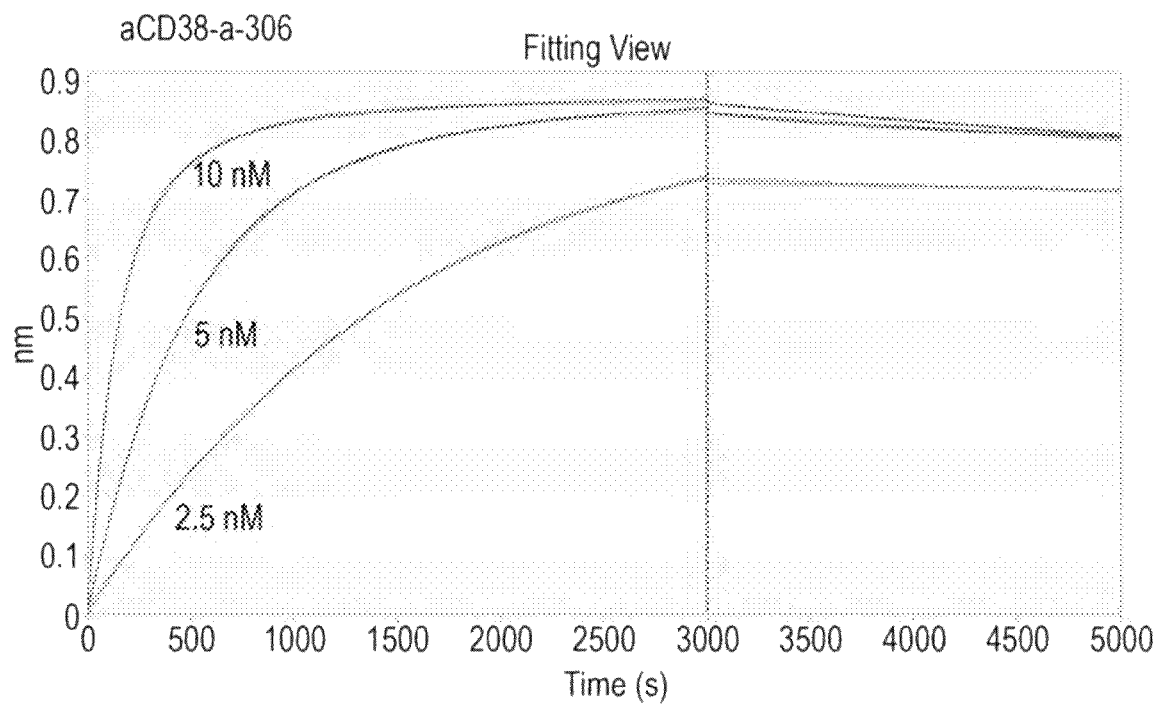
Figure 30D:
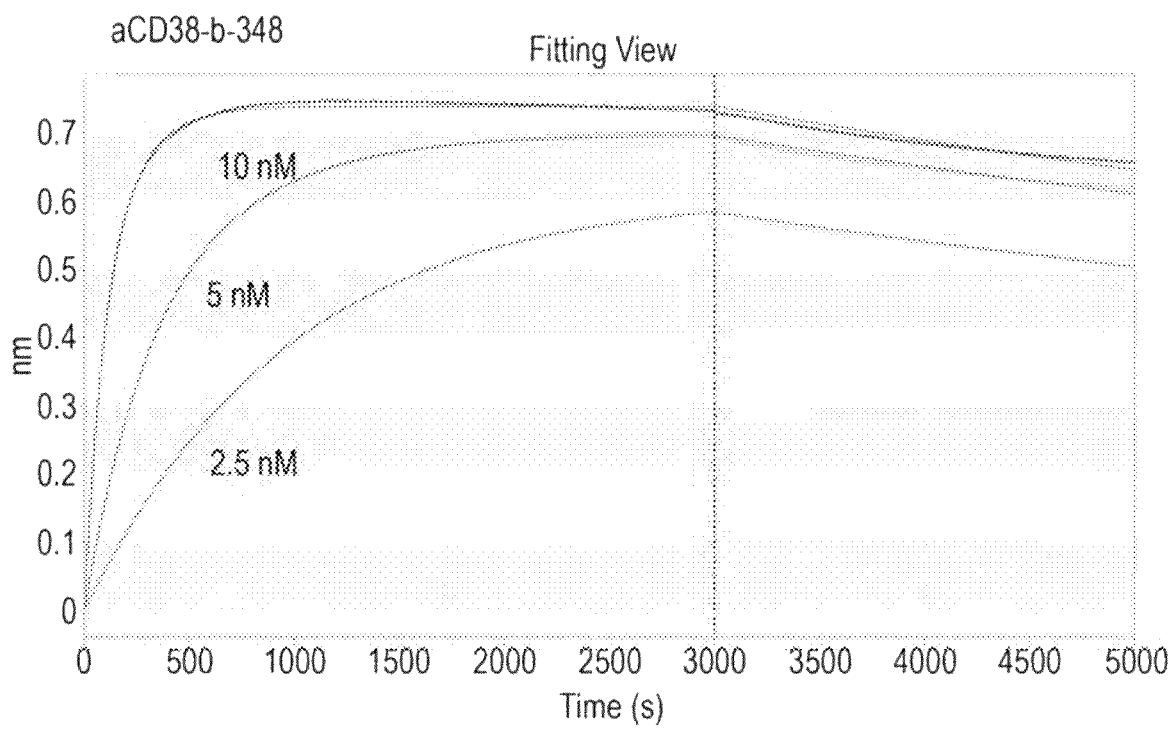
Figure 30E:
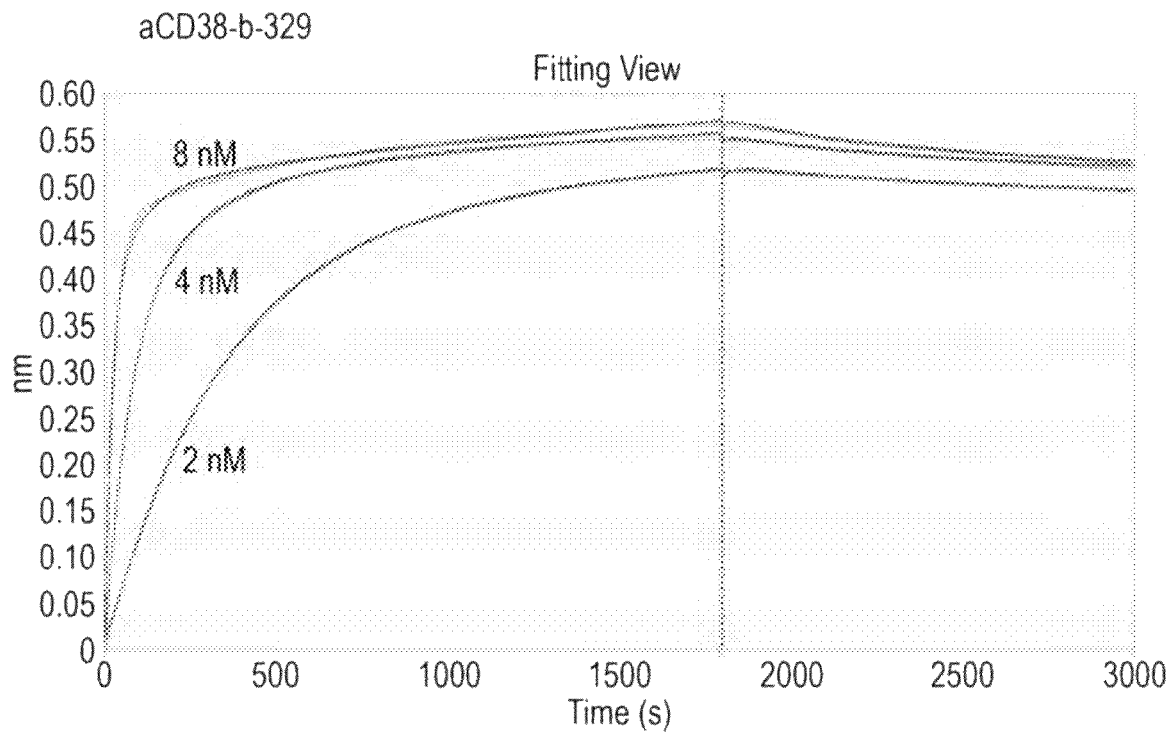
Figure 30F:
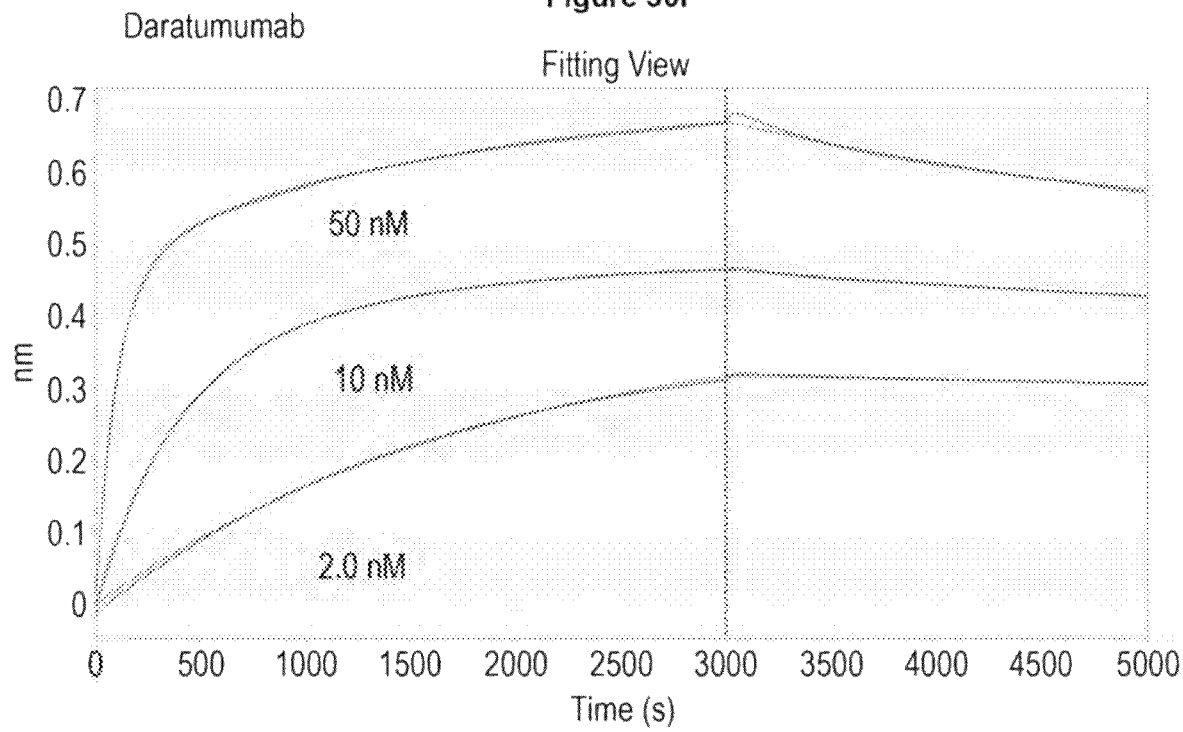

FIG. 29: functional characterization of aCD38-b-348, compared to Daratumumab (DARA) or negative control antibodies (human IgG1 isotype), in a NFAT signalling luc_reporter assay in Jurkat cells. The NFAT signalling (measured as Relative luminescence units (RLU)) of the antibody is at least 30% higher than that of daratumumab, when the cells are stimulated with antibody concentrations between 10 and 20 ug/ml and when the RLU of CD3-only stimulation is used as baseline of assay (RLU of CD3-only conditions is subtracted from the other conditions).

FIG. 30: shows the binding of anti-CD38 antibodies aCD38-a-323 (FIG. 30A), aCD38-a-327 (FIG. 30B), aCD38-a-306 (FIG. 30C) aCD38-b-348 (FIG. 30D) and aCD38-b-329 (FIG. 30E) as compared to daratumumab (FIG. 30F) to recombinant human CD38 his tagged measured by biolayer interferometry on the Octet Red 96 instrument. 4.2 nM of rhCD38-his was loaded to the Ni-NTA biosensor followed by varying concentrations of antibody (as shown in the Figures) and then let them to dissociate in Kinetics Buffer.

FIG. 31: shows the CDC of aCD38-b-348 and aCD38-a-327 compared to Dara and human IgG1 isotype control antibody in Raji cells with 10% complement. aCD38-b-348 exhibits reduced CDC compared to Dara and aCD38-a-327 exhibits no CDC.

FIG. 32: Low dose anti-CD38 antibody aCD38-b-348 increases T cell activation in non-human primates. aCD38-b-348 was administered at a dose of 0.03 mg/kg to cynomolgus monkeys and T cell activation was assessed.

FIG. 33: Relevant heavy and light chain protein sequences of variant aCD38-b-329 antibodies A) aCD38-b-329-m6 and B) aCD38-b-329-m7. Each CDR for the heavy and the light chain is underlined, within the frame sequence, aCD38-b-329-m6-HCDR123 (SEQ ID NO: 20) and aCD38-b-329-m6-LCDR123 (SEQ ID NO: 62), respectively for aCD38-b-329-m6, and aCD38-b-329-m7-HCDR123 (SEQ ID NO: 20) and aCD38-b-329-m7-LCDR123 (SEQ ID NO: 63), respectively for aCD38-b-329-m7.

Figure 34:
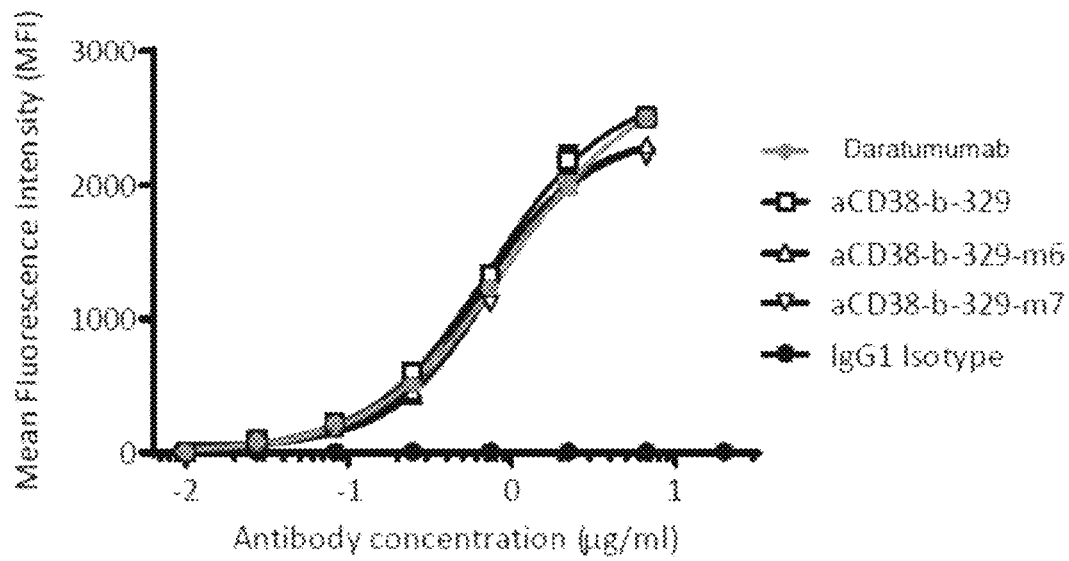

FIG. 34: Binding of variant sequences to Daudi cells, in comparison with Dara and IgG1 control. Binding to CD38 expression human cell line (Daudi) was examined by adding anti-CD38 primary antibodies at 20 μg/mL followed by a semi-log dilution series (7 points) followed by staining with a secondary antibody. aCD38-b-329 variants show similar binding to Daudi cells as the parental aCD38-b-329 and as DARA.

Figure 35:
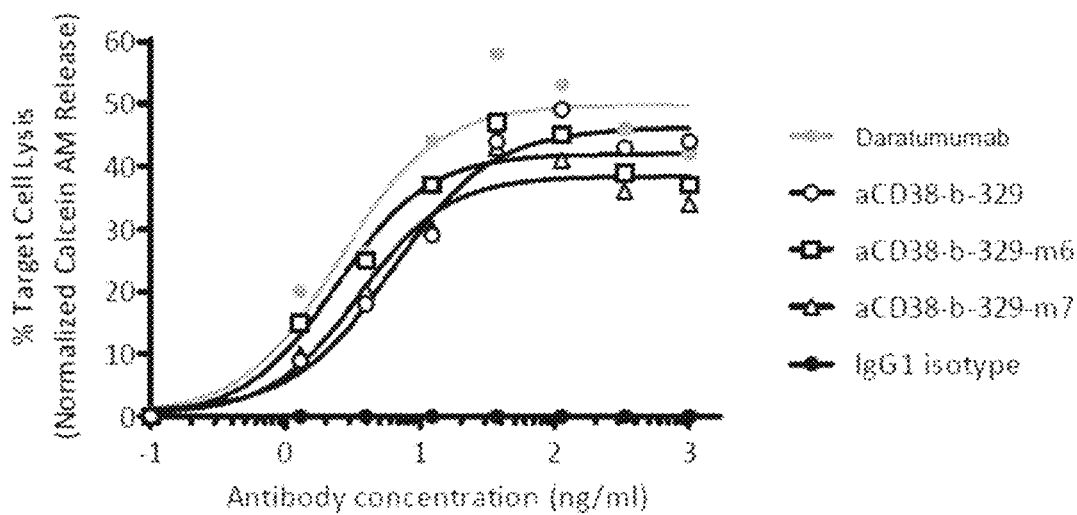

FIG. 35: Functional characterization of aCD38-b-329 and its variant sequences compared to DARA with respect to cytotoxicity. aCD38-b-329 and its variant sequences as well as DARA induce killing of CD38+ cell line (Daudi) by antibody-dependent cell-mediated cytotoxicity (ADCC) with no detectable differences in the activity (EC50 or maximum lysis).

FIG. 36: Relevant heavy and light chain protein sequences of variant aCD38-b-348 antibodies A) aCD38-b-348-m1, B) aCD38-b-348-m2, C) aCD38-b-348-m3 and D) aCD38-b-348-m4. Each CDR for the heavy and the light chain is underlined, within the frame sequence, aCD38-b-348-m1-HCDR123 (SEQ ID NO: 28) and aCD38-b-348-m1-LCDR123 (SEQ ID NO: 58), respectively for aCD38-b-348-m1, aCD38-b-348-m2-HCDR123 (SEQ ID NO: 28) and aCD38-b-348-m2-LCDR123 (SEQ ID NO: 59), respectively for aCD38-b-348-m2, aCD38-b-348-m3-HCDR123 (SEQ ID NO: 28) and aCD38-b-348-m3-LCDR123 (SEQ ID NO: 60), respectively for aCD38-b-348-m3, and aCD38-b-348-m4-HCDR123 (SEQ ID NO: 28) and aCD38-b-348-m4-LCDR123 (SEQ ID NO: 61), respectively for aCD38-b-348-m4.

Figure 37:
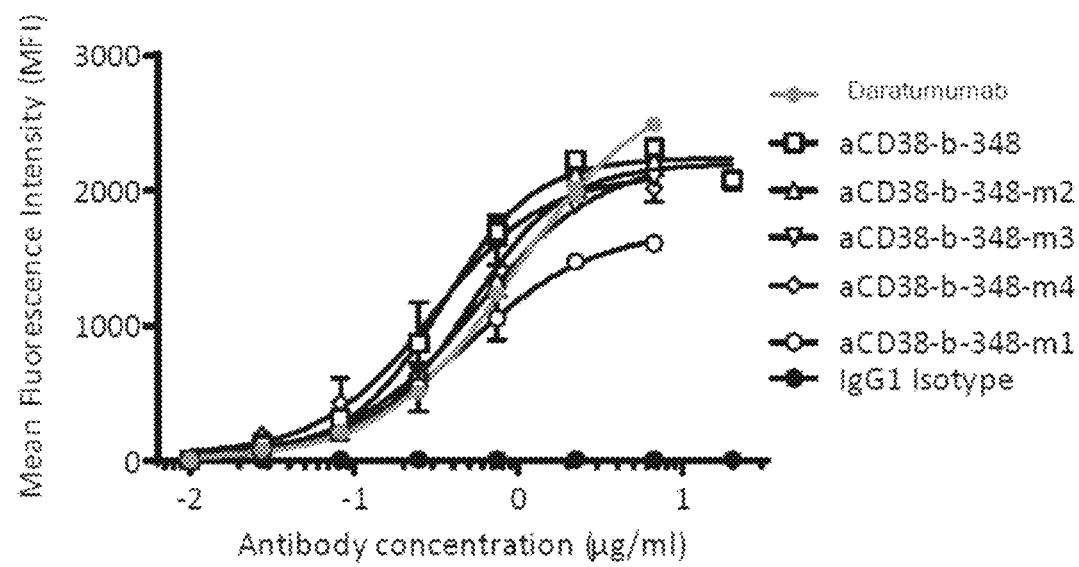

FIG. 37: Binding of variant sequences to Daudi cells, in comparison with Dara and IgG1 control. Binding to CD38 expression human cell line (Daudi) was examined by adding anti-CD38 primary antibodies at 20 μg/mL followed by a semi-log dilution series (7 points) followed by staining with a secondary antibody. aCD38-b-348 variants show similar binding to Daudi cells as the parental aCD38-b-348 and as DARA.

Figure 38:
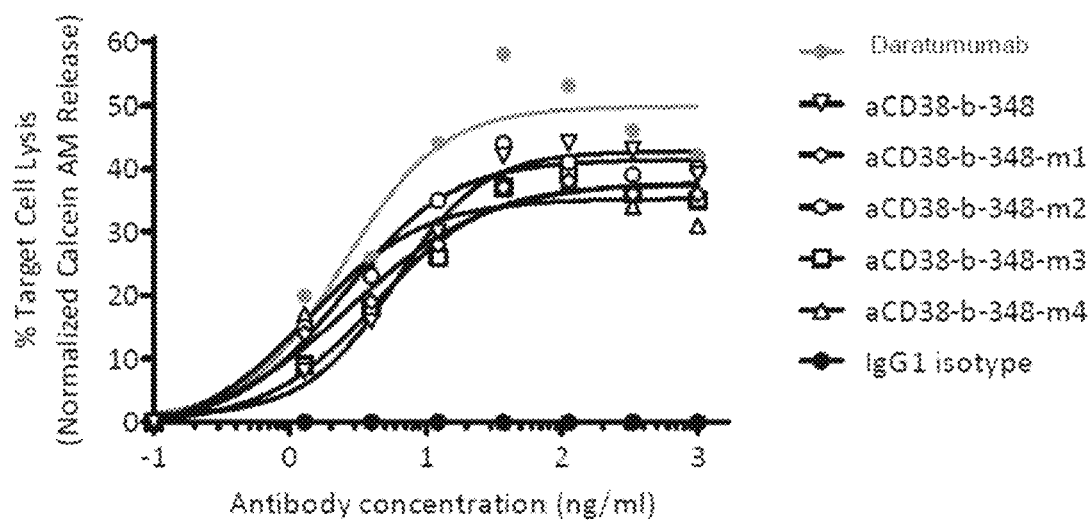

FIG. 38: Functional characterization of aCD38-b-348 and its variant sequences compared to DARA with respect to cytotoxicity. aCD38-b-348 and its variant sequences as well as DARA induce killing of CD38+ cell line (Daudi) by antibody-dependent cell-mediated cytotoxicity (ADCC) with no detectable differences in the activity (EC50 or maximum lysis).

FIG. 39: Functional characterization of aCD38-b-329 and variants aCD38-b-329-m6 and aCD38-b-329-m7 (all administered at 10 mg/kg), as well as aCD38-b-348 and its variant aCD38-b-348-m2 with respect to animal survival in two cancer models based on the intra-venous administration of Raji Cells (A) and Ramos cells (B) over the indicated number of days. The treatment with aCD38-b-329 and with aCD38-b-348-m2 increases animal survival when compared to negative control in both models. The treatment with aCD38-b-348, as well as with the variants aCD38-b-329-m6 and a-CD38-b-329-m7 increases animal survival when compared to negative control as well as when compared to Daratumumab (DARA) in both models.

Figure 40:
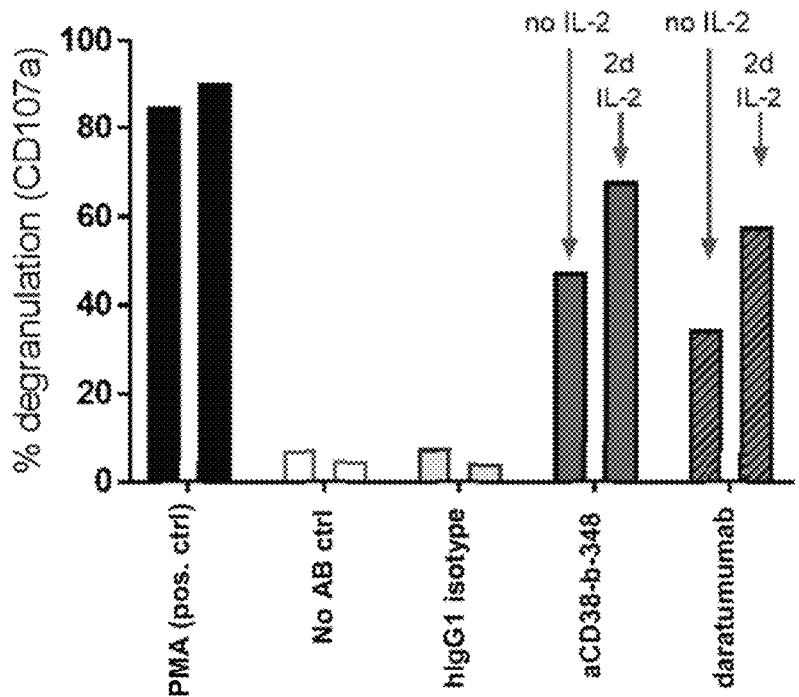

FIG. 40: Degranulation of unactivated or IL-2 pre-activated human NK cells by aCD38-b-348 compared to hIgG1 isotype, daratumumab and controls.

Figure 41:
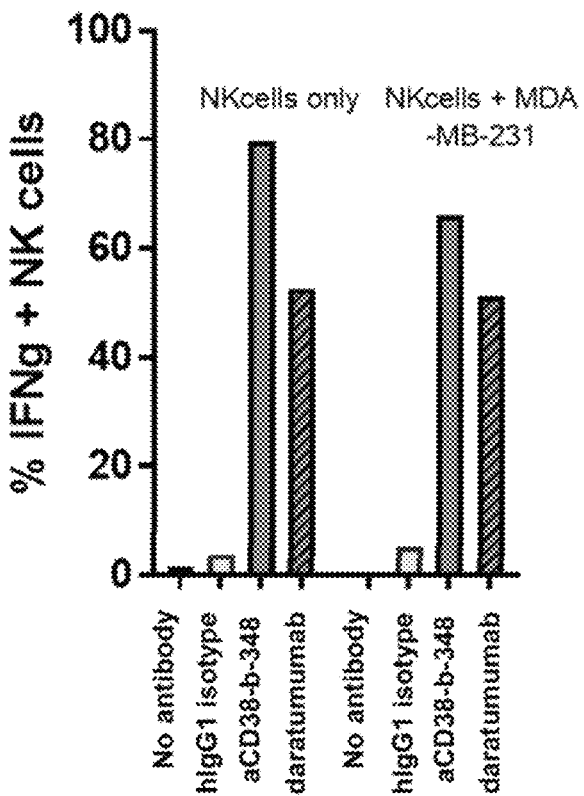

FIG. 41: IFNγ production of NK cells in the presence or absence of a tumor target (MDA-MB-231 cells) by aCD38-b-348 compared to hIgG1 isotype and daratumumab.

FIG. 42: NK cell proliferation of human NK cells in the presence of MDA-MB-231 tumor cells by aCD38-b-348 compared to hIgG1 isotype and daratumumab. A) Antibodies tested at 10 μg/ml. B) dose titration of antibodies from 0.4 μg/ml to 10 μg/ml tested.

Figure 43:
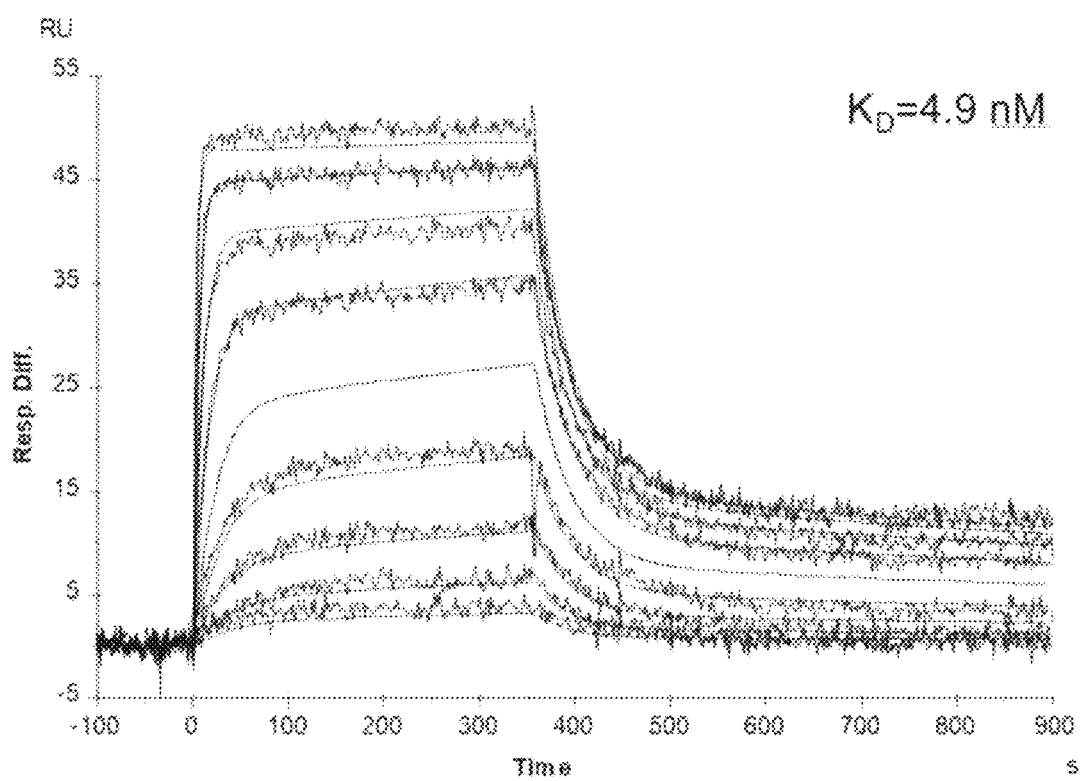

FIG. 43: SPR based analysis of purified antibodies (IgG1) to rhCD38 his tagged on the Biacore 2000. A) aCD38-a-323, B) aCD38-a-327, C) aCD38-b-348, D) aCD38-b-348-m1, E) aCD38-b-348-m2, F) aCD38-b-348m3, G) aCD38-b-348-m4, H) aCD38-a-306, I) aCD38-b-329, J) aCD38-b-329-m6, and K) aCD38-b-329-m7

FIG. 44: Competition Assays in the Octet with aCD38-b-329, aCD38-b-348, aCD38-a-327 and daratumumab. Binding of a first antibody to the immobilized rhCD38 is followed by either first antibody again (as control) or a second Antibody. Non-competitor antibodies will bind to CD38 in the presence of the other antibody (FIGS. 43 A, B and C) while antibodies binding the same epitope will compete, and no additional binding will be observed (Figure D).

DETAILED DESCRIPTION OF CERTAIN EMBODIMENTS

Below are provided certain definitions of terms, technical means, and embodiments used herein, many or most of which confirm common understanding of those skilled in the art.

Administration: As used herein, the term "administration" refers to the administration of a composition to a subject. Administration to an animal subject (e.g., to a human) may be by any appropriate route. For example, in some embodiments, administration may be bronchial (including by bronchial instillation), buccal, enteral, intra-arterial, intra-dermal, intra-gastric, intra-medullary, intra-muscular, intra-nasal, intra-peritoneal, intra-thecal, intra-venous, intra-ventricular, within a specific organ or tissue (e.g. intra-hepatic, intra-tumoral, peri-tumoral, etc.), mucosal, nasal, oral, rectal, subcutaneous, sublingual, topical, tracheal (including by intra-tracheal instillation), transdermal, vaginal and vitreal. The administration may involve intermittent dosing. Alternatively, administration may involve continuous dosing (e.g., perfusion) for at least a selected period of time. As is known in the art, antibody therapy is commonly administered parenterally, e.g. by intravenous, subcutaneous, or intratumoral injection (e.g., particularly when high doses within a tumor are desired).

Agent: The term "agent" as used herein may refer to a compound or entity of any chemical class including, for example, polypeptides, nucleic acids, saccharides, small molecules, metals, or combinations thereof. Specific embodiments of agents that may be utilized in accordance with the present invention include small molecules, drugs, hormones, antibodies, antibody fragments, aptamers, nucleic acids (e.g., siRNAs, shRNAs, antisense oligonucleotides, ribozymes), peptides, peptide mimetics, etc. An agent may be or comprise a polymer.

Antibody: As used herein, the term "antibody" refers to a polypeptide that includes canonical immunoglobulin sequence elements sufficient to confer specific binding to a particular target antigen, such as CD38, human CD38 in particular, and human CD38 extracellular. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long), an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally produced antibodies are also glycosylated, typically on the CH2 domain, and each domain has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3; as understood in the art, for example determined according to Kabat numbering scheme) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen-binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification that can improve the developability of the antibody (Jarasch A et al., 2015).

In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal or oligoclonal, that is generated as a panel of antibodies, each associated to a single antibody sequence and binding a more or less distinct epitopes within an antigen (such as different epitopes within human CD38 extracellular domain that are associated to different reference anti-CD38 antibodies).

Polyclonal or oligoclonal antibodies can be provided in a single preparation for medical uses as described in the literature (Kearns J D et al., 2015). In some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation, for instance as antigen-binding fragments as defined below. For example, an antibody utilized in accordance with the present invention is in a format selected from, but not limited to, intact IgG, IgE and IgM, bi- or multi-specific antibodies (e.g., Zybodies®, etc.), single chain variable domains (scFv), polypeptide-Fc fusions, Fabs, cameloid antibodies, heavy-chain shark antibody (IgNAR), masked antibodies (e.g., Probodies®), or fusion proteins with polypeptides that allow expression and exposure on the cell surface (as scFv within constructs for obtaining artificial T cell receptors that are used to graft the specificity of a monoclonal antibody onto a T cell). A masked antibody can comprise a blocking or "mask" peptide that specifically binds to the antigen binding surface of the antibody and interferes with the antibody's antigen binding. The mask peptide is linked to the antibody by a cleavable linker (e.g. by a protease). Selective cleavage of the linker in the desired environment, e.g. in the tumour environment, allows the masking/blocking peptide to dissociate, enabling antigen binding to occur in the tumour, and thereby limiting potential toxicity issues. In some embodiments, an antibody may lack a covalent modification (e.g., attachment of a glycan) that it would have if produced naturally. Alternatively, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]).

Antigen: The term "antigen", as used herein, refers to an agent that elicits an immune response and/or that binds to a T cell receptor (e.g., when presented by an MHC molecule) and/or B cell receptor. An antigen that elicits a humoral response involve the production of antigen-specific antibodies or, as shown in the Examples for CD38 extracellular domain, can be used for screening antibody libraries and identifying candidate antibody sequences to be further characterized.

Antigen-binding Fragment: As used herein, the term "Antigen-binding Fragment" encompasses agents that include or comprise one or more portions of an antibody as described herein sufficient to confer on the antigen-binding fragment and ability to specifically bind to the Antigen targeted by the antibody. For example, in some embodiments, the term encompasses any polypeptide or polypeptide complex that includes immunoglobulin structural elements sufficient to confer specific binding. Exemplary antigen-binding fragments include, but are not limited to Small Modular ImmunoPharmaceuticals ("SMIPs™"), single chain antibodies, cameloid antibodies, single domain antibodies (e.g., shark single domain antibodies), single chain or Tandem diabodies (TandAb®), VHHs, Anticalins®, Nanobodies®, minibodies, BiTE®s, ankyrin repeat proteins or DARPINs®, Avimers®, a DART, a TCR-like antibody, Adnectins®, Affilins®, Trans-bodies®, Affibodies®, a TrimerX®, MicroProteins, Centyrins®, CoVX bodies, BiCyclic peptides, Kunitz domain derived antibody constructs, or any other antibody fragments so long as they exhibit the desired biological activity. In some embodiments, the term encompasses other protein structures such as stapled peptides, antibody-like binding peptidomimetics, antibody-like binding scaffold proteins, monobodies, and/or other non-antibody proteins scaffold, for example as reviewed in the literature (Vazquez-Lombardi R et al., 2015). In some embodiments, an antigen-binding fragment is or comprises a polypeptide whose amino acid sequence includes one or more structural elements recognized by those skilled in the art as a complementarity determining region (CDR). In some embodiments an antigen-binding fragment is or comprises a polypeptide whose amino acid sequence includes at least one reference CDR (e.g., at least one heavy chain CDR and/or at least one light chain CDR) that is substantially identical to one found in an anti-CD38 antibody as described herein (e.g., in an aCD38-a-323 amino acid sequence element, an aCD38-a-306 amino acid sequence element, an aCD38-b-329 amino acid sequence element, an aCD38-a-327 amino acid sequence element or an aCD38-b-348 amino acid sequence element), and in particular at least one heavy chain CDR, such as an HCDR3 (e.g., an aCD38-a-323-HCDR3 sequence, an aCD38-a-306-HCDR3 sequence, an aCD38-b-329-HCDR3 sequence, an aCD38-a-327-HCDR3 sequence or an aCD38-b-348-HCDR3 sequence). In some embodiments an antigen-binding fragment is or comprises a polypeptide whose amino acid sequence includes at least one CDR (e.g., at least one heavy chain CDR and/or at least one light chain CDR) that is either identical in sequence or contains a small number (e.g., 1, 2, 3, or 4) more amino acid alterations (e.g., substitutions, additions, or deletions; in many cases, substitutions) relative to such a reference CDR, while maintaining binding to the target of the antibody (e.g., aCD38-a-323, aCD38-a-306, aCD38-b-329, aCD38-a-327 or aCD38-b-348) from which the reference CDR was derived. In some embodiments, an antigen-binding fragment is or comprises a polypeptide or complex thereof that includes all three CDRs (or, in some embodiments, sequences substantially identical thereto) from a heavy or light chain of a reference antibody (e.g., from aCD38-a-323, aCD38-a-306, aCD38-b-329, aCD38-a-327 or aCD38-b-348); in some embodiments, an antigen-binding fragment is or comprises a polypeptide or complex thereof that includes all six CDRs (or, in some embodiments, sequences substantially identical thereto) from a reference antibody (e.g., from aCD38-a-323, aCD38-a-306, aCD38-b-329, aCD38-a-327, or aCD38-b-348). In some embodiments, an antigen-binding fragment is or comprises a polypeptide or complex thereof that includes the heavy and/or light chain variable domains (or, in some embodiments, sequences substantially identical thereto) of a reference antibody (e.g., of aCD38-a-323, aCD38-a-306, aCD38-b-329, aCD38-a-327, or aCD38-b-348). In some embodiments, the term "antigen-binding fragment" encompasses non-peptide and non-protein structures, such as nucleic acid aptamers, for example, RNA aptamers and DNA aptamers. An aptamer is an oligonucleotide (e.g., DNA, RNA, or an analog or derivative thereof) that binds to a particular target, such as a polypeptide. Aptamers are short synthetic single-stranded oligonucleotides that specifically bind to various molecular targets such as small molecules, proteins, nucleic acids, and even cells and tissues. These small nucleic acid molecules can form secondary and tertiary structures capable of specifically binding proteins or other cellular targets, and are essentially a chemical equivalent of antibodies. Aptamers are highly specific, relatively small in size, and non-immunogenic. Aptamers are generally selected from a biopanning method known as SELEX (Systematic Evolution of Ligands by Exponential enrichment) (See for example Ellington et al. Nature. 1990; 346(6287): 818-822; Tuerk et al., Science. 1990; 249(4968):505-510; Ni et al., Curr Med Che 2011; 18(27):4206-14). Methods of generating an aptamer for any given target are well known in the art. Peptide aptamers including affimers are also encompassed. An affimer is a small, highly stable protein engineered to display peptide loops which provide a high affinity binding surface for a specific target protein. It is a protein of low molecular weight, 12-14 kDa, derived from the cysteine protease inhibitor family of cystatins. Affimer proteins are composed of a scaffold, which is a stable protein based on the cystatin protein fold. They display two peptide loops and an N-terminal sequence that can be randomized to bind different target proteins with high affinity and specificity similar to antibodies. Stabilization of the peptide upon the protein scaffold constrains the possible conformations which the peptide may take, thus increasing the binding affinity and specificity compared to libraries of free peptides.

Percent (%) sequence identity: Percent (%) "sequence identity" between two sequences can be determined using those methods known in the art. Sequence identity with respect to a peptide, polypeptide or antibody sequence can be defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, including gapped BLAST, and BLASTp (for proteins), (Altschul S F et al (1997)), or FASTA, using the default parameters.

Biological Sample. As used herein, the terms "biological sample" or "sample" typically refers to a sample obtained or derived from a biological source (e.g., a tissue or organism or cell culture) of interest, as described herein. A source of interest may be an organism, such as an animal or human. The biological sample may comprise biological tissue or fluid.

Cancer. The terms "cancer", "malignancy", "neoplasm", "tumor", "tumour", and "carcinoma", are used interchangeably herein to refer to cells that exhibit relatively abnormal, uncontrolled, and/or autonomous growth, so that they exhibit an aberrant growth phenotype characterized by a significant loss of control of cell proliferation. In general, cells of interest for detection or treatment in the present application include precancerous (e.g., benign), malignant, pre-metastatic, metastatic, and non-metastatic cells. The teachings of the present disclosure may be relevant to any and all cancers. To give but a few, non-limiting examples, in some embodiments, teachings of the present disclosure are applied to one or more cancers such as, for example, hematopoietic cancers including leukemias, lymphomas (Hodgkins and non-Hodgkins), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like. The antibodies of the invention can be used in the treatment of CD38+ expressing tumours.

CD38 Modulating Antibody Agent The term "CD38 Modulating Antibody Agent" is used herein to refer to those CD38 Modulating Antibody Agents (e.g., anti-CD38 antibodies) that demonstrate particular properties as described herein. In many embodiments, desirable CD38 Modulating Antibody Agents as described herein are characterized in that they stimulate immune effector cells and/or modify immune cells function and are cytotoxic towards or induce phagocytosis of CD38 expressing cells (e.g. expressing high levels of CD38) such as immune suppressive cells or tumour cells (e.g., in each case, that express CD38 on their surfaces). In some embodiments, a CD38 Modulating Antibody Agent is characterized by an activity (e.g., level and/or type) reasonably comparable to that of aCD38-a-323, aCD38-a-306, aCD38-b-329, aCD38-a-327, or aCD38-b-348 with respect to immune cells (e.g., when contacted with immune cells, and particularly with immune cells that express CD38) and tumour cells. In some embodiments, a relevant activity is or comprises ADCP, ADCC in absence of CDC, direct killing, depletion of certain CD38-expressing cells (e.g., high-expressing cells), effector immune cell activation, promotion of T cell, B cell or NK cell expansion, modulation of immune cells activity (e.g. repolarization of suppressive macrophages into inflammatory macrophages), skewing of T cell repertoire, etc., and combinations thereof. In some embodiments, CD38 Modulating Antibody Agents are entities or moieties whose presence or level correlates with level and/or activity of CD38, and/or with one or more features or results characteristic of CD38 activity. In some embodiments, an increased level and/or activity is assessed or determined relative to that observed under otherwise comparable conditions in absence of the entity(ies) or moiety(ies). Alternatively or additionally, in some embodiments, an increased level and/or activity is comparable to or greater than that observed under comparable conditions when a reference CD38 Modulating Antibody Agent (e.g., an appropriate reference anti-CD38 antibody, which in many embodiments is a CD38 agonist antibody, such as IB4) is present. In many embodiments, a CD38 Modulating Antibody Agent for use in accordance with the present disclosure is or comprises an entity or moiety that binds, directly or indirectly, to CD38, typically to its extracellular domain. In some embodiments, a CD38 Modulating Antibody Agent is, comprises, or competes for binding to CD38 with an anti-CD38 antibody as exemplified herein, an antigen-binding fragment (e.g., comprising one or more CDRs, all heavy chain CDRs, all light chain CDRs, all CDRs, a heavy chain variable region, a light chain variable region, or both heavy and light chain variable regions) thereof, an affinity matured variant thereof (or an antigen-binding fragment thereof), or any alternative format (e.g., chimeric, humanized, multispecific, alternate isotype, etc.) of any of the foregoing. Alternatively or additionally, in some embodiments, a CD38 Modulating Antibody Agent as described herein may be characterized by one or more features that may be features that are advantageous for screening, manufacturing, (pre-) clinical testing, and/or for identifying relevant epitope within human CD38), and/or for formulation, administration, and/or efficacy in particular contexts (e.g., for cancer therapy), as disclosed herein.

Combination Therapy: As used herein, the term "combination therapy" refers to those situations in which a subject is simultaneously exposed to two or more therapeutic regimens (e.g., two or more therapeutic agents). In some embodiments, two or more agents may be administered simultaneously. Alternatively, such agents may be administered sequentially; otherwise, such agents are administered in overlapping dosing regimens.

Comparable: As used herein, the term "comparable" refers to two or more agents, entities, situations, effects, sets of conditions, etc., that may not be identical to one another but that are sufficiently similar to permit comparison (e.g., by level and/or type of activity) there between so that conclusions may reasonably be drawn based on differences or similarities observed. Such comparable sets of conditions, effects, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, effects, or populations, etc. to be considered comparable.

Comprising: A composition or method described herein as "comprising" one or more named elements or steps is open-ended, meaning that the named elements or steps are essential, but other elements or steps may be added within the scope of the composition or method. It is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method.

Daratumumab: As used herein, the term "daratumumab" includes an antibody having, VH and VL sequences as published in WO2006/099875 and being a human IgG1 monoclonal antibody. For example having variable heavy and light chain sequences comprising the respective sequences as provided below:

```
Heavy Chain:
                                            (SEQ ID NO: 70)
EVQLLESGGGLVQPGGSLRLSCAVSGFTFNSFAMSWVRQAPGKGLEWV

SAISGSGGGTYYADSVKGRFTISRDNSKNTLYLQMNSLRAEDTAVYFC

AKDKILWFGEPVFDYWGQGTLVTVSSASTKGPSVFPLAPSSKSTSGGT

AALGCLVKDYFPEPVTVSWNSGALTSGVHTFPAVLQSSGLYSLSSVVT

VPSSSLGTQTYICNVNHKPSNTKVDKRVEPKSCDKTHTCPPCPAPELL

GGPSVFLFPPKPKDTLMISRTPEVTCVVVDVSHEDPEVKFNWYVDGVE

VHNAKTKPREEQYNSTYRVVSVLTVLHQDWLNGKEYKCKVSNKALPAP

IEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSV

MHEALHNHYTQKSLSLSPGK

Light Chain
                                            (SEQ ID NO: 71)
EIVLTQSPATLSLSPGERATLSCRASQSVSSYLAWYQQKPGQAPRLLI

YDASNRATGIPARFSGSGSGTDFTLTISSLEPEDFAVYYCQQRSNWPP

TFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC
```

Dosage Form: As used herein, the term "dosage form" refers to a physically discrete unit of an active agent (e.g., a therapeutic or diagnostic agent) for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing Regimen: As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length. Alternatively, a dosing regimen comprises a plurality of doses and at least two different time periods separating individual doses. In some embodiments, all doses within a dosing regimen are of the same unit dose amount. Alternatively, different doses within a dosing regimen are of different amounts. In some embodiments, a dosing regimen comprises a first dose in a first dose amount, followed by one or more additional doses in a second dose amount different from the first dose amount. A dosing regimen may comprise a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Epitope: As used herein, the term "epitope" refers to a portion of an antigen that is bound by an antibody or antigen-binding fragment. In some embodiments, where the antigen is a polypeptide, an epitope is conformational in that it is comprised of portions of an antigen that are not covalently contiguous in the antigen but that are near to one another in three-dimensional space when the antigen is in a relevant conformation. For example, for CD38, conformational epitopes are those comprised of amino acid residues that are not contiguous in CD38 extracellular domain; linear epitopes are those comprised of amino acid residues that are contiguous in CD38 extracellular domain. In some embodiments, epitopes utilized in accordance with the present invention are provided by means of reference to those bound by CD38 Modulating Antibody Agents provided herein (e.g., by aCD38-a-323, by aCD38-a-306, by aCD38-a-327 and as defined by aCD38ep-a and aCD38ep-b, by aCD38-b-329 and defined as aCD38-b-ep, or by aCD38-b-348 and defined as aCD38-b-ep). Means for determining the exact sequence and/or particularly amino acid residues of the epitope for aCD38-a-323, aCD38-a-306, aCD38-b-329, aCD38-a-327, or aCD38-b-348, are known in the literature and in the Examples, including competition with peptides, from antigen sequences, binding to CD38 sequence from different species, truncated, and/or mutagenized (e.g. by alanine scanning or other site-directed mutagenesis), phage display-based screening, or (co-)crystallography techniques.

Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. A patient may display one or more symptoms of a disorder or condition, or may have been diagnosed with one or more disorders or conditions (such as cancer, or presence of one or more tumors). In some embodiments, the patient is receiving or has received certain therapy to diagnose and/or to treat such disease, disorder, or condition.

Pharmaceutically Acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Pharmaceutical Composition: As used herein, the term "pharmaceutical composition" refers to a composition in which an active agent is formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. A pharmaceutical compositions may be formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous, intratumoral, or epidural injection as a sterile solution or suspension, or sustained-release formulation; topical application, for example, as a cream, ointment, or a controlled release patch or spray applied to skin, lungs, or oral cavity; intravaginally, intrarectally, sublingually, ocularly, transdermally, nasally, pulmonary, and to other mucosal surfaces.

Solid Tumor. As used herein, the term "solid tumor" refers to an abnormal mass of tissue that usually does not contain cysts or liquid areas. Solid tumors may be benign or malignant. Different types of solid tumors are named for the type of cells that form them. Examples of solid tumors are sarcomas (including cancers arising from transformed cells of mesenchymal origin in tissues such as cancellous bone, cartilage, fat, muscle, vascular, hematopoietic, or fibrous connective tissues), carcinomas (including tumors arising from epithelial cells), melanomas, lymphomas, mesothelioma, neuroblastoma, retinoblastoma, etc. Cancers involving solid tumors include, without limitations, brain cancer, lung cancer, stomach cancer, duodenal cancer, esophagus cancer, breast cancer, colon and rectal cancer, renal cancer, bladder cancer, kidney cancer, pancreatic cancer, prostate cancer, ovarian cancer, melanoma, mouth cancer, sarcoma, eye cancer, thyroid cancer, urethral cancer, vaginal cancer, neck cancer, lymphoma, and the like.

Therapeutically Effective Amount: As used herein, the term "therapeutically effective amount" means an amount (e.g., of an agent or of a pharmaceutical composition) that is sufficient, when administered to a population suffering from or susceptible to a disease and/or condition in accordance with a therapeutic dosing regimen, to treat such disease and/or condition. A therapeutically effective amount is one that reduces the incidence and/or severity of, stabilizes, and/or delays onset of, one or more symptoms of the disease, disorder, and/or condition. Those of ordinary skill in the art will appreciate that a "therapeutically effective amount" does not in fact require successful treatment be achieved in a particular subject.

Treatment: As used herein, the term "treatment" (also "treat" or "treating") refers to any administration of a substance (e.g., a provided CD38 Modulating Antibody Agent, as exemplified by aCD38-a-323, aCD38-a-306, aCD38-b-329, aCD38-a-327, or aCD38-b-348 or any other agent) that partially or completely alleviates, ameliorates, relives, inhibits, delays onset of, reduces severity of, and/or reduces incidence of one or more symptoms. In some embodiments, treatment may involve the direct administration of a CD38 Modulating Antibody Agent such as aCD38-a-323, aCD38-a-306, aCD38-b-329, aCD38-a-327, or aCD38-b-348 (for example, as an injectable, aqueous composition, optionally comprising a pharmaceutically acceptable carrier, excipient and/or adjuvant, for use for intravenous, intratumoral or peritumoral injection) or the administration using a regimen comprising obtaining cells from the subject (e.g. from the blood, a tissue, or a tumor, with or without a selection on the basis of presence, or absence, of the expression of a marker), contacting said cells with a CD38 Modulating Antibody Agent such as aCD38-a-323, aCD38-a-306, aCD38-b-329, aCD38-a-327 or aCD38-b-348 ex vivo, and administering such cells to the subject (with or without a selection on the basis of presence, or absence, of the expression of a marker).

Dosing and Administration. Pharmaceutical compositions comprising a CD38 Modulating Antibody Agent as described herein (e.g., an anti-CD38 or antigen-binding fragment thereof, for example comprising the aCD38-a-323-HCDR3, aCD38-a-306-HCDR3, aCD38-b-329-HCDR3, aCD38-a-327-HCDR3, or aCD38-b-348-HCDR3 amino acid sequence) for use in accordance with the present invention may be prepared for storage and/or delivery using any of a variety of techniques and/or technologies known and/or available to those skilled in the art. In some embodiments, a provided CD38 Modulating Antibody Agent is administered according to a dosing regimen approved by a regulatory authority such as the United States Food and Drug Administration (FDA) and/or the European Medicines Agency (EMEA), e.g., for the relevant indication. In some embodiments, a provided CD38 Modulating Antibody Agent is administered in combination with one or more other agents or therapies, which may themselves be administered according to a dosing regimen approved by a regulatory authority such as the United States Food and Drug Administration (FDA) and/or the European Medicines Agency (EMEA), e.g., for the relevant indication. In some embodiments however, use of a provided CD38 Modulating Antibody Agent may permit reduced dosing (e.g., lower amount of active in one or more doses, smaller number of doses, and/or reduced frequency of doses) of an approved agent or therapy used in combination with the CD38 Modulating Antibody Agent therapy. In some embodiments, dosing and/or administration may be adapted to other drugs that also administered, the patient status, and/or the format of CD38 Modulating Antibody Agent (e.g. modified as an immunoconjugate, a single domain antibody, or a bispecific antibody).

Moreover, in some embodiments, it may be desirable to tailor dosing regimens, and particularly to design sequential dosing regimens, based on timing and/or threshold expression levels of CD38, whether for particular cell types, particular tumors or types thereof, or particular patient populations (e.g., carrying genetic markers). In some such embodiments, therapeutic dosing regimens may be combined with or adjusted in light of detection methods that assess expression of one or more inducible markers or other criteria prior to and/or during therapy.

In some embodiments, dosing and administration according to the present invention utilizes active agent having a desired degree of purity combined with one or more physiologically acceptable carriers, excipients or stabilizers in any or variety of forms. These include, for example, liquid, semi-solid and solid dosage forms, such as liquid solutions (e.g., injectable and infusible solutions), dispersions or suspensions, tablets, pills, powders, liposomes and suppositories. A preferred form may depend on the intended mode of administration and/or therapeutic application, typically in the form of injectable or infusible solutions, such as compositions similar to those used for treating of human subjects with antibodies.

In some embodiments, ingredient(s) can be prepared with carriers that protect the agent(s) against rapid release and/or degradation, such as a controlled release formulation, including implants, transdermal patches, and microencapsulated delivery systems. Biodegradable, biocompatible polymers can be used, such as polyanhydrides, polyglycolic acid, polyorthoesters, and polylactic acid. In general, each active agent is formulated, dosed, and administered in therapeutically effective amount using pharmaceutical compositions and dosing regimens that are consistently with good medical practice and appropriate for the relevant agent(s) (e.g., for agents such as antibodies). Pharmaceutical compositions containing active agents can be administered by any appropriate method known in the art, including, without limitation, oral, mucosal, byinhalation, topical, buccal, nasal, rectal, or parenteral (e.g. intravenous, infusion, intratumoral, intranodal, subcutaneous, intraperitoneal, intramuscular, intradermal, transdermal, or other kinds of administration involving physical breaching of a tissue of a subject and administration of the pharmaceutical composition through such breach).

In some embodiments, a dosing regimen for a particular active agent may involve intermittent or continuous (e.g., by perfusion or slow release system) administration, for example to achieve a particular desired pharmacokinetic profile or other pattern of exposure in one or more tissues or fluids of interest in the subject. In some embodiments, different agents administered in combination may be administered via different routes of delivery and/or according to different schedules. Alternatively, or additionally, in some embodiments, one or more doses of a first active agent is administered substantially simultaneously with, and in some embodiments via a common route and/or as part of a single composition with, one or more other active agents.

Factors to be considered when optimizing routes and/or dosing schedule for a given therapeutic regimen may include, for example, the particular cancer being treated (e.g., type, stage, location, etc.), the clinical condition of a subject (e.g., age, overall health, weight, etc.), the site of delivery of the agent, the nature of the agent (e.g. an antibody or other protein-based compound), the mode and/or route of administration of the agent, the presence or absence of combination therapy, and other factors known to medical practitioners.

Those skilled in the art will appreciate, for example, that a specific route of delivery may impact dose amount and/or required dose amount may impact route of delivery. For example, where particularly high concentrations of an agent within a particular site or location (e.g., within a tissue or organ) are of interest, focused delivery (e.g., intratumoral delivery) may be desired and/or useful. In some embodiments, one or more features of a particular pharmaceutical composition and/or of a utilized dosing regimen may be modified over time (e.g., increasing or decreasing amount of active in any individual dose, increasing or decreasing time intervals between doses, etc.), for example in order to optimize a desired therapeutic effect or response (e.g., a therapeutic or biological response that is related to the functional features of a CD38 Modulating Antibody Agent as described herein). In general, type, amount, and frequency of dosing of active agents in accordance with the present invention in governed by safety and efficacy requirements that apply when relevant agent(s) is/are administered to a mammal, preferably a human. In general, such features of dosing are selected to provide a particular, and typically detectable, therapeutic response as compared with what is observed absent therapy. In context of the present invention, an exemplary desirable therapeutic response may involve, but is not limited to, inhibition of and/or decreased tumor growth, tumor size, metastasis, one or more of the symptoms and side effects that are associated with the tumor, as well as increased apoptosis of cancer cells, therapeutically relevant decrease or increase of one or more cell marker or circulating markers and the like. Such criteria can be readily assessed by any of a variety of immunological, cytological, and other methods that are disclosed in the literature. For example, the therapeutically effective amount of CD38 Modulating Antibody Agent, alone or in combination with a further agent, can be determined as being sufficient to enhance killing of cancer cells as described in the Examples.

A therapeutically effective amount of a CD38 Modulating Antibody Agent as active agent or composition comprising such agent can be readily determined using techniques available in the art including, for example, considering one or more factors such as the disease or condition being treated, the stage of the disease, the age and health and physical condition of the mammal being treated, the severity of the disease, the particular compound being administered, and the like.

In some embodiments, therapeutically effective amount is an effective dose (and/or a unit dose) of an active agent that may be at least about 0.01 mg/kg body weight, at least about 0.05 mg/kg body weight; at least about 0.1 mg/kg body weight, at least about 1 mg/kg body weight, at least about 5 mg/kg body weight, at least about 10 mg/kg body weight, or more (e.g. 0.01, 0.1, 0.3, 0.5, 1, 2, 3, 4, 5, 6, 7, 8, 9, 10, 20, 30, 40, or 50 mg/kg body weight). It will be understood by one of skill in the art that in some embodiments such guidelines may be adjusted for the molecular weight of the active agent. The dosage may also be varied for route of administration, the cycle of treatment, or consequently to dose escalation protocol that can be used to determine the maximum tolerated dose and dose limiting toxicity (if any) in connection to the administration of the isolated antibody or antigen-binding fragment thereof comprising the aCD38-a-323-HCDR3, aCD38-a-306-HCDR3, aCD38-b-329-HCDR3, aCD38-a-327-HCDR3, or aCD38-b-348-HCDR3 amino acid sequence at increasing doses.

Therapeutic compositions typically should be sterile and stable under the conditions of manufacture and storage. The composition can be formulated as a solution, microemulsion, dispersion, liposome, or other ordered structure suitable to high drug concentration. Sterile injectable solutions can be prepared by incorporating the antibody in the required amount in an appropriate solvent with one or a combination of ingredients enumerated above, followed by filtered sterilization. Generally, dispersions are prepared by incorporating the active compound into a sterile vehicle that contains a basic dispersion medium and other required ingredients from those enumerated above. In the case of powders for preparing sterile injectable solutions, the preferred methods of preparation are vacuum drying and freeze drying that yields a powder of the active ingredient plus any additional desired ingredient from a previously sterile filtered solution. The proper fluidity of a solution can be maintained, for example, by using a coating, by the maintenance of the required particle size in the case of dispersion and by the use of surfactants. Prolonged absorption of injectable compositions can be brought about by including in the composition an agent that delays absorption, for example, monostearate salts and gelatin.

The formulation of each agent should desirably be sterile, as can be accomplished by filtration through sterile filtration membranes, and then packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations as discussed herein. Sterile injectable formulations may be prepared using a non-toxic parenterally acceptable diluent or solvent, such as water or 1,3 butanediol. Other parentally-administrable formulations which are useful include those which comprise the active ingredient in microcrystalline form, in a liposomal preparation, or as a component of biodegradable polymer systems. Compositions for sustained release or implantation may comprise pharmaceutically acceptable polymeric or hydrophobic materials such as an emulsion, an ion exchange resin, a sparingly soluble polymer or salt.

Each pharmaceutical composition for use in accordance with the present invention may include pharmaceutically acceptable dispersing agents, wetting agents, suspending agents, isotonic agents, coatings, antibacterial and antifungal agents, carriers, excipients, salts, or stabilizers are non-toxic to the subjects at the dosages and concentrations employed. A non-exhaustive list of such additional pharmaceutically acceptable compounds includes buffers such as phosphate, citrate, and other organic acids; antioxidants including ascorbic acid and methionine; salts containing pharmacologically acceptable anions (such as acetate, benzoate, bicarbonate, bisulfate, isothionate, lactate, lactobionate, laurate, malate, maleate, salicylate, stearate, subacetate, succinate, tannate, tartrate, teoclate, tosylate, thiethiodode, and valerate salts); preservatives (such as octadecyidimethylbenzyl ammonium chloride; hexamethonium chloride; benzalkonium chloride, benzethonium chloride; sodium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin; hydrophilic polymers such as polyvinylpyrrolidone; amino acids such as glycine, glutamine, asparagine, glutamic acid, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG).

In some embodiments, where two or more active agents are utilized in accordance with the present invention, such agents can be administered simultaneously or sequentially. In some embodiments, administration of one agent is specifically timed relative to administration of another agent. In some embodiments, desired relative dosing regimens for agents administered in combination may be assessed or determined empirically, for example using ex vivo, in vivo and/or in vitro models; in some embodiments, such assessment or empirical determination is made in vivo, in a particular patient or patient population (e.g., so that a correlation is made).

In some embodiments, one or more active agents utilized in practice of the present invention is administered according to an intermittent dosing regimen comprising at least two cycles. Where two or more agents are administered in combination, and each by such an intermittent, cycling, regimen, individual doses of different agents may be interdigitated with one another. In some embodiments, one or more doses of the second agent is administered a period of time after a dose of a CD38 Modulating Antibody Agent as described herein. In some embodiments, each dose of the second agent is administered a period of time after a dose of CD38 Modulating Antibody Agent as described herein. In some embodiments, a CD38 Modulating Antibody Agent as described herein can be also administered in regimens that involve not only subsequent administration by the same route but also by alternating administration routes such as by sub-cutaneous (or intramuscular) administration and intra-tumoral administration, within one or more cycles of treatments over one, two, four or more weeks, repeating such cycle with the same regimen (or by extending the interval between administrations), depending of patient responses. Also, in some embodiments, the precise regimen followed (e.g., number of doses, spacing of doses (e.g., relative to each other or to another event such as administration of another therapy), amount of doses, etc. may be different for one or more cycles as compared with one or more other cycles.

By using any of the routes of administrations, dosages, and/or regimens as described herein, a CD38 Modulating Antibody Agent as described herein can be identified, characterized, and/or validated, for example, taking into account one or more criteria that are measured in the patients using biopsies, blood samples, and/or other clinical criteria. In some embodiments, as an alternative or in addition to direct evaluation of tumor size and/or metastasis, therapeutic efficacy of a CD38 Modulating Antibody Agent as described herein can be determined in methods wherein one or more different general criteria are evaluated (for example increase in activation markers or other phenotypic markers on immune cells, or a measurement of cytokines and chemokines): direct cytotoxicity on cancer cells (apoptosis and necrosis of cancer cells), increase of tumor infiltrating, immune cells (such as CD4-positive and/or CD8-positive tumor infiltrating T cells), increase in immune cells that circulates in blood (total populations or specific subpopulations of lymphocytes, NK cells, monocytes, dendritic cells, macrophages, B cells, etc.), and/or presenting some differential expression pre-versus post-treatment only in either responding or non-responding patients (as determined by RNA sequencing, mass flow cytometry, and/or other mass sequencing approach). Alternatively or additionally, in some embodiments, such identification, characterization, and/or validation may involve the follow-up at molecular level by screening the mRNA and/or protein expression of one or more specific proteins or sets of proteins. In some embodiments, one or more such techniques may allow identification or relevant information for evaluating the response to a CD38 Modulating Antibody Agent as described herein, for example that may be is related to tissue distribution and/or markers for specific cell populations within (or nearby) the tumor and/or circulating in blood.

Such approaches and immune-biological data may allow determination not only of one or more efficacy and/or safety parameters or characteristics, but in some embodiments, can provide a rationale for choosing a particular dose, route or dosing regimen, for example that may be utilized in one or more clinical trials for a given indication, alone and/or in combination with other drugs, standard-of-care protocols, or immunotherapies that can provide further therapeutic benefits. Thus, in a series of further embodiments of the invention, a CD38 Modulating Antibody Agent as described herein is used in a method of treating a patient suffering from a disease (such as cancer) or preventing a disease (such as cancer) after determining the combined presence (and/or absence) of expression at RNA and/or protein level for one or more genes in cells or tissues of the patient (such as a tumor, a blood sample, or a blood fraction), post- or pre-treatment with such a formulation. Such methods may allow therefore defining a one or more biomarkers, or a more complex gene expression signature (or cell population distribution) that is associated to the therapeutically effective amount of a desirable CD38 Modulating Antibody Agent, the therapeutically relevant biomarker(s) that predicts that a subject may have an anti-tumor or anti-infective response after the treatment with a CD38 Modulating Antibody Agent as described herein, or the therapeutically relevant biomarker(s) that predicts that a subject may respond to the treatment with a compound after the treatment with a CD38 Modulating Antibody Agent.

Alternatively or additionally, in some embodiments, dosing and administration for a particular CD38 Modulating Antibody Agent as disclosed herein can be preliminarily established and/or later evaluated in view of CD38 expression in human cancers and/or other human tissues, for example by gathering data about CD38 distribution in stromal and/or immune subsets in various cancers, tissues, and/or patients. Such data can be generated by using common technologies (such as flow cytometry, mass cytometry, immunohistochemistry or mRNA expression libraries) across common cancer types and/or tissues (central nervous system, Esophagus, Stomach, Liver, Colon, Rectum, Lung, Bladder, Heart, Kidney, Thyroid, Pancreas, Uterus, Skin, Breast, Ovary, Prostate and testis) for identifying relationship between CD38 expression in various immune and non-immune subpopulations and/or its relation with cell infiltrate measures and/or cancer-relevant markers associated with sub-sets of cancer cells or immune cells (such as Foxp3 and PD-1/PD-L1). CD38 expression can be confined (or not) to immune subsets in tumor tissue (such as in NK cells and other effector or regulatory immune cells), and correlations between CD38 expression and immune checkpoint inhibitors can be determined if being positive, thus suggesting appropriate uses of CD38 Modulating Antibody Agents in combinations with compounds targeting such immune checkpoint inhibitors.

Articles of Manufacture and Kits; In some embodiments of the invention, a CD38 Modulating Antibody Agent as described herein is provided in a separate article of manufacture. In some embodiments of the invention, an article of manufacture containing a CD38 Modulating Antibody Agent is provided in or with a container with a label. Suitable containers may include, for example, bottles, vials, syringes, and test tubes. In some embodiments, a container may be formed from any or a variety of materials such as glass or plastic. In some embodiments, a container holds a composition that is effective for treating a particular disease, disorder, or condition, or stage or type thereof. In some embodiments, a container may have a sterile access port (for example the container may be an intravenous solution bag or a vial having a stopper pierceable by a hypodermic injection needle). For example, in some embodiments, a composition comprising a CD38 Modulating Antibody Agent as described herein is packaged in clear glass vials with a rubber stopper and an aluminium seal. The label on, or associated with, the container indicates that the composition is used for treating the condition of choice.

In some embodiments, an article of manufacture may further comprise a separate container comprising a pharmaceutically acceptable buffer, such as phosphate-buffered saline, Ringer's solution and dextrose solution and/or may further include other materials desirable from a commercial and user standpoint, including other buffers, diluents, filters, needles, syringes, and package inserts with instructions for use. For example, in some embodiments, an article of manufacture may allow providing each or the agent in an intravenous formulation as a sterile aqueous solution containing a total of 2 mg, 5 mg, 10 mg, 20 mg, 50 mg, or more that are formulated, with appropriate diluents and buffers, at a final concentration of 0.1 mg/ml, 1 mg/ml, 10 mg/ml, or at a higher concentration.

In some embodiments, a CD38 Modulating Antibody Agent as described herein can be provided within the kits-of-parts in the form of lyophilized is to be reconstituted with any appropriate aqueous solution that provided or not with the kits, or other types of dosage unit using any compatible pharmaceutical carrier. One or more unit dosage forms of a CD38 Modulating Antibody Agent may be provided in a pack or dispenser device. Such a pack or device may, for example, comprise metal or plastic foil, such as a blister pack. In order to use correctly such kits-of-parts, it may further comprise buffers, diluents, filters, needles, syringes, and package inserts with instructions for use in the treatment of cancer.

In some embodiments, instructions that are associated with an article of manufacture or the kits as described herein may be in the form of a label, a leaflet, a publication, a recording, a diagram, or any other means that can be used to inform about the correct use and/or monitoring of the possible effects of the agents, formulations, and other materials in the article of manufacture and/or in the kit. Instructions may be provided together with the article of manufacture and/or in the kit.

EXAMPLES

Example 1: Generation of Antibodies that Bind CD38 In Vitro

Materials & Methods

CD38 antigen preparation. Recombinant, Histidine-tagged extracellular domain of human, Cynomolgus monkey (Cyno), and murine CD38 proteins were purchased from Sino Biological Inc. Protein reagent biotinylation was done using the EZ-Link Sulfo-NHS-Biotinylation Kit (Thermo Scientific, Cat #21425). The CD38 antigen was concentrated to ~1 mg/mL and buffer exchanged into PBS before addition of 1:7.5 molar ratio biotinylation reagents (EZ-Link Sulfo-NHS-Biotinylation Kit, Thermo Scientific, Cat #21425). The mixture was held at 4° C. overnight prior to another buffer exchange to remove free biotin in the solution. Biotinylation was confirmed through Streptavidin sensor binding of the labelled proteins.

Library interrogation and selection methodology for isolation of anti-CD38 antibodies. Eight naïve human synthetic yeast libraries each of ~109 diversity were designed, generated, and propagated for high-throughput screening and selection of yeast cell lines expressing monoclonal antibodies as described previously (Xu Y et al, 2013; WO2009036379; WO2010105256; WO2012009568). Eight parallel selections were performed, using the eight naïve libraries for monomeric human CD38-based selection.

For the first two rounds of selection, a magnetic bead sorting technique utilizing the Miltenyi MACs system was performed, essentially as described (Siegel et al., 2004). Briefly, yeast cells (~$10^{10}$ cells/library) were incubated with 3 ml of 100 nM biotinylated monomeric human CD38 antigen for 15 minutes at room temperature in FACS wash buffer PBS with 0.1% BSA. After washing once with 50 ml ice-cold wash buffer, the cell pellet was re-suspended in 40 mL wash buffer, and 500 µl Streptavidin MicroBeads (Miltenyi Biotec, Germany. Cat #130-048-101) were added to the yeast cells and incubated for 15 minutes at 4° C. Next, the yeast cells were pelleted, resuspended in 5 mL wash buffer, and loaded onto a MACS LS column (Miltenyi Biotec, Germany. Cat. No. 130-042-401). After the 5 mL was loaded, the column was washed 3 times with 3 ml FACS wash buffer. Column was removed from magnetic field, yeast cells were eluted with 5 mL growth media, and then grown overnight.

Subsequent to the two MACS rounds, five rounds of sorting were performed using flow cytometry (FACS). For the first round of FACS selection, approximately $4 \times 10^7$ yeast cells were pelleted, washed three times with wash buffer, and incubated with 100 nM of each the biotinylated monomeric human, murine, and Cyno CD38 antigen for 10 minutes at room temperature. Yeast cells were then washed twice and stained with goat anti-human F(ab')2 kappa-FITC diluted 1:100 (Southern Biotech, USA; Cat. No. 2062-02) and either streptavidin-Alexa Fluor 633 (Life Technologies, USA; Cat. No. S21375) diluted 1:500, or Extravidin-phycoerthyrin (Sigma-Aldrich, USA; Cat. No. E4011) diluted 1:50, secondary reagents for 15 minutes at 4° C. After washing twice with ice-cold wash buffer, cell pellets were resuspended in 0.4 mL wash buffer and transferred to strainer-capped sort tubes. Sorting was performed using a FACS ARIA sorter (BD Biosciences) and sort gates were determined to select only CD38 binding. Murine- and Cyno-selected populations from the first FACS round were combined into two pools. These pools were then sorted for human CD38 binding to identify cross-reactive binders in the second FACS round to decrease reagent polyspecific binders (Xu Y et al., 2013). The fourth FACS round consisted predominantly of positive selection using 100 nM biotinylated monomeric CD38 as antigen. A sample of the selected clones were plated and sequenced.

Affinity Maturation of clones identified in naïve selections. Heavy chains from the fourth FACS sorting selection round outputs were used to prepare light chain diversification libraries used for four additional selection rounds. The first selection round involved Miltenyi MACs beads conjugated with either 100 nM biotinylated monomeric human CD38 as antigen or 200 nM biotinylated monomeric murine CD38 as antigen. Subsequent to the MACs bead selections, three rounds of FACS sorting were performed. The first FACS round involved either human CD38 at 100 nM or 10 nM or murine CD38 at 200 nM. In parallel to the second FACS round described above, competition selections were performed with 75-100 nM of competitor IgG. After a selection round, a third positive sort with human CD38 at 1 or 10 nM was done before plating. Individual colonies from each FACS selection round were picked for sequencing IgG.

IgG and Fab production & purification. Yeast clones were grown to saturation and then induced for 48 hrs at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over CaptureSelect IgG-CH1 affinity matrix (Life Technologies; Cat. No. 1943200250).

Producing afucosylated aCD38 human IgG1 antibodies expressed in mammalian cells:

Synthesis of codon optimized VH and VL coding sequences for the antibody is performed and cDNAs of variable regions are cloned into the antibody expression vector (Evitria, Switzerland) using conventional (non-PCR based) cloning techniques. cDNA for oxidoreductase GDP-6-deoxy-d-lyxo-4-hexulose reductase (RMD) enzyme is cloned into an expression vector (Evitria, Switzerland). Plasmid DNA is prepared under low-endotoxin conditions based on anion exchange chromatography. Evitria uses suspension-adapted CHO K1 cells (originally received from ATCC and adapted to serum-free growth in suspension culture at Evitria) for production. The seed is grown in eviGrow medium, a chemically defined, animal-component free, serum-free medium. Cells is transfected with expression vectors for the IgG1 and the RMD enzyme using eviFect, Evitria's custom-made, proprietary transfection reagent. Cells are grown after transfection in eviMake2, an animal-component free, serum-free medium. Supernatant is harvested by centrifugation and subsequent filtration (0.2 µm filter). The antibody is purified using MabSelect™ SuRe™. The glycosylation pattern of the antibodies is characterized using LC/MS and showed >99% of a-fucosylation.

Affinity Measurements of anti-CD38 Antibodies The affinity for the CD38 antibodies was determined by measuring their $K_D$ by Forte Bio. Forte Bio affinity measurements were performed by loading IgGs on-line onto AHQ sensors as described (Estep P et al., 2013). Briefly, sensors were equilibrated off-line in assay buffer for 30 minutes and then monitored on-line for 60 seconds for baseline establishment. For avid binding measurement, sensors with loaded IgGs were exposed to 200 nM of human, cyno, or murine CD38 for 3 minutes, afterwards they were transferred to assay buffer for 3 minutes for off-rate measurement. Monovalent binding measurements were obtained by loading biotinylated CD38 monomer on SA sensors followed by exposure to 200 nM Fab. Kinetics data were fit using a 1:1 binding model of data analysis software provided by Forte Bio. The Kd values that were established in this assay for the reference agonistic anti-CD38 antibodies are the following: for IB4, $0.9 \times 10^{-8}$M for human CD38 and no binding to cynomolgus CD38, for IB4.

Avidity binding measurements of anti-CD38 Antibodies: Ni-NTA sensors were equilibrated off-line in assay buffer for 30 minutes and then monitored on-line for 60 seconds for baseline establishment. They were loaded with 4.2 nM antigen (recombinant human CD38 HIS tagged) for 50 minutes, afterwards they were transferred to assay buffer for 0.5 min for wash and again for 1 minutes in assay buffer for base line determination. Then the antibody was associated at different concentrations (as described in FIGS. 25 and 30) for 30-50 minutes. Afterwards they were transferred to assay buffer for 20-30 min for off-rate measurement. Kinetics data were fit using a 1:1 binding model in the data analysis software provided by ForteBio.

Alternatively the affinity for the anti human CD38 antibodies was determined by measuring their $K_D$ by SPR in a Biacore 2000 using a CM-5 Sensor chip with an ambient experiment temperature of 25° C. Anti-human antibody was initially immobilised across all flow cells in analysis buffer (pH 7.4, 10 mM HEPES, 150 mM NaCl, 3 mM EDTA, 0.05% Tween 20) to an RU of between 12,000-14,000 over 10 minutes. The ligand (antibody test articles) was sub sequentially loaded to a capture level between 54-208 RU. The analyte (recombinant human CD38 his tagged) was then associated in analysis buffer from a 2-fold dilution starting at 3200 nM with a lowest concentration of 0.78 nM for 6 minutes. Dissociation was performed in analysis buffer over 10 minutes. Regeneration steps between sample concentrations were performed in 3M $MgCl_2$, three times for 0.5 minutes. A flow rate of 25 µl/min was maintained throughout the process. Kinetics data were fit using a global fit on the analysis software provided by Biacore with reference subtraction.

Epitope Binning: Epitope binning of antibodies can be performed on a Forte Bio Octet Red384 system (Pall Forte Bio Corp., USA) using a standard sandwich binning assay. The anti-human CD38 antibody can be loaded onto AHQ sensors and unoccupied Fc-binding sites on the sensor and blocked with a non-relevant human IgG1 antibody. Sensors can be exposed to 100 nM target antigen followed by a second anti-CD38 antibody, the reference monoclonal agonistic mouse anti-human CD38 antibodies (IB4). Data can be processed using Forte Bio Data Analysis Software 7.0. Additional binding by a second antibody after antigen association indicates an unoccupied epitope, while no binding indicates epitope blocking.

Binding of anti-CD38 Antibodies to CD38-expressing cells The candidate hits are evaluated by analysing the binding to purified cynomolgus T cells. To this aim cynomolgus pan T cells were stained with 20 µg/ml of aCD38-a-323, aCD38-a-306, aCD38-b-348 or isotype control followed by a semi-log serial dilution (7 points) for 30 minutes on ice.

Unbound primary antibody was removed by washing followed by staining with a secondary antibody (5 µg/ml) 30 minutes on ice. All samples were stained in triplicates with appropriate CD3, CD4 and CD8 cross-reactive antibodies. Samples were measured by flow cytometry. For data analysis live cells were gated using FSC vs SSC parameters during sample acquisition. Mean fluorescence intensities (MFI) of stained cells were plotted on an XY chart, graphing MFI against the log of the concentration and the data fit to a non-linear regression curve from which the EC50 was calculated.

Alternatively binding was evaluated in human PBMC. To this aim, PBMCs were prepared from whole blood from 3 human donors and incubated for 30 mins with aCD38-a-323, aCD38-a-306, aCD38-b-329, aCD38-b-348, aCD38-a-327, DARA or isotype control at final concentrations of 1 µM, 200 nM, 40 nM, 8 nM, 1.6 nM, 320 pM, 64 pM, 13 pM and 2.5 pM. Cells were then washed and labelled with an AF488 secondary antibody. Cells were then incubated with additional surface staining antibodies: anti-CD3 PE-Cy7, anti-CD4 APC and anti-CD8 BV451. Sample acquisition was performed using 8-colour (three laser) BD FACSCanto II cytometer, running on the BD FACSDiva software (BD Biosciences). Post-analysis processing and was conducted using FCS Express (v3.0) software (DeNovo software). The relative proportions (%) of the different cell populations and Median Fluorescence Intensity (MFI) data were reported to 2 decimal places.

Recloning, producing, and characterizing of aCD38-a-323, aCD38-a-306, aCD38-b-329, aCD38-a-327 and aCD38-b-348 as human IgG1 expressed in mammalian cells. Synthesis of codon optimized VH and VL coding sequences for the antibody was performed by Genewiz. cDNAs of variable regions were cloned into the antibody expression vector (Icosagen, EST) containing human IgG1 heavy chain and kappa light chain constant regions (P01857 and P01834 respectively). Full length heavy and light chain cDNAs were verified by sequencing in final vectors and then recloned for expressing them using the QMCF Technology (Icosagen) a stable episomal expression system that uses CHO-based cells (CHOEBNALT85) and appropriate vectors for production of recombinant proteins, antibodies, CHOEBNALT85 cells were transfected with 1 µg of the expression plasmids for antibody production. 48 h after the transfection 700 µg/ml of G418 was added to select plasmid containing cell population. For the production, temperature was shifted to 30° C. and the cultures were additionally fed. At the end of the production the culture supernatants were clarified by centrifugation (1000 g, 30 min, and 15° C.), PMSF was added and supernatants were processed or frozen until purification. hIgG1 antibodies were purified by Mab-Select SuRe affinity chromatography followed by Superdex 200 gel filtration into either 25 mM NaOAc pH 5,5; 50 mM NaCl, PBS or PBS 100 nM L-Arg. Human IgG1 antibodies produced in CHOEBNALT85 cells were characterized for affinity towards recombinant human CD38, cross reactivity towards murine, rat, rabbit and cyno CD38 using recombinant rabbit CD38 (65003-TO8H-20; Sino Biological) and recombinant rat CD38: (80229-R0H8H-20; Sino Biological).

aCD38-b-348 epitope mapping Different sets of linear, single loop, β-turn mimics, disulfide bridge mimics, discontinuous disulfide bridges, discontinuous epitope mimics peptides representing the human CD38 sequence (Uniprot record no. P28907) were synthesized using solid-phase Fmoc synthesis (Pepscan BV, The Netherlands; Timmermann P et al., 2007; Langedijk J P et al., 2011). The binding of antibody to each of the synthesized peptides was tested in a pepscan-based ELISA (Pepscan, The Netherlands). The peptide arrays were incubated with primary antibody solution (overnight at 4° C.). After washing, the peptide arrays were incubated with a 1/1000 dilution of an appropriate antibody peroxidase conjugate (2010-05; Southern Biotech) for one hour at 25° C. After washing, the peroxidase substrate 2,2'-azino-di-3-ethylbenzthiazoline sulfonate (ABTS) and 20 µl/ml of 3 percent H2O2 were added. After one hour, the color development was measured. The color development was quantified with a charge coupled device (CCD)—camera and an image processing system. The values obtained from the CCD camera range from 0 to 3000 mAU, similar to a standard 96-well plate ELISA-reader. To verify the quality of the synthesized peptides, a separate set of positive and negative control peptides was synthesized in parallel and screened with irrelevant, control antibodies.

Alanine scanning was performed to confirm the epitope. Alanine scanning was performed using Integral Molecular's epitope mapping platform based on Shotgun Mutagenesis to further characterize the epitopes of the mAbs. The coding region for full-length CD38 protein was successfully codon-optimized, synthesized, and subcloned into a mammalian high-expression vector. This parental construct was then sequence-verified and validated for mammalian cell expression by immunodetection. Conditions for binding and screening of aCD38-b-348 (mAb and Fab) using high-throughput flow cytometry were optimized using wild-type CD38 cloned into a proprietary vector and expressed in HEK-293T cells.

In order to map the epitopes of the antibody an alanine-scan library of CD38 was constructed. The antibodies (mAb and Fab) were then screened for binding to each individual CD38 variant, allowing identification of the CD38 contact residues critical for the test mAbs binding.

aCD38-b-329 epitope mapping Different sets of linear, single loop, β-turn mimics, disulfide bridge mimics, discontinuous disulfide bridges, discontinuous epitope mimics peptides representing the human CD38 sequence (Uniprot record no. P28907) were synthesized using solid-phase Fmoc synthesis (Pepscan BV, The Netherlands; Timmermann P et al., 2007; Langedijk J P et al., 2011). The binding of antibody to each of the synthesized peptides was tested in a pepscan-based ELISA (Pepscan, The Netherlands). The peptide arrays were incubated with primary antibody solution (overnight at 4° C.). After washing, the peptide arrays were incubated with a ¹⁄₁₀₀₀ dilution of an appropriate antibody peroxidase conjugate (2010-05; Southern Biotech) for one hour at 25° C. After washing, the peroxidase substrate 2,2'-azino-di-3-ethylbenzthiazoline sulfonate (ABTS) and 20 µl/ml of 3 percent $H_2O_2$ were added. After one hour, the color development was measured. The color development was quantified with a charge coupled device (CCD)—camera and an image processing system. The values obtained from the CCD camera range from 0 to 3000 mAU, similar to a standard 96-well plate ELISA-reader. To verify the quality of the synthesized peptides, a separate set of positive and negative control peptides was synthesized in parallel and screened with irrelevant, control antibodies.

aCD38-a-327 epitope mapping Different sets of linear, single loop, β-turn mimics, disulfide bridge mimics, discontinuous disulfide bridges, discontinuous epitope mimics peptides representing the human CD38 sequence (Uniprot record no. P28907) were synthesized using solid-phase Fmoc synthesis (Pepscan BV, The Netherlands; Timmermann P et al., 2007; Langedijk J P et al., 2011). The binding of the a-327 antibody to each of the synthesized peptides was tested in an ELISA (Pepscan, The Netherlands). The peptide arrays were incubated with primary antibody solution (overnight at 4° C.). After washing, the peptide arrays were incubated with a ¹⁄₁₀₀₀ dilution of an appropriate antibody peroxidase conjugate (2010-05; Southern Biotech) for one hour at 25° C. After washing, the peroxidase substrate 2,2'-azino-di-3-ethylbenzthiazoline sulfonate (ABTS) and 20 µl/ml of 3 percent H2O2 were added. After one hour, the color development was measured. The color development was quantified with a charge coupled device (CCD)—camera and an image processing system. The values obtained from the CCD camera range from 0 to 3000 mAU, similar to a standard 96-well plate ELISA reader. To verify the quality of the synthesized peptides, a separate set of positive and negative control peptides was synthesized in parallel and screened with irrelevant, control antibodies. Alanine scanning was performed by Integral Molecular to confirm the epitope as discussed above.

Anti-human CD38 Ab Competition Assays: Antibody competitions were performed on a Forte Bio Octet Red96 system (Pall Forte Bio Corp., USA) using a standard sequential binding assay. 0.625 ug/mL of recombinant human CD38his tagged was loaded onto Ni-NTA Biosensors for 300 s. After wash for 15 s and a base line step for 60 s on kinetic buffer sensors were exposed to 66.6 nM of first antibody for 600 s followed by a second anti-CD38 antibody (also at 66.6 nM for 600 s). Data was processed using Forte Bio Data Analysis Software 9.0. Additional binding by a second antibody indicates an unoccupied epitope (no competition for the epitope), while no binding indicates epitope blocking (competition) for the epitope.

Results

Monoclonal antibodies (mAb) binding to recombinant human CD38 extracellular protein sequence (rhCD38) have been isolated using a yeast-based antibody presentation library as described in the Materials & Methods. These antibodies were sequenced and unique clones were produced in yeast cells (Barnard G C et al., 2010). The cell culture supernatants for each yeast clone expressing a unique antibody sequence were screened for rhCD38 binding.

The $K_D$ values (for affinity and avidity measurements) and crossing binning analysis for selected antibodies are provided in Table 1:

TABLE 1A

| Antibody | Epitope Cross-binning group | Affinity | | | Avidity | |
| --- | --- | --- | --- | --- | --- | --- |
| | | $K_D$ Human CD38-HIS Monovalent (M) (Octet) | Isotype | $K_D$ Human CD38-HIS Monovalent (M) (Biacore) | $K_D$ Human CD38-HIS Monovalent (M) | Isotype |
| aCD38-a-323 | E | 1.65E−08 | IgG4 | | 9.57E−11 | IgG1 |
| aCD38-a-323 | E | — | IgG1 | 0.90E−09 | | |
| aCD38-a-327 | A | 2.30E−09 | IgG1 | 1.00E−09 | 1.81E−11 | IgG1 |
| aCD38-a-327 | A | 2.99E−09 | IgG4 | | — | — |
| aCD38-b-329 | B | 3.38E−09 | IgG1 | 0.62E−09 | | |
| aCD38-b-348 | B | 8.81E−09 | IgG1 | 2.00E−09 | 1.77E−10 | IgG1 |
| aCD38-b-348 | B | 9.24E−09 | IgG4 | | — | — |
| aCD38-a-306 | H | 4.80E−08 | Yeast produced | | 7.35E−11 | IgG1 |
| aCD38-a-306 | H | — | IgG1 | 1.20E−09 | — | — |
| Daratumumab | F | 8.28E−08 | IgG1 | | 1.80E−10 | IgG1 |

Binding of anti-CD38 antibodies to recombinant monovalent human CD38 measured by Octet and compared to Daratumumab, is shown in FIGS. 25 and 30. Binding affinity of anti-CD38 antibodies (IgG1) to recombinant monovalent human CD38 was also measured by Biacore (which is considered to produce more reliable data). The results are shown in Table 1A and FIG. 42.

The results of the epitope mapping and confirmation by alanine scanning are shown in Table 1B.

TABLE 1B

| Antibody | Alanine Scanning | Pepscan |
|---|---|---|
| aCD38-b-348 and aCD38-b-329 | R78 | $_{65}$ARCVKYTEIHPEMRH$_{79}$ |
| aCD38-a-327 | R58, L64, A65, V68 | $_{126}$SRIKDLAHQFTQV$_{138}$ $_{47}$RQQWSGPGTTKRFPETVLAR$_{66}$ |
| aCD38-a-323 | N120, K121, D141 W241 | — |

Based on the binding to rhCD38, sequence uniqueness and expression levels a panel of mAbs was identified. These antibodies were further characterized for binding to recombinant Cynomolgus monkey and mouse CD38 extracellular domain protein sequences. In addition, epitope binning was performed to determine whether the antibodies aCD38-b-329 and aCD38-b-348 bind to epitopes overlapping with those of the reference agonistic anti-CD38 antibody IB4 (Ausiello C M et al., 2000; Ferrero E et al., 2004). The clones were characterized presenting IgG binding values to monovalent rhCD38 and/or recombinant cynomolgus CD38 extracellular protein sequences that is comprised between $10^{-8}$M and $10^{-10}$M. In addition, antibodies were characterized as competing or not with reference agonistic anti-CD38 antibody IB4 or to the commercially available Daratumumab, DARA). All selected antibodies belong to different cross binning groups, as shown on Table 1. The antibody clones were also evaluated at the level of binding to human cells strongly expressing CD38, such as lymphoblast-like, Raji cells by flow cytometry, using CHO-S cells as negative control. Further, for aCD38-a-323 binding to human PBMC (FIG. 3B) but not cynomolgus pan T cells (FIG. 3A) was confirmed. For aCD38-a-306 binding to human CD4 and CD8 T cells (FIG. 8B), but not to cynomolgus T cells (FIG. 8A) was confirmed. For aCD38-b-329, binding to human PBMC (FIG. 12) was confirmed. For aCD38-b-348, binding to cynomolgus pan T cells (FIG. 17A) and human PBMC (FIG. 17B) was confirmed.

Finally, in order to eliminate antibody sequences that would be prone to aggregation and non-specific interaction, the antibodies were screened in a Poly Specific Reagent (PSR) assay and Affinity-Capture Self-Interaction Nanoparticle Spectroscopy (AC-SINS), an approach that allows high-throughput screening for early-stage antibody development (Liu Y et al., 2014). None of the selected antibodies scored positive in the latter assays and as such were not removed from the panel.

Among the selected hits that were sequenced and characterized as described above, the clone aCD38-a-323 is an antibody presenting novel complementarity determining regions (CDRs; FIG. 2) and binds human CD38 extracellular protein sequences with a Kd value in the $10^{-8}$M to $10^{-11}$M range. Alanine scanning indicated that aCD38-a-323 binds amino acid residues 12, 121, 141 and 241 of human CD38 (SEQ ID NO: 47), or at least these residues are required for antibody binding.

Thus, the aCD38-a-323 sequences (FIG. 2) identify antibodies that specifically bind CD38, and whose agonistic activities associated to the functional features defining CD38 Modulating Antibody Agents, as that term is used herein, can be functionally evaluated by cell-based assays or animal models.

The clone aCD38-a-306 is an antibody presenting novel complementarity determining regions (CDRs; FIG. 7) and binds human CD38 extracellular protein sequences with a Kd value in the $10^{-8}$M to $10^{-11}$M range.

Thus, the aCD38-a-306 sequences (FIG. 7A) identify antibodies that specifically bind CD38, and whose agonistic activities associated to the functional features defining CD38 Modulating Antibody Agents, as that term is used herein, can be functionally evaluated by cell-based assays or animal models.

The clone aCD38-b-329 is an antibody presenting novel complementarity determining regions (CDRs; FIG. 11A) that competes for human CD38 binding neither with IB4 nor with Daratumumab. Indeed, the epitope mapping study that has been performed using Pepscan technology would indicate that aCD38-b-329 binds human CD38 in a region that is not only distinct from the one published for Daratumumab (two beta-strands containing amino acids 233-246 and 267-280; FIG. 11B) or the ones that are reported for other anti-human CD38 antibodies (see table 2 in WO2015123687) and binds human CD38 extracellular protein sequences with a Kd value in the $10^{-9}$ M range. The antibody competition assay showed that Daratumumab does not compete with aCD38-b-329 for the same epitope (FIG. 44B), however the assay showed that aCD38-b-329 and aCD38-b-348 do compete with each other for the same epitope (FIG. 44D).

Thus, the aCD38-b-329 sequences (FIG. 11A) identify antibodies that specifically bind CD38, and whose agonistic activities associated to the functional features defining CD38 Modulating Antibody Agents, as that term is used herein, can be functionally evaluated by cell-based assays or animal models. The analysis of aCD38-b-329-LCDR3s shows the presence of a DG (Asp-Gly) motif which represents a potential target for modification during manufacturing that may affect some of the antibody properties. At this scope, aCD38-b-329-based antibody libraries in which either one or both residues are substituted and, among all such mutants, only a limited number of them maintained the binding to human CD38, for example as expressed on the surface of Daudi cells (see Example 2). In this manner, the corresponding aCD38-b-329-based antibody variants can be tested as maintaining full properties of CD38 Modulating Antibody Agents, or simply having CD38 binding properties. Further validation of these variants may be pursued by using the assays disclosed in the Examples.

The clone aCD38-b-348 is an antibody presenting novel complementarity determining regions (CDRs; FIG. 16A) that competes for human CD38 binding neither with IB4 nor with Daratumumab. Indeed, the epitope mapping study that has been performed using Pepscan technology would indicate that aCD38-b-348 binds human CD38 in a region that is not only distinct from the one published for Daratumumab (two beta-strands containing amino acids 233-246 and 267-280; FIG. 16B) or the ones that are reported for other anti-human CD38 antibodies (see table 2 in WO2015123687) and binds human and cyno CD38 extracellular protein sequences with a Kd value in the $10^{-9}$ M to $10^{-10}$M range. The alanine scanning confirms the epitope region for aCD38-b-348 and in particular that amino acid residue 78 of human CD38 is involved in binding. The antibody competition assay showed that Daratumumab does not compete with aCD38-b-348 for the same epitope (FIG. 44A), however the assay showed that aCD38-b-329 and aCD38-b-348 do compete with each other for the same epitope (FIG. 44 D).

Thus, the aCD38-b-348 sequences (FIG. 16A) identify antibodies that specifically bind CD38, and whose agonistic activities associated to the functional features defining CD38 Modulating Antibody Agents, as that term is used herein, can be functionally evaluated by cell-based assays or animal models. The analysis of aCD38-b-348-LCDR3s shows the presence of a DG (Asp-Gly) motif which represents a potential target for modification during manufacturing that may affect some of the antibody properties. At this scope, aCD38-b-348-based antibody libraries in which either one or both residues are substituted and, among all such mutants, only a limited number of them maintained the binding to human CD38, for example as expressed on the surface of Daudi cells (see Example 2). In this manner, the corresponding aCD38-b-348-based antibody variants can be tested as maintaining full properties of CD38 Modulating Antibody Agents, or simply having CD38 binding properties. Further validation of these variants may be pursued by using the assays disclosed in the Examples.

aCD38-a-327 is an antibody presenting novel complementarity determining regions (CDRs; FIG. 21A) that competes for human CD38 binding neither with IB4 nor with Daratumumab. Indeed, the epitope mapping study that has been performed using Pepscan technology would indicate that aCD38-a-327 binds human CD38 in the region from amino acids 47-66 and 126-138; (FIG. 21B) and binds human CD38 extracellular protein sequences with a Kd value in the $10^{-9}$M range. Alanine scanning confirms the epitope region for aCD38-b-348 and in particular that amino acid residues 58, 64 and 65 of human CD38 are involved in binding. Amino acid residue 68 was also indicated as being involved. As this residue is sufficiently close to the epitope identified by the Pepscan data, this would indicate that the correct epitope has been identified.

The antibody competition assay showed that Daratumumab does not compete with aCD38-b-327 for the same epitope (FIG. 44C).

Thus, the aCD38-a-327 sequences (FIG. 21A) identify antibodies that specifically bind CD38, and whose agonistic activities associated to the functional features defining CD38 Modulating Antibody Agents, as that term is used herein, can be functionally evaluated by cell-based assays or animal models.

Example 2: Cell-Based Models for Validating CD38 Modulating Antibody Agents Materials & Methods In vitro T cell activation assay: Previously frozen primary human pan T cells (Stemcell Technologies) were labelled with eFluor450 fluorescent dye (Life Technologies) and $0.15 \times 10^6$ cells per well were incubated for 72 hrs in 96-well flat bottom plates pre-coated with anti-CD3 antibody (0.5 or 0.1 µg/ml coating concentration, as indicated in the figures, clone OKT3, eBiosciences) and anti-CD38 modulating antibodies coated at concentrations of 10, 5 and 2.5 µg/ml in RPMI 1640 (Life Technologies) containing 10% FBS (Sigma), 2 mM LGlutamine (Life Technologies) and 10,000 U/ml Pen-Strep (Sigma). Readout of T cell proliferation was done by acquisition on the flow cytometer, excluding dead cells labelled with a viability dye (Zombie NIR, BioLegend) and discriminating surface markers by staining with fluorochrome labelled antibodies (CD8-FITC clone HIT8a eBiosciences, CD25-PE clone M-A251 Biolegend, CD4-BV510 clone RPA-T4 BioLegend, CD38-PE-Cy7 clone HB7, eBiosciences, CD137-APC clone 4B4-1 BioLegend). Cytokine analysis in supernatants was conducted using the Meso Scale Discovery MSD platform, determining the expression of IFNg, IL2, IL10, TNFa, and GM-CSF according to the manufacturer's instructions (Multiplex assay kits, Meso Scale Discovery; asterisk in figure indicates values above fit curve range).

In vitro T cell activation by NFAT signalling assay: Jurkat cells stably transfected with a luciferase reporter system (BPS Biosciences) were incubated at 4° C. for 20 minutes in PBS (GIBCO) with different concentrations of mAbs (0.2, 1, 5, 10, 20, 40 ug/ml) against CD38 (or control IgG), followed by cell pelleting, removal of the PBS supernatant and resuspension of the cells in cold growth medium (RPMI (ATCC)+10% FBS (SIGMA)) supplemented with 40 ug/ml F(Ab')2-fragment cross-linking Ab (Jackson ImmunoResearch) and in the presence of 1 ug/ml soluble CD3 mAbs. 10 minutes after the cross-linking antibody has been added, the cells were transferred to 37° C. incubation. 24 h after the 37° C. incubation started, the cells were lysed and the luciferase activity was measured by mean of luminescence release from the hydrolysis of a specific luciferase substrate, following manufacturer instruction (BPS Bioscience one-step luciferase assay kit). NFAT signalling is measured as Relative luminescence units (RLU).

In vitro NK cell activation assay. Human PBMC were labelled with Cell Trace violet proliferation dye (Life Technologies) and cultured in the presence of MDA-MB-231 cells in a ratio of 100:1 (culture medium IMDM, Life Technologies, 10% human serum heat-inactivated, Sigma, 10,000 U/ml Pen-Strep, Sigma) for 5 days. Anti-CD38 antibody was added or control cells were left untreated. Readout for proliferation quantified by dilution of fluorescent dye was done by FACS analysis. Cells were labelled with fluorochrome conjugated antibodies and NK cells were gated by excluding dead cells (Zombie NIR dye, Biolegend), gating on CD45+ hematopoietic cells (CD45-PE-Cy7, Biolegend), further gating on CD3 negative CD56 positive cells (CD56-BV711 clone H130 Biolegend; CD3-BV510 clone OKT3 Biolegend).

In vitro ADCP assay. Antibody-dependent cell-mediated phagocytosis (ADCP) was performed for the characterization of anti-human CD38 antibodies using in-vitro differentiated Tregs as target cells and monocyte-derived macrophages as the effector cells. Different effector to target ratios were evaluated. Target cells were added at $1 \times 10^4$ cells/well while the effector cells were added at ($1 \times 10^4$, $2.5 \times 10^4$, $5 \times 10^4$ or $1 \times 10^5$ cells/well). Anti-human CD38 antibodies were evaluated at 3 concentrations (1 µg/ml; 10 µg/ml and 50 µg/ml). The assay performed using the following protocol: PBMC were isolated from leucocyte cones by Ficoll gradient centrifugation. CD14+ cells were isolated using CD14 Microbeads (CDK006, Miltenyi Biotec). Monocytes were cultured for 7 days in the presence of 50 ng/mlM-CSF in RPMI 1640 (Life Technologies) containing 10% FBS (Sigma), 2 mM L-Glutamine (Life Technologies) and 10,000 U/ml Pen-Strep (Sigma), fresh media containing M-CSF was added after 4 days. Regulatory T cells (Treg) were isolated using the Human Treg Cell Differentiation Kit (130-050-201, R&D Systems). These cells were incubated in a 37° C., 5% $CO_2$ humidified incubator for 5 days. At day 7 macrophages and eFluor450 labelled (eBiosciences) Tregs were cocultured overnight in ratios described above in the presence of CD38 or control antibodies. Phagocytosis of Tregs was determined by flow cytometry gating on CD14+ cells (stained with CD14-PE-Cy7 clone MfP9 BD Biosciences) positive for the Treg label (eFluor450 dye).

In vitro ADCP reporter assay: Promega Bioassay core kit G9901 was used. 5000 Raji cells/well of target wells were plated in 25 ul medium per well using a 96 well white polystyrene plate (Costar Cat #3917). Test antibodies were serial diluted 1:3 in a separate plate. 25 ul serial diluted antibody was added to the cells. 50000 cells/well of the effector cells were added to the plate (25 ul/well). Plates were incubated over night for 20 hours at 37° C. The next day the plate was removed from the incubator and kept at room temperature for 20 minutes. 60 ul Bio-Glo Luciferase assay substrate were added to each well, incubated for 30 minutes. Luminsence was read using the GloMax Multi Detection System. Cell culture medium: RPMI+4% Low IgG Serum.

In vitro ADCC assay: Antibody-dependent cell-mediated cytotoxicity assays (ADCC assays) were performed for the characterization of anti-human CD38 antibodies using Daudi (CD38 positive) human cell line as a target cell with human PBMC as the source of effector cells. Effector to Target ratios would be evaluated at 50 to 1 or 25 to 1 with test articles (anti-CD38 primary antibodies or Daratumumab (or Rituximab) as a control) to be evaluated with top concentration of 10 µg/ml followed by a log series (7 points) in triplicate for 4 hours at 37° C. 5% CO2. PBMCs were primed with IL-2 and IL-2 was present during co-culture assays. Prior to in-vitro culture, target cell lines were labelled with 1 µM Calcein AM and incubated with 2.5 mM probenecid. Lysed cells release the loaded Calcein into the supernatant, which allows for fluorescent measurement. Calcein AM release was analysed by excel and GraphPad software analysis to generate dose response curves by normalization where 1% saponin treatment values will be used to determine maximal lysis. Percentage target cell lysis was plotted on an XY chart, graphing normalized Calcein AM percentage release against the log of the concentration, and the data fit to a no-linear regression curve from which the EC50 was calculated.

In vitro CDC assay: CDC activity to CD38 expressing human cell lines (Daudi) was examined by treating cells with test articles (anti-CD38 primary antibodies or daratumumab (or Rituximab) as control) at a top concentration of 10 µg/ml followed by a log dilution series (7 points) in triplicate with a final concentration of 10% normal human serum complement. Samples were cultured for 3 hours at 37° C. 5% CO2. Following culture conditions, cells washed and re-suspended in 1×PBS with propidium iodide (PI) at a final concentration of 5 µg/ml prior to flow cytometry analysis. Total cells were examined by flow cytometry during sample acquisition. Percentage of PI positive cells were plotted on an XY chart, graphing percentage PI against the log of the concentration, and the data fit to a non-linear regression curve from which the EC50 is calculated.

Direct cell death assay. Direct proapoptotic activity to CD38 expressing human cell lines (Daudi) was examined by treating cells with test articles (anti-CD38 primary antibodies) or daratumumab (or Rituximab) as a control at a top concentration of 10 µg/ml followed by a log dilution series (7 points) in triplicate. Cell death by Fcγ receptor-mediated cross-linking activity was examined by treating cells with test articles (anti-CD38 primary antibodies or Rituximab) as a control at a top concentration of 10 µg/ml followed by a log serial dilution (7 points) in triplicate followed by 5 µg/ml rabbit anti-human Fcγ F(ab')2 (secondary antibody). Samples were cultured for 24 hours at 37° C. 5% CO2. Following culture conditions, cells were washed and resuspended in Annexin V binding buffer and 7-AAD to examine cell death by flow cytometry analysis. Total cells were examined by flow cytometry during sample acquisition. Percentage of late apoptotic cells were plotted on an XY chart, graphing percentage Annexin V-positive and 7-AAD-positive cells against the log of the concentration and the data fit to a non-linear regression from which the EC50 is calculated.

Enzymatic activities of CD38 on the cell surface (cyclase and NADase/hydrolase activities): both cyclase and NADase activity of CD38 were measured on the cell surface of Daudi cells and in Jurkat cells by monitoring the CD38-dependent conversion of NGD+ (Sigma) and E-NAD+ (Sigma) into their respective fluorescent products: cGDPR (cyclic product from NDG+) and 5'-eAMP (hydrolysis product of E-NAD+). 150 thousand Daudi cells were incubated for 20 minutes on ice with 10 µg/ml antibodies in 75 ul of PBS (Thermo Fisher); after 20 minutes, 75 µl of enzymatic reaction buffer (or control buffers) were added and the cells were incubated at 37° C. for 45 minutes for Daudi cells and for 60 minutes for Jurkat cells. The enzymatic reaction buffer included 20 mM UltraPure Tris-HCl Buffer (Thermo Fisher), pH 7.5 in PBS, (Thermo Fisher) and 200 µM of either NGD+ or E-NAD+. After the incubation at 37° C., the cells were pelleted by mean of centrifugation at 550×g and 100 ul of supernatant was utilised for fluorescence measurements in a Molecular Device SpectraMax MiniMax 300 plate reader (excitation wavelength 300 and emission wavelength 410).

Statistics. Prism software (GraphPad) was used to perform curve fitting and to determine EC50 values and maximal activity.

Results

The EC50 values and percentage lysis results from the ADCC and CDC assays are shown in Tables 2, 3 and 4, compared to the results for daratumumab in the same experiment:

TABLE 2

ADCC data for Target Daudi cells:

| Antibody | Experiment | EC50 ug/ml | Max. lysis % | EC50 ug/ml DARA | Max. Lysis DARA |
|---|---|---|---|---|---|
| aCD38-b-329 | 1 | 0.011 | 50 | 0.004 | 36 |
| aCD38-b-329 | 2 | 0.0062 | 49 | 0.0025 | 58 |
| aCD38-a-323 | 3 | 0.0113 | 53 | 0.0139 | 68 |
| aCD38-a-327 | 4 | 0.03 | 55 | 0.004 | 36 |
| aCD38-a-306 | 5 | 0.0013 | 43 | 0.0014 | 30 |
| aCD38-b-348 | 6 | 0.00032 | 60 | 0.00194 | 45 |
| aCD38-b-348 | 7 | 0.0008 | 39 | 0.00317 | 31 |
| aCD38-b-348 | 8 | 0.00042 | 50 | — | — |

TABLE 3

CDC data—10% complement, target Daudi cells:

| Antibody | Experiment | EC50 ug/ml | Max. lysis % | EC50 ug/ml DARA | Max. Lysis DARA |
|---|---|---|---|---|---|
| aCD38-b-329 | 9 | NA | NA | 0.11 | 92 |
| aCD38-a-323 | 10 | 0.05 | 43 | 0.11 | 93.5 |
| aCD38-a-323 | 11 | 0.04 | 31.2 | 0.07 | 91.3 |
| aCD38-a-327 | 12 | No CDC | 10 (background) | 0.11 | 92 |
| aCD38-a-327 | 13 | No CDC | 11 | 0.13 | 87.7 |
| aCD38-a-306 | 14 | 0.19 | 16.9 | 0.13 | 96.8 |

TABLE 3-continued

CDC data—10% complement, target Daudi cells:

| Antibody | Experiment | EC50 ug/ml | Max. lysis % | EC50 ug/ml DARA | Max. Lysis DARA |
|---|---|---|---|---|---|
| aCD38-b-348 | 15 | 0.17 | 97.1 | 0.05 | 97.8 |
| aCD38-b-348 | 16 | 0.34 | 87.8 | 0.13 | 96.8 |
| aCD38-b-348 | 17 | 0.26 | 89.9 | 0.13 | 96.8 |

TABLE 4

CDC data—10% complement, target Raji cells:

| Antibody | EC50 ug/ml | Max. lysis % | EC50 ug/ml DARA | Max. Lysis DARA |
|---|---|---|---|---|
| aCD38-a-327 | No CDC | No CDC | 0.04 | 54.7 |
| aCD38-b-348 | 0.3 | 41.7 | 0.04 | 54.7 |
| aCD38-b-348 (repeat) | 0.17 | 44.4 | 0.04 | 41.7 |

The aCD38-a-323 candidate antibody, has been further evaluated with respect to immune cells. In a first series of experiments, aCD38-a-323 shows dose dependent binding to human T cells (FIG. 3B). When tested using T cells, for instance when aCD38-a-323 is used for coating a plate for culturing such cells, aCD38-a-323 strongly increases human T cell activation in the presence of anti-CD3 stimulation while the reference anti-CD38 antibody (DARA) is displaying weaker agonist activity (FIG. 4A). The agonist activity of aCD38-a-323 is further emphasized by stronger proinflammatory cytokine secretion by human T cells triggered by aCD38-a-323 when compared to DARA (FIG. 4B). aCD38-a-323 and DARA show comparable activity in ADCC assays (FIG. 5A). The lower CDC effect triggered by aCD38-323 compared to DARA (FIG. 5B) would provide an anti-CD38 antibody having increased safety due to reduced infusion site reactions. aCD38-a-323 was also shown to have reduced or no ADCP as compared daratumumab (FIG. 26). In addition to the killing activities in vitro, aCD38-a-323 strongly increases the cyclase activity of CD38 (FIG. 6A and FIG. 27A), while DARA inhibits the latter activity in both the Daudi cell assay and the Jurkat cell assay. aCD38-a-323 decreases the NADase (NAD+ hydrolase) activity of CD38, while DARA does not (FIG. 6B) in Daudi cell assay. In the Jurkat cell assay whilst aCD38-a-323 decreases the NADase (NAD+ hydrolase) activity of CD38, while DARA increases the activity (FIG. 27B).

In conclusion, aCD38-a-323 has been characterized as an exemplary anti-CD38 antibody that presents the activities of a CD38 Modulating Antibody Agent with respect to immune cells in different experimental set ups.

Figure 1:
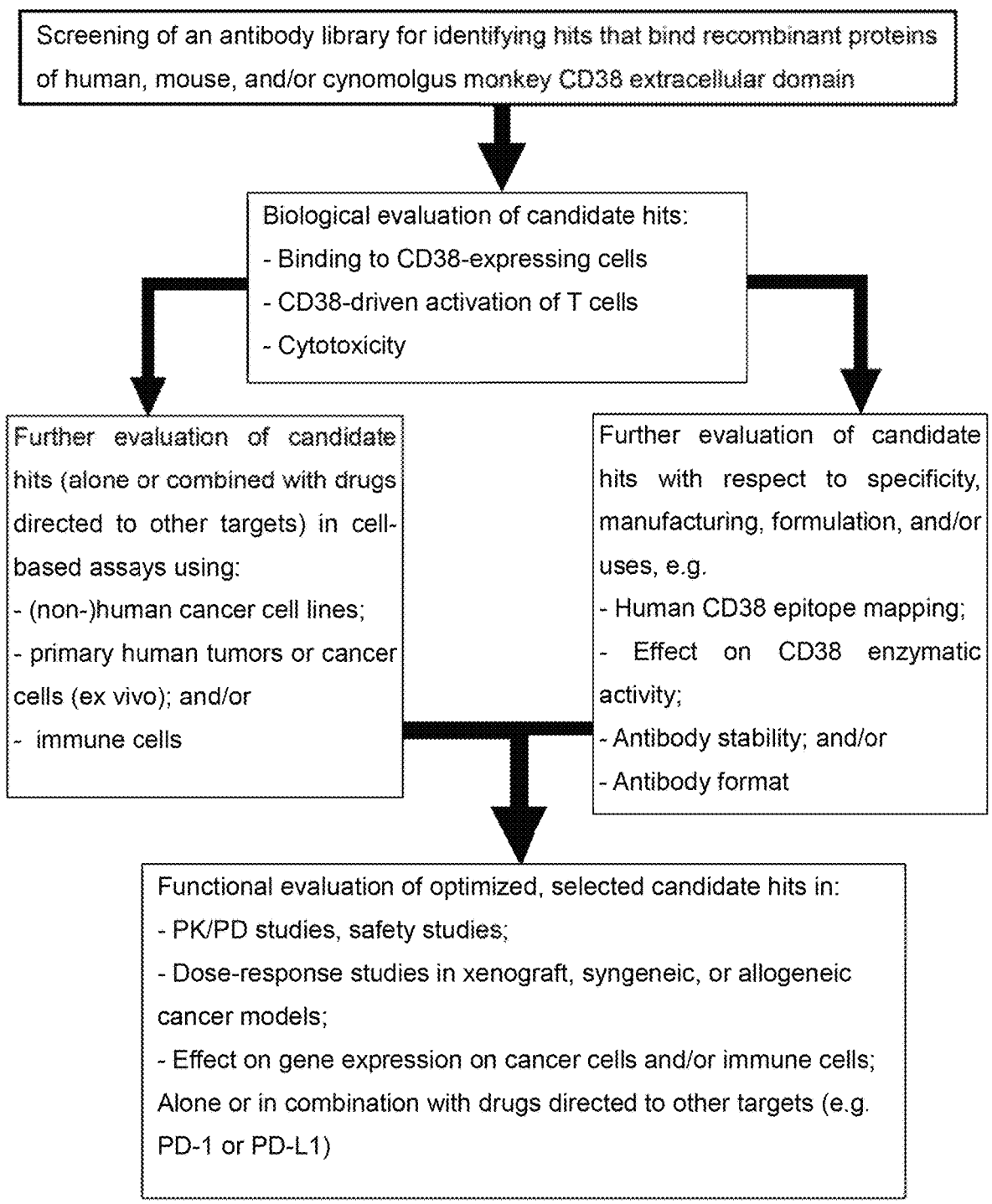
FIG. 1: flowchart summarizing the screening procedure for identifying aCD38-a-323, aCD38-a-306, aCD38-b-329, aCD38-a-327, and aCD38-b-348 as agonistic anti-CD38 antibodies having one or more properties according to the present invention, in particular those described herein as characteristic of CD38 Modulating Antibody Agents of particular interest: pharmaceutically relevant targeted cell killing (e.g. as measured in ADCC, ADCP, and CDC assays), effects on immune cells (such as Treg, CD8 and CD4 T cells, NK cells, dendritic cells, MDSC, macrophages, and/or monocytes, for measuring properties such as cell viability and/or proliferation, cytokine secretion, and/or activation markers), effects on CD38 enzymatic activities or CD38-mediated signalling, effects on cancer cells expressing (or not) CD38, combinations with other drugs (e.g. antibodies targeting a tumor antigen or other anticancer drugs) and/or antibody sequence and format, for identifying stability issues related to aggregation-prone sequences, presence of glycosylation sites or free Cysteines in variable domain and/or effects (e.g. within a human IgG1 frame, as Fabs, nanobodies, bi/multispecific antibodies, or within non-antibody scaffolds).
Figure 9:
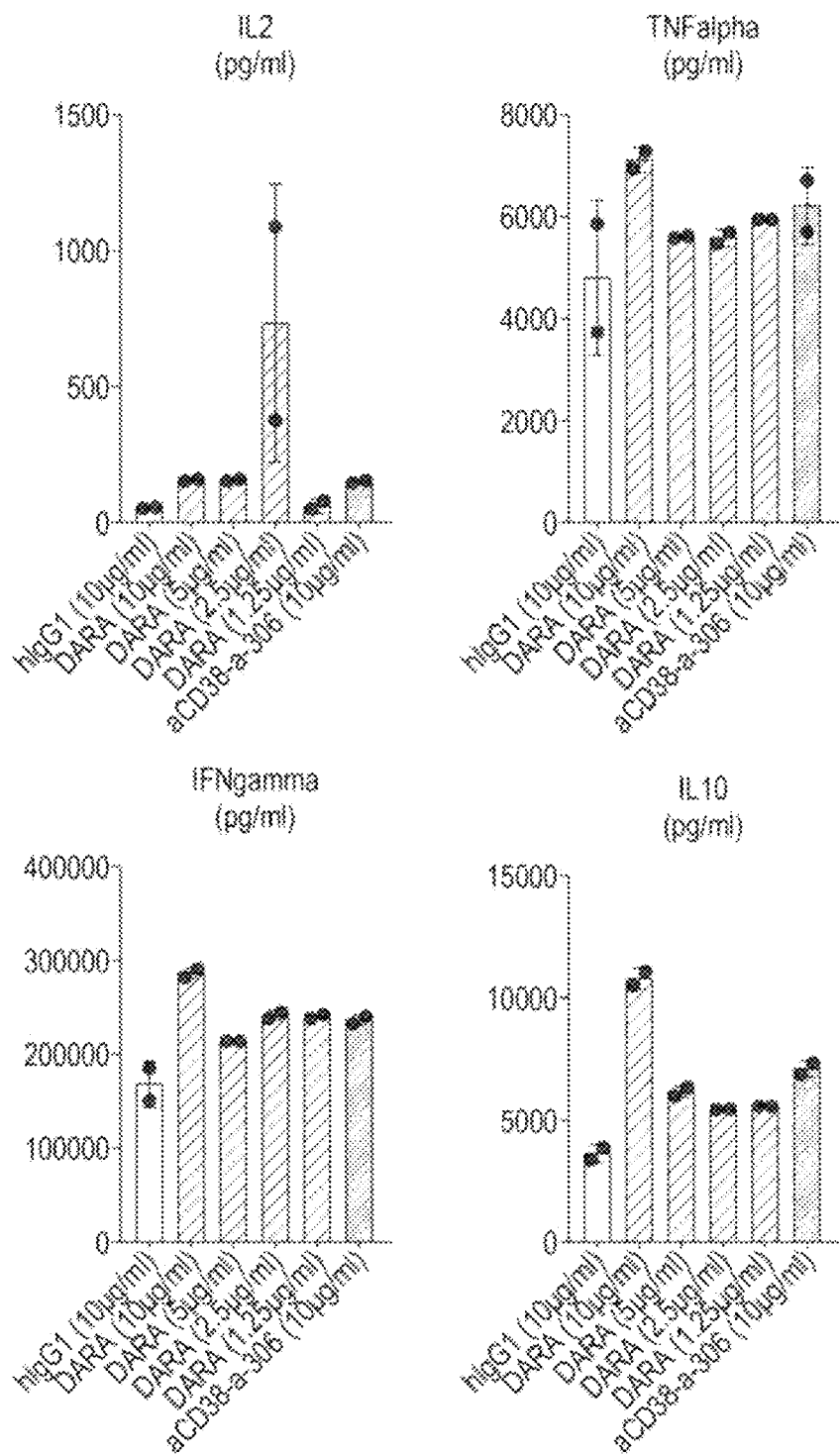
FIG. 9: Functional characterization of aCD38-a-306 compared to Daratumumab (DARA) or negative control antibodies (anti-human CD3 or human IgG1 isotype), in cell-based models independently from the administration of any further tumor targeting antibody. (A) aCD38-a-306 increases the percentage of TCR-mediated CD8 and CD4 T cell proliferation, as indicated in each graph. (Daratumumab is tested at 10-5-2.5-1.25 µg/ml; aCD38-a-306 and hIgG1 are tested at 10 µg/ml, anti-CD3 is tested at 0.5 µg/ml). (B) aCD38-a-306 does not increase the secretion of selected cytokines by TCR-activated CD4/CD8 T cells (similar pattern in 3 out of 3 donors tested). Antibodies tested at the same concentrations.

The aCD38-a-306 candidate antibody has been further evaluated with respect to immune cells. In a first series of experiments, aCD38-a-306 shows dose dependent binding to human but not cynomolgus T cells (FIGS. 8A and B). When tested using T cells, for instance when aCD38-a-306 is used for coating a plate for culturing such cells, aCD38-a-306 increases human T cell activation while the reference anti-CD38 antibody (DARA) is displaying weaker agonist activity (FIG. 9A).

Proinflammatory cytokine secretion is similar to DARA (FIG. 9B). aCD38-a-306 and DARA show comparable activity in ADCC assays (FIG. 10A), but only the latter one presents CDC activity (FIG. 10B). The lack of CDC effect triggered by aCD38-a-306 would provide an anti-CD38 antibody having increased safety due to reduced infusion site reaction. aCD38-a-323 and aCD38-a-306 were also shown to have no or reduced ADCP as compared daratumumab in an ADCP reporter cell assay (FIG. 26).

In addition to the killing activities in vitro, aCD38-a-306 was shown to decrease the cyclase activity of CD38 (FIG. 27A) to a lower extent than DARA, which more strongly inhibits the cyclase activity in the Jurkat cell assay. aCD38-a-306 strongly decreases the NADase (NAD+ hydrolase) activity of CD38, while DARA increases the activity in the Jurkat cell assay (FIG. 27B).

In conclusion, aCD38-a-306 has been characterized as an exemplary anti-CD38 antibody that presents the activities of a CD38 Modulating Antibody Agent with respect to immune cells in different experimental set ups.

Figure 12:
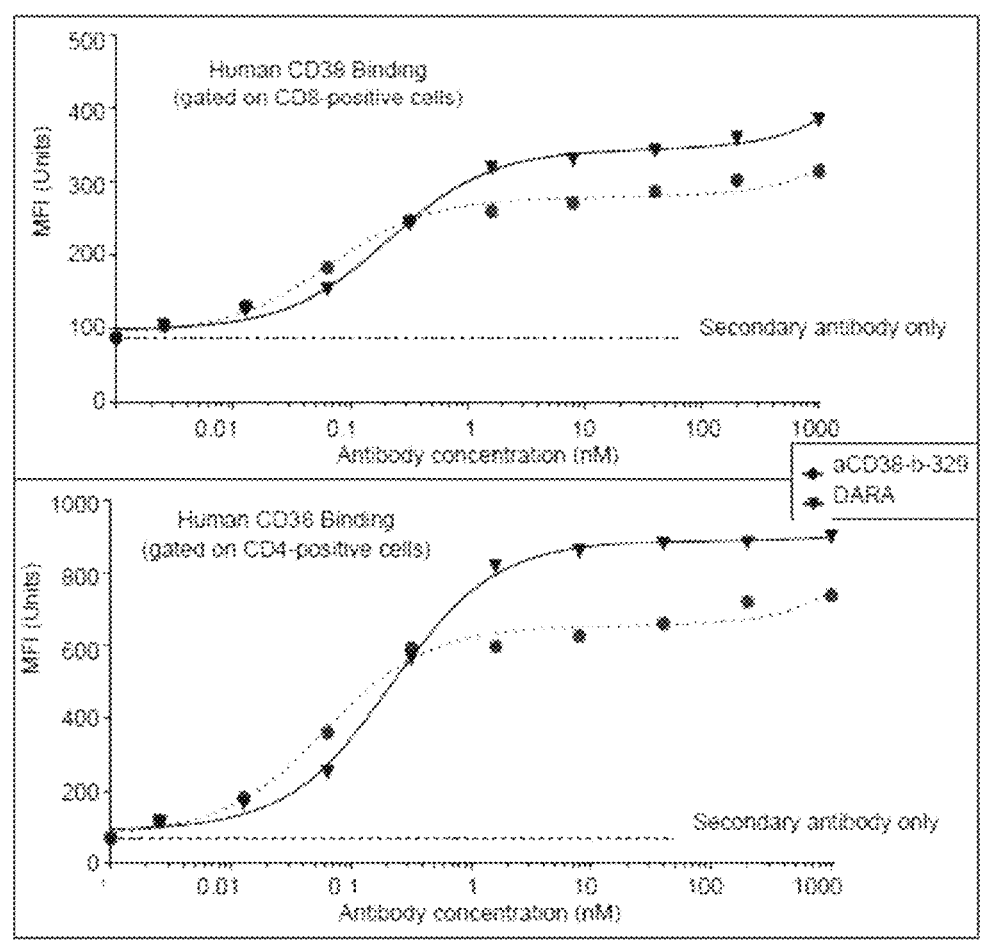
FIG. 12: characterization of aCD38-b-329 binding to CD38 expressed in PBMCs, using cells of human origin at increasing antibody concentration and by restricting the analysis to CD8-positive or CD4-positive cells and comparing with either human IgG1 isotype control, Daratumumab (DARA), or in absence of a primary antibody.

The aCD38-b-329 candidate antibody has been further evaluated with respect to immune cells. In a first series of experiments, aCD38-b-329 shows dose dependent binding to human T cells (FIG. 12). When tested using T cells, for instance when aCD38-b-329 is used for coating a plate for culturing such cells, aCD38-b-329 strongly increases human T cell activation while the reference anti-CD38 antibody (DARA) is displaying weaker agonist activity (FIG. 13A). The agonist activity of aCD38-b-329 is further emphasized by stronger proinflammatory cytokine secretion by human T cells triggered by aCD38-b-329 when compared to DARA (FIG. 13B). In addition, aCD38-b-329 and DARA show comparable activity in ADCC assays, but aCD38-b-329 presents less CDC activity (FIG. 14A). The reduced CDC effect triggered by aCD38-b-329 would provide an anti-CD38 antibody having increased safety due to reduced infusion site reaction. DARA and aCD38-b-329 show also comparable activity in killing of CD38 expressing tumour cells (Daudi) by human PBMC, even though only the activity of aCD38-b-329 appears enhanced by antibody cross-linking (FIG. 14B).

In conclusion, aCD38-b-329 has been characterized as an exemplary anti-CD38 antibody that presents the activities of a CD38 Modulating Antibody Agent with respect to immune cells in different experimental set ups.

The aCD38-b-348 candidate antibody has been further evaluated with respect to immune cells. In a first series of experiments, aCD38-b-348 shows dose dependent binding to human and cynomolgus T cells (FIGS. 17A and B). When tested using T cells, for instance when aCD38-b-348 is used for coating a plate for culturing such cells, aCD38-b-348 strongly increases human T cell activation while the reference anti-CD38 antibody (DARA) is displaying much weaker agonist activity (FIG. 18A and FIG. 29). When aCD38-b-348 is tested in solution, this antibody induces proliferation and activation of human primary NK cells co-cultured with a breast cancer cell line (FIG. 18B). The agonist activity of aCD38-b-348 is further emphasized by stronger proinflammatory cytokine secretion by human T cells triggered by aCD38-b-348 when compared to DARA (FIG. 18C). Killer activities of aCD38-b-348 appears exerted via inducing macrophage mediated phagocytosis of CD38 expression target cells (FIG. 19A), e.g. regulatory T cells. This effect is comparable to DARA. In addition, aCD38-b-348 and DARA show comparable activity in ADCC assays, but the latter presents higher CDC activity (FIG. 19B). The decreased CDC effect triggered by aCD38-b-348 would provide an anti-CD38 antibody having increased safety due to reduced infusion site reaction. DARA and aCD38-b-348 show also comparable activity in killing of CD38 expressing tumour cells (Daudi) by human PBMC, even though only the activity of aCD38-b-348 appears enhanced by antibody cross-linking (FIG. 19C). aCD38-b-348 was also shown to have increased ADCP as compared daratumumab in a reporter cell assay (FIG. 26).

In addition to the killing activities in vitro, aCD38-b-348 was shown to slightly decrease the cyclase activity of CD38 (FIG. 27A), however DARA more strongly inhibits the cyclase activity in the Jurkat cell assay. aCD38-b-348 showed no effect on the NADase (NAD+ hydrolase) activity of CD38, while DARA increases the activity in the Jurkat cell assay (FIG. 27B)

In conclusion, aCD38-b-348 has been characterized as an exemplary anti-CD38 antibody that presents the activities of a CD38 Modulating Antibody Agent with respect to immune cells in different experimental set ups.

The aCD38-a-327 candidate antibody has been further evaluated with respect to immune cells. aCD38-a-327 and DARA show comparable activity in ADCC assays (FIG. 23A). CDC is not triggered by aCD38-327 (FIG. 23B), which in comparison to DARA would provide an anti-CD38 antibody having increased safety due to reduced infusion site reactions. aCD38-a-327 shows week induction of apoptosis when crosslinked on target cells (FIGS. 23C and D).

In addition to the killing activities in vitro, aCD38-a-327 slightly decreases the cyclase activity of CD38 (FIG. 24A), while DARA inhibits the latter activity stronger in both the Daudi and Jurkat cell assays (reduction to 75% activity by aCD38-a-327, and to 16% activity by DARA in the Daudi cell assay). aCD38-a-327 has no influence on NADase (NAD+ hydrolase) activity of CD38 (FIGS. 24B and 27B) while DARA induces an increase of NADase activity in the Daudi cell assay and in the Jurkat cell assay.

In conclusion, aCD38-a-327 has been characterized as an exemplary anti-CD38 antibody that presents the activities of a CD38 Modulating Antibody Agent with respect to immune cells in different experimental set ups The same assays can be carried out on the variant antibodies provided herein (i.e. variants of aCD38-a-348 and aCD38-a-329 having altered DG motifs).

Example 3: Validation of CD38 Modulating Antibody Agent in Animal Models Materials & Methods Lymphoma cells-based models.

Daudi and Ramos human Burkitt Lymphoma cells were cultured in RPMI 1640 containing 2 mM L-glutamine supplemented with 10% fetal bovine serum+1 mM Na Pyruvate+4.5 g/L Glucose+10 mM Hepes. Healthy female cb17 SCID mice were obtained from Charles River. Tumors were induced by intravenous injection of $5 \times 10^5$ Daudi cells or $10^6$ Ramos cells in 200 µL of RPMI 1640 into the caudal vein of the animals. Cell injection was performed 24 to 72 hours after a whole body irradiation with a γ-source (1.44 Gy/mouse, 60Co, BioMep, Breteniéres, France). Mice were randomized into treatment groups by bodyweight, 8 mice per group. Animals from group 1 received intravenous injections of vehicle at 5 ml/kg twice a week for three consecutive weeks (TW×3). Animals from group 2 received intravenous injections of DARA at 10 mg/kg/inj. twice a week for three consecutive weeks (TW×3). Animals from groups 3 and 4 received intravenous injections of aCD38-b-348 or aCD38-b-329, respectively, at 10 mg/kg/inj. twice a week for three consecutive weeks (TW×3). Mice were sacrificed after a maximum of 72 days.

Solid Tumour model

Female CB.17 SCID mice were injected with $1 \times 10^7$ Ramos tumour cells in 0% Matrigel subcutaneously in the flank, n=10 per group. Treatment started when tumours reached 100-130 mm³ size for twice a week for three weeks. Mice were treated with 10 mg/kg intra venously with the antibodies aCD38-a-323, aCD38-a-306, aCD38-b-348 compared to daratumumab and a vehicle control. Mice were sacrificed when the tumour volume reached 2000 mm² or 60 days, whichever was reached first.

Results

The therapeutic properties of aCD38-a-323, aCD38-a-306, aCD38-b-348 can be tested in animal model for human cancer, in particular using immunocompromised mice where the properties of a CD38 Modulating Antibody Agent with respect to the killing of human tumor cells can be more appropriately evaluated.

aCD38-b-329 shows remarkable potency to increase survival of mice intravenously injected with two different types of human lymphoma cells, an effect that is potentially superior to Daratumumab (DARA) (FIG. 15).

aCD38-b-348 shows remarkable potency to increase survival of mice intravenously injected with two different types of human lymphoma cells, an effect that is superior to Daratumumab (DARA) (FIG. 20).

These properties, not only in terms of animal survival but also with concurrent immunological effects can be further investigated in other in vivo models for human tumors (in particular solid cancers) that are based on the injection with either human cancer lines or human primary cancer cells, in which solid tumors grow subcutaneously, as described in the literature (Morton J J et al. 2016; Holzapfel B M et al., 2015).

aCD38-b-348 and aCD38-a-306 showed enhanced antitumor activity against subcutaneously injected Ramos cells when compared to daratumumab. aCD38-a-323 showed equivalent anti-tumor activity against subcutaneously injected Ramos cells when compared to daratumumab (FIG. 28).

Properties can be further investigated in ex vivo models based on the use of tumour samples directly isolated from patients from which tumour cells and immune cells are isolated and tested in vitro for their response to the anti-CD38 antibodies, as measured by cell activation, proliferation, cytokine production and/or cell death. Additional features such as changes in gene expression in selected tissues or biological materials can be evaluated, possibly by administering aCD38-a-323, aCD38-a-306, aCD38-a-323, aCD38-b-348 in different doses and/or in combination with other anti-cancer agents (such as inhibitors of kinases or of other enzymes, antibodies, radio/chemo-therapy, adjuvants, or vaccines).

The same assays can be carried out on the variant antibodies provided herein (i.e. variants of aCD38-a-348 and aCD38-a-329 having altered DG motifs).

Example 4: Low Dose Anti-CD38 Antibody Increases T Cell Activation in Non-Human Primates Non-human primates (cynomolgus monkeys) were treated with 0.03 mg/kg aCD38-b-348 i.v. on days 1 and 8. Peripheral T cell frequencies and activation markers (CD69, CD137 and HLA-DR) were analysed before the first dose, as well as 24 hrs and 5 days after the second dose. T cells showed signs of increased activation after dosing, most prominently by upregulation of CD69 and CD137 on CD4

T cells, and HLA-DR on CD8 T cells. No immune activation-related adverse reactions were observed. The results are shows in FIGS. 32A to F.

These results demonstrate that the antibodies could be used therapeutically at a dosage of equal to or less than 1 mg/kg in human patients, which is below the current therapeutic dosages used for daratumumab.

Example 5: Generation of Variants of CD38 Modulating Antibody Agents

Variants of aCD38-b-329

To prevent aspartate isomerisation, a library of potential substitutions for the VL CDR3 DG sequence was generated. Two yeast libraries were generated for aCD38-b-329 in order to remove a DG motif. The first library was based on degenerate primers NNKNNK around both the aspartate and the glycine. This library had a diversity of 400. The second library was based on a degenerate primer NNK focused on the aspartate while preserving the glycine, with a diversity of 20. These libraries were sorted in a single round on human CD38 monomer at 10 nM and a PSR-negative sort was performed. 96 from each lineage were sequenced, produced, and characterized as above. Additionally, a total of five 96-well plates were picked from the NNKNNK libraries to screen for binding to rhCD38 in Octet. A limited number of substitutions were tolerated and the variants showing the best affinities were selected and the variants tested for binding the rhCD3 in Octet. Variants showing the best affinities were selected for mammalian production and further characterisation using the assays as described above in Example 2.

Results

The CDR1-FR2-CDR2-FR3-CDR3 sequence of the VH and VL chains of the variant antibodies are shown in FIG. 33. Daudi cell binding experiments confirmed that binding of the variant antibodies to CD38 was comparable with the parental clones and with daratumumab (FIG. 34 and FIG. 43).

TABLE 5

| Antibody | LCDR3 Sequence | Octect Affinity $K_D$ (M) | Biacore Affinity $K_D$ (M) | EC50 ug/ml | Max MFI |
|---|---|---|---|---|---|
| aCD38-b-329 | QQDGAVFT (SEQ ID NO: 23) | 2.38E-09 | 0.62E-09 | 0.734 | 2508 |
| aCD38-b-329-m6 | QQDEAVFT (SEQ ID NO: 41) | 1.99E-08 | 4.70E-09 | 0.651 | 2297 |
| aCD38-b-329-m7 | QQDSAVFT (SEQ ID NO: 42) | 2.60E-08 | 4.90E-09 | 0.745 | 2213 |
| Daratumumab | — | — | — | 0.945 | 2495 |

The variants showed comparable ADCC activity to the parental clones and daratumumab (FIG. 35). The variants had a lower EC50 ug/ml for ADCC activity than the parental strain but comparable maximum lysis (Table 6).

TABLE 6

| ADCC target lysis: | | |
|---|---|---|
| Antibody | EC50 ug/ml | Max. % lysis |
| aCD38-b-329 | 0.0062 | 49 |
| aCD38-b-329-m6 | 0.0024 | 47 |
| aCD38-b-329-m7 | 0.0035 | 43 |
| Daratumumab | 0.0025 | 58 |
| IgG1 Isotype | NA | 0 |

Peptide mapping samples were prepared through DTT reduction and iodoacetamide alkylation, digested using trypsin and analyzed on a LC-UV-MS system. The level of isomerized and non-isomerized peptides were determined and % of isomerized peptide are shown in Table 7:

TABLE 7

| Antibody | % isoD |
|---|---|
| aCD38-b-329 | 7.4% |
| aCD38-b-329-m6 | 0.0% |
| aCD38-b-329-m7 | 0.0% |

Variants of aCD38-b-348

To prevent aspartate isomerisation, a library of potential substitutions for the VL CDR3 DG sequence was generated. Two yeast libraries were generated for aCD38-b-348 in order to remove a DG motif. The first library was based on degenerate primers NNKNNK around both the aspartate and the glycine. This library had a diversity of 400. The second library was based on a degenerate primer NNK focused on the aspartate while preserving the glycine, with a diversity of 20. These libraries were sorted in a single round on human CD38 monomer at 10 nM and a PSR-negative sort was performed. 96 from each lineage were sequenced, produced, and characterized as above. Additionally, a total of five 96-well plates were picked from the NNKNNK libraries to screen for binding to rhCD38 in Octet. A limited number of substitutions were tolerated and the variants showing the best affinities were selected and the variants tested for binding the rhCD3 in Octet. Variants showing the best affinities were selected for mammalian production and further characterisation using the assays as described above in Example 2.

Results

The CDR1-FR2-CDR2-FR3-CDR3 sequence of the VH and VL chains of the variant antibodies are shown in FIG. 36. Daudi cell binding experiments confirmed that binding of the variant antibodies to CD38 was comparable with the parental clones and with daratumumab (FIG. 37).

TABLE 8

| Antibody | LCDR3 Sequence | Octet Affinity $K_D$ (M) | Biacore Affinity KD (M) | EC 50 ug/ml | Max MFI |
|---|---|---|---|---|---|
| aCD38-b-348 | QQDGNVYT (SEQ ID NO: 31) | 5.79E-09 | 2.0E-9 | 0.341 | 2324 |
| aCD38-b-348-m1 | QQEANVYT (SEQ ID NO: 43) | 2.47E-08 | 6.30E-08 | 0.485 | 1612 |
| aCD38-b-348-m2 | QQDSNVYT (SEQ ID NO: 44) | 3.99E-08 | 6.80E-09 | 0.499 | 2221 |

TABLE 8-continued

| Antibody | LCDR3 Sequence | Octet Affinity $K_D$(M) | Biacore Affinity KD(M) | EC 50 ug/ml | Max MFI |
|---|---|---|---|---|---|
| aCD38-b-348-m3 | QQDANVYT (SEQ ID NO: 45) | 5.51E-08 | 2.80E-08 | 0.558 | 2098 |
| aCD38-b-348-m4 | QQEGNYVT (SEQ ID NO: 46) | 7.01E-08 | 2.70E-08 | 0.299 | 2020 |
| Daratumumab | — | — | — | 0.945 | 2495 |

The variants showed comparable ADCC activity to the parental clones and daratumumab (FIG. 38). The variants had a lower EC50 ug/ml for ADCC activity than the parental strain but comparable maximum lysis (Table 9).

TABLE 9

ADCC target lysis:

| Antibody | EC50 ug/ml | Max. % lysis |
|---|---|---|
| aCD38-b-348 | 0.0059 | 44 |
| aCD38-b-348-m1 | 0.0028 | 38 |
| aCD38-b-348-m2 | 0.0025 | 44 |
| aCD38-b-348-m3 | 0.0043 | 39 |
| aCD38-b-348-m4 | 0.0014 | 38 |
| Daratumumab | 0.0025 | 58 |
| IgG1 Isotype | NA | 0 |

Peptide mapping samples were prepared through DTT reduction and iodoacetamide alkylation, digested using trypsin and analyzed on a LC-UV-MS system. The level of isomerized and non-isomerized peptides were determined and % of isomerized peptide are shown in Table 10:

TABLE 10

| Antibody | Isotype | % isoD |
|---|---|---|
| aCD38-b-348 | IgG4 | 13.0% |
| aCD38-b-348 | IgG1 | 15.5% |
| aCD38-b-348-m2 | IgG1 | 0.0% |
| aCD38-b-348-m3 | IgG1 | 0.0% |

Functional characterization of variants: Lymphoma cells-based models Raji and Ramos human Burkitt Lymphoma cells were cultured in RPMI 1640 containing 2 mM L-glutamine supplemented with 10% fetal bovine serum+1 mM Na Pyruvate+4.5 g/L Glucose+10 mM Hepes. Healthy female cb17 SCID mice were obtained from Charles River. Tumors were induced by intravenous injection of $5 \times 10^5$ Raji cells or $10^6$ Ramos cells in 200 µL of RPMI 1640 into the caudal vein of the animals. Cell injection was performed 24 to 72 hours after a whole body irradiation with a γ-source (1.44 Gy/mouse, 60Co, BioMep, Bretenieres, France). Mice were randomized into treatment groups by bodyweight, 10 mice per group. Animals from group 1 received intravenous injections of vehicle at 5 ml/kg twice a week for three consecutive weeks (TW×3). Animals from group 2 received intravenous injections of DARA at 10 mg/kg/inj. twice a week for three consecutive weeks (TW×3). Animals from group 3 received intravenous injections of aCD38-b-329 at 10 mg/kg/inj. twice a week for three consecutive weeks (TW×3). Mice from group 4 received intravenous injections of aCD38-b-329-m6 at 10 mg/kg/inj. twice a week for three consecutive weeks (TW×3), and mice from group 5 received intravenous injections of aCD38-b-329-m7 at 10 mg/kg/inj. twice a week for three consecutive weeks (TW×3). Animals from group 6 received intravenous injections of aCD38-b-348 at 10 mg/kg/inj. twice a week for three consecutive weeks (TW×3), and animals from group 7 received intravenous injections of aCD38-b-348-m2 at 10 mg/kg/inj. twice a week for three consecutive weeks (TW×3). Mice were sacrificed at the time indicated in the figure.

Results: The therapeutic properties of aCD38 antibodies and their variants were tested in animal models for human cancer, in particular using immunocompromised mice where the properties of a CD38 Modulating Antibody Agent with respect to the killing of human tumour cells can be more appropriately evaluated. aCD38-b-329 variants, aCD38-b-329-m6 and aCD38-b-329-m7, show remarkable potency to increase survival of mice intravenously injected with two different types of human lymphoma cells, an effect that is superior to Daratumumab (DARA) both models (Raji and Ramos) (FIG. 39). Variant of aCD38-b-348, aCD38-b-348-m2 shows remarkable potential to increase survival of mice in both models (Raji and Ramos) over the isotype control (FIG. 39).

Example 6: Analysis of aCD38-b-348 in NK Cells

NK Cell Degranulation:
NK cells isolated from buffy coats of healthy volunteers were either stimulated for 2 days with 500 U/ml IL-2 at $2 \times 10^6$ cells/ml in RPM11640 media containing 10% FCS, or used freshly isolated without prior IL-2 stimulation. For the functional assay 1 to $1.5 \times 10^6$ NK cells were resuspended in DMEM complete media, 100 µl cell suspension were seeded per well in 20 wells of a 96-well plate. 20 µl of media containing CD107a antibody (14 µl antibody pre-mixed in 140 µl media) were added to all wells except to unstained/unstimulated control conditions. Test antibodies aCD38-b-348, daratumumab, and human IgG1 isotype control were added at 10 µg/ml. For positive control 50 ml media containing PMA (50 ng/ml) and Ionomycin (1 mg/ml) were added to positive control wells, in addition, media only was added for negative control conditions. Cells were incubated at 37° C., 5% $CO_2$ for 45 minutes. 10 µl Golgi Stop were added to each well, and cells were incubated for further 4 hours. For readout, cells were harvested, transferred to FACS tubes, washed twice with FACS buffer, and labelled with anti-CD56-BV-570 and near infrared dead cell marker. After 20 minutes incubation cells were washed, resuspended in fresh buffer, and run on the flow cytometer.

NK Cell IFNγ Production:
NK cells isolated from buffy coats of healthy volunteers were stimulated for 48 hrs with 500 U/ml IL-2 in DMEM media containing 10% FBS. Cells were harvested, washed twice with PBS, resuspended at $1 \times 10^6$ cells/ml in DMEM complete media. 100 µl cell suspension were seeded per well in 96-well plates. 20 ml of media were added to all samples, either containing media only (negative control), or aCD38-b-348, daratumumab or isotype control to reach a final concentration of 10 g/ml in each test well. The positive control contained PMA/Ionomycin. The same conditions were set up for wells containing a co-culture of MDA-MB-231 tumour cells (100 000 cells/well) and NK cells (as above). GolgiPlug and GolgiStop were added to all wells (10 ul). Cells were incubated at 37° C., 5% $CO_2$ for 6 hours. For readout, cells were harvested, washed, transferred to FACS tubes, stained with anti-CD56-FITC and Aqua Dead cell maker for 20 minutes. After wash with FACS buffer cells were fixed for 20 minutes with fixation buffer, permeabilised and stained with anti-IFNγ-APC for 30 minutes. Cells were washed and resuspended for readout at flow cytometer.

NK Cell Proliferation:

NK cells isolated from buffy coats of healthy volunteers were stimulated for 48 hrs with 500 U/ml IL-2 in DMEM media containing 10% FBS. NK cells were harvested, washed, and labelled with CFSE proliferation dye: 8×10$^6$ cells were resuspended in 1 ml PBS in a falcon tube. 110 μl PBS were added as 1 drop to the side of the tube held horizontally, 0.2 μl CFSE were added into the PBS drop. Tube was vortex to mix cell suspension and CSFE solution, and incubated for 20 minutes at 37° C., 5% CO$_2$. 5 ml DMEM media were added, cells were further incubated for 5 minutes, spun down, washed, resuspended in complete media at 1×10$^6$ cells/ml. 100 μl cell suspension was seeded per well in 96-well plates. MDA-MB-231 cells were added at a 50:1 ratio in 80 μl media per well. 20 μl media containing aCD38-b-348, daratumumab, or IgG1 isotype control were added to result in a final concentration of 0.4, 2, or 10 μg/ml. Cells were incubated for 6 days and proliferation was assessed by flow cytometry looking at dilution of proliferation dye CFSE in the NK cell population.

Results

Soluble aCD38-b-348 or daratumumab (10 μg/ml) increase degranulation of un-activated or IL2 pre-activated human NK cells (FIG. 40). Soluble aCD38-b-348 or daratumumab (10 μg/ml) increase IFNγ production of NK cells in the presence or absence of a tumour target (MDA-MB-231 cells), FIG. 41. Soluble aCD38-b-348 but not daratumumab increases proliferation of human NK cells, as compared to control, in the presence of MDA-MB-231 tumour cells (FIG. 42).

The results show that soluble aCD38-b-348 antibody induces strong activation of primary human NK cells in vitro, defined by degranulation, IFNγ-production and proliferation. No further stimulation of NK cells in needed for these effects. daratumumab induces similar NK cell degranulation and IFNγ-production, but no NK cell proliferation.

Example 7: Antibody Binding to Mutant CD38

Materials and Methods: Two mutant version of human CD38 were constructed. In one version D was mutated to G at position 202 (D202G) and in the second version S was mutated to F at position 274 (S274F).

The binding of aCD38-b348, aCD38-b-329, aCD38-a-323, aCD38-a-327 and aCD38-a-306 to each of the mutated CD38 proteins was assessed, and compared to daratumumab.

Results

|  | Binding Reactivity (% WT) | |
| --- | --- | --- |
| Antibody | Mutation—D202G | Mutation—S274F |
| aCD38-b348 Fab HS | 66.8 (12) | 106.1 (9) |
| aCD38-a-323 Fab | 26.1 (2) | 94.6 (37) |
| aCD38-a-327 Fab | 113 (5) | 96.9 (44) |
| aCD38-a-306 Fab | 106.4 (15) | 14.3 (1) |
| Daratumumab | 39.9 (8) | 6.8 (6) |

The results showed that binding of aCD38-b348, aCD38-b-329 (results not shown), aCD38-a-323 and aCD38-a-327 was not affected by the introduction of mutation D202G or mutation S274F into human CD38. The binding of aCD38-a-306 was not affected by the introduction of mutation D202G but was affected by the introduction of mutation S274F into human CD38. This compares to Daratumumab where antibody binding was affected by the introduction of mutation S274F, but was not affected by the introduction of mutation D202G into human CD38. These results confirm that aCD38-b348, aCD38-b-329, aCD38-a-323, aCD38-a-327 bind to different epitopes than daratumumab.

The present invention also relates to the following:

1. An antibody or antigen-binding fragment thereof comprising the aCD38-a-323-HCDR3 amino acid sequence as variable heavy chain complementarity determining region 3.

2. The antibody or antigen-binding fragment thereof according to clause 1, further comprising
   a) aCD38-a-323-HCDR1 amino acid sequence as variable heavy chain complementarity determining region 1; and
   b) aCD38-a-323-HCDR2 amino acid sequence as variable heavy chain complementarity determining region 2.

3. The antibody or antigen-binding fragment thereof of according to clause 1 or 2, further comprising:
   a) aCD38-a-323-LCDR1 amino acid sequence as variable light chain complementarity determining region 1;
   b) aCD38-a-323-LCDR2 amino acid sequence as variable light chain complementarity determining region 2; and
   c) aCD38-a-323-LCDR3 amino acid sequence as variable light chain complementarity determining region 3.

4. The antibody or antigen-binding fragment thereof of according to clause 1, 2 or 3, wherein the antibody or antigen-binding fragment thereof comprises a variable heavy chain comprising aCD38-a-323-HCDR123 amino acid sequence.

5. The antibody or antigen-binding fragment thereof according to any one of clauses 1 to 4, wherein the antibody or antigen-binding fragment thereof further comprises a variable light chain comprising aCD38-a-323-LCDR123 amino acid.

6. The antibody or antigen-binding fragment thereof according to any one of clauses 1 to 5 wherein the antibody or an antigen-binding fragment thereof is selected from the group consisting of:
   a) an antibody or antigen binding fragment thereof comprising an HCDR1 comprising the sequence of SEQ ID NO: 1, an HCDR2 comprising the sequence of SEQ ID NO: 2, an HCDR3 comprising the sequence of SEQ ID NO 3, an LCDR1 comprising the sequence of SEQ ID NO: 5, an LCDR2 comprising the sequence of SEQ ID NO: 6, and an LCDR3 comprising the sequence of SEQ ID NO: 7;
   b) an antibody or antigen binding fragment thereof comprising a heavy chain variable region comprising the sequence of SEQ ID NO: 4 and a light chain variable region comprising the sequence of SEQ ID NO: 8;
   e) an antibody or antigen binding fragment thereof comprising a heavy chain variable region comprising the sequence of SEQ ID NO: 48 and a light chain variable region comprising the sequence of SEQ ID NO: 49; and
   d) an antibody or antigen binding fragment thereof comprising a heavy chain variable region comprising the sequence of SEQ ID NO: 72 and a light chain variable region comprising the sequence of SEQ ID NO: 73.

7. An antibody or antigen-binding fragment thereof comprising the aCD38-a-306-HCDR3 amino acid sequence as variable heavy chain complementarity determining region 3.

8. The antibody or antigen-binding fragment thereof according to clause 7, further comprising
   a) aCD38-a-306-HCDR1 amino acid sequence as variable heavy chain complementarity determining region 1; and
   b) aCD38-a-306-HCDR2 amino acid sequence as variable heavy chain complementarity determining region 2.
9. The antibody or antigen-binding fragment thereof of according to clause 7 or 8, further comprising:
   a) aCD38-a-306-LCDR1 amino acid sequence as variable light chain complementarity determining region 1;
   b) aCD38-a-306-LCDR2 amino acid sequence as variable light chain complementarity determining region 2; and
   c) aCD38-a-306-LCDR3 amino acid sequence as variable light chain complementarity determining region 3.
10. The antibody or antigen-binding fragment thereof of according to clause 7, 8 or 9, wherein the antibody or antigen-binding fragment thereof comprises a variable heavy chain comprising aCD38-a-306-HCDR123 amino acid sequence.
11. The antibody or antigen-binding fragment thereof according to any one of clauses 7 to 10, wherein the antibody or antigen-binding fragment thereof further comprises a variable light chain comprising aCD38-a-306-LCDR123 amino acid.
12. The antibody or antigen-binding fragment thereof according to any one of clauses 7 to 11 wherein the antibody or an antigen-binding fragment thereof is selected from the group consisting of:
   a) an antibody or antigen binding fragment thereof comprising an HCDR1 comprising the sequence of SEQ ID NO: 9, an HCDR2 comprising the sequence of SEQ ID NO: 10, an HCDR3 comprising the sequence of SEQ ID NO 11, an LCDR1 comprising the sequence of SEQ ID NO: 13, an LCDR2 comprising the sequence of SEQ ID NO: 14, and an LCDR3 comprising the sequence of SEQ ID NO: 15;
   b) an antibody or antigen binding fragment thereof comprising a heavy chain variable region comprising the sequence of SEQ ID NO: 12 and a light chain variable region comprising the sequence of SEQ ID NO: 16;
   c) an antibody or antigen binding fragment thereof comprising a heavy chain variable region comprising the sequence of SEQ ID NO: 50 and a light chain variable region comprising the sequence of SEQ ID NO: 51; and
   d) an antibody or antigen binding fragment thereof comprising a heavy chain variable region comprising the sequence of SEQ ID NO: 74 and a light chain variable region comprising the sequence of SEQ ID NO: 75.
13. An antibody or antigen-binding fragment thereof comprising the aCD38-b-329-HCDR3 amino acid sequence as variable heavy chain complementarity determining region 3.
14. The antibody or antigen-binding fragment thereof according to clause 13, further comprising
   a) aCD38-b-329-HCDR1 amino acid sequence as variable heavy chain complementarity determining region 1; and
   b) aCD38-a-309-HCDR2 amino acid sequence as variable heavy chain complementarity determining region 2.
15. The antibody or antigen-binding fragment thereof of according to clause 13 or 14, further comprising:
   a) aCD38-b-329-LCDR1 amino acid sequence as variable light chain complementarity determining region 1;
   b) aCD38-b-329-LCDR2 amino acid sequence as variable light chain complementarity determining region 2; and
   c) aCD38-b-329-LCDR3 amino acid sequence as variable light chain complementarity determining region 3.
16. The antibody or antigen-binding fragment thereof of according to clause 13, 14, or 15, wherein the antibody or antigen-binding fragment thereof comprises a variable heavy chain comprising aCD38-b-329-HCDR123 amino acid sequence.
17. The antibody or antigen-binding fragment thereof according to any one of clauses 13 to 16, wherein the antibody or antigen-binding fragment thereof further comprises a variable light chain comprising aCD38-b-329-LCDR123 amino acid.
18. The antibody or antigen-binding fragment thereof according to any one of clauses 15 to 17, wherein the antibody or antigen-binding fragment thereof is mutated to remove the DG motif in the LCDR3 region.
19. The antibody or antigen-binding fragment thereof according to clause 18, wherein the antibody or antigen-binding fragment thereof comprises an LCDR3 region selected from the group consisting of QQDEAVFT and QQDSAVFT.
20. The antibody or antigen-binding fragment thereof according to any one of clauses 13 to 19 wherein the antibody or an antigen-binding fragment thereof is selected from the group consisting of:
   a) an antibody or antigen binding fragment thereof comprising an HCDR1 comprising the sequence of SEQ ID NO: 17, an HCDR2 comprising the sequence of SEQ ID NO: 18, an HCDR3 comprising the sequence of SEQ ID NO 19, an LCDR1 comprising the sequence of SEQ ID NO: 21, an LCDR2 comprising the sequence of SEQ ID NO: 22, and an LCDR3 comprising the sequence of SEQ ID NO: 23;
   b) an antibody or antigen binding fragment thereof comprising an HCDR1 comprising the sequence of SEQ ID NO: 17, an HCDR2 comprising the sequence of SEQ ID NO: 18, an HCDR3 comprising the sequence of SEQ ID NO 19, an LCDR1 comprising the sequence of SEQ ID NO: 21, an LCDR2 comprising the sequence of SEQ ID NO: 22, and an LCDR3 comprising the sequence of SEQ ID NO: 41;
   c) an antibody or antigen binding fragment thereof comprising an HCDR1 comprising the sequence of SEQ ID NO: 17, an HCDR2 comprising the sequence of SEQ ID NO: 18, an HCDR3 comprising the sequence of SEQ ID NO 19, an LCDR1 comprising the sequence of SEQ ID NO: 21, an LCDR2 comprising the sequence of SEQ ID NO: 22, and an LCDR3 comprising the sequence of SEQ ID NO: 42;
   d) an antibody or antigen binding fragment thereof comprising a heavy chain variable region comprising the sequence of SEQ ID NO: 20 and a light chain variable region comprising the sequence of SEQ ID NO: 24.
   e) an antibody or antigen binding fragment thereof comprising a heavy chain variable region comprising the sequence of SEQ ID NO: 20 and a light chain variable region comprising the sequence of SEQ ID NO: 62.
   f) an antibody or antigen binding fragment thereof comprising a heavy chain variable region comprising the sequence of SEQ ID NO: 20 and a light chain variable region comprising the sequence of SEQ ID NO: 63.
   g) an antibody or antigen binding fragment thereof comprising a heavy chain variable region comprising the sequence of SEQ ID NO: 52 and a light chain variable region comprising the sequence of SEQ ID NO: 53;
   h) an antibody or antigen binding fragment thereof comprising a heavy chain variable region comprising the sequence of SEQ ID NO: 52 and a light chain variable region comprising the sequence of SEQ ID NO: 68;
i) an antibody or antigen binding fragment thereof comprising a heavy chain variable region comprising the sequence of SEQ ID NO: 52 and a light chain variable region comprising the sequence of SEQ ID NO: 69.

21. An antibody or antigen-binding fragment thereof comprising the aCD38-b-348-HCDR3 amino acid sequence as variable heavy chain complementarity determining region 3.

22. The antibody or antigen-binding fragment thereof according to clause 21, further comprising
    a) aCD38-b-348-HCDR1 amino acid sequence as variable heavy chain complementarity determining region 1; and
    b) aCD38-b-348-HCDR2 amino acid sequence as variable heavy chain complementarity determining region 2.

23. The anti-CD38 antibody or antigen-binding fragment thereof of according to clause 21 or 22, further comprising:
    a) aCD38-b-348-LCDR1 amino acid sequence as variable light chain complementarity determining region 1;
    b) aCD38-b-348-LCDR2 amino acid sequence as variable light chain complementarity determining region 2; and
    c) aCD38-b-348-LCDR3 amino acid sequence as variable light chain complementarity determining region 3.

24. The anti-CD38 antibody or antigen-binding fragment thereof of according to clause 21, 22, or 23, wherein the antibody or antigen-binding fragment thereof comprises a variable heavy chain comprising aCD38-b-348-HCDR123 amino acid sequence.

25. The anti-CD38 antibody or antigen-binding fragment thereof according to any one of clauses 21 to 24 wherein the antibody or antigen-binding fragment thereof further comprises a variable light chain comprising aCD38-b-348-LCDR123 amino acid.

26. The antibody or antigen-binding fragment thereof according to any one of clauses 23 to 25, wherein the antibody or antigen-binding fragment thereof is mutated to remove the DG motif in the LCDR3 region.

27. The antibody or antigen-binding fragment thereof according to clause 26, wherein the antibody or antigen-binding fragment thereof comprises an LCDR3 region selected from the group consisting of QQEANVYT, QQDSNVYT, QQDANVYT and QQEGNVYT.

28. The antibody or antigen-binding fragment thereof according to any one of clauses 21 to 27 wherein the antibody or an antigen-binding fragment thereof is selected from the group consisting of:
    a) an antibody or antigen binding fragment thereof comprising an HCDR1 comprising the sequence of SEQ ID NO: 25, an HCDR2 comprising the sequence of SEQ ID NO: 26, an HCDR3 comprising the sequence of SEQ ID NO 27, an LCDR1 comprising the sequence of SEQ ID NO: 29, an LCDR2 comprising the sequence of SEQ ID NO: 30, and an LCDR3 comprising the sequence of SEQ ID NO: 31;
    b) an antibody or antigen binding fragment thereof comprising an HCDR1 comprising the sequence of SEQ ID NO: 25, an HCDR2 comprising the sequence of SEQ ID NO: 26, an HCDR3 comprising the sequence of SEQ ID NO 27, an LCDR1 comprising the sequence of SEQ ID NO: 29, an LCDR2 comprising the sequence of SEQ ID NO: 30, and an LCDR3 comprising the sequence of SEQ ID NO: 43;
    c) an antibody or antigen binding fragment thereof comprising an HCDR1 comprising the sequence of SEQ ID NO: 25, an HCDR2 comprising the sequence of SEQ ID NO: 26, an HCDR3 comprising the sequence of SEQ ID NO 27, an LCDR1 comprising the sequence of SEQ ID NO: 29, an LCDR2 comprising the sequence of SEQ ID NO: 30, and an LCDR3 comprising the sequence of SEQ ID NO: 44;
    d) an antibody or antigen binding fragment thereof comprising an HCDR1 comprising the sequence of SEQ ID NO: 25, an HCDR2 comprising the sequence of SEQ ID NO: 26, an HCDR3 comprising the sequence of SEQ ID NO 27, an LCDR1 comprising the sequence of SEQ ID NO: 29, an LCDR2 comprising the sequence of SEQ ID NO: 30, and an LCDR3 comprising the sequence of SEQ ID NO: 45
    e) an antibody or antigen binding fragment thereof comprising an HCDR1 comprising the sequence of SEQ ID NO: 25, an HCDR2 comprising the sequence of SEQ ID NO: 26, an HCDR3 comprising the sequence of SEQ ID NO 27, an LCDR1 comprising the sequence of SEQ ID NO: 29, an LCDR2 comprising the sequence of SEQ ID NO: 30, and an LCDR3 comprising the sequence of SEQ ID NO: 46;
    f) an antibody or antigen binding fragment thereof comprising a heavy chain variable region comprising the sequence of SEQ ID NO: 28 and a light chain variable region comprising the sequence of SEQ ID NO: 32.
    g) an antibody or antigen binding fragment thereof comprising a heavy chain variable region comprising the sequence of SEQ ID NO: 28 and a light chain variable region comprising the sequence of SEQ ID NO: 58.
    h) an antibody or antigen binding fragment thereof comprising a heavy chain variable region comprising the sequence of SEQ ID NO: 28 and a light chain variable region comprising the sequence of SEQ ID NO: 59.
    i) an antibody or antigen binding fragment thereof comprising a heavy chain variable region comprising the sequence of SEQ ID NO: 28 and a light chain variable region comprising the sequence of SEQ ID NO: 60;
    j) an antibody or antigen binding fragment thereof comprising a heavy chain variable region comprising the sequence of SEQ ID NO: 28 and a light chain variable region comprising the sequence of SEQ ID NO: 61;
    k) an antibody or antigen binding fragment thereof comprising a heavy chain variable region comprising the sequence of SEQ ID NO: 54 and a light chain variable region comprising the sequence of SEQ ID NO: 55;
    l) an antibody or antigen binding fragment thereof comprising a heavy chain variable region comprising the sequence of SEQ ID NO: 54 and a light chain variable region comprising the sequence of SEQ ID NO: 64;
    m) an antibody or antigen binding fragment thereof comprising a heavy chain variable region comprising the sequence of SEQ ID NO: 54 and a light chain variable region comprising the sequence of SEQ ID NO: 65;
    n) an antibody or antigen binding fragment thereof comprising a heavy chain variable region comprising the sequence of SEQ ID NO: 54 and a light chain variable region comprising the sequence of SEQ ID NO: 66;
    o) an antibody or antigen binding fragment thereof comprising a heavy chain variable region comprising the sequence of SEQ ID NO: 54 and a light chain variable region comprising the sequence of SEQ ID NO: 67.

29. An antibody or antigen-binding fragment thereof comprising the aCD38-a-327-HCDR3 amino acid sequence as variable heavy chain complementarity determining region 3.
30. The antibody or antigen-binding fragment thereof according to clause 29, further comprising
    a) aCD38-a-327-HCDR1 amino acid sequence as variable heavy chain complementarity determining region 1; and
    b) aCD38-a-327-HCDR2 amino acid sequence as variable heavy chain complementarity determining region 2.
31. The antibody or antigen-binding fragment thereof of according to clause 29 or 30, further comprising:
    a) aCD38-a-327LCDR1 amino acid sequence as variable light chain complementarity determining region 1;
    b) aCD38-a-327-LCDR2 amino acid sequence as variable light chain complementarity determining region 2; and
    c) aCD38-a-327-LCDR3 amino acid sequence as variable light chain complementarity determining region 3.
32. The antibody or antigen-binding fragment thereof of according to clause 29, 30 or 31, wherein the antibody or antigen-binding fragment thereof comprises a variable heavy chain comprising aCD38-a-327-HCDR123 amino acid sequence.
33. The antibody or antigen-binding fragment thereof according to any one of clauses 29 to 32, wherein the antibody or antigen-binding fragment thereof further comprises a variable light chain comprising aCD38-a-327-LCDR123 amino acid.
34. The antibody or antigen-binding fragment thereof according to any one of clauses 29 to 33 wherein the antibody or an antigen-binding fragment thereof is selected from the group consisting of:
    a) an antibody or antigen binding fragment thereof comprising an HCDR1 comprising the sequence of SEQ ID NO: 33, an HCDR2 comprising the sequence of SEQ ID NO: 34, an HCDR3 comprising the sequence of SEQ ID NO 35, an LCDR1 comprising the sequence of SEQ ID NO: 37, an LCDR2 comprising the sequence of SEQ ID NO: 38, and an LCDR3 comprising the sequence of SEQ ID NO: 39;
    b) an antibody or antigen binding fragment thereof comprising a heavy chain variable region comprising the sequence of SEQ ID NO: 36 and a light chain variable region comprising the sequence of SEQ ID NO: 40;
    c) an antibody or antigen binding fragment thereof comprising a heavy chain variable region comprising the sequence of SEQ ID NO: 56 and a light chain variable region comprising the sequence of SEQ ID NO: 57; and
    d) an antibody or antigen binding fragment thereof comprising a heavy chain variable region comprising the sequence of SEQ ID NO: 76 and a light chain variable region comprising the sequence of SEQ ID NO: 77.
35. The antibody or antigen-binding fragment thereof of any one of clauses 1 to 34, wherein the antibody or antigen-binding fragment thereof is a monoclonal antibody, a domain antibody, a single chain antibody, a Fab fragment, a F(ab')2 fragment, a single chain variable fragment (scFv), a scFv-Fc fragment, a single chain antibody (scAb), or a single domain antibody.
36. The antibody or antigen-binding fragment thereof of any one of clauses 1 to 35, wherein the antibody or antigen-binding fragment thereof is a rabbit, mouse, chimeric, humanized or fully human antigen-binding antibody.
37. The antibody or antigen-binding fragment thereof of any one of clauses 1 to 36, wherein the antibody is selected from the group consisting of IgG1, IgG2, IgG3, and IgG4 isotype antibodies.
38. The antibody or antigen-binding fragment thereof of any one of clauses 1 to 37, wherein the antibody or antigen-binding fragment thereof is comprised in a bispecific antibody, a multispecific antibody, or an immunoconjugate further comprising a therapeutic or diagnostic agent.
39. The antibody or antigen-binding fragment thereof of any one of clauses 1 to 38, wherein the antibody or antigen-binding fragment thereof binds the extracellular domain of human CD38.
40. The antibody or antigen-binding fragment thereof of any one of clauses 1 to 39, wherein the antibody or antigen-binding fragment thereof binds cells expressing human CD38 on their surface and is a CD38 Modulating Antibody Agent.
41. The antibody or antigen-binding fragment thereof of any one of clauses 1 to 40 wherein the antibody or antigen-binding fragment is a-fucosylated.
42. An antibody or antigen-binding fragment that specifically binds to an epitope of human CD38, wherein the epitope comprises one or more amino acid residues comprised in amino acids 65-79, 47-66 and 126-138 of SEQ ID NO: 47.
43. The antibody or antigen or antigen-binding fragment of clause 42 wherein the epitope comprises amino acids 65-79 of SEQ ID NO: 47.
44. The antibody or antigen or antigen-binding fragment of clause 42 wherein the epitope comprises amino acids 47-66 and 126-138 of SEQ ID NO: 47.
45. The antibody or antigen or antigen-binding fragment of clause 42 or clause 44 wherein the antibody further binds amino acid 68 of SEQ ID NO: 47.
46. An antibody or antigen-binding fragment that specifically binds to an epitope of human CD38, wherein the epitope comprises amino acid residues 120, 121 and 141 of SEQ ID NO:47.
47. The antibody or antigen-binding fragment of clause 46 wherein the epitope further comprises amino acid residue 241 of SEQ ID NO: 47.
48. An affinity matured variant of an antibody or antigen-binding fragment thereof of any one of clauses 1 to 47.
49. A nucleic acid molecule encoding the antibody or antigen-binding fragment thereof of any of the any one of clauses 1 to 48.
50. A nucleic acid vector comprising the nucleic acid molecule of clause 49.
51. A host cell comprising the nucleic acid vector of clause 50.
52. A method for producing an antibody or antigen-binding fragment thereof of any one of clauses 1 to 48 by culturing a host cell of clause 46.
53. A composition comprising an antibody or antigen-binding fragment thereof of any one of clauses 1 to 48.
54. The composition of clause 53 that further comprises a pharmaceutically acceptable carrier or excipient.
55. The pharmaceutical composition of clause 53 or clause 54, wherein said composition is for use in the treatment of cancer.
56. Use of an antibody or antigen-binding fragment thereof of any one of clauses 1 to 48, or of a composition of clause 53 in the manufacture of a medicament for treating a cancer.
57. Use of an antibody or antigen-binding fragment thereof that competes with an antibody according to anyone of clauses 1 to 48 for the binding of CD38 in the manufacture of a medicament for treating cancer.

58. A method of treating cancer in a subject, comprising administering to the subject an effective amount of the composition of clause 53 or clause 54.
59. A method of treating cancer in a subject, comprising administering to the subject an effective amount of an antibody or antigen-binding fragment thereof that competes with an antibody according to anyone of clause 1 to 48 for the binding of CD38.
60. The method of clause 58 or 59, further comprising administering, simultaneously or sequentially in any order, a second agent to the subject.
61. The method of clause 58, 59 or 60 wherein the subject has a solid tumour.
62. The method according to anyone of clauses 58, 59, 60 wherein the subject has a haematological cancer.
63. An antibody or antigen-binding fragment that competes with an antibody according to anyone of clauses 1 to 48 for the binding of CD38 for use in the treatment of cancer.
64. A kit comprising the composition of clauses 53 or clause 54 in a container.
65. A method of preparing an anti-CD38 antibody comprising providing an antibody according to any one of clauses 1 to 47, and subjecting the antibody to affinity maturation, wherein the anti-CD38 antibody produced has a greater affinity to CD38 than the parental antibody.
66. A method of preparing a pharmaceutical composition comprising providing an antibody prepared according to a method of clause 65 and co-formulating the antibody with at least one or more pharmaceutically acceptable excipients.

The present invention also provides antibodies or antibody fragments thereof having the activity profiles as defined herein, wherein the antibody or antibody fragment thereof is an antibody or antibody fragment defined according to any one of clauses 1 to 61.

A summary of the sequences included in the application is provided below:

| SEQ ID NO | Description of antibody sequences | Also referred to as |
|---|---|---|
| 1 | aCD38-a-323 variable heavy chain CDR1 | aCD38-a-323-HCDR1 |
| 2 | aCD38-a-323 variable heavy chain CDR2 | aCD38-a-323-HCDR2 |
| 3 | aCD38-a-323 variable heavy chain CDR3 | aCD38-a-323-HCDR3 |
| 4 | aCD38-a-323 variable heavy chain CDR 1, 2, 3 and FR 2, 3, 4 | aCD38-a-323-HCDR123 |
| 5 | aCD38-a-323 variable light chain CDR1 | aCD38-a-323-LCDR1 |
| 6 | aCD38-a-323 variable light chain CDR2 | aCD38-a-323-LCDR2 |
| 7 | aCD38-a-323 variable light chain CDR3 | aCD38-a-323-LCDR3 |
| 8 | aCD38-a-323 variable light chain CDR 1, 2, 3 and FR 2, 3, 4 | aCD38-a-323-LCDR123 |
| 9 | aCD38-a-306 variable heavy chain CDR1 | aCD38-a-306 HCDR1 |
| 10 | aCD38-a-306 variable heavy chain CDR2 | aCD38-a-306 HCDR2 |
| 11 | aCD38-a-306 variable heavy chain CDR3 | aCD38-a-306-HCDR3 |
| 12 | aCD38-a-306 variable heavy chain CDR 1, 2, 3 and FR 2, 3, 4 | aCD38-a-306-HCDR123 |
| 13 | aCD38-a-306 variable light chain CDR1 | aCD38-a-306-LCDR1 |
| 14 | aCD38-a-306 variable light chain CDR2 | aCD38-a-306-LCDR2 |
| 15 | aCD38-a-306 variable light chain CDR3 | aCD38-a-306-LCDR3 |
| 16 | aCD38-a-306 variable light chain CDR 1, 2, 3 and FR 2, 3, 4 | aCD38-a-306-LCDR123 |
| 17 | aCD38-b-329 variable heavy chain CDR1 | aCD38-b-329-HCDR1 |
| 18 | aCD38-b-329 variable heavy chain CDR2 | aCD38-b-329-HCDR2 |
| 19 | aCD38-b-329 variable heavy chain CDR3 | aCD38-b-329-HCDR3 |
| 20 | aCD38-b-329 variable heavy chain CDR 1, 2, 3 and FR 2, 3 | aCD38-b-329-HCDR123<br>aCD38-b-329-m6-HCDR123<br>aCD38-b-329-m7-HCDR123 |
| 21 | aCD38-b-329 variable light chain CDR1 | aCD38-b-329-LCDR1 |
| 22 | aCD38-b-329 variable light chain CDR2 | aCD38-b-329-LCDR2 |
| 23 | aCD38-b-329 variable light chain CDR3 | aCD38-b-329-LCDR3 |
| 24 | aCD38-b-329 variable light chain CDR 1, 2, 3 and FR 2, 3 | aCD38-b-329-LCDR123 |
| 25 | aCD38-b-348 variable heavy chain CDR1 | aCD38-b-348-HCDR1 |
| 26 | aCD38-b-348 variable heavy chain CDR2 | aCD38-b-348-HCDR2 |
| 27 | aCD38-b-348 variable heavy chain CDR3 | aCD38-b-348-HCDR3 |
| 28 | aCD38-b-348 variable heavy chain CDR 1, 2, 3 and FR 2, 3 | aCD38-b-348-HCDR123<br>aCD38-b-348-m1-HCDR123<br>aCD38-b-348-m2-HCDR123<br>aCD38-b-348-m3-HCDR123<br>aCD38-b-348-m4-HCDR123 |
| 29 | aCD38-b-348 variable light chain CDR1 | aCD38-b-348-LCDR1 |
| 30 | aCD38-b-348 variable light chain CDR2 | aCD38-b-348-LCDR2 |
| 31 | aCD38-b-348 variable light chain CDR3 | aCD38-b-348-LCDR3 |
| 32 | aCD38-b-348 variable light chain CDR 1, 2, 3 and FR 2, 3 | aCD38-b-348-LCDR123 |
| 33 | aCD38-a-327 variable heavy chain CDR1 | aCD38-a-327 HCDR1 |
| 34 | aCD38-a-327 variable heavy chain CDR2 | aCD38-a-327 HCDR2 |
| 35 | aCD38-a-327 variable heavy chain CDR3 | aCD38-a-327-HCDR3 |
| 36 | aCD38-a-327 variable heavy chain CDR 1, 2, 3 and FR 2, 3, 4 | aCD38-a-327-HCDR123 |
| 37 | aCD38-a-327 variable light chain CDR1 | aCD38-a-327-LCDR1 |
| 38 | aCD38-a-327 variable light chain CDR2 | aCD38-a-327-LCDR2 |
| 39 | aCD38-a-327 variable light chain CDR3 | aCD38-a-327-LCDR3 |
| 40 | aCD38-a-327 variable light chain CDR 1, 2, 3 and FR 2, 3, 4 | aCD38-a-327-LCDR123 |
| 41 | aCD38-b-329-m6 variable light chain CDR3 | aCD38-b-329-m6 |
| 42 | aCD38-b-329-m7 variable light chain CDR3 | aCD38-b-329-m7 |
| 43 | aCD38-b-348-m1 variable light chain CDR3 | aCD38-b-348-m1 |
| 44 | aCD38-b-348-m2 variable light chain CDR3 | aCD38-b-348-m2 |
| 45 | aCD38-b-348-m3 variable light chain CDR3 | aCD38-b-348-m3 |

-continued

| SEQ ID NO | Description of antibody sequences | Also referred to as |
|---|---|---|
| 46 | aCD38-b-348-m4 variable light chain CDR3 | aCD38-b-348-m4 |
| 47 | Human CD38 | Uniprot code P28907 |
| 48 | aCD38-a-323 variable heavy chain CDR 1, 2,3 and FR 1, 2, 3, 4 | aCD38-a-323-VH |
| 49 | aCD38-a-323 variable light chain CDR 1, 2, 3 and FR 1, 2, 3, 4 | aCD38-a-323-VL |
| 50 | aCD38-a-306 variable heavy chain CDR 1, 2,3 and FR 1, 2, 3, 4 | aCD38-a-306-VH |
| 51 | aCD38-a-306 variable light chain CDR 1, 2, 3 and FR 1, 2, 3, 4 | aCD38-a-306-VL |
| 52 | aCD38-b-329 variable heavy chain CDR 1, 2,3 and FR 1, 2, 3, 4 | aCD38-b-329-VH |
| 53 | aCD38-b-329 variable light chain CDR 1, 2, 3 and FR 1, 2, 3, 4 | aCD38-b-329-VL |
| 54 | aCD38-b-348 variable heavy chain CDR 1, 2, 3 and FR 1, 2, 3, 4 | aCD38-b-348-VH |
| 55 | aCD38-b-348 variable light chain CDR 1, 2, 3 and FR 1, 2, 3, 4 | aCD38-b-348-VL |
| 56 | aCD38-a-327 variable heavy chain CDR 1, 2, 3 and FR 1, 2, 3, 4 | aCD38-a-327-VH |
| 57 | aCD38-a-327 variable light chain CDR 1, 2, 3 and FR 1, 2, 3, 4 | aCD38-a-327-VL |
| 58 | aCD38-b-348-m1 variable light chain CDR 1, 2, 3 and FR 2, 3 | aCD38-b-348-m1-LCDR123 |
| 59 | aCD38-b-348-m2 variable light chain CDR 1, 2, 3 and FR 2, 3 | aCD38-b-348-m2-LCDR123 |
| 60 | aCD38-b-348-m3 variable light chain CDR 1, 2, 3 and FR 2, 3 | aCD38-b-348-m3-LCDR123 |
| 61 | aCD38-b-348-m4 variable light chain CDR 1, 2, 3 and FR 2, 3 | aCD38-b-348-m4-LCDR123 |
| 62 | aCD38-b-329-m6 variable light chain CDR 1, 2, 3 and FR 2, 3 | aCD38-b-329-m6LCDR123 |
| 63 | aCD38-b-329-m7 variable light chain CDR 1, 2, 3 and FR 2, 3 | aCD38-b-329-m7-LCDR123 |
| 64 | aCD38-b-348-m1 variable light chain CDR 1, 2, 3 and FR 1, 2, 3, 4 | aCD38-b-348-m1-VL |
| 65 | aCD38-b-348-m2 variable light chain CDR 1, 2, 3 and FR 1, 2, 3, 4 | aCD38-b-348-m2-VL |
| 66 | aCD38-b-348-m3 variable light chain CDR 1, 2, 3 and FR 1, 2, 3, 4 | aCD38-b-348-m3-VL |
| 67 | aCD38-b-348-m4 variable light chain CDR 1, 2, 3 and FR 1, 2, 3, 4 | aCD38-b-348-m4-VL |
| 68 | aCD38-b-329-m6 variable light chain CDR 1, 2, 3 and FR 1, 2, 3, 4 | aCD38-b-329-m6-VL |
| 69 | aCD38-b-329-m7 variable light chain CDR 1, 2, 3 and FR 1, 2, 3, 4 | aCD38-b-329-m7-VL |
| 70 | Daratumumab variable heavy chain | |
| 71 | Daratumumab variable light chain | |
| 72 | aCD38-a-323 variable heavy chain CDR 1, 2, 3 and FR 2, 3 | |
| 73 | aCD38-a-323 variable light chain CDR 1, 2, 3 and FR 2, 3 | |
| 74 | aCD38-a-306 variable heavy chain CDR 1, 2, 3 and FR 2, 3 | |
| 75 | aCD38-a-306 variable light chain CDR 1, 2, 3 and FR 2, 3 | |
| 76 | aCD38-a-327 variable heavy chain CDR 1, 2, 3 and FR 2, 3 | |
| 77 | aCD38-a-327 variable light chain CDR 1, 2, 3 and FR 2, 3 | |

EQUIVALENTS AND SCOPE

Those skilled in the art will appreciate that the present invention is defined by the appended claims and not by the Examples or other description of certain embodiments included herein.

Similarly, the singular forms "a", "an", and "the" include plural referents unless the context clearly dictates otherwise.

Unless defined otherwise above, all technical and scientific terms used herein have the same meaning as commonly understood by one of ordinary skill in the art to which this invention belongs. Any methods and materials similar or equivalent to those described herein can also be used in the practice or testing of the present invention. Generally, nomenclatures used in connection with, and techniques of, cell and tissue culture, molecular biology, immunology, genetics and protein and nucleic acid chemistry described herein are those well known and commonly used in the art, or according to manufacturers specifications.

All publications mentioned herein are incorporated herein by reference to disclose and describe the methods and/or materials in connection with which the publications are cited.

REFERENCES

Ausiello C M et al., 2000. Tissue Antigens. 56:539-47.
Barnard G C et al., 2010. J Ind Microbiol Biotechnol. 37:961-71.
Beck A et al., 2017. Nat Rev Drug Discov. 16:315-337.
Chevrier S et al. 2017. Cell. 169:736-749.
de Weers M et al., 2011. J Immunol. 186:1840-8.
Estep P et al., 2013 MAbs. 5:270-8.
Ferrero E et al., 2004. BMC Immunol. 5:21.
Frasca L et al, 2006. Blood 107: 2392-2399.
Hara-Yokoyama M et al., 2008. Int Immunopharmacol. 8:59-70.
Holzapfel B M et al., 2015. Stem Cells. 33:1696-704.
Horenstein A L et al., 2017. Hum Antibodies. 25:75-85.
Jarasch A et al., 2015. J Pharm Sci. 104:1885-1898.
Kamphorst A O et al., 2017. Proc Natl Acad Sci USA. 114:4993-4998.
Karakasheva T et al., 2015. Cancer Res 75: 4074-85.
Kearns J D et al., 2015. Mol Cancer Ther. 14:1625-36.
Kijanka M et al., 2015. Nanomedicine. 10:161-174.
Langedijk J P et al., 2011. Analytical Biochemistry. 417: 149-155.
Liu L, 2015. J Pharm Sci. 104:1866-84.
Liu Y et al., 2014. MAbs. 6:483-92.
Malavasi F et al., 2008. Physiol Rev. 88: 841-86.
Morandi F et al., 2015. J Immunol. 195:965-72.
Morton J J et al. 2016. Cancer Res. 76:6153-6158.
Quarona V et al., 2013. Cytometry B Clin Cytom. 84:207-17.
Rah S Y et al., 2015. Sci Rep. 5:9482.
Redman J M et al., 2015. Mol Immunol. 67: 28-45.
Siegel R W et al., 2004. J Immunol Methods. 286:141-53.
Sliwkowski M & Mellman I, 2013. Science. 341:1192-8.
Sydow J et al. 2014. PLoS One. 9:e100736.
Timmermann P et al., 2007, J. Mol. Recognit., 20, 283-99.
van de Donk N W et al., 2016. Immunol Rev. 270: 95-112.
Vazquez-Lombardi R et al., 2015. Drug Discov Today. 20:1271-83.
Xu Y et al., 2013. Protein Eng Des Sel. 26:663-70
Wei W et al., 2014. World J Biol Chem. 5: 58-67
Rajpal et al., Proc Natl Acad Sci USA, 2005, 102(24):8466-71.
Steinwand et al., MAbs, 2014, 6(1):204-18.
Ellington et al. Nature. 1990; 346(6287): 818-822.
Tuerk et al., Science. 1990; 249(4968):505-510.
Ni et al., Curr Med Che 2011; 18(27):4206-14.

The invention claimed is:

1. An anti-CD38 antibody or antigen-binding fragment thereof, wherein the antibody or antigen-binding fragment thereof comprises:
   a) the amino acid sequence of SEQ ID NO: 11 as variable heavy chain complementarity determining region 3;
   b) amino acid sequence of SEQ ID NO: 9 as variable heavy chain complementarity determining region 1;
   c) amino acid sequence of SEQ ID NO: 10 as variable heavy chain complementarity determining region 2;
   d) amino acid sequence of SEQ ID NO: 13 as variable light chain complementarity determining region 1;
   e) amino acid sequence of SEQ ID NO: 14 as variable light chain complementarity determining region 2; and
   f) amino acid sequence of SEQ ID NO: 15 as variable light chain complementarity determining region 3.

2. The anti-CD38 antibody or antigen-binding fragment thereof according to claim 1, wherein the antibody or antigen-binding fragment thereof is a monoclonal antibody, a Fab fragment, a F(ab')2 fragment, a single chain variable fragment (scFv), a scFv-Fc fragment, or a single chain antibody (scAb).

3. The anti-CD38 antibody or antigen-binding fragment thereof according to claim 1, wherein the antibody or antigen-binding fragment thereof is a rabbit, mouse, chimeric, humanized or fully human antigen-binding antibody.

4. The anti-CD38 antibody or antigen-binding fragment thereof according to claim 1, wherein the antibody is selected from the group consisting of IgG1, IgG2, IgG3, and IgG4 isotype antibodies.

5. The anti-CD38 antibody or antigen-binding fragment thereof according to claim 1, wherein the antibody or antigen-binding fragment thereof is comprised in a bispecific antibody, a multispecific antibody, or an immunoconjugate further comprising a therapeutic or diagnostic agent.

6. The anti-CD38 antibody or antigen-binding fragment thereof of according to claim 1, wherein the antibody or antigen-binding fragment thereof comprises a variable heavy chain sequence having at least 95% sequence identity to the amino acid sequence as set forth in SEQ ID NO: 12.

7. The anti-CD38 antibody or antigen-binding fragment thereof according to claim 1, wherein the antibody or antigen-binding fragment thereof further comprises a variable light chain sequence having at least 95% sequence identity to the amino acid as set forth in SEQ ID NO: 16.

8. The anti-CD38 antibody or an antigen-binding fragment thereof according to claim 1 wherein the antibody or antigen-binding fragment thereof is afucosylated.

9. A nucleic acid molecule encoding the antibody or antigen-binding fragment thereof according to claim 1.

10. A nucleic acid vector comprising the nucleic acid molecule of claim 9.

11. A host cell comprising the nucleic acid vector of claim 10.

12. A method of producing an antibody or antigen binding fragment thereof, wherein the antibody or fragment thereof:
   exhibits antibody-dependent cell-mediated cytotoxicity (ADCC) activity against CD38+ target cells;
   exhibits no complement dependent cytotoxicity (CDC) or reduced CDC activity against a CD38+ target cell as compared to daratumumab under the same or substantially the same conditions; and
   induces immune effector cell activation,
   comprising culturing a host cell of claim 11.

13. A composition comprising an antibody or antigen-binding fragment thereof according to claim 1 and a pharmaceutically acceptable carrier or excipient.

14. A method of treating cancer in a subject, comprising administering to the subject an effective amount of the composition of claim 13.

15. The method of claim 14, further comprising administering, simultaneously or sequentially in any order, a second agent to the subject.

16. The method of claim 14 wherein the subject has a solid tumour.

17. The method of claim 14 wherein the subject has a haematological cancer.

* * * * *

SEQUENCE LISTING

<160> NUMBER OF SEQ ID NOS: 77

<210> SEQ ID NO 1
<211> LENGTH: 11
<212> TYPE: PRT
<213> ORGANISM: Homo sapiens

<400> SEQUENCE: 1

Gly Ser Ile Ser Ser Gly Ser Tyr Tyr Trp Ser
1               5                   10

<210> SEQ ID NO 2
<211> LENGTH: 16
<212> TYPE: PRT
<213> ORGANISM: Homo sapiens

<400> SEQUENCE: 2

Tyr Ile Tyr Tyr Ser Gly Ser Thr Tyr Tyr Asn Pro Ser Leu Lys Ser
1               5                   10                  15

<210> SEQ ID NO 3
<211> LENGTH: 16
<212> TYPE: PRT
<213> ORGANISM: Homo sapiens

<400> SEQUENCE: 3

Ala Arg Gly Ser Pro Tyr Arg Trp Tyr Asn Tyr Tyr Met Asp Val
1               5                   10                  15

<210> SEQ ID NO 4
<211> LENGTH: 98
<212> TYPE: PRT
<213> ORGANISM: Homo sapiens
<220> FEATURE:
<221> NAME/KEY: HCDR1
<222> LOCATION: (1)..(11)
<220> FEATURE:
<221> NAME/KEY: HCDR2
<222> LOCATION: (26)..(41)
<220> FEATURE:
<221> NAME/KEY: HCDR3
<222> LOCATION: (72)..(87)

<400> SEQUENCE: 4

Gly Ser Ile Ser Ser Gly Ser Tyr Tyr Trp Ser Trp Ile Arg Gln His
1               5                   10                  15

Pro Gly Lys Gly Leu Glu Trp Ile Gly Tyr Ile Tyr Tyr Ser Gly Ser
            20                  25                  30

Thr Tyr Tyr Asn Pro Ser Leu Lys Ser Arg Val Thr Ile Ser Val Asp
        35                  40                  45

Thr Ser Lys Asn Gln Phe Ser Leu Lys Leu Ser Ser Val Thr Ala Ala
    50                  55                  60

Asp Thr Ala Val Tyr Tyr Cys Ala Arg Gly Ser Pro Tyr Arg Trp Tyr
65                  70                  75                  80

Asn Tyr Tyr Met Asp Val Trp Gly Lys Gly Thr Thr Val Thr Val
                85                  90                  95

Ser Ser

<210> SEQ ID NO 5
<211> LENGTH: 11
<212> TYPE: PRT
<213> ORGANISM: Homo sapiens

<400> SEQUENCE: 5

Arg Ala Ser Gln Ser Ile Ser Ser Trp Leu Ala
1               5                   10

<210> SEQ ID NO 6
<211> LENGTH: 7
<212> TYPE: PRT
<213> ORGANISM: Homo sapiens

<400> SEQUENCE: 6

Asp Ala Ser Ser Leu Glu Ser
1               5

<210> SEQ ID NO 7
<211> LENGTH: 9
<212> TYPE: PRT
<213> ORGANISM: Homo sapiens

<400> SEQUENCE: 7

Gln Gln His Arg Ser Tyr Pro Pro Thr
1               5

<210> SEQ ID NO 8
<211> LENGTH: 84
<212> TYPE: PRT
<213> ORGANISM: Homo sapiens
<220> FEATURE:
<221> NAME/KEY: LCDR1
<222> LOCATION: (1)..(11)
<220> FEATURE:
<221> NAME/KEY: LCDR2
<222> LOCATION: (27)..(33)
<220> FEATURE:
<221> NAME/KEY: LCDR3
<222> LOCATION: (66)..(74)

<400> SEQUENCE: 8

Arg Ala Ser Gln Ser Ile Ser Ser Trp Leu Ala Trp Tyr Gln Gln Lys
1               5                   10                  15

Pro Gly Lys Ala Pro Lys Leu Leu Ile Tyr Asp Ala Ser Ser Leu Glu
                20                  25                  30

Ser Gly Val Pro Ser Arg Phe Ser Gly Ser Gly Ser Gly Thr Glu Phe
        35                  40                  45

Thr Leu Thr Ile Ser Ser Leu Gln Pro Asp Asp Phe Ala Thr Tyr Tyr
    50                  55                  60

Cys Gln Gln His Arg Ser Tyr Pro Pro Thr Phe Gly Gly Gly Thr Lys
65                  70                  75                  80

Val Glu Ile Lys

<210> SEQ ID NO 9
<211> LENGTH: 9
<212> TYPE: PRT
<213> ORGANISM: Homo sapiens

<400> SEQUENCE: 9

Tyr Thr Phe Thr Gly Tyr Tyr Met His
1               5

<210> SEQ ID NO 10
<211> LENGTH: 17
<212> TYPE: PRT
<213> ORGANISM: Homo sapiens

<400> SEQUENCE: 10

Trp Ile Asn Pro Asn Ser Gly Gly Thr Asn Tyr Ala Gln Lys Phe Gln
1               5                   10                  15

Gly

<210> SEQ ID NO 11
<211> LENGTH: 12
<212> TYPE: PRT
<213> ORGANISM: Homo sapiens

<400> SEQUENCE: 11

Ala Arg Asp Gln Ala His Gln Arg Ser Ser Tyr Asp
1               5                   10

<210> SEQ ID NO 12
<211> LENGTH: 93
<212> TYPE: PRT
<213> ORGANISM: Homo sapiens
<220> FEATURE:
<221> NAME/KEY: HCDR1
<222> LOCATION: (1)..(9)
<220> FEATURE:
<221> NAME/KEY: HCDR2
<222> LOCATION: (24)..(40)
<220> FEATURE:
<221> NAME/KEY: HCDR3
<222> LOCATION: (71)..(82)

<400> SEQUENCE: 12

Tyr Thr Phe Thr Gly Tyr Tyr Met His Trp Val Arg Gln Ala Pro Gly
1               5                   10                  15

Gln Gly Leu Glu Trp Met Gly Trp Ile Asn Pro Asn Ser Gly Gly Thr
            20                  25                  30

Asn Tyr Ala Gln Lys Phe Gln Gly Arg Val Thr Met Thr Arg Asp Thr
        35                  40                  45

Ser Ile Ser Thr Ala Tyr Met Glu Leu Ser Arg Leu Arg Ser Asp Asp
    50                  55                  60

Thr Ala Val Tyr Tyr Cys Ala Arg Asp Gln Ala His Gln Arg Ser Ser
65                  70                  75                  80

Tyr Asp Trp Gly Gln Gly Thr Leu Val Thr Val Ser Ser
                85                  90

<210> SEQ ID NO 13
<211> LENGTH: 11
<212> TYPE: PRT
<213> ORGANISM: Homo sapiens

<400> SEQUENCE: 13

Arg Ala Ser Gln Ser Ile Ser Ser Tyr Leu Asn
1               5                   10

<210> SEQ ID NO 14
<211> LENGTH: 7
<212> TYPE: PRT
<213> ORGANISM: Homo sapiens

<400> SEQUENCE: 14

Gly Ala Ser Ser Leu Gln Ser
1               5

<210> SEQ ID NO 15
<211> LENGTH: 9
<212> TYPE: PRT
<213> ORGANISM: Homo sapiens

```
<400> SEQUENCE: 15

Gln Gln Arg Ser Ser Thr Pro Ile Thr
1               5

<210> SEQ ID NO 16
<211> LENGTH: 84
<212> TYPE: PRT
<213> ORGANISM: Homo sapiens
<220> FEATURE:
<221> NAME/KEY: LCDR1
<222> LOCATION: (1)..(11)
<220> FEATURE:
<221> NAME/KEY: LCDR2
<222> LOCATION: (27)..(33)
<220> FEATURE:
<221> NAME/KEY: LCDR3
<222> LOCATION: (66)..(74)

<400> SEQUENCE: 16

Arg Ala Ser Gln Ser Ile Ser Ser Tyr Leu Asn Trp Tyr Gln Gln Lys
1               5                   10                  15

Pro Gly Lys Ala Pro Lys Leu Leu Ile Tyr Gly Ala Ser Ser Leu Gln
            20                  25                  30

Ser Gly Val Pro Ser Arg Phe Ser Gly Ser Gly Ser Thr Asp Phe
        35                  40                  45

Thr Leu Thr Ile Ser Ser Leu Gln Pro Glu Asp Phe Ala Thr Tyr Tyr
    50                  55                  60

Cys Gln Gln Arg Ser Ser Thr Pro Ile Thr Phe Gly Gly Gly Thr Lys
65                  70                  75                  80

Val Glu Ile Lys

<210> SEQ ID NO 17
<211> LENGTH: 11
<212> TYPE: PRT
<213> ORGANISM: Homo sapiens

<400> SEQUENCE: 17

Gly Ser Ile Ser Ser Ser Asp Tyr Tyr Trp Gly
1               5                   10

<210> SEQ ID NO 18
<211> LENGTH: 16
<212> TYPE: PRT
<213> ORGANISM: Homo sapiens

<400> SEQUENCE: 18

Ser Ile Tyr Tyr Ser Gly Ser Thr Tyr Tyr Asn Pro Ser Leu Lys Ser
1               5                   10                  15

<210> SEQ ID NO 19
<211> LENGTH: 16
<212> TYPE: PRT
<213> ORGANISM: Homo sapiens

<400> SEQUENCE: 19

Ala Arg Gly Gln Tyr Ser Ser Gly Trp Tyr Ala Tyr Pro Phe Asp Met
1               5                   10                  15

<210> SEQ ID NO 20
<211> LENGTH: 87
<212> TYPE: PRT
<213> ORGANISM: Homo sapiens
<220> FEATURE:
<221> NAME/KEY: HCDR1
```

```
<222> LOCATION: (1)..(11)
<220> FEATURE:
<221> NAME/KEY: HCDR2
<222> LOCATION: (26)..(41)
<220> FEATURE:
<221> NAME/KEY: HCDR3
<222> LOCATION: (72)..(87)

<400> SEQUENCE: 20

Gly Ser Ile Ser Ser Asp Tyr Tyr Trp Gly Trp Ile Arg Gln Pro
1               5                   10                  15

Pro Gly Lys Gly Leu Glu Trp Ile Gly Ser Ile Tyr Tyr Ser Gly
                20                  25                  30

Thr Tyr Tyr Asn Pro Ser Leu Lys Ser Arg Val Thr Ile Ser Val Asp
                35                  40                  45

Thr Ser Lys Asn Gln Phe Ser Leu Lys Leu Ser Ser Val Thr Ala Ala
    50                  55                  60

Asp Thr Ala Val Tyr Tyr Cys Ala Arg Gly Gln Tyr Ser Ser Gly Trp
65                  70                  75                  80

Tyr Ala Tyr Pro Phe Asp Met
                85

<210> SEQ ID NO 21
<211> LENGTH: 12
<212> TYPE: PRT
<213> ORGANISM: Homo sapiens

<400> SEQUENCE: 21

Arg Ala Ser Gln Ser Val Arg Ser Ser Tyr Leu Ala
1               5                   10

<210> SEQ ID NO 22
<211> LENGTH: 7
<212> TYPE: PRT
<213> ORGANISM: Homo sapiens

<400> SEQUENCE: 22

Gly Ala Ser Ser Arg Ala Thr
1               5

<210> SEQ ID NO 23
<211> LENGTH: 8
<212> TYPE: PRT
<213> ORGANISM: Homo sapiens

<400> SEQUENCE: 23

Gln Gln Asp Gly Ala Val Phe Thr
1               5

<210> SEQ ID NO 24
<211> LENGTH: 74
<212> TYPE: PRT
<213> ORGANISM: Homo sapiens
<220> FEATURE:
<221> NAME/KEY: LCDR1
<222> LOCATION: (1)..(12)
<220> FEATURE:
<221> NAME/KEY: LCDR2
<222> LOCATION: (28)..(34)
<220> FEATURE:
<221> NAME/KEY: LCDR3
<222> LOCATION: (67)..(74)

<400> SEQUENCE: 24

Arg Ala Ser Gln Ser Val Arg Ser Ser Tyr Leu Ala Trp Tyr Gln Gln
```

```
                1               5                  10                 15
Lys Pro Gly Gln Ala Pro Arg Leu Leu Ile Tyr Gly Ala Ser Ser Arg
            20                  25                 30

Ala Thr Gly Ile Pro Asp Arg Phe Ser Gly Ser Gly Ser Gly Thr Asp
        35                  40                 45

Phe Thr Leu Thr Ile Ser Arg Leu Glu Pro Glu Asp Phe Ala Val Tyr
    50                  55                 60

Tyr Cys Gln Gln Asp Gly Ala Val Phe Thr
65                  70

<210> SEQ ID NO 25
<211> LENGTH: 11
<212> TYPE: PRT
<213> ORGANISM: Homo sapiens

<400> SEQUENCE: 25

Gly Ser Ile Ser Ser Asp Tyr Tyr Trp Gly
1               5                  10

<210> SEQ ID NO 26
<211> LENGTH: 16
<212> TYPE: PRT
<213> ORGANISM: Homo sapiens

<400> SEQUENCE: 26

Ser Ile Tyr Tyr Ser Gly Ser Thr Tyr Tyr Asn Pro Ser Leu Lys Ser
1               5                  10                 15

<210> SEQ ID NO 27
<211> LENGTH: 16
<212> TYPE: PRT
<213> ORGANISM: Homo sapiens

<400> SEQUENCE: 27

Ala Arg Gly Gln Tyr Ser Ser Gly Trp Tyr Ala Tyr Pro Phe Asp Met
1               5                  10                 15

<210> SEQ ID NO 28
<211> LENGTH: 87
<212> TYPE: PRT
<213> ORGANISM: Homo sapiens
<220> FEATURE:
<221> NAME/KEY: HCDR1
<222> LOCATION: (1)..(11)
<220> FEATURE:
<221> NAME/KEY: HCDR2
<222> LOCATION: (26)..(41)
<220> FEATURE:
<221> NAME/KEY: HCDR3
<222> LOCATION: (72)..(87)

<400> SEQUENCE: 28

Gly Ser Ile Ser Ser Asp Tyr Tyr Trp Gly Trp Ile Arg Gln Pro
1               5                  10                 15

Pro Gly Lys Gly Leu Glu Trp Ile Gly Ser Ile Tyr Tyr Ser Gly Ser
            20                  25                 30

Thr Tyr Tyr Asn Pro Ser Leu Lys Ser Arg Val Thr Ile Ser Val Asp
        35                  40                 45

Thr Ser Lys Asn Gln Phe Ser Leu Lys Leu Ser Ser Val Thr Ala Ala
    50                  55                 60

Asp Thr Ala Val Tyr Tyr Cys Ala Arg Gly Gln Tyr Ser Ser Gly Trp
65                  70                 75                 80
```

Tyr Ala Tyr Pro Phe Asp Met
            85

<210> SEQ ID NO 29
<211> LENGTH: 12
<212> TYPE: PRT
<213> ORGANISM: Homo sapiens

<400> SEQUENCE: 29

Arg Ala Ser Gln Ser Val Arg Ser Ser Tyr Leu Ala
1               5                   10

<210> SEQ ID NO 30
<211> LENGTH: 7
<212> TYPE: PRT
<213> ORGANISM: Homo sapiens

<400> SEQUENCE: 30

Gly Ala Ser Ser Arg Ala Thr
1               5

<210> SEQ ID NO 31
<211> LENGTH: 8
<212> TYPE: PRT
<213> ORGANISM: Homo sapiens

<400> SEQUENCE: 31

Gln Gln Asp Gly Asn Val Tyr Thr
1               5

<210> SEQ ID NO 32
<211> LENGTH: 74
<212> TYPE: PRT
<213> ORGANISM: Homo sapiens
<220> FEATURE:
<221> NAME/KEY: LCDR1
<222> LOCATION: (1)..(12)
<220> FEATURE:
<221> NAME/KEY: LCDR2
<222> LOCATION: (28)..(34)
<220> FEATURE:
<221> NAME/KEY: LCDR3
<222> LOCATION: (67)..(74)

<400> SEQUENCE: 32

Arg Ala Ser Gln Ser Val Arg Ser Ser Tyr Leu Ala Trp Tyr Gln Gln
1               5                   10                  15

Lys Pro Gly Gln Ala Pro Arg Leu Leu Ile Tyr Gly Ala Ser Ser Arg
            20                  25                  30

Ala Thr Gly Ile Pro Asp Arg Phe Ser Gly Ser Gly Ser Gly Thr Asp
        35                  40                  45

Phe Thr Leu Thr Ile Ser Arg Leu Glu Pro Glu Asp Phe Ala Val Tyr
    50                  55                  60

Tyr Cys Gln Gln Asp Gly Asn Val Tyr Thr
65                  70

<210> SEQ ID NO 33
<211> LENGTH: 11
<212> TYPE: PRT
<213> ORGANISM: Homo sapiens

<400> SEQUENCE: 33

Gly Ser Ile Ser Ser Gly Gly Tyr Tyr Trp Ser
1               5                   10

<210> SEQ ID NO 34
<211> LENGTH: 16
<212> TYPE: PRT
<213> ORGANISM: Homo sapiens

<400> SEQUENCE: 34

Tyr Ile Tyr Tyr Ser Gly Ser Thr Tyr Tyr Asn Pro Ser Leu Lys Ser
1               5                   10                  15

<210> SEQ ID NO 35
<211> LENGTH: 17
<212> TYPE: PRT
<213> ORGANISM: Homo sapiens

<400> SEQUENCE: 35

Ala Arg Ala Lys Ser Glu Leu Val Leu Pro Tyr Tyr Tyr Tyr Met Asp
1               5                   10                  15

Val

<210> SEQ ID NO 36
<211> LENGTH: 99
<212> TYPE: PRT
<213> ORGANISM: Homo sapiens
<220> FEATURE:
<221> NAME/KEY: HCDR1
<222> LOCATION: (1)..(11)
<220> FEATURE:
<221> NAME/KEY: HCDR2
<222> LOCATION: (26)..(41)
<220> FEATURE:
<221> NAME/KEY: HCDR3
<222> LOCATION: (72)..(88)

<400> SEQUENCE: 36

Gly Ser Ile Ser Ser Gly Gly Tyr Tyr Trp Ser Trp Ile Arg Gln His
1               5                   10                  15

Pro Gly Lys Gly Leu Glu Trp Ile Gly Tyr Ile Tyr Tyr Ser Gly Ser
                20                  25                  30

Thr Tyr Tyr Asn Pro Ser Leu Lys Ser Arg Val Thr Ile Ser Val Asp
            35                  40                  45

Thr Ser Lys Asn Gln Phe Ser Leu Lys Leu Ser Ser Val Thr Ala Ala
        50                  55                  60

Asp Thr Ala Val Tyr Tyr Cys Ala Arg Ala Lys Ser Glu Leu Val Leu
65                  70                  75                  80

Pro Tyr Tyr Tyr Met Asp Val Trp Gly Lys Gly Thr Thr Val Thr
                85                  90                  95

Val Ser Ser

<210> SEQ ID NO 37
<211> LENGTH: 17
<212> TYPE: PRT
<213> ORGANISM: Homo sapiens

<400> SEQUENCE: 37

Lys Ser Ser Gln Ser Val Leu Phe Ser Ser Asn Asn Lys Asn Tyr Leu
1               5                   10                  15

Ala

<210> SEQ ID NO 38
<211> LENGTH: 7
<212> TYPE: PRT
<213> ORGANISM: Homo sapiens

<400> SEQUENCE: 38

Trp Ala Ser Thr Arg Glu Ser
1               5

<210> SEQ ID NO 39
<211> LENGTH: 9
<212> TYPE: PRT
<213> ORGANISM: Homo sapiens

<400> SEQUENCE: 39

Gln Gln Tyr Tyr Ser Leu Pro Pro Thr
1               5

<210> SEQ ID NO 40
<211> LENGTH: 90
<212> TYPE: PRT
<213> ORGANISM: Homo sapiens
<220> FEATURE:
<221> NAME/KEY: LCDR1
<222> LOCATION: (1)..(17)
<220> FEATURE:
<221> NAME/KEY: LCDR2
<222> LOCATION: (33)..(39)
<220> FEATURE:
<221> NAME/KEY: LCDR3
<222> LOCATION: (72)..(80)

<400> SEQUENCE: 40

Lys Ser Ser Gln Ser Val Leu Phe Ser Ser Asn Asn Lys Asn Tyr Leu
1               5                   10                  15

Ala Trp Tyr Gln Gln Lys Pro Gly Gln Pro Pro Lys Leu Leu Ile Tyr
            20                  25                  30

Trp Ala Ser Thr Arg Glu Ser Gly Val Pro Asp Arg Phe Ser Gly Ser
        35                  40                  45

Gly Ser Gly Thr Asp Phe Thr Leu Thr Ile Ser Ser Leu Gln Ala Glu
    50                  55                  60

Asp Val Ala Val Tyr Tyr Cys Gln Gln Tyr Tyr Ser Leu Pro Pro Thr
65                  70                  75                  80

Phe Gly Gly Gly Thr Lys Val Glu Ile Lys
                85                  90

<210> SEQ ID NO 41
<211> LENGTH: 8
<212> TYPE: PRT
<213> ORGANISM: Homo sapiens

<400> SEQUENCE: 41

Gln Gln Asp Glu Ala Val Phe Thr
1               5

<210> SEQ ID NO 42
<211> LENGTH: 8
<212> TYPE: PRT
<213> ORGANISM: Homo sapiens

<400> SEQUENCE: 42

Gln Gln Asp Ser Ala Val Phe Thr
1               5

<210> SEQ ID NO 43
<211> LENGTH: 8
<212> TYPE: PRT
<213> ORGANISM: Homo sapiens

<400> SEQUENCE: 43

Gln Gln Glu Ala Asn Val Tyr Thr
1               5

<210> SEQ ID NO 44
<211> LENGTH: 8
<212> TYPE: PRT
<213> ORGANISM: Homo sapiens

<400> SEQUENCE: 44

Gln Gln Asp Ser Asn Val Tyr Thr
1               5

<210> SEQ ID NO 45
<211> LENGTH: 8
<212> TYPE: PRT
<213> ORGANISM: Homo sapiens

<400> SEQUENCE: 45

Gln Gln Asp Ala Asn Val Tyr Thr
1               5

<210> SEQ ID NO 46
<211> LENGTH: 8
<212> TYPE: PRT
<213> ORGANISM: Homo sapiens

<400> SEQUENCE: 46

Gln Gln Glu Gly Asn Val Tyr Thr
1               5

<210> SEQ ID NO 47
<211> LENGTH: 300
<212> TYPE: PRT
<213> ORGANISM: Homo sapiens

<400> SEQUENCE: 47

Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
                20                  25                  30

Leu Ile Leu Val Val Leu Ala Val Val Pro Arg Trp Arg Gln
            35                  40                  45

Gln Trp Ser Gly Pro Gly Thr Thr Lys Arg Phe Pro Glu Thr Val Leu
        50                  55                  60

Ala Arg Cys Val Lys Tyr Thr Glu Ile His Pro Glu Met Arg His Val
65                  70                  75                  80

Asp Cys Gln Ser Val Trp Asp Ala Phe Lys Gly Ala Phe Ile Ser Lys
                85                  90                  95

His Pro Cys Asn Ile Thr Glu Glu Asp Tyr Gln Pro Leu Met Lys Leu
                100                 105                 110

Gly Thr Gln Thr Val Pro Cys Asn Lys Ile Leu Leu Trp Ser Arg Ile
            115                 120                 125

Lys Asp Leu Ala His Gln Phe Thr Gln Val Gln Arg Asp Met Phe Thr
        130                 135                 140

Leu Glu Asp Thr Leu Leu Gly Tyr Leu Ala Asp Asp Leu Thr Trp Cys
145                 150                 155                 160

Gly Glu Phe Asn Thr Ser Lys Ile Asn Tyr Gln Ser Cys Pro Asp Trp
                165                 170                 175

```
Arg Lys Asp Cys Ser Asn Asn Pro Val Ser Val Phe Trp Lys Thr Val
            180                 185                 190

Ser Arg Arg Phe Ala Glu Ala Ala Cys Asp Val Val His Val Met Leu
            195                 200                 205

Asn Gly Ser Arg Ser Lys Ile Phe Asp Lys Asn Ser Thr Phe Gly Ser
            210                 215                 220

Val Glu Val His Asn Leu Gln Pro Glu Lys Val Gln Thr Leu Glu Ala
225                 230                 235                 240

Trp Val Ile His Gly Gly Arg Glu Asp Ser Arg Asp Leu Cys Gln Asp
                245                 250                 255

Pro Thr Ile Lys Glu Leu Glu Ser Ile Ile Ser Lys Arg Asn Ile Gln
            260                 265                 270

Phe Ser Cys Lys Asn Ile Tyr Arg Pro Asp Lys Phe Leu Gln Cys Val
            275                 280                 285

Lys Asn Pro Glu Asp Ser Ser Cys Thr Ser Glu Ile
            290                 295                 300

<210> SEQ ID NO 48
<211> LENGTH: 124
<212> TYPE: PRT
<213> ORGANISM: Homo sapiens
<220> FEATURE:
<221> NAME/KEY: HCDR1
<222> LOCATION: (27)..(37)
<220> FEATURE:
<221> NAME/KEY: HCDR2
<222> LOCATION: (52)..(67)
<220> FEATURE:
<221> NAME/KEY: HCDR3
<222> LOCATION: (98)..(113)

<400> SEQUENCE: 48

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Ser Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Ser Pro Tyr Arg Trp Tyr Asn Tyr Tyr Met Asp
            100                 105                 110

Val Trp Gly Lys Gly Thr Thr Val Thr Val Ser Ser
            115                 120

<210> SEQ ID NO 49
<211> LENGTH: 107
<212> TYPE: PRT
<213> ORGANISM: Homo sapiens
<220> FEATURE:
<221> NAME/KEY: LCDR1
<222> LOCATION: (24)..(34)
<220> FEATURE:
<221> NAME/KEY: LCDR2
<222> LOCATION: (50)..(56)
<220> FEATURE:
<221> NAME/KEY: LCDR3
```

<222> LOCATION: (89)..(97)

<400> SEQUENCE: 49

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln His Arg Ser Tyr Pro Pro
                85                  90                  95

Thr Phe Gly Gly Gly Thr Lys Val Glu Ile Lys
            100                 105

<210> SEQ ID NO 50
<211> LENGTH: 119
<212> TYPE: PRT
<213> ORGANISM: Homo sapiens
<220> FEATURE:
<221> NAME/KEY: HCDR1
<222> LOCATION: (27)..(35)
<220> FEATURE:
<221> NAME/KEY: HCDR2
<222> LOCATION: (50)..(66)
<220> FEATURE:
<221> NAME/KEY: HCDR3
<222> LOCATION: (97)..(108)

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Gln Ala His Gln Arg Ser Ser Tyr Asp Trp Gly Gln Gly
            100                 105                 110

Thr Leu Val Thr Val Ser Ser
        115

<210> SEQ ID NO 51
<211> LENGTH: 107
<212> TYPE: PRT
<213> ORGANISM: Homo sapiens
<220> FEATURE:
<221> NAME/KEY: LCDR1
<222> LOCATION: (24)..(34)
<220> FEATURE:
<221> NAME/KEY: LCDR2
<222> LOCATION: (50)..(56)
<220> FEATURE:
<221> NAME/KEY: LCDR3

<222> LOCATION: (89)..(97)

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Ser Ser Thr Pro Ile
                85                  90                  95

Thr Phe Gly Gly Gly Thr Lys Val Glu Ile Lys
            100                 105

<210> SEQ ID NO 52
<211> LENGTH: 124
<212> TYPE: PRT
<213> ORGANISM: Homo sapiens
<220> FEATURE:
<221> NAME/KEY: HCDR1
<222> LOCATION: (27)..(37)
<220> FEATURE:
<221> NAME/KEY: HCDR2
<222> LOCATION: (52)..(67)
<220> FEATURE:
<221> NAME/KEY: HCDR3
<222> LOCATION: (98)..(113)

<400> SEQUENCE: 52

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gln Tyr Ser Ser Gly Trp Tyr Ala Tyr Pro Phe Asp
            100                 105                 110

Met Trp Gly Gln Gly Thr Met Val Thr Val Ser Ser
        115                 120

<210> SEQ ID NO 53
<211> LENGTH: 107
<212> TYPE: PRT
<213> ORGANISM: Homo sapiens
<220> FEATURE:
<221> NAME/KEY: LCDR1
<222> LOCATION: (24)..(35)
<220> FEATURE:
<221> NAME/KEY: LCDR2
<222> LOCATION: (51)..(57)
<220> FEATURE:
<221> NAME/KEY: LCDR3

```
<222> LOCATION: (90)..(97)

<400> SEQUENCE: 53

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Gly Ala Val Phe
                85                  90                  95

Thr Phe Gly Gly Gly Thr Lys Val Glu Ile Lys
            100                 105

<210> SEQ ID NO 54
<211> LENGTH: 124
<212> TYPE: PRT
<213> ORGANISM: Homo sapiens
<220> FEATURE:
<221> NAME/KEY: HCDR1
<222> LOCATION: (27)..(37)
<220> FEATURE:
<221> NAME/KEY: HCDR2
<222> LOCATION: (52)..(67)
<220> FEATURE:
<221> NAME/KEY: HCDR3
<222> LOCATION: (98)..(113)

<400> SEQUENCE: 54

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asp Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gln Tyr Ser Ser Gly Trp Tyr Ala Tyr Pro Phe Asp
            100                 105                 110

Met Trp Gly Gln Gly Thr Met Val Thr Val Ser Ser
        115                 120

<210> SEQ ID NO 55
<211> LENGTH: 107
<212> TYPE: PRT
<213> ORGANISM: Homo sapiens
<220> FEATURE:
<221> NAME/KEY: LCDR1
<222> LOCATION: (24)..(35)
<220> FEATURE:
<221> NAME/KEY: LCDR2
<222> LOCATION: (51)..(57)
<220> FEATURE:
<221> NAME/KEY: LCDR3
```

<222> LOCATION: (90)..(107)

<400> SEQUENCE: 55

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Gly Asn Val Tyr
                85                  90                  95

Thr Phe Gly Gly Gly Thr Lys Val Glu Ile Lys
            100                 105

<210> SEQ ID NO 56
<211> LENGTH: 125
<212> TYPE: PRT
<213> ORGANISM: Homo sapiens
<220> FEATURE:
<221> NAME/KEY: HCDR1
<222> LOCATION: (27)..(36)
<220> FEATURE:
<221> NAME/KEY: HCDR2
<222> LOCATION: (52)..(67)
<220> FEATURE:
<221> NAME/KEY: HCDR3
<222> LOCATION: (98)..(114)

<400> SEQUENCE: 56

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Lys Ser Glu Leu Val Leu Pro Tyr Tyr Tyr Tyr Met
            100                 105                 110

Asp Val Trp Gly Lys Gly Thr Thr Val Thr Val Ser Ser
        115                 120                 125

<210> SEQ ID NO 57
<211> LENGTH: 113
<212> TYPE: PRT
<213> ORGANISM: Homo sapiens
<220> FEATURE:
<221> NAME/KEY: LCDR1
<222> LOCATION: (24)..(40)
<220> FEATURE:
<221> NAME/KEY: LCDR2
<222> LOCATION: (56)..(62)
<220> FEATURE:
<221> NAME/KEY: LCDR3

<222> LOCATION: (95)..(103)

<400> SEQUENCE: 57

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Phe Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Leu Pro Pro Thr Phe Gly Gly Gly Thr Lys Val Glu Ile
            100                 105                 110

Lys

<210> SEQ ID NO 58
<211> LENGTH: 74
<212> TYPE: PRT
<213> ORGANISM: Homo sapiens
<220> FEATURE:
<221> NAME/KEY: LCDR1
<222> LOCATION: (1)..(12)
<220> FEATURE:
<221> NAME/KEY: LCDR2
<222> LOCATION: (28)..(34)
<220> FEATURE:
<221> NAME/KEY: LCDR3
<222> LOCATION: (67)..(74)

<400> SEQUENCE: 58

Arg Ala Ser Gln Ser Val Arg Ser Ser Tyr Leu Ala Trp Tyr Gln Gln
1               5                   10                  15

Lys Pro Gly Gln Ala Pro Arg Leu Leu Ile Tyr Gly Ala Ser Ser Arg
            20                  25                  30

Ala Thr Gly Ile Pro Asp Arg Phe Ser Gly Ser Gly Ser Gly Thr Asp
        35                  40                  45

Phe Thr Leu Thr Ile Ser Arg Leu Glu Pro Glu Asp Phe Ala Val Tyr
    50                  55                  60

Tyr Cys Gln Gln Glu Ala Asn Val Tyr Thr
65                  70

<210> SEQ ID NO 59
<211> LENGTH: 74
<212> TYPE: PRT
<213> ORGANISM: Homo sapiens
<220> FEATURE:
<221> NAME/KEY: LCDR1
<222> LOCATION: (1)..(12)
<220> FEATURE:
<221> NAME/KEY: LCDR2
<222> LOCATION: (28)..(34)
<220> FEATURE:
<221> NAME/KEY: LCDR3
<222> LOCATION: (67)..(74)

<400> SEQUENCE: 59

Arg Ala Ser Gln Ser Val Arg Ser Ser Tyr Leu Ala Trp Tyr Gln Gln
1               5                   10                  15

```
Lys Pro Gly Gln Ala Pro Arg Leu Leu Ile Tyr Gly Ala Ser Ser Arg
            20                  25                  30

Ala Thr Gly Ile Pro Asp Arg Phe Ser Gly Ser Gly Ser Gly Thr Asp
            35                  40                  45

Phe Thr Leu Thr Ile Ser Arg Leu Glu Pro Glu Asp Phe Ala Val Tyr
        50                  55                  60

Tyr Cys Gln Gln Asp Ser Asn Val Tyr Thr
65                  70
```

<210> SEQ ID NO 60
<211> LENGTH: 74
<212> TYPE: PRT
<213> ORGANISM: Homo sapiens
<220> FEATURE:
<221> NAME/KEY: LCDR1
<222> LOCATION: (1)..(12)
<220> FEATURE:
<221> NAME/KEY: LCDR2
<222> LOCATION: (28)..(34)
<220> FEATURE:
<221> NAME/KEY: LCDR3
<222> LOCATION: (67)..(74)

<400> SEQUENCE: 60

```
Arg Ala Ser Gln Ser Val Arg Ser Ser Tyr Leu Ala Trp Tyr Gln Gln
1               5                   10                  15

Lys Pro Gly Gln Ala Pro Arg Leu Leu Ile Tyr Gly Ala Ser Ser Arg
            20                  25                  30

Ala Thr Gly Ile Pro Asp Arg Phe Ser Gly Ser Gly Ser Gly Thr Asp
            35                  40                  45

Phe Thr Leu Thr Ile Ser Arg Leu Glu Pro Glu Asp Phe Ala Val Tyr
        50                  55                  60

Tyr Cys Gln Gln Asp Ala Asn Val Tyr Thr
65                  70
```

<210> SEQ ID NO 61
<211> LENGTH: 74
<212> TYPE: PRT
<213> ORGANISM: Homo sapiens
<220> FEATURE:
<221> NAME/KEY: LCDR1
<222> LOCATION: (1)..(12)
<220> FEATURE:
<221> NAME/KEY: LCDR2
<222> LOCATION: (28)..(34)
<220> FEATURE:
<221> NAME/KEY: LCDR3
<222> LOCATION: (67)..(74)

<400> SEQUENCE: 61

```
Arg Ala Ser Gln Ser Val Arg Ser Ser Tyr Leu Ala Trp Tyr Gln Gln
1               5                   10                  15

Lys Pro Gly Gln Ala Pro Arg Leu Leu Ile Tyr Gly Ala Ser Ser Arg
            20                  25                  30

Ala Thr Gly Ile Pro Asp Arg Phe Ser Gly Ser Gly Ser Gly Thr Asp
            35                  40                  45

Phe Thr Leu Thr Ile Ser Arg Leu Glu Pro Glu Asp Phe Ala Val Tyr
        50                  55                  60

Tyr Cys Gln Gln Glu Gly Asn Val Tyr Thr
65                  70
```

<210> SEQ ID NO 62
<211> LENGTH: 74

```
<212> TYPE: PRT
<213> ORGANISM: Homo sapiens
<220> FEATURE:
<221> NAME/KEY: LCDR1
<222> LOCATION: (1)..(12)
<220> FEATURE:
<221> NAME/KEY: LCDR2
<222> LOCATION: (28)..(34)
<220> FEATURE:
<221> NAME/KEY: LCDR3
<222> LOCATION: (67)..(74)

<400> SEQUENCE: 62

Arg Ala Ser Gln Ser Val Arg Ser Ser Tyr Leu Ala Trp Tyr Gln Gln
 1               5                   10                  15

Lys Pro Gly Gln Ala Pro Arg Leu Leu Ile Tyr Gly Ala Ser Ser Arg
            20                  25                  30

Ala Thr Gly Ile Pro Asp Arg Phe Ser Gly Ser Gly Ser Gly Thr Asp
        35                  40                  45

Phe Thr Leu Thr Ile Ser Arg Leu Glu Pro Glu Asp Phe Ala Val Tyr
    50                  55                  60

Tyr Cys Gln Gln Asp Glu Ala Val Phe Thr
65                  70

<210> SEQ ID NO 63
<211> LENGTH: 74
<212> TYPE: PRT
<213> ORGANISM: Homo sapiens
<220> FEATURE:
<221> NAME/KEY: LCDR1
<222> LOCATION: (1)..(12)
<220> FEATURE:
<221> NAME/KEY: LCDR2
<222> LOCATION: (28)..(34)
<220> FEATURE:
<221> NAME/KEY: LCDR3
<222> LOCATION: (67)..(74)

<400> SEQUENCE: 63

Arg Ala Ser Gln Ser Val Arg Ser Ser Tyr Leu Ala Trp Tyr Gln Gln
 1               5                   10                  15

Lys Pro Gly Gln Ala Pro Arg Leu Leu Ile Tyr Gly Ala Ser Ser Arg
            20                  25                  30

Ala Thr Gly Ile Pro Asp Arg Phe Ser Gly Ser Gly Ser Gly Thr Asp
        35                  40                  45

Phe Thr Leu Thr Ile Ser Arg Leu Glu Pro Glu Asp Phe Ala Val Tyr
    50                  55                  60

Tyr Cys Gln Gln Asp Ser Ala Val Phe Thr
65                  70

<210> SEQ ID NO 64
<211> LENGTH: 107
<212> TYPE: PRT
<213> ORGANISM: Homo sapiens
<220> FEATURE:
<221> NAME/KEY: LCDR1
<222> LOCATION: (24)..(35)
<220> FEATURE:
<221> NAME/KEY: LCDR2
<222> LOCATION: (51)..(57)
<220> FEATURE:
<221> NAME/KEY: LCDR3
<222> LOCATION: (90)..(97)

<400> SEQUENCE: 64

Glu Ile Val Leu Thr Gln Ser Pro Gly Thr Leu Ser Leu Ser Pro Gly
```

```
                1               5                    10                   15
Glu Arg Ala Thr Leu Ser Cys Arg Ala Ser Gln Ser Val Arg Ser Ser
                20                       25                      30

Tyr Leu Ala Trp Tyr Gln Gln Lys Pro Gly Gln Ala Pro Arg Leu Leu
            35                          40                     45

Ile Tyr Gly Ala Ser Ser Arg Ala Thr Gly Ile Pro Asp Arg Phe Ser
        50                       55                      60

Gly Ser Gly Ser Gly Thr Asp Phe Thr Leu Thr Ile Ser Arg Leu Glu
65                       70                      75                      80

Pro Glu Asp Phe Ala Val Tyr Tyr Cys Gln Gln Glu Ala Asn Val Tyr
                    85                      90                      95

Thr Phe Gly Gly Gly Thr Lys Val Glu Ile Lys
                100                     105
```

<210> SEQ ID NO 65
<211> LENGTH: 107
<212> TYPE: PRT
<213> ORGANISM: Homo sapiens
<220> FEATURE:
<221> NAME/KEY: LCDR1
<222> LOCATION: (24)..(35)
<220> FEATURE:
<221> NAME/KEY: LCDR2
<222> LOCATION: (51)..(57)
<220> FEATURE:
<221> NAME/KEY: LCDR3
<222> LOCATION: (90)..(97)

<400> SEQUENCE: 65

```
Glu Ile Val Leu Thr Gln Ser Pro Gly Thr Leu Ser Leu Ser Pro Gly
1               5                    10                  15

Glu Arg Ala Thr Leu Ser Cys Arg Ala Ser Gln Ser Val Arg Ser Ser
                20                       25                      30

Tyr Leu Ala Trp Tyr Gln Gln Lys Pro Gly Gln Ala Pro Arg Leu Leu
            35                          40                     45

Ile Tyr Gly Ala Ser Ser Arg Ala Thr Gly Ile Pro Asp Arg Phe Ser
        50                       55                      60

Gly Ser Gly Ser Gly Thr Asp Phe Thr Leu Thr Ile Ser Arg Leu Glu
65                       70                      75                      80

Pro Glu Asp Phe Ala Val Tyr Tyr Cys Gln Gln Asp Ser Asn Val Tyr
                    85                      90                      95

Thr Phe Gly Gly Gly Thr Lys Val Glu Ile Lys
                100                     105
```

<210> SEQ ID NO 66
<211> LENGTH: 107
<212> TYPE: PRT
<213> ORGANISM: Homo sapiens
<220> FEATURE:
<221> NAME/KEY: LCDR1
<222> LOCATION: (24)..(35)
<220> FEATURE:
<221> NAME/KEY: LCDR2
<222> LOCATION: (51)..(57)
<220> FEATURE:
<221> NAME/KEY: LCDR3
<222> LOCATION: (90)..(97)

<400> SEQUENCE: 66

```
Glu Ile Val Leu Thr Gln Ser Pro Gly Thr Leu Ser Leu Ser Pro Gly
1               5                    10                  15

Glu Arg Ala Thr Leu Ser Cys Arg Ala Ser Gln Ser Val Arg Ser Ser
```

```
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Asp Ala Asn Val Tyr
                85                  90                  95

Thr Phe Gly Gly Gly Thr Lys Val Glu Ile Lys
            100                 105

<210> SEQ ID NO 67
<211> LENGTH: 107
<212> TYPE: PRT
<213> ORGANISM: Homo sapiens
<220> FEATURE:
<221> NAME/KEY: LCDR1
<222> LOCATION: (24)..(35)
<220> FEATURE:
<221> NAME/KEY: LCDR2
<222> LOCATION: (51)..(57)
<220> FEATURE:
<221> NAME/KEY: LCDR3
<222> LOCATION: (90)..(97)

<400> SEQUENCE: 67

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Glu Gly Asn Val Tyr
                85                  90                  95

Thr Phe Gly Gly Gly Thr Lys Val Glu Ile Lys
            100                 105

<210> SEQ ID NO 68
<211> LENGTH: 107
<212> TYPE: PRT
<213> ORGANISM: Homo sapiens
<220> FEATURE:
<221> NAME/KEY: LCDR1
<222> LOCATION: (24)..(35)
<220> FEATURE:
<221> NAME/KEY: LCDR2
<222> LOCATION: (51)..(57)
<220> FEATURE:
<221> NAME/KEY: LCDR3
<222> LOCATION: (90)..(97)

<400> SEQUENCE: 68

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ser Ser
            20                  25                  30

Tyr Leu Ala Trp Tyr Gln Gln Lys Pro Gly Gln Ala Pro Arg Leu Leu
```

```
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Asp Glu Ala Val Phe
                 85                  90                  95

Thr Phe Gly Gly Gly Thr Lys Val Glu Ile Lys
            100                 105

<210> SEQ ID NO 69
<211> LENGTH: 107
<212> TYPE: PRT
<213> ORGANISM: Homo sapiens
<220> FEATURE:
<221> NAME/KEY: LCDR1
<222> LOCATION: (24)..(35)
<220> FEATURE:
<221> NAME/KEY: LCDR2
<222> LOCATION: (51)..(57)
<220> FEATURE:
<221> NAME/KEY: LCDR3
<222> LOCATION: (90)..(97)

<400> SEQUENCE: 69

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Arg Ser Ser
             20                  25                  30

Tyr Leu Ala Trp Tyr Gln Gln Lys Pro Gly Gln Ala Pro Arg Leu Leu
         35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Asp Ser Ala Val Phe
                 85                  90                  95

Thr Phe Gly Gly Gly Thr Lys Val Glu Ile Lys
            100                 105

<210> SEQ ID NO 70
<211> LENGTH: 452
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
  1               5                  10                  15

Ser Leu Arg Leu Ser Cys Ala Val Ser Gly Phe Thr Phe Asn Ser Phe
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Phe Cys
                 85                  90                  95

Ala Lys Asp Lys Ile Leu Trp Phe Gly Glu Pro Val Phe Asp Tyr Trp
```

```
            100                 105                 110
Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 71
<211> LENGTH: 214
<212> TYPE: PRT
<213> ORGANISM: Homo sapiens

<400> SEQUENCE: 71

Glu Ile Val Leu Thr Gln Ser Pro Ala Thr Leu Ser Leu Ser Pro Gly
1               5                   10                  15
```

-continued

```
Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 72
<211> LENGTH: 87
<212> TYPE: PRT
<213> ORGANISM: Homo sapiens
<220> FEATURE:
<221> NAME/KEY: HCDR1
<222> LOCATION: (1)..(11)
<220> FEATURE:
<221> NAME/KEY: HCDR2
<222> LOCATION: (26)..(41)
<220> FEATURE:
<221> NAME/KEY: HCDR3
<222> LOCATION: (72)..(87)

<400> SEQUENCE: 72

Gly Ser Ile Ser Ser Gly Ser Tyr Tyr Trp Ser Trp Ile Arg Gln His
 1               5                  10                  15

Pro Gly Lys Gly Leu Glu Trp Ile Gly Tyr Ile Tyr Tyr Ser Gly Ser
             20                  25                  30

Thr Tyr Tyr Asn Pro Ser Leu Lys Ser Arg Val Thr Ile Ser Val Asp
         35                  40                  45

Thr Ser Lys Asn Gln Phe Ser Leu Lys Leu Ser Ser Val Thr Ala Ala
     50                  55                  60

Asp Thr Ala Val Tyr Tyr Cys Ala Arg Gly Ser Pro Tyr Arg Trp Tyr
 65                  70                  75                  80

Asn Tyr Tyr Tyr Met Asp Val
                 85

<210> SEQ ID NO 73
<211> LENGTH: 74
<212> TYPE: PRT
<213> ORGANISM: Homo sapiens
```

```
<220> FEATURE:
<221> NAME/KEY: LCDR1
<222> LOCATION: (1)..(11)
<220> FEATURE:
<221> NAME/KEY: LCDR2
<222> LOCATION: (27)..(33)
<220> FEATURE:
<221> NAME/KEY: LCDR3
<222> LOCATION: (66)..(74)

<400> SEQUENCE: 73

Arg Ala Ser Gln Ser Ile Ser Ser Trp Leu Ala Trp Tyr Gln Gln Lys
1               5                   10                  15

Pro Gly Lys Ala Pro Lys Leu Leu Ile Tyr Asp Ala Ser Ser Leu Glu
            20                  25                  30

Ser Gly Val Pro Ser Arg Phe Ser Gly Ser Gly Ser Gly Thr Glu Phe
        35                  40                  45

Thr Leu Thr Ile Ser Ser Leu Gln Pro Asp Asp Phe Ala Thr Tyr Tyr
    50                  55                  60

Cys Gln Gln His Arg Ser Tyr Pro Pro Thr
65                  70

<210> SEQ ID NO 74
<211> LENGTH: 82
<212> TYPE: PRT
<213> ORGANISM: Homo sapiens
<220> FEATURE:
<221> NAME/KEY: HCDR1
<222> LOCATION: (1)..(9)
<220> FEATURE:
<221> NAME/KEY: HCDR2
<222> LOCATION: (24)..(40)
<220> FEATURE:
<221> NAME/KEY: HCDR3
<222> LOCATION: (71)..(82)

<400> SEQUENCE: 74

Tyr Thr Phe Thr Gly Tyr Tyr Met His Trp Val Arg Gln Ala Pro Gly
1               5                   10                  15

Gln Gly Leu Glu Trp Met Gly Trp Ile Asn Pro Asn Ser Gly Gly Thr
            20                  25                  30

Asn Tyr Ala Gln Lys Phe Gln Gly Arg Val Thr Met Thr Arg Asp Thr
        35                  40                  45

Ser Ile Ser Thr Ala Tyr Met Glu Leu Ser Arg Leu Arg Ser Asp Asp
    50                  55                  60

Thr Ala Val Tyr Tyr Cys Ala Arg Asp Gln Ala His Gln Arg Ser Ser
65                  70                  75                  80

Tyr Asp

<210> SEQ ID NO 75
<211> LENGTH: 74
<212> TYPE: PRT
<213> ORGANISM: Homo sapiens
<220> FEATURE:
<221> NAME/KEY: LCDR1
<222> LOCATION: (1)..(11)
<220> FEATURE:
<221> NAME/KEY: LCDR2
<222> LOCATION: (27)..(33)
<220> FEATURE:
<221> NAME/KEY: LCDR3
<222> LOCATION: (66)..(74)

<400> SEQUENCE: 75

Arg Ala Ser Gln Ser Ile Ser Ser Tyr Leu Asn Trp Tyr Gln Gln Lys
```

```
                1               5                   10                  15
Pro Gly Lys Ala Pro Lys Leu Leu Ile Tyr Gly Ala Ser Ser Leu Gln
                20                  25                  30

Ser Gly Val Pro Ser Arg Phe Ser Gly Ser Gly Ser Gly Thr Asp Phe
            35                  40                  45

Thr Leu Thr Ile Ser Ser Leu Gln Pro Glu Asp Phe Ala Thr Tyr Tyr
        50                  55                  60

Cys Gln Gln Arg Ser Ser Thr Pro Ile Thr
65                  70

<210> SEQ ID NO 76
<211> LENGTH: 88
<212> TYPE: PRT
<213> ORGANISM: Homo sapiens
<220> FEATURE:
<221> NAME/KEY: LCDR1
<222> LOCATION: (1)..(11)
<220> FEATURE:
<221> NAME/KEY: LCDR2
<222> LOCATION: (26)..(41)
<220> FEATURE:
<221> NAME/KEY: LCDR3
<222> LOCATION: (72)..(88)

<400> SEQUENCE: 76

Gly Ser Ile Ser Ser Gly Gly Tyr Tyr Trp Ser Trp Ile Arg Gln His
1               5                   10                  15

Pro Gly Lys Gly Leu Glu Trp Ile Gly Tyr Ile Tyr Tyr Ser Gly Ser
                20                  25                  30

Thr Tyr Tyr Asn Pro Ser Leu Lys Ser Arg Val Thr Ile Ser Val Asp
            35                  40                  45

Thr Ser Lys Asn Gln Phe Ser Leu Lys Leu Ser Ser Val Thr Ala Ala
        50                  55                  60

Asp Thr Ala Val Tyr Tyr Cys Ala Arg Ala Lys Ser Glu Leu Val Leu
65                  70                  75                  80

Pro Tyr Tyr Tyr Tyr Met Asp Val
                85

<210> SEQ ID NO 77
<211> LENGTH: 80
<212> TYPE: PRT
<213> ORGANISM: Homo sapiens
<220> FEATURE:
<221> NAME/KEY: LCDR1
<222> LOCATION: (1)..(17)
<220> FEATURE:
<221> NAME/KEY: LCDR2
<222> LOCATION: (33)..(39)
<220> FEATURE:
<221> NAME/KEY: LCDR3
<222> LOCATION: (72)..(80)

<400> SEQUENCE: 77

Lys Ser Ser Gln Ser Val Leu Phe Ser Asn Asn Lys Asn Tyr Leu
1               5                   10                  15

Ala Trp Tyr Gln Gln Lys Pro Gly Gln Pro Lys Leu Leu Ile Tyr
                20                  25                  30

Trp Ala Ser Thr Arg Glu Ser Gly Val Pro Asp Arg Phe Ser Gly Ser
            35                  40                  45

Gly Ser Gly Thr Asp Phe Thr Leu Thr Ile Ser Ser Leu Gln Ala Glu
        50                  55                  60
```

```
Asp Val Ala Val Tyr Tyr Cys Gln Gln Tyr Tyr Ser Leu Pro Pro Thr
 65                  70                  75                  80
```